US008024036B2

(12) United States Patent
Ferren et al.

(10) Patent No.: US 8,024,036 B2
(45) Date of Patent: **\*Sep. 20, 2011**

(54) LUMEN-TRAVELING BIOLOGICAL INTERFACE DEVICE AND METHOD OF USE

(75) Inventors: Bran Ferren, Beverly Hills, CA (US); W. Daniel Hillis, Encino, CA (US); Roderick A. Hyde, Redmond, WA (US); Muriel Y. Ishikawa, Livermore, CA (US); Edward K. Y. Jung, Bellevue, WA (US); Eric C. Leuthardt, St. Louis, MO (US); Nathan P. Myhrvold, Medina, WA (US); Clarence T. Tegreene, Bellevue, WA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 34 days.

This patent is subject to a terminal disclaimer.

(21) Appl. No.: 12/319,881

(22) Filed: Jan. 12, 2009

(65) Prior Publication Data
US 2009/0131737 A1 May 21, 2009

Related U.S. Application Data

(62) Division of application No. 11/726,031, filed on Mar. 19, 2007.

(51) Int. Cl.
*A61N 1/362* (2006.01)
(52) U.S. Cl. .............................. 607/2; 607/9
(58) Field of Classification Search .............. 607/2, 9
See application file for complete search history.

(56) References Cited

U.S. PATENT DOCUMENTS

| 3,391,697 | A | | 7/1968 | Greatbatch |
| 3,837,339 | A | | 9/1974 | Aisenberg et al. |
| 4,267,831 | A | | 5/1981 | Aguilar |
| 4,367,741 | A | | 1/1983 | Michaels |
| 4,585,652 | A | | 4/1986 | Miller et al. |
| 4,628,928 | A | | 12/1986 | Lowell |
| 4,714,460 | A | | 12/1987 | Calderon |
| 4,717,381 | A | * | 1/1988 | Papantonakos ............... 607/122 |
| 4,763,667 | A | | 8/1988 | Manzo |

(Continued)

FOREIGN PATENT DOCUMENTS
CN 99810271.7 10/2001
(Continued)

OTHER PUBLICATIONS

UK Intellectual Property Office Examination Report Under Section 18(3); App. No. GB0706802.6; bearing a date of Dec. 1, 2008; pp. 1-2.

(Continued)

*Primary Examiner* — Eric D. Bertram

(57) ABSTRACT

Lumen-traveling biological interface devices and associated methods and systems are described. Lumen-traveling biological interface devices capable of traveling within a body lumen may include a propelling mechanism to produce movement of the lumen-traveling device within the lumen, electrodes or other electromagnetic transducers for detecting biological signals and electrodes, coils or other electromagnetic transducers for delivering electromagnetic stimuli to stimulus responsive tissues. Lumen-traveling biological interface devices may also include additional components such as sensors, an active portion, and/or control circuitry.

17 Claims, 91 Drawing Sheets

U.S. PATENT DOCUMENTS

| | | | |
|---|---|---|---|
| 4,769,006 A * | 9/1988 | Papantonakos | 604/95.02 |
| 4,771,772 A | 9/1988 | DeWitt | |
| 4,800,898 A | 1/1989 | Hess et al. | |
| 4,817,601 A | 4/1989 | Roth et al. | |
| 4,871,351 A | 10/1989 | Feingold | |
| 4,905,689 A | 3/1990 | Stack et al. | |
| 4,944,659 A | 7/1990 | Labbe et al. | |
| 4,994,071 A | 2/1991 | MacGregor | |
| 5,019,372 A | 5/1991 | Folkman et al. | |
| 5,153,827 A | 10/1992 | Coutre et al. | |
| 5,176,638 A | 1/1993 | Don Michael | |
| 5,188,111 A | 2/1993 | Yates et al. | |
| 5,234,457 A | 8/1993 | Andersen | |
| 5,269,303 A | 12/1993 | Wernicke et al. | |
| 5,279,607 A | 1/1994 | Schentag et al. | |
| 5,310,404 A | 5/1994 | Gyory et al. | |
| 5,314,451 A | 5/1994 | Mulier | |
| 5,335,657 A | 8/1994 | Terry, Jr. et al. | |
| 5,337,732 A | 8/1994 | Grundfest et al. | |
| 5,338,625 A | 8/1994 | Bates et al. | |
| 5,339,051 A | 8/1994 | Koehler et al. | |
| 5,353,807 A | 10/1994 | DeMarco | |
| 5,374,285 A | 12/1994 | Vaiani et al. | |
| 5,386,741 A | 2/1995 | Rennex | |
| 5,395,390 A | 3/1995 | Simon et al. | |
| 5,398,670 A | 3/1995 | Ortiz et al. | |
| 5,403,311 A | 4/1995 | Abele et al. | |
| 5,411,551 A | 5/1995 | Winston et al. | |
| 5,437,660 A | 8/1995 | Johnson et al. | |
| 5,476,450 A | 12/1995 | Ruggio | |
| 5,497,147 A | 3/1996 | Arms et al. | |
| 5,522,394 A | 6/1996 | Zurbrügg | |
| 5,551,953 A | 9/1996 | Lattin et al. | |
| 5,554,914 A | 9/1996 | Miyazawa | |
| 5,569,968 A | 10/1996 | Lal et al. | |
| 5,574,347 A | 11/1996 | Neubauer | |
| 5,593,434 A | 1/1997 | Williams | |
| 5,599,324 A | 2/1997 | McAlister et al. | |
| 5,610,488 A | 3/1997 | Miyazawa | |
| 5,624,398 A | 4/1997 | Smith et al. | |
| 5,632,754 A | 5/1997 | Farley et al. | |
| 5,643,296 A | 7/1997 | Hundertmark et al. | |
| 5,662,587 A | 9/1997 | Grundfest et al. | |
| 5,669,874 A | 9/1997 | Feiring | |
| 5,674,276 A | 10/1997 | Andersen et al. | |
| 5,688,269 A | 11/1997 | Newton et al. | |
| 5,695,457 A | 12/1997 | St. Goar et al. | |
| 5,697,967 A | 12/1997 | Dinh et al. | |
| 5,702,432 A | 12/1997 | Chen et al. | |
| 5,705,293 A | 1/1998 | Hobson | |
| 5,728,089 A | 3/1998 | Lal et al. | |
| 5,735,276 A | 4/1998 | Lemelson | |
| 5,737,279 A | 4/1998 | Carter | |
| 5,782,798 A | 7/1998 | Rise | |
| 5,804,563 A | 9/1998 | Still et al. | |
| 5,807,395 A | 9/1998 | Mulier et al. | |
| 5,819,736 A | 10/1998 | Avny et al. | |
| 5,827,190 A | 10/1998 | Palcic et al. | |
| 5,830,179 A | 11/1998 | Mikus et al. | |
| 5,830,207 A | 11/1998 | Leeb et al. | |
| 5,831,012 A | 11/1998 | Nilsson et al. | |
| 5,833,603 A | 11/1998 | Kovacs et al. | |
| 5,843,139 A | 12/1998 | Goedeke et al. | |
| 5,855,801 A | 1/1999 | Lin et al. | |
| 5,865,754 A | 2/1999 | Sevick-Muraca et al. | |
| 5,873,835 A | 2/1999 | Hastings et al. | |
| 5,908,027 A | 6/1999 | Butterfield et al. | |
| 5,921,982 A | 7/1999 | Lesh et al. | |
| 5,947,119 A | 9/1999 | Reznick | |
| 5,951,600 A | 9/1999 | Lemelson | |
| 5,954,675 A | 9/1999 | Dellagatta | |
| 5,964,773 A | 10/1999 | Greenstein | |
| 6,004,269 A | 12/1999 | Crowley et al. | |
| 6,016,449 A | 1/2000 | Fischell et al. | |
| 6,019,729 A | 2/2000 | Itoigawa et al. | |
| 6,022,316 A | 2/2000 | Eppstein et al. | |
| 6,053,873 A | 4/2000 | Govari et al. | |
| 6,086,528 A | 7/2000 | Adair | |
| 6,102,845 A | 8/2000 | Woodard et al. | |
| 6,111,520 A | 8/2000 | Allen et al. | |
| 6,128,538 A | 10/2000 | Fischell et al. | |
| 6,134,474 A | 10/2000 | Fischell et al. | |
| 6,149,603 A | 11/2000 | Parker | |
| 6,159,230 A | 12/2000 | Samuels | |
| 6,164,284 A | 12/2000 | Schulman et al. | |
| 6,170,488 B1 | 1/2001 | Spillman, Jr. et al. | |
| 6,179,789 B1 | 1/2001 | Tu et al. | |
| 6,185,452 B1 | 2/2001 | Schulman et al. | |
| 6,186,986 B1 | 2/2001 | Berg et al. | |
| 6,187,599 B1 | 2/2001 | Asher et al. | |
| 6,197,013 B1 | 3/2001 | Reed et al. | |
| 6,219,577 B1 | 4/2001 | Brown, III et al. | |
| 6,221,099 B1 | 4/2001 | Andersen et al. | |
| 6,240,312 B1 * | 5/2001 | Alfano et al. | 600/476 |
| 6,240,316 B1 | 5/2001 | Richmond et al. | |
| 6,248,345 B1 | 6/2001 | Goldenheim et al. | |
| 6,249,076 B1 | 6/2001 | Madden et al. | |
| 6,255,361 B1 | 7/2001 | Rajagopalan et al. | |
| 6,278,379 B1 | 8/2001 | Allen et al. | |
| 6,280,386 B1 | 8/2001 | Alfano et al. | |
| 6,295,990 B1 | 10/2001 | Lewis et al. | |
| 6,296,638 B1 | 10/2001 | Davison et al. | |
| 6,322,532 B1 | 11/2001 | D'Sa et al. | |
| 6,337,997 B1 | 1/2002 | Rise | |
| 6,372,248 B1 | 4/2002 | Qin et al. | |
| 6,383,162 B1 | 5/2002 | Sugarbaker | |
| 6,384,741 B1 | 5/2002 | O'Leary, Sr. | |
| 6,385,472 B1 | 5/2002 | Hall et al. | |
| 6,398,280 B1 | 6/2002 | Parker et al. | |
| 6,402,678 B1 | 6/2002 | Fischell et al. | |
| 6,409,674 B1 | 6/2002 | Brockway et al. | |
| 6,436,120 B1 | 8/2002 | Meglin | |
| 6,442,413 B1 | 8/2002 | Silver | |
| 6,450,937 B1 | 9/2002 | Mercereau et al. | |
| 6,453,199 B1 | 9/2002 | Kobozev | |
| 6,464,687 B1 | 10/2002 | Ishikawa et al. | |
| 6,475,639 B2 | 11/2002 | Shahinpoor et al. | |
| 6,490,483 B2 | 12/2002 | Willis | |
| 6,497,714 B1 | 12/2002 | Ishikawa et al. | |
| 6,500,174 B1 | 12/2002 | Maguire et al. | |
| 6,512,949 B1 | 1/2003 | Combs et al. | |
| 6,512,950 B2 | 1/2003 | Li et al. | |
| 6,514,237 B1 | 2/2003 | Maseda | |
| 6,530,950 B1 | 3/2003 | Alvarado et al. | |
| 6,547,825 B1 | 4/2003 | Shimizu et al. | |
| 6,548,982 B1 | 4/2003 | Papanikolopoulos et al. | |
| 6,554,798 B1 | 4/2003 | Mann et al. | |
| 6,575,969 B1 | 6/2003 | Rittman, III et al. | |
| 6,585,763 B1 | 7/2003 | Keilman et al. | |
| 6,591,137 B1 | 7/2003 | Fischell et al. | |
| 6,592,567 B1 | 7/2003 | Levin et al. | |
| 6,597,954 B1 | 7/2003 | Pless et al. | |
| 6,607,553 B1 | 8/2003 | Healy et al. | |
| 6,616,676 B2 | 9/2003 | Bashiri et al. | |
| 6,623,519 B2 | 9/2003 | Edwin et al. | |
| 6,632,216 B2 | 10/2003 | Houzego et al. | |
| 6,638,273 B1 | 10/2003 | Farley et al. | |
| 6,648,908 B2 | 11/2003 | Dobak, III et al. | |
| 6,666,860 B1 | 12/2003 | Takahashi | |
| 6,669,683 B2 | 12/2003 | Santini, Jr. et al. | |
| 6,673,042 B1 | 1/2004 | Samson et al. | |
| 6,673,363 B2 | 1/2004 | Luo et al. | |
| 6,679,893 B1 | 1/2004 | Tran | |
| 6,709,388 B1 * | 3/2004 | Mosse et al. | 600/114 |
| 6,711,423 B2 | 3/2004 | Colvin, Jr. | |
| 6,712,835 B2 | 3/2004 | Mazzocchi et al. | |
| 6,719,684 B2 | 4/2004 | Kim et al. | |
| 6,733,485 B1 | 5/2004 | Whitehurst et al. | |
| 6,735,474 B1 | 5/2004 | Loeb et al. | |
| 6,735,475 B1 | 5/2004 | Whitehurst et al. | |
| 6,743,211 B1 | 6/2004 | Prausnitz et al. | |
| 6,754,536 B2 | 6/2004 | Swoyer et al. | |
| 6,755,802 B2 | 6/2004 | Bell | |
| 6,755,803 B1 | 6/2004 | Le et al. | |
| 6,764,441 B2 | 7/2004 | Chiel et al. | |
| 6,770,071 B2 | 8/2004 | Woloszko et al. | |
| 6,773,429 B2 | 8/2004 | Sheppard, Jr. et al. | |

| | | |
|---|---|---|
| 6,797,522 B1 | 9/2004 | Still et al. |
| 6,802,811 B1 | 10/2004 | Slepian |
| 6,824,508 B2 | 11/2004 | Kim et al. |
| 6,824,510 B2 | 11/2004 | Kim et al. |
| 6,824,561 B2 | 11/2004 | Soykan et al. |
| 6,849,183 B2 | 2/2005 | Gorsuch et al. |
| 6,855,115 B2 | 2/2005 | Fonseca et al. |
| 6,860,867 B2 | 3/2005 | Seward et al. |
| 6,861,001 B2 | 3/2005 | Lee et al. |
| 6,869,430 B2 | 3/2005 | Balbierz et al. |
| 6,875,209 B2 | 4/2005 | Zvuloni et al. |
| 6,882,881 B1 | 4/2005 | Lesser et al. |
| 6,889,091 B2 * | 5/2005 | Hine et al. ............... 607/119 |
| 6,890,303 B2 | 5/2005 | Fitz |
| 6,898,464 B2 | 5/2005 | Edell et al. |
| 6,911,004 B2 | 6/2005 | Kim et al. |
| 6,911,496 B2 | 6/2005 | Rhee et al. |
| 6,920,359 B2 | 7/2005 | Meadows et al. |
| 6,921,413 B2 | 7/2005 | Mahadevan-Jansen et al. |
| 6,925,357 B2 | 8/2005 | Wang et al. |
| 6,929,636 B1 | 8/2005 | von Alten |
| 6,936,003 B2 | 8/2005 | Iddan |
| 6,939,290 B2 | 9/2005 | Iddan |
| 6,939,376 B2 | 9/2005 | Shulze et al. |
| 6,950,707 B2 | 9/2005 | Whitehurst |
| 6,953,589 B1 | 10/2005 | Trautman et al. |
| 6,958,034 B2 | 10/2005 | Iddan |
| 6,959,215 B2 | 10/2005 | Gliner et al. |
| 6,960,227 B2 | 11/2005 | Jones et al. |
| 6,963,792 B1 | 11/2005 | Green |
| 6,991,617 B2 | 1/2006 | Hektner et al. |
| 7,003,352 B1 | 2/2006 | Whitehurst |
| 7,013,177 B1 | 3/2006 | Whitehurst et al. |
| 7,037,343 B2 | 5/2006 | Imran |
| 7,042,184 B2 | 5/2006 | Oleynikov et al. |
| 7,066,180 B2 | 6/2006 | Aylsworth et al. |
| 7,101,386 B2 | 9/2006 | Dobak, III |
| 7,115,109 B2 | 10/2006 | Gerdts et al. |
| 7,125,382 B2 | 10/2006 | Zhou et al. |
| 7,131,979 B2 | 11/2006 | DiCarlo et al. |
| 7,160,258 B2 | 1/2007 | Imran et al. |
| 7,181,261 B2 | 2/2007 | Silver et al. |
| 7,195,641 B2 | 3/2007 | Palmaz et al. |
| 7,228,162 B2 | 6/2007 | Ward et al. |
| 7,236,821 B2 | 6/2007 | Cates et al. |
| 7,245,954 B2 | 7/2007 | Glukhovsky |
| 7,297,113 B1 | 11/2007 | Russell et al. |
| 7,341,577 B2 | 3/2008 | Gill |
| 7,365,509 B2 | 4/2008 | Park et al. |
| 7,383,071 B1 | 6/2008 | Russell et al. |
| 7,572,228 B2 | 8/2009 | Wolinsky et al. |
| 7,625,338 B2 | 12/2009 | Gilad et al. |
| 7,684,840 B2 | 3/2010 | Palti |
| 7,713,196 B2 | 5/2010 | Baker, Jr. |
| 7,736,300 B2 | 6/2010 | Ziegler et al. |
| 7,744,542 B2 | 6/2010 | Piaget et al. |
| 7,801,626 B2 | 9/2010 | Moser |
| 7,840,271 B2 | 11/2010 | Kieval et al. |
| 7,857,767 B2 | 12/2010 | Ferren et al. |
| 2001/0029348 A1 | 10/2001 | Willis |
| 2001/0051766 A1 | 12/2001 | Gazdzinski |
| 2002/0065509 A1 | 5/2002 | Lebel et al. |
| 2002/0068080 A1 | 6/2002 | Lerner |
| 2002/0090388 A1 | 7/2002 | Humes et al. |
| 2002/0116029 A1 | 8/2002 | Miller et al. |
| 2002/0116034 A1 | 8/2002 | Miller et al. |
| 2002/0147480 A1 | 10/2002 | Mamayek |
| 2002/0156462 A1 | 10/2002 | Stultz |
| 2002/0165592 A1 | 11/2002 | Glukhovsky et al. |
| 2002/0169436 A1 | 11/2002 | Gurm et al. |
| 2002/0171385 A1 | 11/2002 | Kim et al. |
| 2002/0188323 A1 | 12/2002 | Penner et al. |
| 2002/0193679 A1 | 12/2002 | Malave et al. |
| 2002/0193874 A1 | 12/2002 | Crowley |
| 2002/0198470 A1 | 12/2002 | Imran et al. |
| 2002/0198521 A1 | 12/2002 | Maguire |
| 2002/0198604 A1 | 12/2002 | Schulman et al. |
| 2003/0023150 A1 | 1/2003 | Yokoi et al. |
| 2003/0024534 A1 | 2/2003 | Silvestri et al. |
| 2003/0040704 A1 | 2/2003 | Dorros et al. |
| 2003/0065358 A1 | 4/2003 | Frecker et al. |
| 2003/0069475 A1 | 4/2003 | Banik et al. |
| 2003/0069523 A1 | 4/2003 | Williams et al. |
| 2003/0151524 A1 | 8/2003 | Clark |
| 2003/0152823 A1 | 8/2003 | Heller |
| 2003/0158584 A1 | 8/2003 | Cates et al. |
| 2003/0163177 A1 | 8/2003 | Eggers et al. |
| 2003/0167000 A1 | 9/2003 | Mullick et al. |
| 2003/0214579 A1 | 11/2003 | Iddan |
| 2003/0214580 A1 | 11/2003 | Iddan |
| 2003/0220556 A1 | 11/2003 | Porat et al. |
| 2004/0008853 A1 | 1/2004 | Pelrine et al. |
| 2004/0018508 A1 | 1/2004 | Friedman |
| 2004/0019374 A1 | 1/2004 | Hojeibane et al. |
| 2004/0064093 A1 | 4/2004 | Hektner et al. |
| 2004/0073177 A1 | 4/2004 | Hickle |
| 2004/0073190 A1 | 4/2004 | Deem et al. |
| 2004/0092825 A1 | 5/2004 | Madar et al. |
| 2004/0097805 A1 | 5/2004 | Verard et al. |
| 2004/0097819 A1 | 5/2004 | Duarte |
| 2004/0098030 A1 | 5/2004 | Makower et al. |
| 2004/0133147 A1 | 7/2004 | Woo |
| 2004/0138517 A1 | 7/2004 | Osorio et al. |
| 2004/0147939 A1 | 7/2004 | Rabkin et al. |
| 2004/0148034 A1 | 7/2004 | Kagan et al. |
| 2004/0162469 A1 | 8/2004 | Imran |
| 2004/0162501 A1 | 8/2004 | Imran |
| 2004/0176664 A1 | 9/2004 | Iddan |
| 2004/0199246 A1 | 10/2004 | Chu et al. |
| 2004/0225325 A1 | 11/2004 | Bonutti |
| 2004/0225326 A1 | 11/2004 | Weiner et al. |
| 2004/0260391 A1 | 12/2004 | Santini, Jr. et al. |
| 2004/0267240 A1 | 12/2004 | Gross et al. |
| 2005/0004553 A1 | 1/2005 | Douk |
| 2005/0021023 A1 | 1/2005 | Guglielmi et al. |
| 2005/0027236 A1 | 2/2005 | Douk |
| 2005/0058701 A1 | 3/2005 | Gross et al. |
| 2005/0065592 A1 | 3/2005 | Holzer |
| 2005/0069925 A1 | 3/2005 | Ford et al. |
| 2005/0079132 A1 | 4/2005 | Wang et al. |
| 2005/0107870 A1 | 5/2005 | Wang et al. |
| 2005/0113460 A1 | 5/2005 | Glick |
| 2005/0121411 A1 | 6/2005 | Cohen |
| 2005/0126916 A1 | 6/2005 | Lockard et al. |
| 2005/0149170 A1 | 7/2005 | Tassel et al. |
| 2005/0151524 A1 | 7/2005 | Sae-Ueng et al. |
| 2005/0177223 A1 | 8/2005 | Palmaz |
| 2005/0182482 A1 | 8/2005 | Wang et al. |
| 2005/0203613 A1 | 9/2005 | Arney et al. |
| 2005/0216074 A1 | 9/2005 | Sahatjian et al. |
| 2005/0221529 A1 | 10/2005 | Bang et al. |
| 2005/0228259 A1 | 10/2005 | Glukhovsky et al. |
| 2005/0234393 A1 | 10/2005 | Wood, Jr. |
| 2005/0234440 A1 | 10/2005 | Wood, Jr. |
| 2005/0238689 A1 | 10/2005 | Carpenter et al. |
| 2005/0272806 A1 | 12/2005 | Falotico et al. |
| 2005/0272974 A1 | 12/2005 | Iddan |
| 2005/0277839 A1 | 12/2005 | Alderman et al. |
| 2005/0278020 A1 | 12/2005 | Wang et al. |
| 2006/0004395 A1 | 1/2006 | Chiel et al. |
| 2006/0009810 A1 | 1/2006 | Mann et al. |
| 2006/0015146 A1 | 1/2006 | Girouard et al. |
| 2006/0037617 A1 | 2/2006 | Walke et al. |
| 2006/0074479 A1 | 4/2006 | Bailey et al. |
| 2006/0119304 A1 | 6/2006 | Farritor et al. |
| 2006/0167339 A1 * | 7/2006 | Gilad et al. ............... 600/101 |
| 2007/0010868 A1 | 1/2007 | Ferren et al. |
| 2007/0088334 A1 | 4/2007 | Hillis et al. |
| 2007/0225634 A1 | 9/2007 | Ferren et al. |
| 2008/0033569 A1 | 2/2008 | Ferren et al. |
| 2008/0063703 A1 | 3/2008 | Gross et al. |
| 2008/0066929 A1 | 3/2008 | Costa et al. |
| 2008/0103440 A1 | 5/2008 | Ferren et al. |
| 2008/0243056 A1 | 10/2008 | Hillis et al. |

FOREIGN PATENT DOCUMENTS

| | | |
|---|---|---|
| EP | 1 245 201 A1 | 10/2002 |
| EP | 1 618 831 A2 | 1/2006 |

| | | |
|---|---|---|
| EP | 2 163 206 A1 | 3/2010 |
| JP | 2001-506871 | 3/1998 |
| JP | 2002-153569 | 5/2002 |
| JP | 2005-74229 | 3/2005 |
| WO | WO 96/39999 | 12/1996 |
| WO | WO 98/09582 | 3/1998 |
| WO | WO 98/14243 | 4/1998 |
| WO | WO 99/20335 | 4/1999 |
| WO | WO 99/44665 | 9/1999 |
| WO | WO 00/69515 | 11/2000 |
| WO | WO 01/08548 A1 | 2/2001 |
| WO | WO 01/24731 A1 | 4/2001 |
| WO | WO 03/072157 A1 | 9/2003 |
| WO | WO 03/090618 A2 | 11/2003 |
| WO | WO 03/106966 A2 | 12/2003 |
| WO | WO 2004/028335 A2 | 4/2004 |
| WO | WO 2004/058041 A2 | 7/2004 |
| WO | WO 2004/086958 A1 | 10/2004 |
| WO | WO 2005/082248 A1 | 9/2005 |

OTHER PUBLICATIONS

UK Intellectual Property Office Examination Report Under Section 18(3); App. No. GB0706802.6; Nov. 23, 2009; pp. 1-2.
UK Intellectual Property Office Examination Report Under Section 18(3); App. No. GB0821519.6; Nov. 12, 2009; 1-4.
UK Intellectual Property Office Examination Report Under Section 18(3); App. No. GB0821526.1; Nov. 11, 2009; 1-5.
UK Intellectual Property Office Examination Report Under Section 18(3), App. No. GB0821523.8; Jul. 2, 2009; pp. 1-2.
UK Examination Report Under Section 18(3); App. No. GB0821524.6; bearing a date of May 6, 2010 (received by our Agent on May 7, 2010); pp. 1-3.
UK Intellectual Property Office Examination Report under Section 18(3); App. No. GB0821521.2; Jan. 12, 2011 (received by our agent on Jan. 13, 2011); 4 pages.
UK Intellectual Property Office Examination Report Under Section 18(3); App. No. GB0821530.3; Aug. 27, 2010 (received by our Agent on Sep. 3, 2010; pp. 1-6.
Japanese Office Action; Japanese App. No. 2007-533572; Sep. 22, 2010 (received by our Agent on Sep. 28, 2010); pp. 1-4; (no English translation currently available).
UK Intellectual Property Office Examination Report Under Section 18(3); App. No. GB0821519.6; Oct. 19, 2010 (received by our Agent on Oct. 19, 2010); 1 page.
UK Intellectual Property Office Combined Search and Examination Report Under Sections 17 & 18(3); App. No. GB1016383.0; Nov. 1, 2010; pp. 1-4.
UK Intellectual Property Office Examination Report Under Section 18(3); App. No. GB0821524.6; Aug. 9, 2010 (received by our Agent on Aug. 10, 2010); pp. 1-2.
UK Intellectual Property Office Examination Report Under Section 18(3); App. No. GB0821519.6; Aug. 9, 2010 (received by our Agent on Aug. 10, 2010); pp. 1-3.
U.S. Appl. No. 12/075,480, Oct. 2, 2008, Hillis et al.
U.S. Appl. No. 11/891,573, Dec. 6, 2007, Wood, Jr., Lowell L.
U.S. Appl. No. 11/891,371, Dec. 6, 2007, Wood, Jr., Lowell L.
U.S. Appl. No. 11/891,356, Apr. 10, 2008, Wood, Jr., Lowell L.
U.S. Appl. No. 11/891,355, Feb. 14, 2008, Wood, Jr., Lowell L.
U.S. Appl. No. 11/891,334, Mar. 6, 2008, Wood, Jr., Lowell L.
U.S. Appl. No. 11/891,333, Feb. 14, 2008, Wood, Jr., Lowell L.
U.S. Appl. No. 11/726,025, Feb. 7, 2008, Ferren et al.
U.S. Appl. No. 11/725,982, May 1, 2008, Ferren et al.
U.S. Appl. No. 11/651,946, Sep. 27, 2007, Ferren et al.
U.S. Appl. No. 11/645,358, Jul. 5, 2007, Ferren et al.
U.S. Appl. No. 11/645,357, Sep. 27, 2007, Ferren et al.
U.S. Appl. No. 11/541,492, Dec. 20, 2007, Jung et al.
U.S. Appl. No. 11/541,542, Dec. 20, 2007, Jung et al.
U.S. Appl. No. 11/541,448, Dec. 20, 2007, Jung et al.
U.S. Appl. No. 11/541,378, Dec. 20, 2007, Jung et al.
U.S. Appl. No. 11/541,377, Dec. 20, 2007, Jung et al.
U.S. Appl. No. 11/526,203, Dec. 20, 2007, Jung et al.
U.S. Appl. No. 11/526,201, Dec. 20, 2007, Jung et al.
U.S. Appl. No. 11/526,144, Dec. 20, 2007, Jung et al.
U.S. Appl. No. 11/526,089, Dec. 20, 2007, Jung et al.
U.S. Appl. No. 11/485,619, Apr. 19, 2007, Hillis et al.
U.S. Appl. No. 11/478,368, Jan. 11, 2007, Ferren et al.
U.S. Appl. No. 11/455,010, Dec. 20, 2007, Jung et al.
U.S. Appl. No. 11/454,343, Apr. 2, 2009, Jung et al.
U.S. Appl. No. 11/417,898, Oct. 7, 2010, Hillis et al.
U.S. Appl. No. 11/403,230, Mar. 22, 2007, Ferren et al.
U.S. Appl. No. 10/949,186, Mar. 30, 2006, Hillis et al.
U.S. Appl. No. 10/827,578, Oct. 20, 2005, Wood, Jr., Lowell L.
U.S. Appl. No. 10/827,576, Oct. 20, 2005, Wood, Jr., Lowell L.
U.S. Appl. No. 10/827,572, Oct. 20, 2005, Wood, Jr., Lowell L.
U.S. Appl. No. 10/827,390, Oct. 20, 2005, Wood, Jr., Lowell L.
"001_08 Comparison of Capsule Cameras: M2A (Given Imaging) vs. NORIKA3 (RF System lab)" RF System lab; bearing dates of 2001-2004; pp. 1-2; located at http://www.rfnorika.com/eng/system/sys_008.html; printed on May 4, 2006.
"A Hydrogel-based CO2 sensor"; BIOS—The lab on a chip group; bearing a date of Aug. 29, 2005; pp. 1-2; located at: http://bios.ewi.utwente.nl/research/analysissystemssenors/ahydrogelbased.doc/index.html;printed on Apr. 25, 2006; University of Twente; The Netherlands.
Agarwal, Abhishek K.; Atencia, Javier; Beebe, David J.; Jiang, Hongrui; "Magnetically-driven temperature-controlled microfluidic actuators"; pp. 1-5; located at: http://www.unl.im.dendai.ac.jp/INSS2004/INSS2004_papers/OralPresentations/C2.pdf.
"Agile new plastics change shape with heat"; MIT News Office; Nov. 20, 2006; pp. 1-4; Massachusetts Institute of Technology; printed on Nov. 22, 2006; located at http://web.mit.edu/newsoffice/2006/triple-shape.html.
"Agile new plastics change shape with heat"; MIT Tech Talk; Nov. 22, 2006; p. 5 (1 page).
Ananthaswamy, Anil; "First robot moved by muscle power"; bearing a date of Feb. 27, 2004; pp. 1-3; New Scientist; located at http://www.newscientist.com/article.ns?id=dn4714;printed on Sep. 12, 2006.
Asari, Vijayan K.; Kumar, Sanjiv; Kassim, Irwan M.; "A Fully Autonomous Microrobotic Endoscopy System"; Journal of Intelligent and Robotic Systems; bearing a date of 2000; pp. 325-341; vol. 28; Kluwer Academic Publishers.
Behkam, Bahareh; Sitti, Metin; "Towards Hybrid Swimming Microrobots: Bacteria Assisted Propulsion of Polystyrene Beads"; Proceedings of the 28$^{th}$ IEEE EMBS Annual International Conference; bearing dates of Aug. 30, 2006-Sep. 3, 2006 and 2006; pp. 2421-2424; IEEE.
Berlinger, Norman T.; "Robotic Surgery—Squeezing into Tight Places"; New England Journal of Medicine; bearing dates of May 17, 2006, May 18, 2006, and 2006; pp. 2099-2101; Massachusetts Medical Society; located at www.nejm.org.
Bezrouk, A.; Hanuš, J.; Záhora, J.; "Temperature Characteristics of Nitinol Spiral Stents"; Scripta Medica (BRNO); bearing dates of Aug. 2005, Oct. 2005; pp. 219-226; vol. 78, No. 4.
Bialek, William; Rieke, Fred; De Ruyter Van Steveninck, Rob R.; Warland, David; "Reading a Neural Code"; Science; bearing a date of Jun. 28, 1991; pp. 1854-1857; vol. 252.
Bucher, Volker; Graf, Michael; Stelzle, Martin; Nisch, Wilfried; "Low-Impedance Thin-Film Polycrystalline Silicon Microelectrodes for Extracellular Stimulation and Recording"; Biosensors and Bioelectronics; bearing a date of 1999; pp. 639-649; vol. 14; Elsevier Science S.A.; located at: www.elsevier.com/locate/bios.
Butson, Christopher R.; McIntyre, Cameron C.; "Role of Electrode Design on the Volume of Tissue Activated During Deep Brain Stimulation"; Journal of Neural Engineering; bearing a date of 2006; vol. 3; pp. 1-8; IOP Publishing Ltd.
Chang, Suk Tai; Paunov, Vesselin N.; Petsev, Dimiter N.; Velev, Orlin D.; "Articles: Remotely Powered Self-Propelling Particles and Micropumps Based on Miniature Diodes"; Nature Materials; bearing a date of 2007; pp. 1-6; Nature Publishing Group; located at: www.nature.com/naturematerials.
Chen, Haitao; Ebner, Armin D.; Ritter, James A.; Kaminski, Michael D.; Rosengart, Axel J.; "Sequestration of Blood-Borne Magnetic Drug Carrier Particles Using Magnetizable Intravascular Stents"; Collaborative Investigators for Applied Nanotechnology in Medicine; pp. 1; Chicago, Illinois, 2004.
Chen, Ting; Barton, Scott Calabrese, Binyamin, Gary; Gao, Zhiqiang; Zhang, Yongchao, Kim, Hyug-Han; Heller, Adam; "A Miniature Biofuel Cell"; Journal of the American Chemical Society; Aug. 11, 2001; pp. 8630-8631; vol. 123; 2001 American Chemical Society.

Christensen, Bill; "Musclebot: Microbot with a Heart"; Technovelgy.com; pp. 1-2; bearing a date of Feb. 27, 2004; located at http://www.technovelgy.com/ct/Science-Fiction-News.asp?NewsNum=46; printed on Sep. 12, 2006.

Christensen, Bill; "Propulsion System for 'Fantastic Voyage' Robot"; Technovelgy.com; pp. 1-4; Technovelgy.com; located http://www.technovelgy.com/ct/Science-Fiction-News.asp?NewsNum=811; printed on Jan. 4, 2007.

Costamagna; Guido M.D.; "PillCam™ SB Capsule Endoscopy"; Given Imaging.com; bearing dates of 2001-2006; pp. 1-4; located at http://www.givenimaging.com/Cultures/en-US/Given/English/Products/CapsuleEndoscopy/; printed on May 4, 2006.

Cui, Xinyan; Hetke, Jamille F.; Wiler, James A.; Anderson, David J.; Martin, David C.; "Electrochemical Deposition and Characterization of Conducting Polymer Polypyrrole/PPS on Multichannel Neural Probes"; Sensors and Actuators A Physical; bearing a date of 2001; pp. 8-18; vol. 93; Elsevier Science B.V.; located at: www.elsevier.com/locate/sna.

Dario, P.; Carrozza, M.C.; Lencioni, L.; Magnani, B.; D'Attanasio, S.; "A Micro Robotic System for Coloscopy"; Proceedings of the 1997 IEEE International Conference on Robotics and Automation; bearing dates of Apr. 1997 and 1997; pp. 1567-1572; IEEE.

Dillier, Norbert; Lai, Wai Kong; Almqvist, Bengt; Frohne, Carolin; Müller-Deile, Joachim; Stecker, Matthias; Von Wallenberg, Ernst; "Measurement of the Electrically Evoked Compound Action Potential Via a Neural Response Telebetry System"; Annals Of Otology Rhinology and Laryngology; bearing a date of May 2002; pp. 407-414; vol. 111, No. 5; Annals Publishing Company.

Donoghue, John P.; "Review: Connecting Cortex to Machines: Recent Advances in Brain Interfaces"; Nature Neuroscience Supplement; bearing a date on Nov. 2002; pp. 1085-1088; vol. 5; Nature Publishing Group; located at: http://www.nature.com/natureneuroscience.

Dongxiang, Chi; Guozheng, Yan; "An earthworm based miniature robot for intestinal inspection"; Proceedings of SPIE; bearing dates of Nov. 7, 2001-Nov. 9, 2001; pp. 396-400; vol. 4601; SPIE.

Fang, Zi-Ping; Mortimer, J. Thomas; "Selective Activation of Small Motor Axons by Quasitrapezoidal Current Pulses"; IEEE Transactions on Biomedical Engineering; bearing a date of Feb. 1991; pp. 168-174; vol. 38, No. 2; IEEE.

Fiaccabrino, G.C.; Tang, X.-M.; Skinner, N.; De Rooij, N.F.; Koudelka-Hep, M.; "Electrochemical Characterization of Thin-Film Carbon Interdigitated Electrode Arrays"; Analytica Chimica Acta; bearing a date of 1996; pp. 155-160; vol. 326; Elsevier Science B.V.

Freitas Jr., Robert A.; "8.2.1.2 Arteriocenous Microcirculation"; "9.4.3.5 Legged Ambulation"; "9.4.3.6 Tank-Tread Rolling"; "9.4.3.7 Amoeboid Locomotion"; "9.4.3.8 Inchworm Locomotion"; "Nanomedicine vol. I: Basic Capabilities"; bearing a date of 1999; pp. 211-214, pp. 316-318; Landes Bioscience; Georgetown, Texas, USA.

Gitter, Alfred H.; Fromm, Michael; Schulzke, Jörg-Dieter; "Impedance Analysis for the Determination of Epithelial and Subepithelial Resistance in Intestinal Tissues"; Journal of Biochemical and Biophysical Methods, bearing a date of 1998; pp. 35-46; vol. 37; Elsevier Science B.V.

Goda, Yukiko; Colicos, Michael A.; "Protocol: Photoconductive Stimulation of Neurons Cultured on Silicon Wafers"; Nature Protocols; bearing a date of 2006; pp. 461-467; vol. 1, No. 1; Nature Publishing Group; located at: http://www.nature.com/natureprotocols.

Gozani, Shai N.; Miller, John P.; "Optimal Discrimination and Classification of Neuronal Action Potential Waveforms from Multiunit, Multichannel Recordings Using Software-Based Linear Filters"; IEEE Transactions on Biomedical Engineering; bearing a date of Apr. 1994; pp. 358-372; vol. 41, No. 4; IEEE.

Gray, Charles M.; Maldonado, Pedro E.; Wilson, Mathew; McNaughton, Bruce; "Tetrodes Markedly Improve the Reliability and Yield of Multiple Single-Unit Isolation from Multi-Unit Recordings in Cat Striate Cortex"; Journal of Neuroscience Methods; bearing a date of 1995; pp. 43-54; vol. 63; Elsevier Science B.V.

Hagleitner, C.; Hierlemann, A.; Lange, D.; Kummer, A.; Kerness, N.; Brand, O.; Baltes, H.; "Smart single-chip gas sensor microsystem"; Nature; Nov. 15, 2001; pp. 293-296; vol. 414; Macmillan Magazines Ltd.; www.nature.com.

Hanna, Darrin M.; Oakley, Barbara A.; Stryker, Gabrielle A.; "Using a System-on-Chip Implantable Device to Filter Circulating Infected Cells in Blood or Lymph"; IEEE Transactions on Biomedical Engineering; bearing dates of Jan. 25, 2003, Mar. 2003; pp. 6-13; vol. 2, No. 1; IEEE.

Hodgkin, A.L.; Huxley, A.F.; "A Quantitative Description of Membrane Current and its Application to Conduction and Excitation in Nerve"; Journal of Physiology; bearing a date of 1952; pp. 500-544; vol. 117.

Høeg, H.D.; Slatkin, A.B.; Burdick, J.W.; Grundfest, Dr. Warren S.; "Biomechanical Modeling of the Small Intestine as Required for the Design and Operation of a Robotic Endoscope"; Proceedings ICRA '00 IEEE International Conference on Robotics and Automation; Apr. 24, 2000-Apr. 28, 2000; pp. 1-8; vol. 2.

Hofmann, U.G.; Folkers, A.; Mösch, F.; Höhl, D.; Kindlundh, M.; Norlin, P.; "A 64(128)-Channel Multisite Neuronal Recording System"; bearing a date of 2002; pp. 1-4.

Ikeuchi, K.; Yoshinaka, K.; Hashimoto, S.; Tomita, N.; "Locomotion of Medical Micro Robot with Spiral Ribs Using Mucus"; Seventh International Symposium on Micro Machine and Human Science; bearing a date of 1996; pp. 217-222; IEEE.

Inmann, Andreas; Haugland, Morten; Haase, Jens; Biering-Sørensen, Fin; Sinkjaer, Thomas; "NeuroReport: Signals from Skin Mechanoreceptors used in Control of a Hand Grasp Neuroprosthesis"; Motor Systems; bearing a date of Sep. 17, 2001; pp. 2817-2819; vol. 12, No. 13; Lippincott Williams & Wilkins.

Janders, M.; Egert, U.; Stelze, M.; Nisch, W.; "Novel Thin Film Titanium Nitride Micro-Electrodes with Excellent Charge Transfer Capability for Cell Stimulation and Sensing Applications"; IEEE Engineering in Medicine and Biology Society; bearing a date of 1996; pp. 245-247; IEEE.

"Japanese Researchers Unveil Medical Mini Robot"; Yahoo! News; bearing a date of Mar. 8, 2007; pp. 1-2; Yahoo! Inc.; located at: http://news.yahoo.com/s/afp/20070308/hl_afp/afplifestyleshealthscience; printed on Mar. 8, 2007.

Ji, Jin; Najafi, Khalil; Wise, Kensall D.; "A Low-Noise Demultiplexing System for Active Multichannel Microelectrode Arrays"; IEEE Transactions of Biomedical Engineering; bearing a date of Jan. 1991; pp. 77-81; vol. 38, No. 1; IEEE.

Kassim, Irwan; Phee, Louis; Ng, Wan S.; Gong, Feng; Dario, Paolo; Mosse, Charles A.; "Locomotion Techniques for Robotic Colonoscopy"; IEEE Engineering in Medicine and Biology Magazine; bearing dates of May/Jun. 2006 and 2006; pp. 49-56; IEEE.

Kennedy, P.R.; Bakay, R.A.E.; Moore, M.M.; Adams, K.; Goldwaithe, J.; "Direct Control of a Computer from the Human Central Nervous System"; IEEE Transactions on Rehabilitation Engineering; bearing a date of Jun. 2000; pp. 198-202; vol. 8, No. 2; IEEE.

Kobetic, Rudi; Triolo, Ronald J.; Uhlir, James P.; Bieri, Carole; Wibowo, Michael; Polando, Gordie; Marsolais, E. Byron; Davis Jr., John A.; Ferguson, Kathleen A.; Sharma, Mukut; "Implanted Functional Electrical Stimulation System for Mobility in Paraplegia: A Follow-Up Case Report"; IEEE Transactions on Rehabilitation Engineering; bearing a date of Dec. 1999; pp. 390-398; vol. 7, No. 4; IEEE.

Krueger, Curtis; "New light on blood testing"; Oct. 20, 2006; pp. 1-2; St. Petersburg Times; printed on Oct. 24, 2006; located at http://www.sptimes.com/2006/10/20news_pf/Tampabay/New_light_on_blood_te.shtml.

Langer, Robert; Peppas, Nicholas A.; "Advances in Biomaterials, Drug Delivery, and Bionanotechnology"; AIChE Journal—Bioengineering, Food, and Natural Products; Dec. 2003; pp. 2990-3006; vol. 49, No. 12.

Loeb, Gerald E.; Peck, Raymond A.; Moore, William H.; Hood, Kevin; "BION System for Distributed Neural Prosthetic Interfaces"; Medical Engineering and Physics; bearing a date of 2001; pp. 9-18; vol. 23; Elsevier Science Ltd.; located at: www.elsevier.com/locate/medengphy.

Loeb, G.E.; Peck, R.A.; Martyniuk, J.; "Toward the Ultimate Metal Microelectrode"; Journal of Neuroscience Methods; bearing a date of 1995; pp. 175-183; vol. 63; Elsevier Science B.V.

Lu, Zhao; Martel, Sylvain; "Preliminary Investigation of Bio-carriers Using Magnetotactic Bacteria"; Proceedings of the 28$^{th}$ IEEE EMBS Annual International Conference; bearing dates of Aug. 30, 2006-Sep. 3, 2006 and 2006; pp. 3415-3418; IEEE.

Mangan, Elizabeth V.; Kingsley, Dan A.; Quinn, Roger D.; Chiel, Hillel J.; "Development of a Peristaltic Endoscope"; IEEE International Conference on Robotics & Automation 2002; pp. 1-6; located at http://biorobots.cwru.edu/publications/ICRA02_Mangan_Endoscope.pdf.

Marks, William B.; Loeb, Gerald E.; "Action Currents, Internodal Potentials, and Extracellular Records of Myelinated Mammalian Nerve Fibers Derived from Node Potentials"; Biophysical Journal; 1976; pp. 655-668; vol. 16.

Martel, Sylvain; "Fundamentals of high-speed piezo-actuated three-legged motion for miniature robots designed for nanometer-scale operations"; pp. 1-8, 2003.

Martel, Sylvain; "Towards MRI-Controlled Ferromagnetic and MC-1 Magnetotactic Bacterial Carriers for Targeted Therapies in Arteriolocapillar Networks Stimulated by Tumoral Angiogenesis"; Proceedings of the 28$^{th}$ IEEE EMBS Annual International Conference; bearing dates of Aug. 30, 2006-Sep. 3, 2006 and 2006; pp. 3399-3402; IEEE.

Martel, Sylvain; Mathieu, Jean-Baptiste; Felfoul, Ouajdi; Chanu, Arnaud; Aboussouan, Eric; Tamaz, Samer; Pouponneau, Pierre; "Automatic Navigation of an Untethered Device in the Artery of a Living Animal using a Conventional Clinical Magnetic Resonance Imaging System"; Applied Physics Letters; 2007; pp. 114105-1-114105-3; vol. 90, No. 114105; American Institute of Physics.

Mathieu, J-B.; Martel, S.; Yahia, L'H.; Soulez, G.; Beaudoin, G.; "MRI Systems as a Mean of Propulsion for a Microdevice in Blood Vessels"; bearing a date of 2003; pp. 3419-3422; IEEE.

Matsui, Takemi; Matsumura, Kouji; Hagisawa, Kousuke; Ishihara, Masayuki; Ishizuka, Toshiaki; Suzuki, Minoru; Kurita, Akira; Kikuchi, Makoto; "A Novel Ferromagnetic Thermo-Stent for Plaque Stabilization That Self-Regulates the Temperature"; IEEE Transactions on Biomedical Engineering; bearing dates of Jun. 2002 and 2002; pp. 621-623; vol. 49, No. 6; IEEE.

McNeal, Donald R.; "Analysis of a Model for Excitation of Myelinated Nerve"; IEEE Transactions on Biomedical Engineering; bearing a date of Jul. 1976; pp. 329-337; vol. BME-23, No. 4.

Meier, P.; Oberthür, S.; Lang, M.; "Development of a compliant device for minimally invasive surgery"; Proceedings of the 28$^{th}$ IEEE EMBS Annual International Conference; bearing dates of Aug. 30, 2006-Sep. 3, 2006 and 2006; pp. 331-334; IEEE.

"MEMS at the cutting edge®, Patent Pending"; Verimetra; pp. 1-2; located at http://www.verimetra.com/flow.htm; printed on May 4, 2006.

Menciassi, A.; Park, Jong-Oh.; Lee, S.; Gorini, S.; Dario, P.; Park, Jong-Oh; "Robotic Solutions and Mechanisms for a Semi-Autonomous Endoscope"; Proceedings of the 2002 IEEE/RSJ International Conference on Intelligent Robots and Systems; bearing a date of 2002; pp. 1379-1384; IEEE.

Mohseni, Kamran; "Biomimetic & Bio-Inspired Aerial and Underwater Vehicles"; bearing a date of Sep. 23, 2006; pp. 1-10; printed on Jan. 4, 2007; located at http://enstrophy.colorado.edu/~mohseni/MicroVehiclesl.html#UUVl#UUV1.

Mosse, Charles; Mills, Tim; Appleyard, Mark; Swain, Paul; "Electrostimulation to move endoscopes in the small bowel"; Proceedings of SPIE; bearing a date of 2001; pp. 24-28; vol. 4158.

Murthy, S. Narasimha; Hiremath, Shobha Rani R.; "Physical and Chemical Permeation Enhancers in Transdermal Delivery of Terbutaline Sulphate"; AAPS PharmSciTech; bearing a date of 2001; pp. 1-5; vol. 2001, 2(1); Technical Note 1; located at 120://www.pharmscitech.com/.

Nakayama, Yasuhide; Ji-Youn, Kim; Nishi, Shogo; Ueno, Hikaru; Matsuda, Takehisa; "Development of high-performance stent: gelatinous photogel-coated stent that permits drug delivery and gene transfer"; J Biomed Mater Res; bearing dates of Nov. 13, 2000, Apr. 23, 2001, May 10, 2001 and 2001; pp. 559-566; vol. 57; John Wiley & Sons, Inc.

Naqvi, Nasir H.; Rudrauf, David; Damasio, Hanna; Bechara, Antoine; "Damage to the Insula Disrupts Addiction to Cigarette Smoking"; Science; bearing a date of Jan. 26, 2007; pp. 531-534; vol. 315, No. 531; located at: www.sciencemag.org; printed on Jan. 25, 2007.

Neto, A.M. Figueiredo; Godinho, M.H.; Toth-Katona, T.; Palffy-Muhoray, P.; "Optical, Magnetic and Dielectric Properties of Non-Liquid Crystalline Elastomers Doped with Magnetic Colloids"; Brazilian Journal of Physics; Bearing a date of Mar. 2005; pp. 184-189; vol. 35, No. 1.

"New Medical Device Combines Wireless and MEMS Technology"; Georgia Institute of Technology; pp. 1-4; PhysOrg.com; located at: http://www.physorg.com/printnews.php?newsid=10533; printed on Feb. 20, 2006.

Nieuwenhuizen-Berkovits, P.; "lubrelastic medical appliance"; Lubrelastic Medical Appliances; pp. 1-4; located at: http://www.xs4all.nl/~plien070/caeng.html; printed on Feb. 20, 2006.

Nyitrai, Zsolt; Illyefalvi-Vitéz, Zsolt; Pinkola, János; "Preparing Stents with Masking & Etching Technology"; 26$^{th}$ International Spring Seminar on Electronics Technology; bearing dates of May 8, 2003-May 11, 2003 and 2003; pp. 321-324; IEEE.

Olsson III, R.H.; Gulari, M.N.; Wise, K.D.; "Poster 114: Silicon Neural Recording Arrays with On-Chip Electronics for In-Vivo Data Acquisition"; Microtechnologies in Medicine and Biology; bearing dates of May 2, 2002-May 4, 2002; pp. 237-240; IEEE.

Oweiss, Karim G.; Anderson, David J.; "A New Technique for Blind Source Separation Using Subband Subspace Analysis in Correlated Multichannel Signal Environments"; bearing a date of 2001; pp. 2813-2816; IEEE.

Patronik, N.A.; Ota, T.; Zenati, M.A.; Riviere, C.N.; "Improved Traction for a Mobile Robot Traveling on the Heart"; Proceedings of the 28$^{th}$ IEEE EMBS Annual International Conference; bearing dates of Aug. 30, 2006-Sep. 3, 2006 and 2006; pp. 339-342; IEEE.

Peckham, P. Hunter; Knutson, Jayme S.; "Functional Electrical Stimulation for Neuromuscular Applications"; Annual Review Biomedical Engineering; bearing a date of 2005; pp. 327-360; vol. 7; Annual Reviews.

Rattay, F.; "The Basic Mechanism for the Electrical Stimulation of the Nervous System"; Neuroscience; 1999; pp. 335-346; vol. 98. No. 2; Elsevier Science Ltd; printed on Mar. 15, 2007.

Rattay, Frank; "Analysis of Models for Extracellular Fiber Stimulation"; IEEE Transactions on Biomedical Engineering; bearing a date of Jul. 1989; pp. 676-682; vol. 36, No. 7; IEEE.

Rattay, Frank, Aberham, Matthias; "Modeling Axon Membranes from Functional Electrical Stimulation"; IEEE Transactions on Biomedical Engineering; bearing a date of Dec. 1993; pp. 1201-1209; vol. 40, No. 12; IEEE.

"Remote-Control Electrostimulation Capsule"; Popular Science; bearing dates of 2002 and 2003; pp. 1-2; located at http://www.popsci.com/popsci/brown/2003/article/0,18881,537028,00.html; printed on May 4, 2006.

"Researchers: Squid-Inspired Vortex Generators Could Mean Better Propulsion for Unmanned Underwater Vehicles"; UnderwaterTimes.com; Dec. 12, 2006; pp. 1-2; UnderwaterTimes.com; printed on Jan. 4, 2007; located at http://www.underwatertimes.com/print.php?article_id=51030782641.

Rice, Mike; "Implantable Neurostimulation Device Market Poised for Explosive Growth"; Future Fab International; Jan. 7, 2006; pp. 1-4; printed on Oct. 6, 2006; located at http://www.future-fab.com/documents.asp?ID=3725.

Rice, Mike; "New Products, Emphasis on Miniaturization Driving Medical Device Innovation"; bearing a date Aug. 23, 2006; pp. 1-3; Advantage Business Media; located at http://www.mdtmag.com/scripts/ShowPR.asp?PUBCODE=046&ACCT=0006109&ISSUE=0603&RELTYPE=PR&PRODCODE=0790&PRODLETT=A; printed on Aug. 23, 2006.

Riedmüller, J.; Bolz, A.; Rebling, H.; Schaldach, M.; "Improvement of Stimulation and Sensing Performance of Bipolar Pacemaker Leads"; IEEE Eng. Med. Biol. Soc.; 1992; pp. 2364-2365; IEEE.

Robinson, David A.; "The Electrical Properties of Metal Microelectrodes"; Proceedings of the IEEE; bearing a date of Jun. 1968; pp. 1065-1071; vol. 56, No. 6.

Rousche, Patrick J.; Pellinen, David S.; Pivin, David P.; Williams, Justin C.; Vetter, Rio J.; Kipke, Daryl R.; "Flexible Polyimide-Based Intracortical Electrode Arrays with Bioactive Capability"; IEEE Transactions on Biomedical Engineering; bearing a date Mar. 2001; pp. 361-371; vol. 48, No. 3; IEEE.

Rutten, Wim; Mouveroux, Jean-Marie; Buitenweg, Jan; Heida, Ciska; Ruardij, Teun; Marani, Enrico; Lakke, Egbert; "Neuroelectronic Interfacing with Cultured Multielectrode Arrays Toward a Cultured Probe"; Proceedings of the IEEE; bearing a date of Jul. 2001; pp. 1013-1029; vol. 89, No. 7; IEEE.

Saltzman, John R.; "Endoscopic Advances—A View Toward the Future"; bearing dates of May 4, 2006, May 17, 2005, and 2005; pp. 1-4; Medscape; located at http://www.medscape.com/viewarticle/505100; printed on May 4, 2006.

Schmidt, W.; Behrens, P.; Behrend, D.; Schmitz, K.-P.; Andresen, R.; "Experimental Study of Peripheral, Balloon-expandable Stent Systems"; Progress in Biomedical Research; bearing a date of May 2001; pp. 246-255.

Schoonhoven, R.; Stegeman, D.F.; "Models and Analysis of Compound Nerve Action Potentials"; Critical Reviews in Biomedical Engineering; bearing a date of 1991; pp. 47-111; vol. 19, No. 1; CRC Press, Inc.

Senel, Sevda; Hincal, A. Atilla; "Drug permeation enhancement via buccal route: possibilities and limitations"; Journal of Controlled Release; bearing a date of 2001; pp. 133-144; vol. 72 (2001); Elsevier; located at www.elsevier.com/locate/jconrel.

Serruya, Mijail D.; Hatsopoulos, Nicholas G.; Paninski, Liam; Fellows, Matthew R.; Donoghue, John P.; "Brief Communications: Instant Neural Control of a Movement Signal"; Nature; bearing a date of Mar. 14, 2002; pp. 141-142; vol. 416; Macmillan Magazines Ltd; located at: www.nature.com.

Serruys, Patrick W.; Kutryk, Michael J.B.; Ong, Andrew T.L.; "Coronary-Artery Stents"; The New England Journal of Medicine; bearing a date of Feb. 15, 2006; pp. 783-495; vol. 354;5; Massachusetts Medical Society.

Shabalovskaya, Svetlana, A.; "Surface, corrosion and biocompatibility aspects of Nitinol as an implant material"; Bio-Medical Materials and Engineering; bearing dates of Apr. 4, 2001, and 2002; pp. 69-109; vol. 12; IOS Press.

Shahinpoor, Mohsen; Kim, Kwang J.; Ionic polymer-metal composites: IV. Industrial and medical applications; Smart Materials and Structures; 2005; pp. 197-214; vol. 14; Institute of Physics Publishing.

Smith, Michael; "PAS: Nasal Spray Flu Vaccine Seems Safe and Effective in Young"; May 2, 2006; pp. 1-2; MedPage Today, LLC; bearing dates of 2004-2006; printed on May 4, 2006; located at http://www.medpagetoday.com/tbprint.cfm?tbid=3213.

Snoek, GJ; Ijzerman, MJ; in 'T Groen, FACG; Stoffers, TS; Zilvold, G; "Use of the Ness Handmaster to Restore Handfunction in Tetraplegia: Clinical Experiences in Ten Patients"; Spinal Cord; bearing a date of 2000; pp. 244-249; vol. 38; International Medical Society of Paraplegia.

Snow, E.S.; Perkins, F.K.; Houser, E.J.; Badescu, S.C.; Reinecke, T. L.; "Chemical Detection with a Single-Walled Carbon Nanotube Capacitor"; Science; Mar. 25, 2005; pp. 1942-1945; vol. 307; www.sciencemag.org.

Stoeckel, Dieter; Pelton, Alan; Duerig, Tom; "Self-expanding nitinol stents: material and design considerations"; European Radiology; bearing dates of Jan. 28, 2003, May 22, 2003, Jul. 1, 2003, Sep. 3, 2003, Feb. 2004 and 2004; pp. 292-301(1-2); vol. 14, No. 2; Springer-Verlag GmbH-SpringerLink—Article; located at: http://www.springerlink.com/(lbegg455gtgjfseqqptyb43m)/app/home/contribution.asp?referrer=parent&backto=issue,17,26;journal,27,147;browsepublicationsresults,444,1551; printed on Feb. 22, 2006.

Strauss, Bradley H., M.D., Ph.D.; LI, Chris, M.D.; Whittingham, Heather A., M.Sc; Tio, Fermin O., M.D.; Kutryk, Michael J.B., M.D., Ph.D.; Janicki, Christian, Ph.D.; Sparkes, John, D., M.Sc.; Turnlund, Todd, B.Sc.; Sweet, William L., M.D.; "Late Effects of Low-Energy Gamma-Emitting Stents in a Rabbit Iliac Artery Model"; Int. J. Radiation Oncology Biol. Phys.; bearing dates of Oct. 23, 2001, May 13, 2002 and May 15, 2002 and 2002; pp. 551-561; vol. 54, No. 2; Elsevier Science Inc.

Struijk, Johannes Jan; "The Extracellular Potential of a Myelinated Nerve Fiber in an Unbounded Medium and in Nerve Cuff Models"; Biophysical Journal; bearing a date of Jun. 1997; pp. 2457-2469; vol. 72; Biophysical Society.

Taylor, Dawn M.; Helms Tillery, Stephen I.; Schwartz, Andrew B.; "Research Article: Direct Cortical Control of 3D Neuroprosthetic Devices"; Science; bearing a date of Jun. 7, 2002; pp. 1829-1832; vol. 296; located at: www.sciencemag.org.

"Tiny Robot Reduces Need for Surgery"; Pink Tentacle; bearing a date of Feb. 26, 2007; p. 1; located at: http://www.pinktentacle.com/2007/02/tiny-robot-reduces-need-for-surgery; printed on Mar. 8, 2007.

"Trying to control pain can be a double-edged sword, say scientists"; PhysOrg.com; printed on Nov. 2, 2006; pp. 1-2; located at http://www.physorg.com/printnews.php?newsid=81599312.

Tummala, R. Lal; Mukherjee, R.; Aslam, D.; XI, Ning; Mahadevan, S.; Weng, J.; "Reconfigurable Adaptable Micro-robot"; IEEE; bearing a date of 1999; pp. 687-691.

Twardoch, U.M.; "Integrity of Ultramicro-Stimulation Electrodes Determined from Electrochemical Measurements"; Journal of Applied Electrochemistry; bearing a date of 1994; pp. 835-857; vol. 24; Chapman & Hall.

Warland, David K.; Reinagel, Pamela; Meister, Markus; "Decoding Visual Information from a Population of Retinal Ganglion Cells"; bearing a date of 1997; pp. 2336-2350; The American Physiological Society.

Weis, Rolf; Müller, Bernt; Fromherz, Peter; "Neuron Adhesion on a Silicon Chip Probed by an Array of Field-Effect Transitors"; Physical Review Letters; bearing a date of Jan. 8, 1996; pp. 327-330; vol. 76, No. 2; The American Physical Society.

Wessberg, Johan; Stambaugh, Christopher R.; Kralik, Jerald D.; Beck, Pamela D.; Laubach, Mark; Chapin, John K.; Kim, Jung; Biggs, S. James; Srinivasan, Mandayam A.; Nicolelis, Miguel A.L.; "Letters to Nature: Real-Time Prediction of Hand Trajectory by Ensembles of Cortical Neurons in Primates"; Nature; bearing a date of Nov. 16, 2000; pp. 361-365; vol. 408; Macmillan Magazines Ltd; located at: www.nature.com.

White, Dave; "Mini Robot Explores, Gives you Medicine from Within"; Mobile Magazine; bearing a date of Feb. 27, 2007; p. 1; located at: http://www.mobilemag.com/content/100/313/C11869/; printed on Mar. 8, 2007.

Yusa, Go; Muraki, Koji; Takashina, Kei; Hashimoto, Katsushi; Hirayama, Yoshiro; "Controlled multiple quantum coherences of nuclear spins in a nanometre-scale device"; Nature; Apr. 21, 2005; pp. 1001-1005; vol. 434; 2005 Nature Publishing Group; www.nature.com/nature.

"Zyvex NanoEffector Microgrippers"; Nanotechnology at Zyvex; printed on Dec. 7, 2006; pp. 1-2; located at http://www.zyvex.com/Products/Grippers_Features.html.

"Zyvex NanoEffector Microgrippers"; Zyvex.com; bearing a date of 2006; pp. 1-2; Zyvex Corporation.

UK Intellectual Property Office Examination Report Under Section 18(3); App. No. GB0821526.1; bearing a date of Jul. 15, 2010; received by our agent Jul. 16, 2010; pp. 1-2.

U.S. Appl. No. 12/928,455, filed Dec. 9, 2010, Wood, Jr., Lowell L.
U.S. Appl. No. 12/930,916, filed Jan. 18, 2011, Wood, Jr., Lowell.
Mosby's Dictionary of Medicine, Nursing & Health Professions; "endoscopy"; 2009; Credo Reference. Web. Jun. 29, 2011; 1 page; Elsevier Health Sciences.

U.S. Appl. No. 13/135,696, Ferren et al.
U.S. Appl. No. 13/135,694, Ferren et al.

* cited by examiner

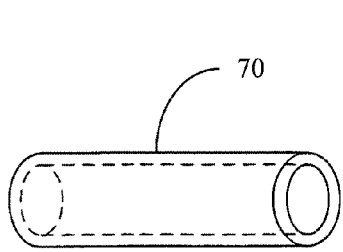 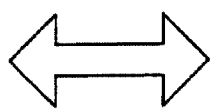 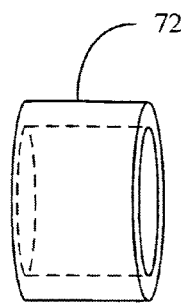
FIG. 4A          FIG. 4B
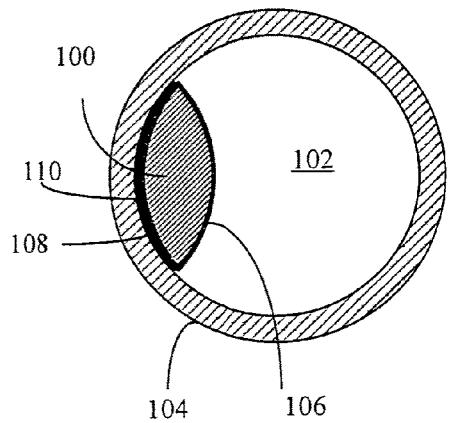
FIG. 5A
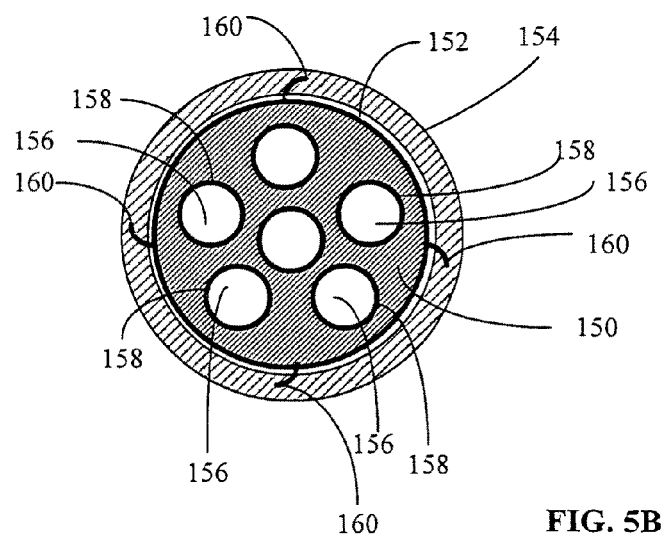
FIG. 5B

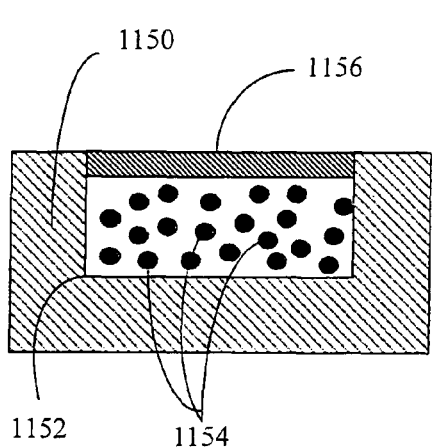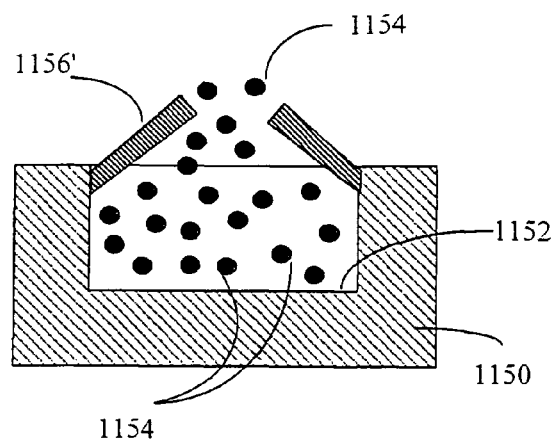
FIG. 19A  FIG. 19B
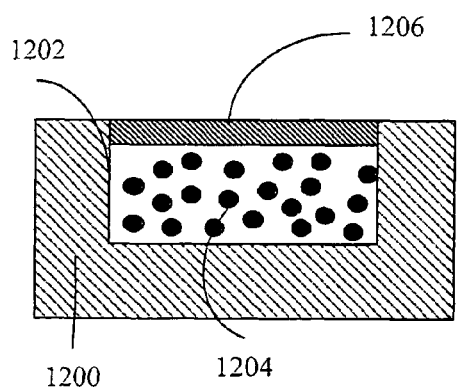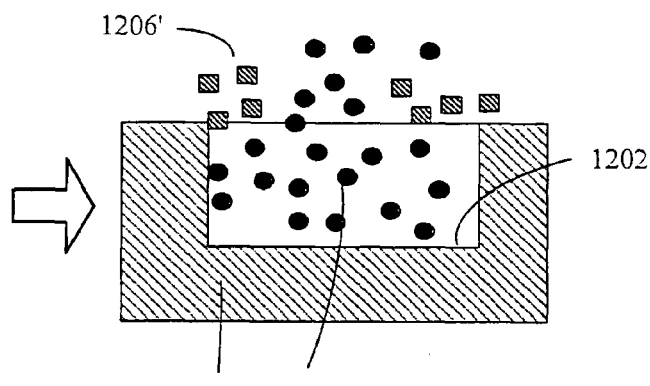
FIG. 20A  FIG. 20B
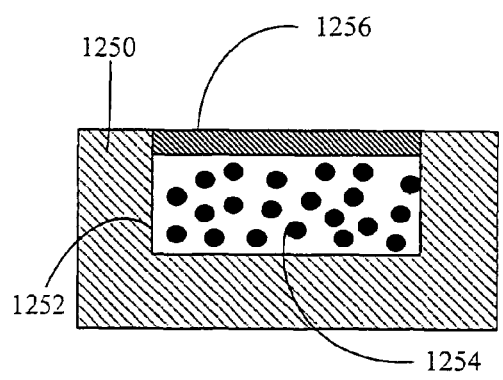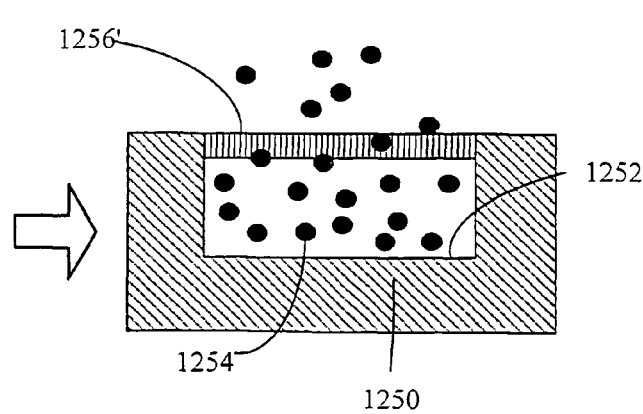
FIG. 21A  FIG. 21B

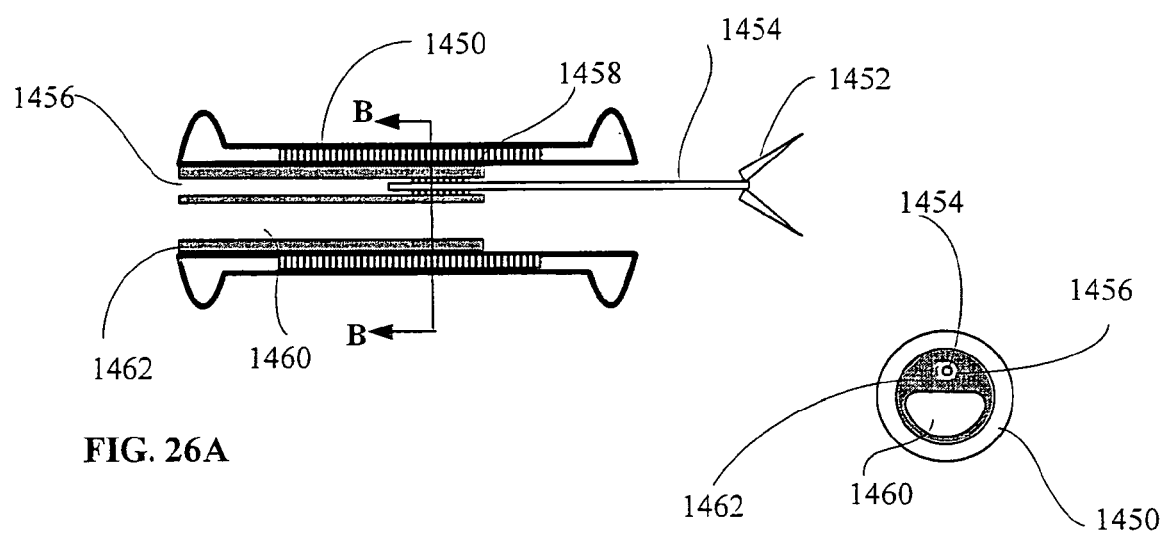
FIG. 26A
FIG. 26B
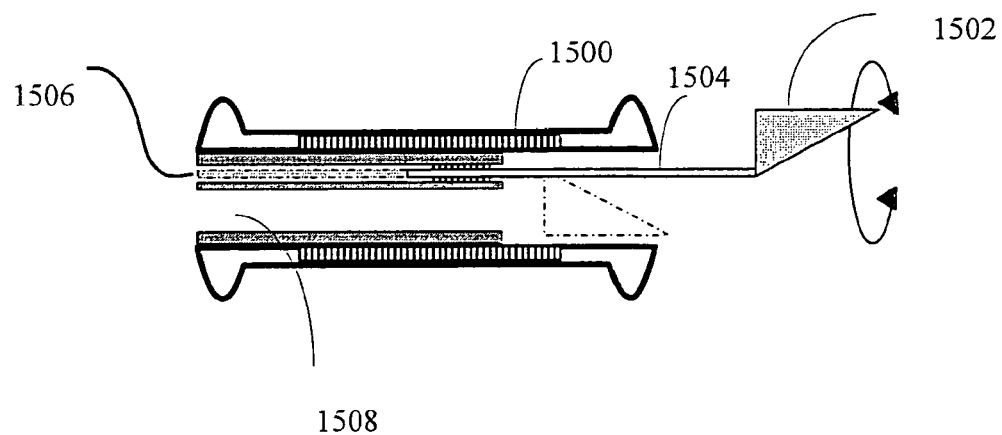
FIG. 27

FIG. 39B

2156 detecting a condition of interest with a sensor on the lumen-traveling device wherein detecting a condition of interest includes detecting a man-made structure. 2186

| wherein detecting a condition of interest includes detecting a pH in the body lumen 2180 | wherein detecting a condition of interest includes detecting an anatomic feature. 2182 | wherein detecting a condition of interest includes detecting a location. 2184 | including delivering a material or structure to the man-made structure. 2190 | including receiving a material or structure from the man-made structure. 2192 | including collecting the man-made structure. 2194 | wherein detecting a condition of interest includes detecting a time. 2188 |

Key To
FIG. 39

| 39A | 39B |

| 40A | 40B | 40C | 40D | 40E | 40F |

Key To
FIG. 40

Start — 2250 propelling the lumen-traveling device through a body lumen — 2252 at least intermittently permitting flow of fluid through the body lumen and past a fluid-contacting portion of the lumen-traveling device — 2254 detecting a condition of interest with a sensor on the lumen-traveling device — 2256 producing a response initiation signal with response initiation circuitry located at least in part on the lumen-traveling device at least partially in response to detection of the condition of interest — 2258 performing an action with an active portion of the lumen-traveling device in response to the response initiation signal — 2260

(A)

wherein performing an action with the active portion includes transmitting a signal to a remote location
2264 wherein performing an action with the active portion includes releasing a material. 2266 wherein the material includes at least one of an adhesive, a filler, a hydrogel, an antibiotic, a pharmaceutical compound, a nutrient, a hormone, a growth factor, a medication, a therapeutic compound, an enzyme, a protein, a genetic material, a vaccine, a vitamin, a neurotransmitter, a neurotropic agent, a neuroactive material, a cytokine, a cell-signaling material, a pro-apoptotic agent, an anti-apoptotic agent, an immunological mediator, an anti-inflammatory agent, a salt, an ion, an antioxidant, an imaging agent, a labeling agent, a diagnostic compound, a nanomaterial, an inhibitor, or a blocker.
2268

End — 2262

| 40A | 40B | 40C | 40D | 40E | 40F |

Key To
FIG. 40

FIG. 40 performing an action with an active portion of the lumen-traveling device in response to the response initiation signal  2260 wherein performing an action with the active portion includes collecting a material from the body lumen  2270 wherein performing an action with the active portion includes collecting a sample from a fluid within the body lumen  2272 wherein performing an action with the active portion includes collecting a sample from a wall region of the body lumen  2274 wherein performing an action with the active portion includes producing heating.  2276 including propelling the lumen-traveling device through the body lumen to a location in the vicinity of the preoptic area, wherein performing an action with the active portion includes producing heating in the vicinity of the preoptic area.  2278 heating in male reproductive system to destroy gametes  2280 wherein performing an action with the active portion includes producing cooling.  2282 wherein performing an action with the active portion includes securing the lumen-traveling device into position within the body lumen.  2284

LUMEN-TRAVELING BIOLOGICAL INTERFACE DEVICE AND METHOD OF USE

CROSS-REFERENCE TO RELATED APPLICATIONS

For purposes of the United States Patent Office (USPTO) extra-statutory requirements, the present application is a DIVISION application of U.S. patent application Ser. No. 11/726,031 titled LUMEN-TRAVELING BIOLOGICAL INTERFACE DEVICE AND METHOD OF USE, naming BRAN FERREN, W. DANIEL HILLIS, RODERICK A. HYDE, MURIEL Y. ISHIKAWA, EDWARD K.Y. JUNG, ERIC C. LEUTHARDT, NATHAN P. MYHRVOLD, CLARENCE T. TEGREENE, LOWELL L. WOOD, JR. AND VICTORIA Y.H. WOOD as inventors, filed 19 Mar. 2007, which is co-pending, or is an application of which a co-pending application is entitled to the benefit of the filing date. The present application claims the benefit of the earliest available effective filing date(s) (i.e., claims earliest available priority dates for other than provisional patent applications or claims benefits under 35 USC §119(e) for provisional patent applications) for any and all applications to which patent application Ser. No. 11/726,031 claims the benefit of priority, including but not limited to U.S. patent application Ser. No. 11/403,230, titled LUMENALLY-ACTIVE DEVICE naming as inventors BRAN FERREN, W. DANIEL HILLIS, RODERICK A. HYDE, MURIEL Y. ISHIKAWA, EDWARD K.Y. JUNG, NATHAN P. MYHRVOLD, ELIZABETH A. SWEENEY, CLARENCE T. TEGREENE, RICHA WILSON, LOWELL L. WOOD, JR., AND VICTORIA Y.H. WOOD, filed 12 Apr. 2006. All subject matter of U.S. patent application Ser. No. 11/403,230 and of any and all applications from which it claims the benefit of the earliest available effective filing date(s) is incorporated herein by reference to the extent such subject matter is not inconsistent herewith. The applicant entity has provided above a specific reference to the application(s) from which priority is being claimed - as required by statute. Applicant entity understands that the statute is unambiguous in its specific reference language and does not require either a serial number or any characterization, such as "continuation" or "continuation-in-part" or "divisional," for claiming priority to U.S. patent applications. Notwithstanding the foregoing, the applicant entity has provided above a specific reference to the application(s) from which priority is being claimed, but expressly points out that such designations are not to be construed in any way as any type of commentary and/or admission as to whether or not the present application contains any new matter in addition to the matter of its parent application(s). Further, any designation that the present application is a "division" should not be construed as an admission that the present application claims subject matter that is patentably distinct from claimed subject matter of its parent application.

BACKGROUND

Devices and systems have been developed for use in various body lumens, particularly in the cardiovascular system, digestive tract, and urogenital tract. Catheters are used for performing a variety of sensing, material delivery or surgical tasks. Stents are implanted in blood vessels for the purpose of preventing stenosis or restenosis of blood vessels. Capsules containing sensing and imaging instrumentation that may be swallowed by a subject and which travel passively through the digestive tract have also been developed. Robotic devices intended to move through the lower portion of the digestive tract under their own power are also under development.

SUMMARY

The present application describes devices, systems, and related methods for performing one or more actions or tasks with a lumen-traveling biological interface device. Embodiments of devices capable of moving through a body lumen to a location and delivering a stimulus to or recording a signal from biological tissue are disclosed.

In addition to the foregoing, other device and system aspects are described in the claims, drawings, and text forming a part of the present disclosure.

In one aspect, a method of emplacing an electrical stimulation device may include, but is not limited to, causing a self-propelling electromagnetic stimulation device to travel within a body tube tree of a subject toward a target site; if a branch point including two or more branches within the body tube tree is reached by the self-propelling electromagnetic stimulation device, causing the self-propelling electromagnetic stimulation device to enter a selected branch; and causing the self-propelling electromagnetic stimulation device to stop traveling upon reaching the target site.

In another aspect, a method of emplacing a neural stimulation device may include causing a self-propelling neural stimulation device to travel within a body tube tree of a subject toward a target site; if a branch point including two or more branches within the body tube tree is reached by the self-propelling neural stimulation device, causing the self-propelling neural stimulation device to enter a branch leading toward the target site; and causing the self-propelling neural stimulation device to stop traveling upon reaching the target site.

In yet another aspect, a method of emplacing a cardiac stimulation device may include causing a self-propelling cardiac stimulation device to travel within a body tube tree of a subject toward a target site; if a branch point including two or more branches within the body tube tree is reached by the self-propelling cardiac stimulation device, causing the self-propelling cardiac stimulation device to enter a branch leading toward the target site; and causing the self-propelling cardiac stimulation device to stop traveling upon reaching the target site.

In one aspect, a method of configuring a bioelectromagnetic interface system may include moving at least one bioelectromagnetic interface device through a body tube tree of a subject toward a target site with a self-propelling lumen-traveling device; detecting the arrival of the at least one bioelectromagnetic interface device at the target site; and moving the self-propelling lumen-traveling device away from the target site while leaving the at least one bioelectromagnetic interface device at the target site.

In another aspect, a method of emplacing a bioelectromagnetic interface system may include introducing a plurality of bioelectromagnetic interface devices into a body tube tree of a subject via at least one introduction site, at least a portion of the bioelectromagnetic interface devices including at least one electromagnetic transducer configured for at least one of producing an output signal representative of a bioelectromagnetic signal sensed from a target tissue or delivering an electromagnetic stimulus to the target tissue; and at least one of a signal processing portion capable of processing the output signal from the electromagnetic transducer or a stimulus source capable of producing an electromagnetic stimulus for delivery to the target tissue with the electromagnetic transducer; and causing the plurality of bioelectromagnetic interface devices to travel within the body tube tree to a plurality of target sites within the body tube tree, at least a portion of the plurality of target sites located in the vicinity of at least one target tissue.

In still another aspect, a method of emplacing a bioelectromagnetic interface system may include introducing a plurality of bioelectromagnetic interface devices into a body tube tree of a subject via at least one introduction site, at least a portion of the bioelectromagnetic interface devices including at least one electromagnetic transducer configured for at least one of producing an output signal representative of a bioelectromagnetic signal sensed from a target tissue or delivering an electromagnetic stimulus to the target tissue; and at least one of a signal processing portion capable of processing the output signal from the electromagnetic transducer or a stimulus source capable of producing an electromagnetic stimulus for delivery to the target tissue with the electromagnetic transducer; causing the plurality of bioelectromagnetic interface devices to travel within the body tube tree to a plurality of target sites within the body tube tree, at least a portion of the plurality of target sites located in the vicinity of at least one target tissue; and delivering an electromagnetic stimulus to the stimulation target with at least a portion of the one or more bioelectromagnetic interface devices.

In addition to the foregoing, other method aspects are described in the claims, drawings, and text forming a part of the present disclosure.

Various aspects of the operation of lumen-traveling biological interface devices may be performed under the control of hardware, software, firmware, or a combination thereof. In one or more aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 4A and 4B are illustrations of a device structure having a variable length and diameter;

FIGS. 5A-5F are cross-sectional views of a number of embodiments of lumen-traveling device structures;

FIGS. 19A and 19B are depictions of the release of a stored deliverable material from a reservoir via a rupturable barrier;

FIGS. 20A and 20B are depictions of the release of a stored deliverable material from a reservoir via a degradable barrier;

FIGS. 21A and 21B are depictions of the release of a stored deliverable material from a reservoir via a barrier having controllable permeability;

FIG. 26A is an illustration of a lumen-traveling device including a cutting tool;

FIG. 26B is a cross-sectional view of the lumen-traveling device of FIG. 26A;

FIG. 27 is an illustration of a lumen-traveling device including a scraping tool;

FIGS. 39A and 39B form a flow diagram showing several variants of a method implemented with a lumen-traveling device;

FIGS. 40A-40F form a flow diagram showing further variants of a method implemented with a lumen-traveling device;

DETAILED DESCRIPTION

Figure 1:
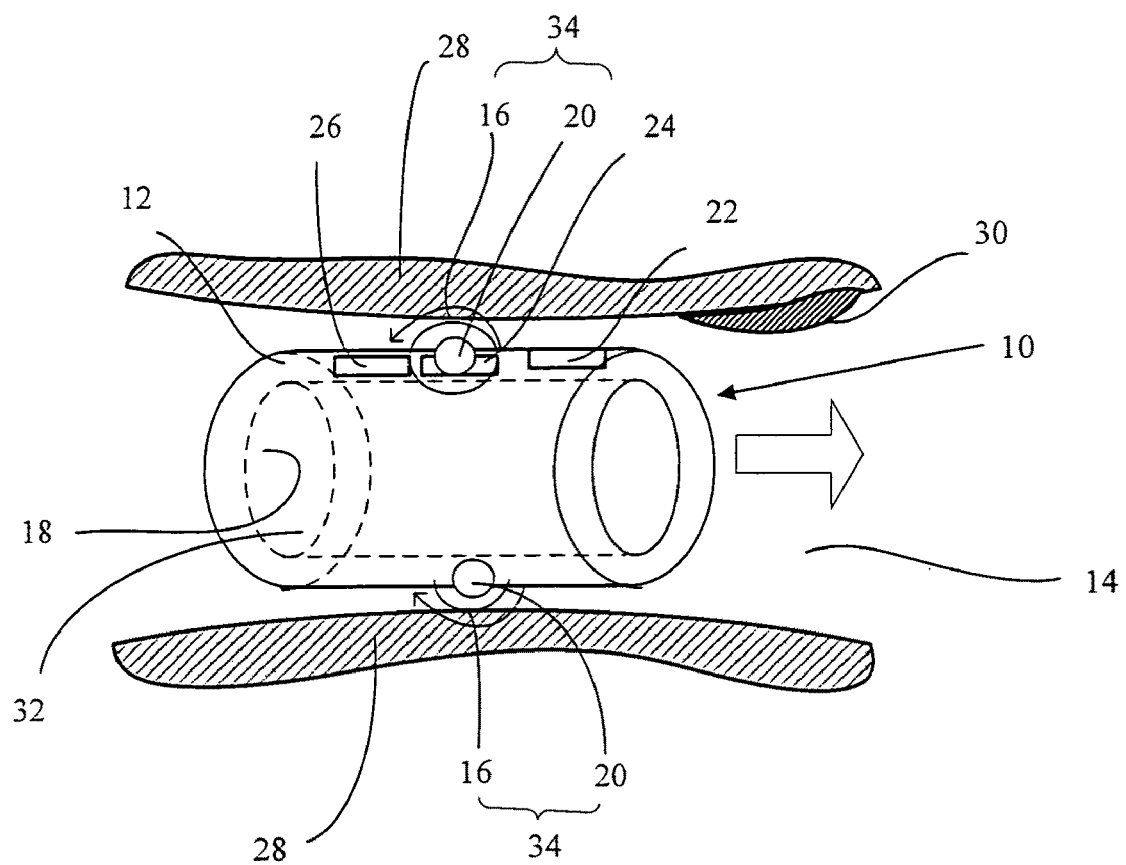
FIG. 1 is an illustration of an embodiment of a lumen-traveling device.

In the following detailed description, reference is made to the accompanying drawings, which form a part hereof In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

A lumen-traveling device is an example of a lumenally active device. Lumenally active devices, and related methods and systems, are described in U.S. patent application Ser. No. 11/403,230, entitled "Lumenally Active Device," filed Apr.

12, 2006, which is incorporated herein by reference. U.S. patent application Ser. No. 11/403,230 describes a lumenally-active system that may include a structural element configured to fit within at least a portion of a body lumen, the structural element including a lumen-wall-engaging portion and a fluid-contacting portion configured to contact fluid within the body lumen; a sensor capable of detecting a condition of interest in the fluid; response initiation circuitry operatively connected to the sensor and configured to generate a response initiation signal upon detection of the condition of interest in the fluid by the sensor; and an active portion operatively connected to the response initiation circuitry and capable of producing a response upon receipt of the response initiation signal.

As illustrated in FIG. 1, an embodiment of a lumen-traveling device 10 may include a structural element 12 configured to fit within at least a portion of a body lumen 14. The structural element 12 may include a lumen-wall-engaging portion 16 and a fluid-contacting portion 18 configured to contact fluid within the body lumen. Lumen-traveling device 10 may also include a propelling mechanism 20 capable of producing movement of the structural element 12 through a body lumen 14 in which the structural element is deployed, a sensor 22 capable of detecting a condition of interest in the body lumen, response initiation circuitry 24 operatively connected to the sensor 22 and configured to generate a response initiation signal upon detection of a condition of interest in the body lumen (e.g., plaque 30); and an active portion 26 operatively connected to the response initiation circuitry and capable of producing a response upon receipt of the response initiation signal. Body lumen 14 is defined by wall portions 28, which may be the walls of a blood vessel or other lumen-containing structure within the body of an organism. In this example, a body fluid flows through lumen 14 in the direction indicated by the arrow. Fluid flows through the central opening 32 of structural element 12, with the interior surface of structural element 12 forming fluid-contacting portion 18. In the embodiment of FIG. 1, sensor 22 and active portion 26 may be located at a fluid-contacting portion 18. Lumen-wall-engaging portions 16 may be, for example, rotating wheels, which function to frictionally engage wall portions 28, and which may also, in combination with a rotary motor 20, function as a propelling mechanism 34 to move lumen-traveling device 10 through body lumen 14. In other embodiments of lumenally traveling devices, other structures and methods for engaging the lumen wall and/or propelling the device through the lumen may be employed.

Embodiments of a lumen-traveling device or system may be configured for use in (e.g., configured to fit within) body lumens of an organism including, for example, the respiratory tract, the cardiovascular system (e.g., a blood vessel), a portion of a CSF-space (cerebro-spinal fluid space) of the nervous system (e.g., the spinal canal, the ventricles of the brain, the sub-arachnoid space, etc.), a portion of the urinary tract (for example a ureter), a portion of the lymphatic system, a portion of the abdominal cavity, a portion of the thoracic cavity, a portion of the digestive tract, a portion of a reproductive tract, either the female reproductive tract (e.g., a lumen of a fallopian tube) or the male reproductive tract (including various lumens including but not limited to the epididymis, vas deferens or ductul deferens, efferent duct, ampulla, seminal duct, ejaculatory duct, or urethra), the biliary tract, a nostril or nasal cavity, the oral cavity, the digestive tract, the tear ducts, or a glandular system. Other body lumens may be found in the auditory or visual system, or in interconnections thereof e.g., the Eustachian tubes. Some of the devices and systems described herein may be used in body lumens through which fluid flows, but it is not intended that such devices or systems are limited to use in tubular lumen-containing structures containing moving fluid; in some applications a lumen-traveling device may be used in a body lumen containing relatively unmoving, or intermittently moving fluid.

The term "body tube tree", as used herein, refers to a body lumen having a branching structure, i.e., that it includes at least one branch point where a first region of a lumen splits into two or more branches, or where a side lumen branches off from a main lumen. "Body tube tree" is not intended to convey any particular structure, configuration, level or organization, or level of complexity, beyond that indicated above. Examples of body tube trees include, but are not limited, the cardiovascular system, the respiratory system, and the CSF-space, for example.

Also included within the scope of the term "body lumen" are man-made lumens within the body, including vascular catheters, spinal fluid shunts, vascular grafts, bowel re-anastomoses, bypass grafts, indwelling stents of various types (e.g., vascular, gastrointestinal, tracheal, respiratory, ureteral, genitourinary, etc.) and surgically created fistulas.

The term fluid, as used herein, may refer to liquids, gases, and other compositions, mixtures, or materials exhibiting fluid behavior. The fluid within a body lumen may include a liquid, or a gas or gaseous mixtures. As used herein, the term fluid may encompass liquids, gases, or mixtures thereof that also include solid particles in a fluid carrier. Liquids may include mixtures of two or more different liquids, solutions, slurries, or suspensions. Body fluids may include components such as, for example, cells, cellular fractions or components, collections or aggregations of cells, bacterial, viral or fungal species, ions, molecules, gas bubbles, dissolved gas, suspended particles, or a variety of other materials that may be present in the body fluid. Body fluid components may be materials that are normally present in the body fluid, materials that are naturally derived but not normally present in the body fluid, or foreign materials that have entered or been introduced to the body fluid (including but not limited to pathogens, toxins, pollutants, or medications, for example). Examples of liquids present within body lumens include blood, lymph, serum, urine, semen, digestive fluids, tears, saliva, mucous, cerebro-spinal fluid, intestinal contents, bile, epithelial exudate, or esophageal contents. Liquids present within body lumens may include synthetic or introduced liquids, such as blood substitutes, or drug, nutrient, or saline solutions. Fluids may include liquids containing dissolved gases or gas bubbles, or gases containing fine liquid droplets or solid particles. Gases or gaseous mixtures found within body lumens may include inhaled and exhaled air, e.g. in the nasal or respiratory tract, or intestinal gases.

A lumen-traveling device may be configured to fit within a particular lumen through appropriate selection of device dimensions, material properties, and propelling mechanism. Configuration aspects may include size, shape, rigidity/flexibility, porosity, and biocompatibility, among others, which may depend on both the materials and construction of the device. Dimensions of a lumen-traveling device may be selected so that the device will be small enough to fit within the smallest expected dimension of the lumen of interest. A material that is both biocompatible and sufficiently durable for use in the lumen of choice may be selected based on standards well known to those of skill in the art. Wherever a lumen-traveling device or system is to be used, the dimensions and mechanical properties (e.g., rigidity) of the lumen-traveling system, and particularly of the structural element of the lumen-traveling system, may be selected for compatibility with the location of use, in order to provide for reliable positioning of the device and to prevent damage to the lumen-containing structure including the body lumen. The propelling mechanism may be selected for the type and nature of the lumen to be traveled. A lumen having a relatively uniform cross-section (height and/or width) over the length to be traveled may be traversed by most propelling mechanisms. A lumen that varies significantly in cross-section over the length to be traveled may pose a challenge for some propelling mechanisms that engage the lumen wall on all sides, but a lumen-traveling device that walks or rolls along one side of a lumen, or employs more than one mode of propulsion, may adapt well to changes in lumen cross-section. A lumen-traveling device that is capable of altering its dimensions (e.g. changing in length and diameter) may also be of utility in some applications. For example, see U.S. Patent Application 2005/0177223, which is incorporated herein by reference in its entirety. However, in many cases it may be possible to design a lumen-traveling device of fixed dimension suited for a particular application, or provide a set of lumen-traveling devices in several sizes, from which the best size can be selected for a particular application or particular patient, to account for variability in lumen dimensions between individual patients. The lumen-traveling device may include a structural element carrying at least one of the propelling mechanism, motion control circuitry, sensor, response initiation circuitry or active portion. Various materials may be used in the construction of the structural element. For example, the structural element may include a self-expanding material, a resilient material, or a mesh-like material. Flexibility may also be conferred by configuration as well as material: for example, the structural element may include a slotted structure. The structural element may include a biocompatible material, as noted above, and may include a bioactive component (such as a drug-releasing coating or bioactive material attached to or incorporated into the structural element).

Figures 2A, 2B:
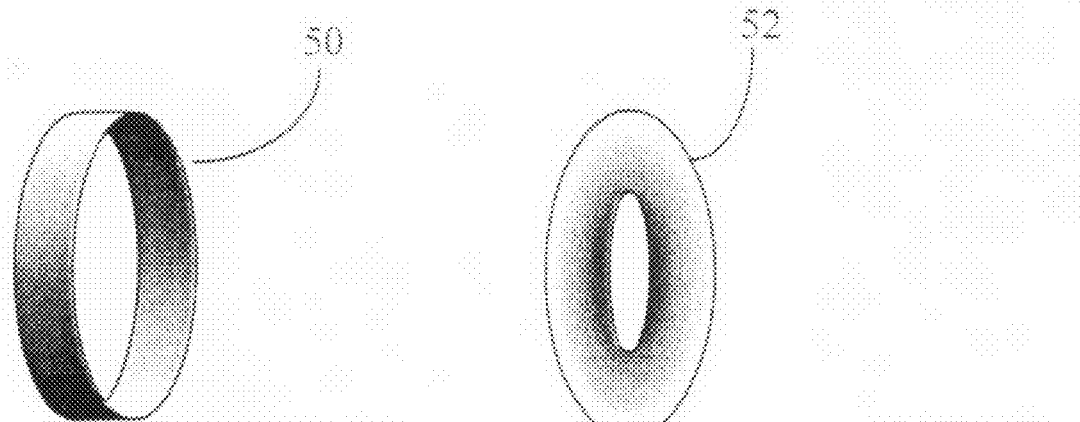
FIGS. 2A-2D are illustrations of several embodiments of lumen-traveling device structural elements.
Figure 2C:
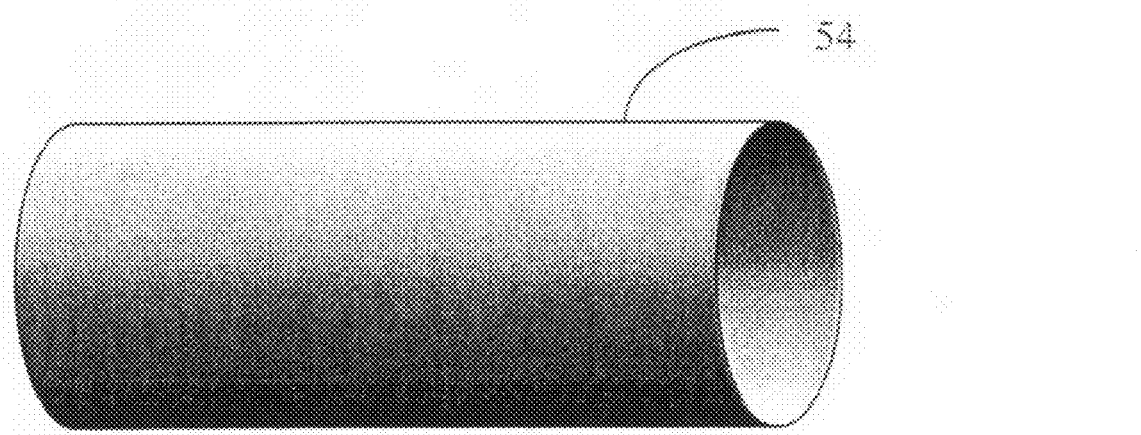
Figure 2D:
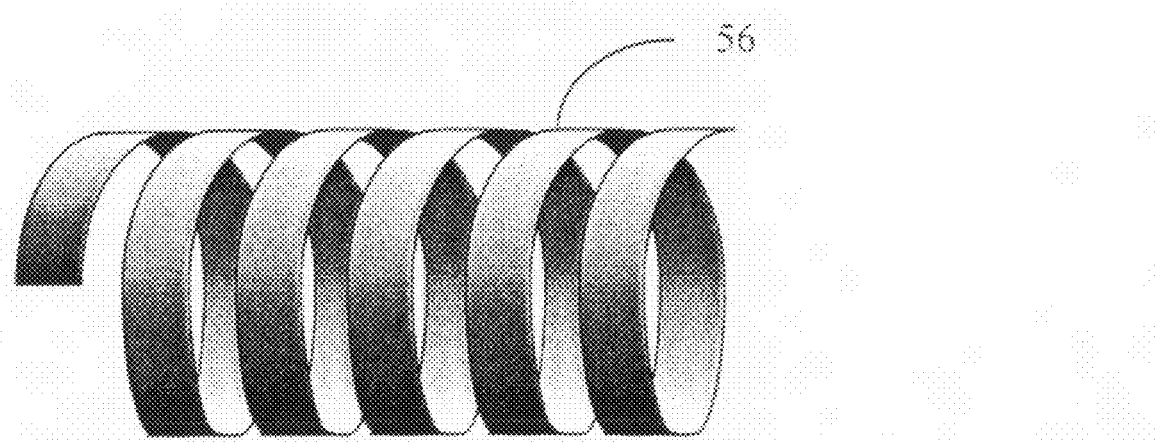

FIGS. 2A-2D depict a number of possible configurations for structural elements of lumen-traveling devices for use in body lumens. In some embodiments, the structural element may be a substantially tubular structure. The structural element may include one or multiple lumens in fluid communication with the body lumen. In some embodiments, the structural element may have an adjustable diameter. Structural elements may have the form of a short cylinder 50, as shown in FIG. 2A; an annulus 52, as shown in FIG. 2B; a cylinder 54, as shown in FIG. 2C; or a spiral 56, as shown in FIG. 2D. A spiral structure is disclosed, for example, in Bezrouk et al, "Temperature Characteristics of Nitinol Spiral Stents"; Scripta Medica (BRNO); bearing dates of August 2005, October 2005; pp. 219-226; Vol. 78, No. 4, which is incorporated herein by reference in its entirety. Elongated forms such as cylinder 54 or spiral 56 may be suitable for use in tubular lumen-containing structures such as, for example, blood vessels.

Structural elements may be formed from various materials, including metals, polymers, fabrics, and various composite materials, including ones of either inorganic or organic character, the latter including materials of both biologic and abiologic origin, selected to provide suitable biocompatibility and mechanical properties. In these, and other examples of structural elements, it is contemplated that additional components, such as sensors, circuitry, and propelling mechanisms, for example, will be attached or connected to, manufactured on, or formed integrally with the structural element, but such additional components are not illustrated in these figures.

In some embodiments, the structural element may include a self-expanding material, or a resilient material. In some embodiments, the form as well as the material of the structural element may contribute to the expanding or flexing properties of the structural element. For example, the structural element may be formed from or include a mesh-like material or a slotted structure.

Figure 3A:
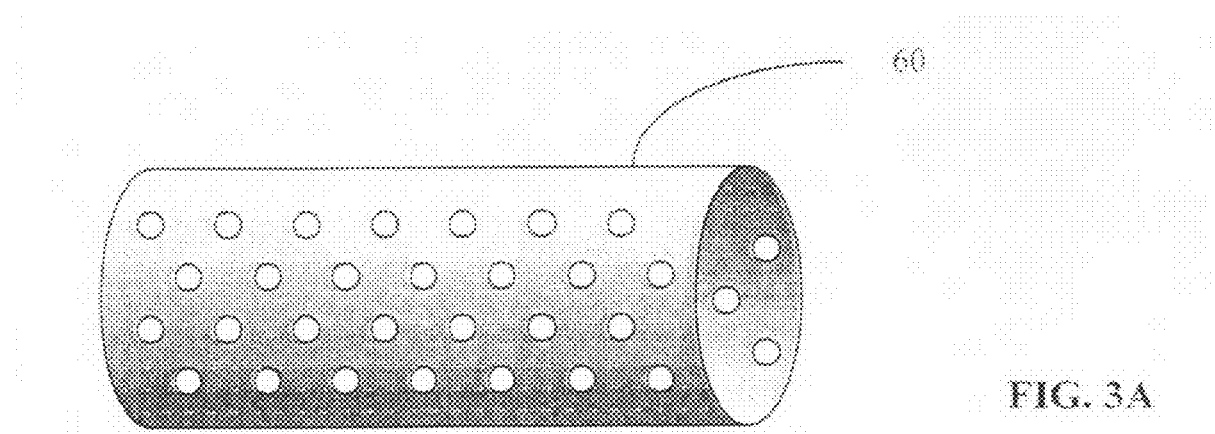
FIGS. 3A-3C are illustrations of several embodiments of lumen-traveling device structural elements.
Figure 3B:
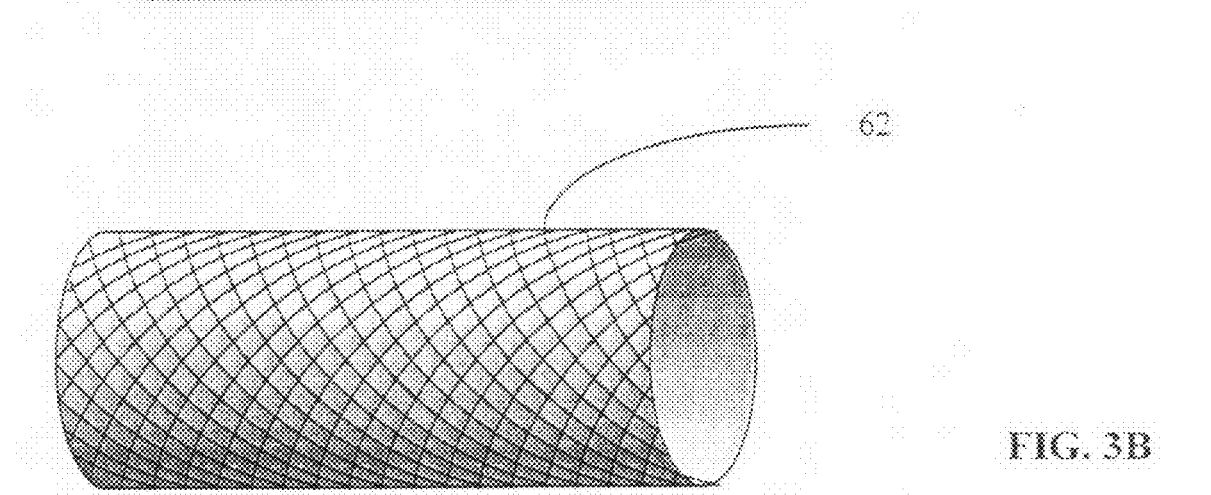
Figure 3C:
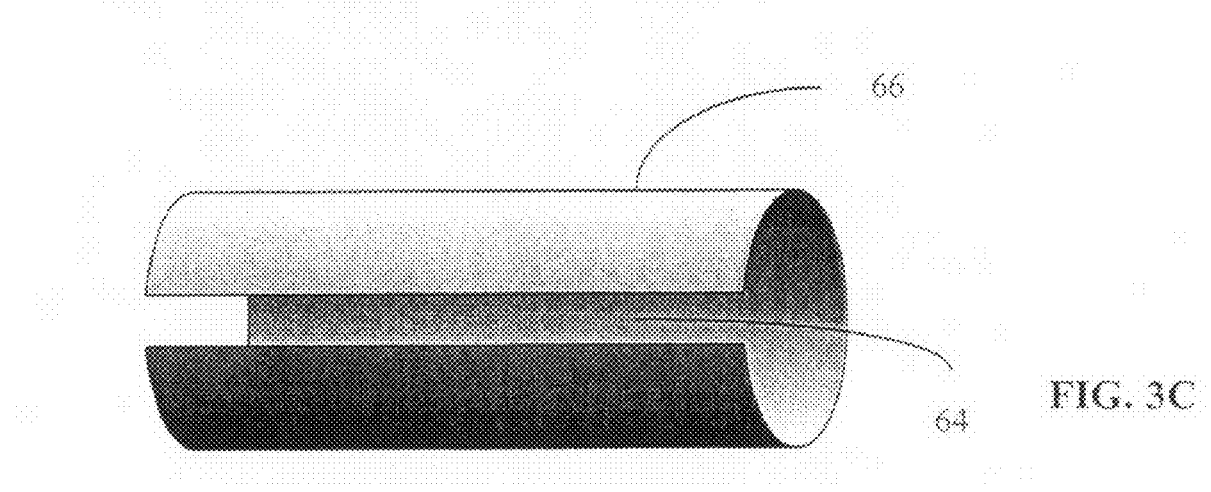

As shown in FIGS. 3A-3C, the basic form of a structural element may be subject to different variations, e.g., by perforations, as shown in structural element 60 in FIG. 3A; a mesh structure, as shown in structural element 62 in FIG. 3B; or the inclusion of one or more slots 64 in structural element 66 in FIG. 3C. Slot 64 runs along the entire length of structural element 66; in other embodiments, one or more slots (or mesh or perforations) may be present in only a portion of the structural element. By using spiral, mesh, or slotted structural elements (as in FIGS. 2D, 3B, and 3C) formed from resilient material, elastic, springy or self-expanding/self-contracting structural elements may be formed. A self-expanding or self-contracting structural element may facilitate positioning of the structural element within a body lumen of an organism. In some embodiments, flexible material having adjustable diameter, taper, and length properties may be used. For example, some materials may change from a longer, narrower configuration 70 as shown in FIG. 4A, to a shorter, wider configuration 72 as shown in FIG. 4B, or may taper over their length. Structural elements that may exhibit this type of expansion/contraction property may include mesh structures formed of various metals or plastics, and some polymeric materials, for example. Examples of possible shape change materials are described in "Agile new plastics change shape with heat"; MIT News Office; Nov. 20, 2006; pp. 1-4; Massachusetts Institute of Technology; printed on Nov. 22, 2006; located at http://web.mit.edu/newsoffice/2006/triple-shape.html;
"Agile new plastics change shape with heat"; MIT Tech Talk; Nov. 22, 2006; p. 5 (1 page); and SHAHINPOOR, MOHSEN; KIM, KWANG J. ("Ionic polymer-metal composites: IV. Industrial and medical applications; Smart Materials and Structures; 2005; pp. 197-214; Vol. 14; Institute of Physics Publishing), all of which are incorporated herein by reference in their entirety.

The exemplary embodiments depicted in FIGS. 2A-2C, 3A-3C, and 4A and 4B are substantially cylindrical, and hollow and tubular in configuration, with a single central opening. Thus, the exterior of the cylindrical structural element may contact and engage the wall of the body lumen, and the interior of the structural element (within the single central opening) may form a fluid-contacting portion of the structural element. Lumen-traveling devices according to various embodiments are not limited to cylindrical structural elements having a single central opening, however. Alternatively, a structural element may be configured to contact and move along a portion of a wall of a body lumen, contacting or engaging the lumen wall over a portion of its cross-section (as opposed to contacting the lumen wall along its entire cross-section) without obstructing the movement of fluid within the body lumen. Such an embodiment may be approximately hemi-spherical or hemi-ellipsoid, with a cross-section as depicted in FIG. 5A. Other embodiments may be pill- or capsule-shaped, adapted to move through a central portion of a body lumen.

Figure 5C:
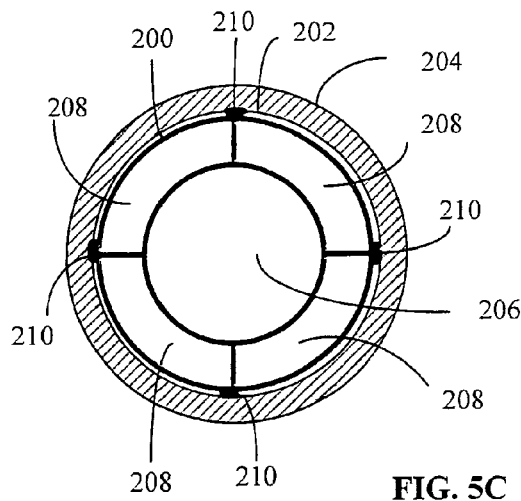

FIGS. 5A through 5F depict a variety of cross-sectional configurations for structural elements of lumen-traveling devices. In FIG. 5A, a lumen-traveling device 100 is positioned in lumen 102 of lumen-containing structure 104. In this embodiment, fluid-contacting portion 106 may be the surface of structural element 100 that faces lumen 102, while the lumen-wall-engaging portion 108 may include a layer of tissue adhesive on surface 110 of structural element 100.

Tissue adhesives may be released from the lumen-traveling device when it has reached its destination. Lumen-traveling device 100 may be approximately hemi-spherical or hemi-ovoid. Lumen-wall-engaging portion 108 may have a curvature that corresponds approximately to the curvature of the lumen.

FIG. 5B depicts in cross-section a further embodiment of a structural element 150 in lumen 152 of lumen-containing structure 154. Structural element 150 includes multiple openings 156, each of which includes an interior surface 158 that forms a fluid-contacting portion. Structural element 150 may include one or more hook or claw-like structures 160 that serve as lumen-wall-engaging portions that maintain structural element 150 in position with respect to lumen-containing structure 154.

FIG. 5C depicts in cross-section an embodiment of a structural element 200 in lumen 202 of lumen-containing structure 204. Structural element 200 includes a large central opening 206 and multiple surrounding openings 208. The interior surface of each opening 206 or 208 serves as a fluid-contacting portion, while projections 210 function as lumen-wall-engaging portions, which may engage frictionally or may project slightly into the interior of the wall of lumen-containing structure 204.

Figure 5D:
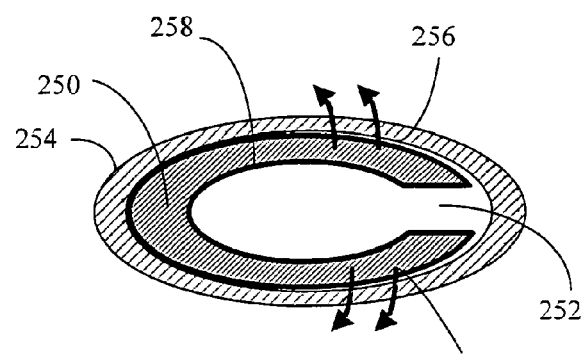

FIG. 5D depicts a further embodiment in which structural element 250 has a substantially oval cross-section and includes a slot 252. Lumen-containing structure 254 may be generally oval in cross section, or may be flexible enough to be deformed to the shape of structural element 250. Structural element 250 may be a compressed spring-like structure that produces outward forces as indicated by the black arrows, so that end portions 256 of structural element 250 thus press against and engage the lumen wall. Interior surface 258 of structural element 250 serves as the fluid-contacting portion of structural element 250.

Figure 5E:
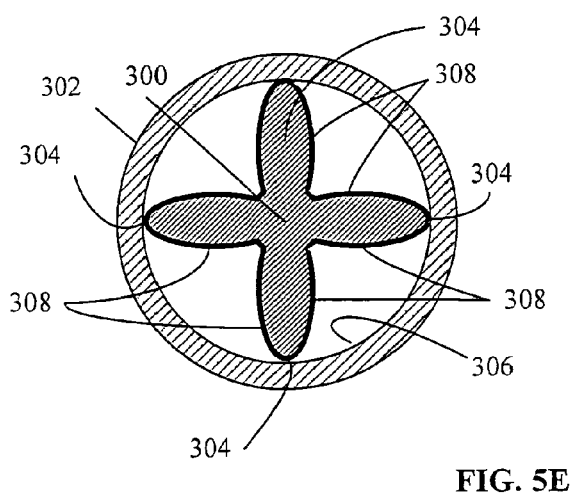

FIG. 5E is a cross-sectional view of a structural element 300 in a lumen-containing structure 302. Structural element 300 includes multiple projecting arms 304 which contact lumen wall 306 of lumen-containing structure 302, and function as lumen-wall-engaging portions. Inner surfaces 308 of arms 304 function as fluid-contacting portions of structural element 300.

Figure 5F:
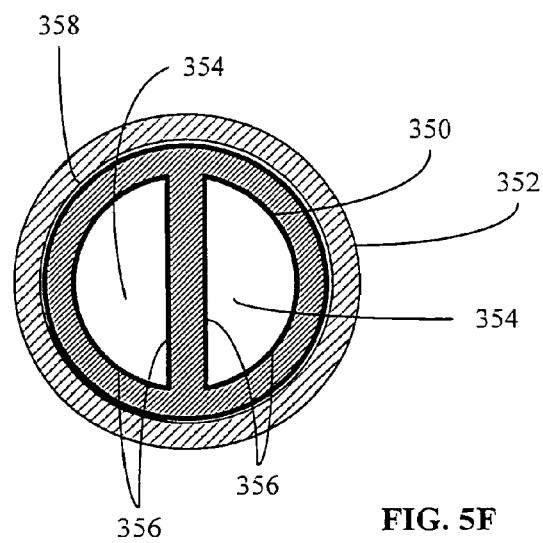

FIG. 5F depicts (in cross-section) another example of a structural element 350 positioned within a lumen-containing structure 352. Structural element 350 includes two openings 354. The interior surfaces 356 of openings 354 function as fluid-contacting portions, while the outer surface 358 of structural element 350 serves as a lumen-wall-engaging portion.

The structural elements depicted in FIGS. 1-5 are intended to serve as examples, and are in no way limiting. The choice of structural element size and configuration appropriate for a particular body lumen may be selected by a person of skill in the art. Structural elements may be constructed by a variety of manufacturing methods, from a variety of materials. Appropriate materials may include metals, ceramics, polymers, and composite materials having suitable biocompatibility, sterilizability, mechanical, and physical properties, as will be known to those of skill in the art. Examples of materials and selection criteria are described, for example, in *The Biomedical Engineering Handbook*, Second Edition, Volume I, J. D. Bronzino, Ed., Copyright 2000, CRC Press LLC, pp. IV-1-43-31. Manufacturing techniques may include injection molding, extrusion, die-cutting, rapid-prototyping, self-assembly, etc., and will depend on the choice of material and device size and configuration. Sensing portions, active portions, and propelling mechanisms or structures of the lumen-traveling device as well as associated circuitry (not depicted in FIGS. 2-5) may be fabricated on the structural element using various microfabrication and/or MEMS techniques, or may be constructed separately and subsequently assembled to the structural element, as one or more distinct components. Examples of microfabrication techniques include, for example, those disclosed in U.S. Patent Applications 2005/0221529, 2005/0121411, 2005/0126916, and NYITRAI, ZSOLT; ILLYEFALVI-VITÉZ, ZSOLT; PINKOLA, JÁNOS; "Preparing Stents with Masking & Etching Technology"; 26th International Spring Seminar on Electronics Technology; bearing dates of May 8, 2003-May 11, 2003 and 2003; pp. 321-324; IEEE, all of which are incorporated by reference in their entirety.

Figure 6:
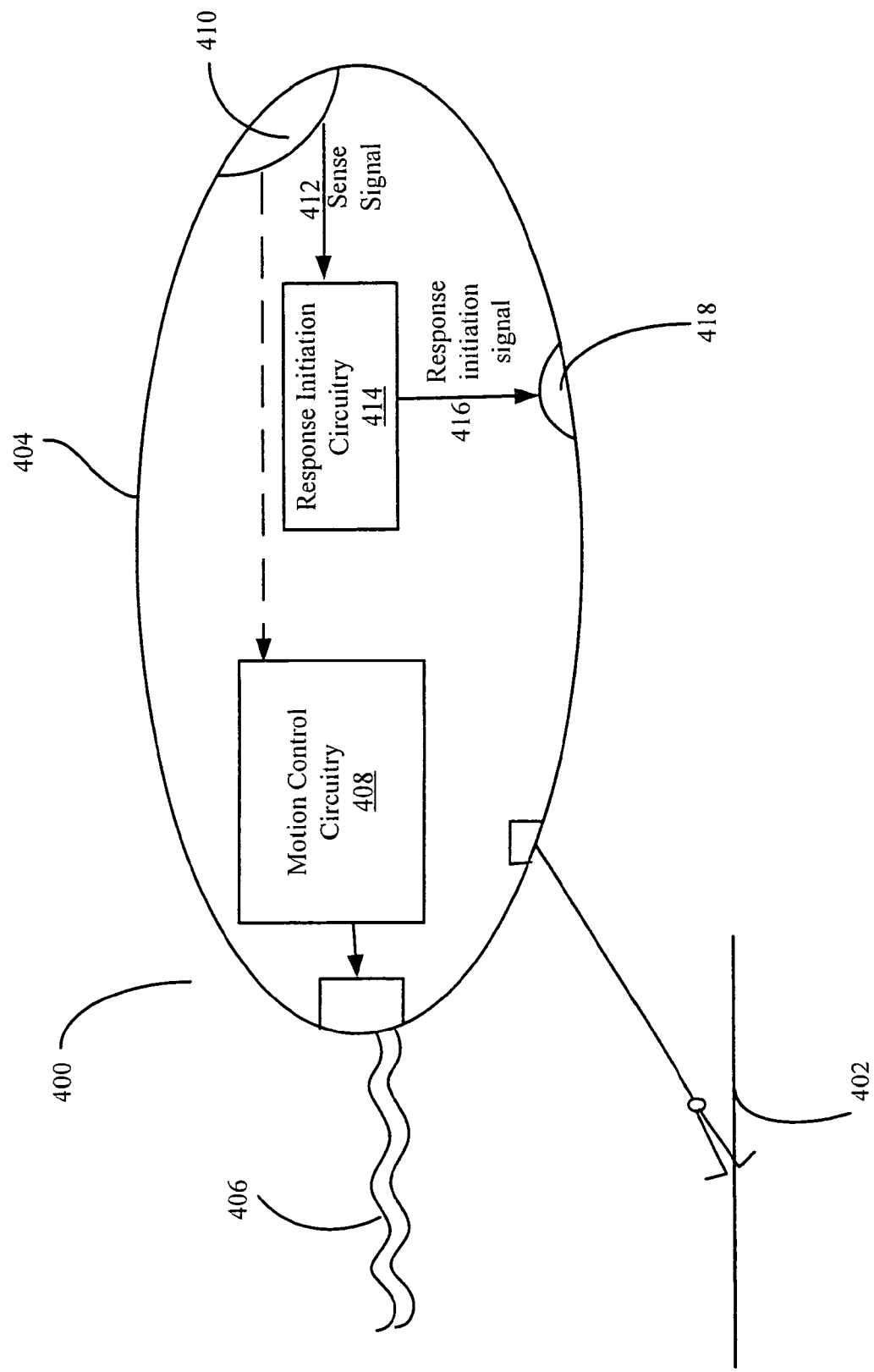
FIG. 6 illustrates an embodiment of a lumen-traveling device including a motion-arresting portion.

According to an embodiment as shown in FIG. 6, a lumen-traveling device 400 may include a motion-arresting portion 402; a fluid-contacting portion 404 configured to contact fluid within a body lumen and to at least intermittently permit flow of fluid through the body lumen; a propelling mechanism 406 capable of producing movement of the lumen-traveling device through a body lumen in which the lumen-traveling device is deployed; motion control circuitry 408 carried at least in part by said lumen-traveling device and configured to control the propelling mechanism 406 to control movement of the lumen-traveling device 400 through the body lumen; a sensor 410 capable of detecting a condition of interest in the body lumen and generating a sense signal 412 indicating detection of the condition of interest; response initiation circuitry 414 operatively connected to the sensor and configured to generate a response initiation signal 416 upon receipt of the sense signal indicating detection of a condition of interest in the body lumen; and an active portion 418 operatively connected to the response initiation circuitry and capable of producing a response upon receipt of the response initiation signal. In some embodiments, the condition of interest may be a local condition of interest (e.g. a condition related to the presence of injured or diseased tissue, an anatomical feature, etc.).

The motion control circuitry may be operatively connected to the sensor and configured to control the propelling mechanism at least in part in response to receipt of the sense signal indicating detection of the condition of interest in the body lumen.

The motion-arresting portion may take various forms, including, for example, an anchor capable of attaching at least temporarily to a wall of the lumen, as shown in FIG. 6; at least one hook or claw, e.g. as depicted in FIG. 5B; at least one adhesive material or glue, as shown in FIG. 5A; a brake to oppose the action of the propelling mechanism, or a shutoff for the propelling mechanism. In some embodiments, the motion-arresting portion may include a reversal mechanism for the propelling mechanism, in that to arrest motion it may be necessary to provide sufficient propulsion in the reverse direction to oppose a flow of fluid through the body lumen. The motion-arresting portion may be a part of, or associated with, the propelling mechanism (e.g. a shutoff for the propelling mechanism) or it may be a separate mechanism (adhesive, hook- or claw-like structure, anchor, etc.).

The lumen-traveling device may include an active portion capable of producing a response upon receipt of the response initiation signal. A lumen-traveling device may include a single active portion or multiple active portions, which may be of the same or different types. Active portions may perform related or complementary functions. A number of different types of active portion may be used in embodiments of the lumen-traveling device; a lumen-traveling device may include one or more active portions, and each active portion may perform one or more actions.

FIGS. 7-27 provide examples of different active portions which may be included in a lumen-traveling device. Some active portions may be most suitable for use in a lumen-traveling device while it is moving, and some active portions may be most suitable for use by a lumen-traveling device that is at rest within a body lumen. Many of the examples of active portions described herein may be adapted for use under either circumstance.

Figure 7A:
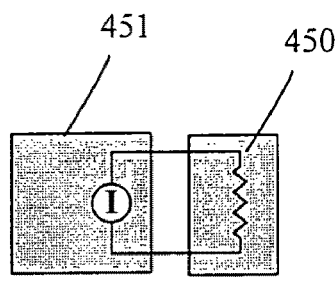
FIGS. 7A-7D are illustrations of several embodiments of lumen-traveling device active portions.

The active portion may include a heating element 450 as depicted in FIG. 7A, operatively coupled to the response initiation circuitry 451 and configured to produce heating in response to receipt of the response initiation signal. The heating element may be a resistive element that produces heat when current is passed through it, or it may be a magnetically active material that produces heat upon exposure to an electromagnetic field. Examples of magnetically active materials include permanently magnetizable materials, ferromagnetic materials such as iron, nickel, cobalt, and alloys thereof, ferrimagnetic materials such as magnetite, ferrous materials, ferric materials, diamagnetic materials such as quartz, paramagnetic materials such as silicate or sulfide, and antiferromagnetic materials such as canted antiferromagnetic materials which behave similarly to ferromagnetic materials; examples of electrically active materials include ferroelectrics, piezoelectrics and dielectrics. In some embodiments, heat may be generated through an exothermic chemical reaction. U.S. Patent Applications 2002/0147480 and 2005/0149170, provide examples of heating and/or cooling mechanisms and structures, and are incorporated herein by reference.

Figure 7B:
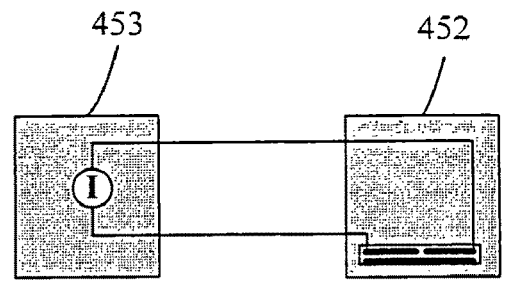

Alternatively, the active portion may include a cooling element 452 as depicted in FIG. 7B, operatively coupled to the response initiation circuitry 453 and configured to produce cooling in response to receipt of the response initiation signal. Cooling may be produced by a number of mechanisms and/or structures. For example, cooling may be produced by an endothermic reaction (such as the mixing of ammonium nitrate and water) initiated by opening of a valve or actuation of a container in response to a control signal. Other methods and/or mechanisms of producing cooling may include, but are not limited to, thermoelectric (Peltier Effect) and liquid-gas-vaporization (Joule-Thomson) devices.

Figure 7C:
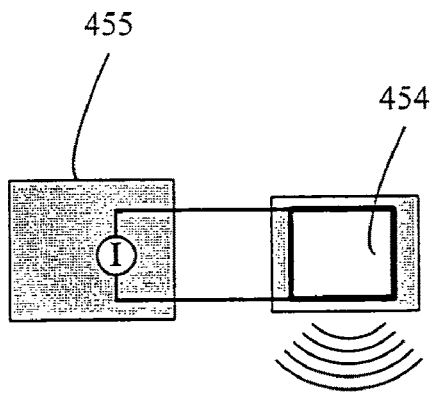

In some embodiments, the active portion may include an electromagnetic radiation source 454 as depicted in FIG. 7C, operatively coupled to the response initiation circuitry 455 and configured to emit electromagnetic radiation in response to receipt of the response initiation signal. Electromagnetic radiation sources may include light sources, for example, such as light emitting diodes and laser diodes, or sources of other frequencies of electromagnetic energy or radiation, radio waves, microwaves, ultraviolet rays, infra-red rays, optical rays, terahertz beams, and the like.

Figure 7D:
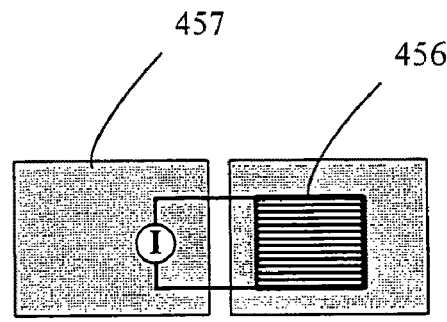

The active portion may include an acoustic energy source 456 (e.g. a piezoelectric element) as depicted in FIG. 7D, operatively coupled to the response initiation circuitry 457 and configured to emit acoustic energy in response to receipt of the response initiation signal. An acoustic energy source may generate pressure pulses of various frequencies, including auditory frequencies, subsonic frequencies, and ultrasonic frequencies. A microscale acoustic transducer may be constructed, for example, in U.S. Pat. No. 5,569,968, which is incorporated herein by reference.

Figure 8A:
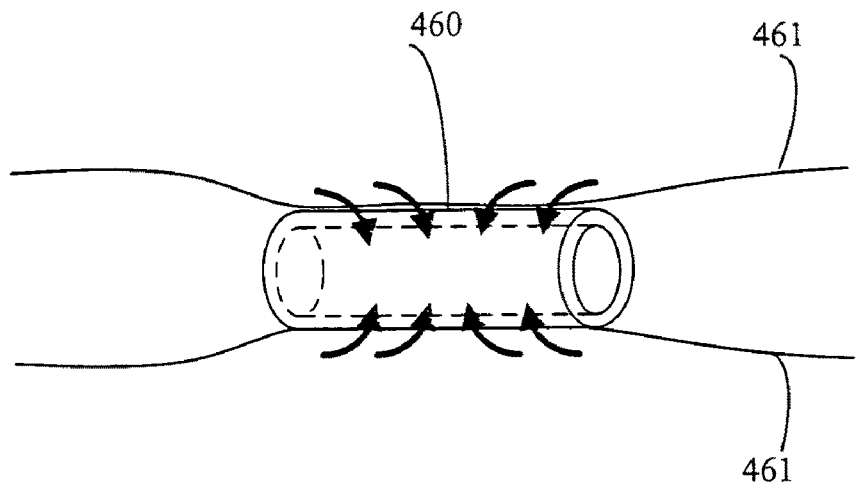
FIGS. 8A and 8B are illustrations of several further embodiments of lumen-traveling device active portions.
Figure 8B:
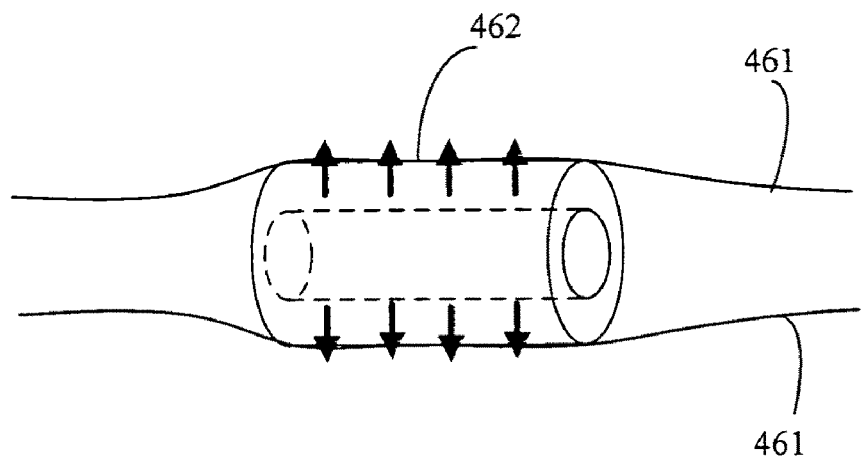

The active portion may include a pressure source operatively coupled to the response initiation circuitry and configured to apply pressure to the body lumen in response to receipt of the response initiation signal. Applied pressure may be positive pressure (e.g., to form a pressure fit of the device with the lumen wall, as described above, or to apply pressure to a particular location, e.g. to stop bleeding) or negative pressure (e.g., a vacuum, to adhere a portion of the lumen wall to the lumen-traveling device, for example to seal off a leak or aneurysm, or to position the device, as described previously). Pressure applied to a body lumen may influence one or both of the lumen walls or the contents of the lumen; in some cases application of pressure to a body lumen may increase (or decrease) the pressure in a fluid (gas or liquid) within the body lumen. A pressure source may include materials that expand through absorption of water or other materials, expand or contract due to generation or consumption of gas, or change conformation by chemical reactions or temperature changes, electrically-engendered Maxwell stresses, osmotic stress-generators, etc. FIG. 8A depicts a negative pressure source 460 capable of applying negative pressure (in this example, substantially radially-inward force) to lumen walls 461, while FIG. 8B depicts a positive pressure (expanding or expansion) source 462, capable of applying positive pressure (in this example, a substantially radially-outward force) to lumen walls 461.

Application of negative pressure to draw the lumen walls inward to form a seal with the lumen-traveling device, as depicted in FIG. 8A, may be useful for repairing or compensating for an aneurysm or other structural damage or imperfection to a lumen wall. Expansion and/or application of positive pressure by the lumen-traveling device may function to open a constricted lumen or secure a lumen-traveling device in place within a lumen, as depicted in FIG. 8B. Expansion of all or a portion of the lumen-traveling device may include expansion of a structural element or a portion thereof, which may be produced by inflation of one or more chambers with liquid or gas, or expansion or change in configuration of a shape-change material, bimetallic structure, etc.

Figure 9B:
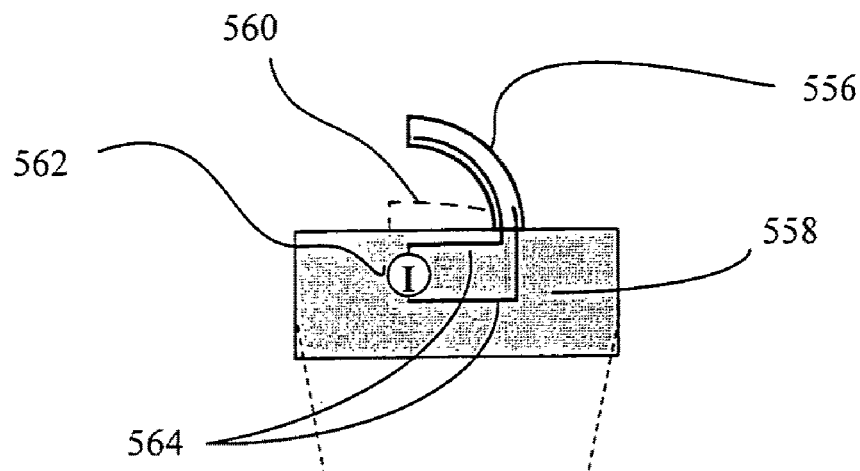
FIGS. 9A and 9B illustrate a positioning mechanism of a lumen-traveling device.
Figure 9A:
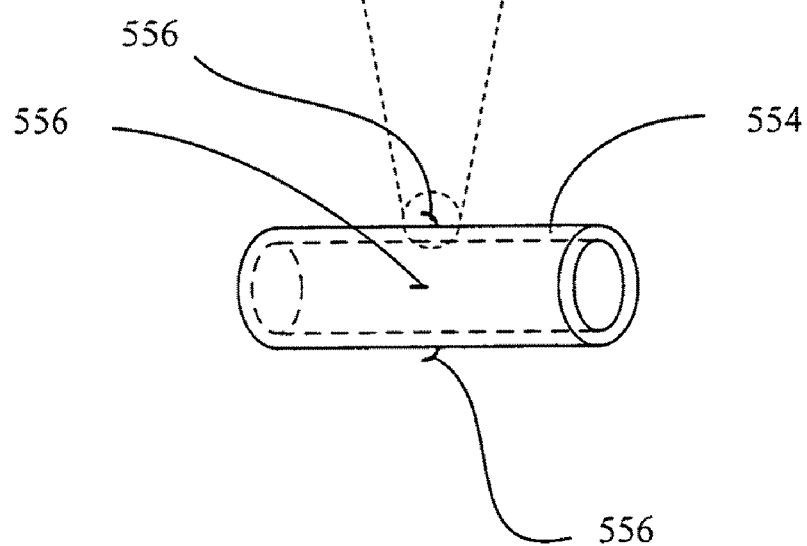

The active portion may include a positioning element operatively coupled to the response initiation circuitry and configured to secure the lumen-traveling device into position within the body lumen in response to receipt of the response initiation signal. A positioning element may be a hook or claw-like structure that may penetrate into or catch on the surface of the lumen wall, as in FIG. 5B, an expanding element that causes the lumen-traveling device to form a pressure-fit with the lumen, as in FIG. 8B, an adhesive material or glue, as in FIG. 5A, or other structure or material that may engage the lumen wall. A positioning element may also include a suction (negative pressure) generating mechanism that causes lumen-traveling device to adhere to the walls of the body lumen by suction, as depicted in FIG. 8A, for example. Claw or hook-like structures may be fixed or movable. Movable structures may include mechanical elements and/or materials that change shape or rigidity in response to temperature, electric field, magnetic field, or various other control signals. As an example, FIGS. 9A and 9B depict a lumen-traveling device 554 that includes positioning elements 556. Positioning elements such as positioning element 556 may be used as active portions in some embodiments of the invention. FIG. 9B is a close up view showing a portion 558 of lumen-traveling device 554, and detail of positioning element 556. Positioning element 556 is shown in an extended configuration (indicated by a solid outline) but may also be retracted (as indicated by the dashed outline and reference number 560). For example, positioning element 556 may change configuration on exposure to an electric current from current source 562 connected to positioning element 556 via circuitry 564. Positioning element 556 may be a claw-like projection that may be moved or extended to cause it to dig into a lumen wall to position lumen-traveling device 554 with respect to a lumen wall. Positioning element 556 may cause the lumen-traveling device to be retained in a desired position within a lumen for brief or extended periods of time. For example positioning elements may be extended to temporarily hold the lumen-traveling device in place and subsequently retracted to permit the lumen-traveling device to continue moving through the lumen. Alternatively, the lumen-traveling device may move through the lumen until it reaches a location of interest, and then the positioning elements may be extended substantially permanently to retain the lumen-traveling device at the location of interest substantially permanently. Various other types of positioning elements may be used, as well. For example, claws, clips, tensioning elements, expanding elements, and adhesives are all examples of positioning elements that may be used to retain a lumen-traveling device in a location. Certain positioning elements may be suited to retaining the lumen-traveling device in a location for extended periods, while other positioning elements may be more suited to retaining the lumen-traveling device in a location only briefly.

Figure 10A:
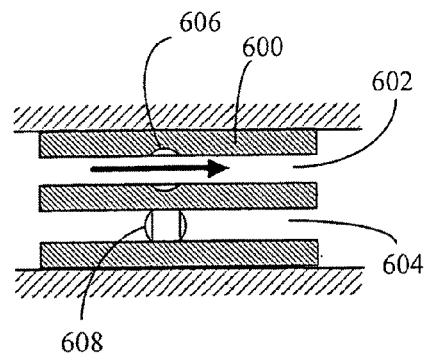
FIGS. 10A-10H depict examples of flow-modulating elements.

The active portion may include a flow-modulating element operatively connected to the response initiation circuitry and configured to modulate the flow of fluid through at least a portion of the body lumen in response to receipt of the response initiation signal. A flow-modulating element may modulate the flow of fluid through the body lumen to modify the amount of turbulence in the flow, the volume rate of flow, the fluid velocity, the direction of flow, or some other flow characteristic. A flow-modulating element may be, for example, a valve, a louver, a flow-directing element, a splitter or flow divider, a filter, a baffle, a channel restriction, a channel widening, or other structure capable of modifying the fluid flow according to principles of fluid dynamics known in the art. FIG. 10A illustrates lumen-traveling device portion 600 including a first channel 602 and a second channel 604, in which are located valves 606 and 608, respectively. Valve 606 is in the open position, allowing fluid flow as indicated by the arrow. Valve 608 is in the closed position, to block the flow of fluid. Valves 606 and 608 may be any of various types of controllable valves or microvalves.

Figure 10B:
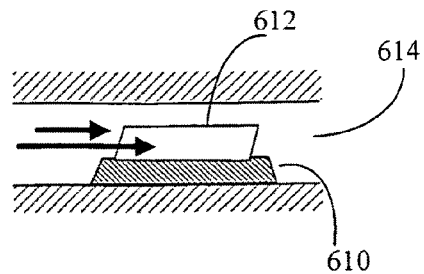

FIG. 10B illustrates a lumen-traveling device 610 including a louver 612, positioned within lumen 614. Louver 612 may modify the flow of fluid within lumen 614, e.g., by reducing turbulent flow or reducing flow velocity. Fluid may flow on either side of louver 612, as indicated by the arrows.

Figure 10C:
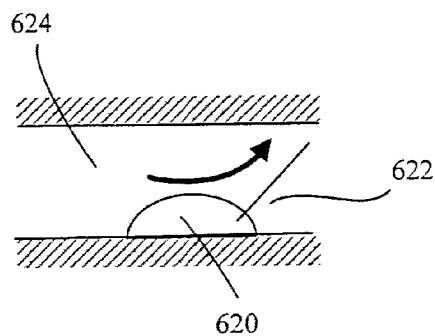

FIG. 10C illustrates a lumen-traveling device 620 including a flow-directing element 622. Flow-directing element 622 may direct the flow of fluid within lumen 624, so that fluid tends to move toward a particular portion of the lumen.

Figure 10D:
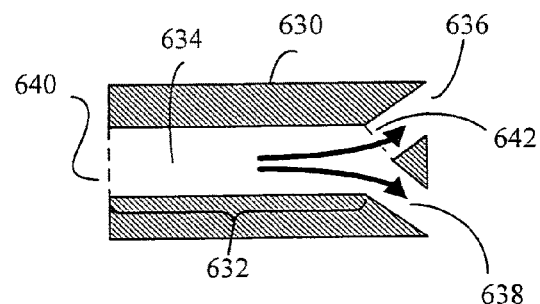

FIG. 10D depicts a portion 630 of a lumen-traveling device that includes a splitter (or flow divider) 632. Fluid may flow into main channel 634 and be divided so that it flows into branch channels 636 and 638, which may lead to additional structures within a lumen-traveling device or within the body lumen (e.g., if the lumen-traveling device was used in the vascular system, branch channels 636 and 638 could lead to particular blood vessels branching off of a larger blood vessel in which the lumen-traveling device resided). A valve placed across main channel entrance 640, or across the entrance of one or both branch channels (e.g., at entrance 642 of branch channel 636) may be used to control the operation of splitter 632.

Figure 10E:
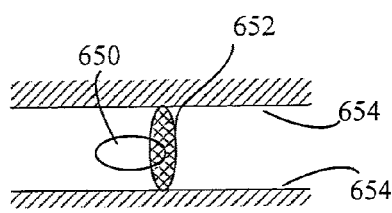

FIG. 10E depicts a lumen-traveling device 650 including a filter 652, in a body lumen defined by lumen walls 654. Filter 652 may be formed of screen, mesh, fibers, a sintered material, or various other materials, selected to remove particles in a particular size range or having particular affinity or binding properties from the fluid flowing though the filter.

Figure 10F:
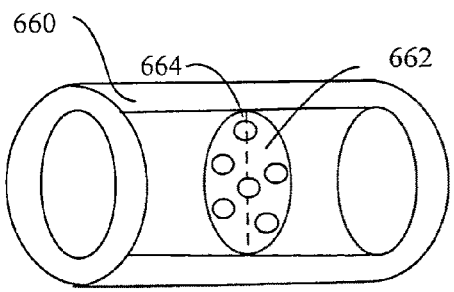

FIG. 10F depicts a lumen-traveling device 660 that include a baffle 662 for modifying the flow of fluid through the central opening 664 of lumen-traveling device 660. In some embodiments, e.g. as depicted in FIG. 10F, baffle 662 may be capable of rotating on axis 664 to move the baffle in an out of the channel to provide controlled modulation of fluid flow.

Figure 10G:
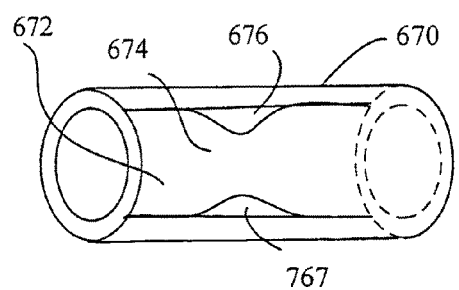

FIG. 10G depicts a lumen-traveling device portion 670 having a central channel 672 with a channel restriction 674. Channel restriction 674 may be formed by a projecting portion 676 extending around the circumference of channel 672. Projecting portion 676 may be an expandable or inflatable structure, to provide a controllable channel restriction.

Figure 10H:
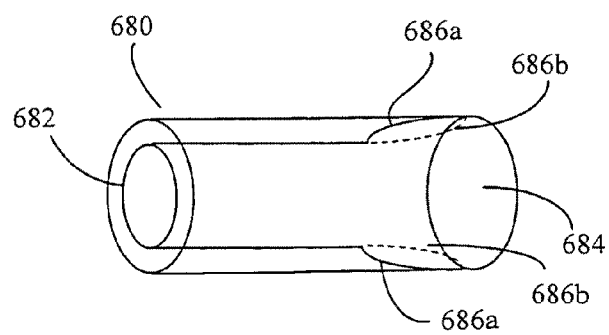

FIG. 10H depicts a lumen-traveling device portion 680 having a central channel 682 leading to a channel widening 684. Channel widening 684 may be formed by retraction of an expandable or inflatable structure 686 extending around the circumference of channel 682. Expandable or inflatable structure 686 is shown in retracted configuration 686a (thus forming channel widening 684) and in expanded configuration 686b, in which substantially no channel widening is formed. Expandable or inflatable structure 686 may be expanded to varying degrees to form varying sizes of channel widenings.

In some embodiments, the active portion of a lumen-traveling device may include a separator operatively connected to the response initiation circuitry and configured to selectively remove specific components from the fluid in response to detection of the condition of interest. A separator may be, for example, a molecular sieve or mechanical filter (including, for example, screen, mesh, fiber, etc., as depicted in FIG. 10E) having openings sized to allow passage of particles or structures of a particular size or size range, or a chemical or biochemical separator based on binding affinity, charge, surface energy, etc. as is well known to those in the art. For example, U.S. Patent Application 2005/0126916, which is incorporated herein by reference, provides an example of a microfabricated mesh. A separator may remove components that are not desired from the fluid (e.g., because they are foreign, harmful, etc.) or it may remove components for the purpose of collecting a sample for analysis. Thus, in related embodiments the active portion may include a sample collector. Either fluid or solid (e.g., tissue) samples may be collected or captured, depending on the type and/or design of the sample collector. Examples of sample collection structures and mechanisms are provided in U.S. Pat. Nos. 6,436,120 and 6,712,835, and HANNA, DARRIN M.; OAKLEY, BARBARA A.; STRYKER, GABRIELLE A.; "Using a System-on-a-Chip Implantable Device to Filter Circulating Infected Cells in Blood or Lymph"; IEEE Transactions on Nanobioscience; bearing dates of Jan. 25, 2003, March 2003; pp. 6-13; Vol. 2, No. 1; IEEE, all of which are incorporated herein by reference in their entirety. Another mechanism for capturing a solid material is a grasper as disclosed in U.S. Pat. No. 6,679,893, which is incorporated herein by reference.

Figure 11:
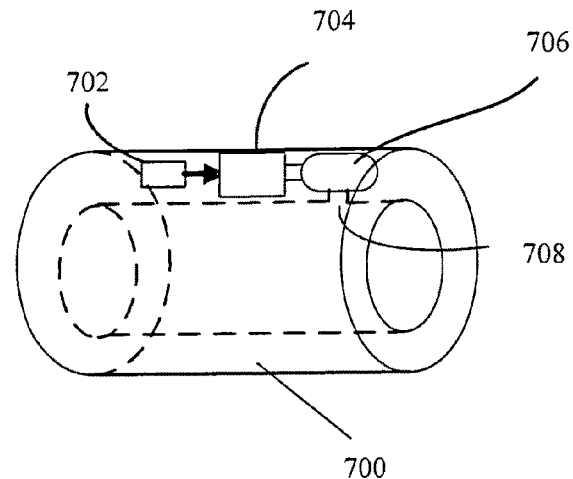
FIG. 11 is a depiction of a lumen-traveling device including a fluid-collection structure.

In some embodiments the active portion may include a fluid capture portion operatively coupled to the response initiation circuitry and configured to capture the detected material of interest. FIG. 11 depicts a device 700 including a fluid capture portion 706. Lumen-traveling device 700 includes sensor 702, response initiation circuitry 704, and fluid capture portion 706. Fluid enters fluid capture portion 706 via inlet 708. Fluid capture portion 706 may be a reservoir, for example, into which fluid is drawn by capillary action or by a negative pressure generated by a pump, for example. Captured fluid may be treated and released, or simply stored. In some applications, stored fluid may be subjected to analysis.

The sample collection portion may be a fluid capture portion configured to passively collect a fluid and/or constituents thereof, including cells or other biologics, within a matrix material, which might be located on the exterior of the lumen-traveling device in some embodiments, or contained in a chamber (e.g., fluid capture portion 706 in FIG. 11) in other embodiments. The matrix material may include an absorbent such as cotton, cellulose, natural or artificial sponge, a gel (a natural gel such as agarose, a natural and/or synthetic polymer gel, a hydrogel), a colloid, a gum base such as acacia gum, or micro particles. The sample collection portion may include a lipid monolayer, lipid bilayer, liposome, dendrimer, ligand affinity resin with conjugated peptide or antibody, ionophore, hydrosol, sol-gel, xerogel, aerogel, smart gel, hydrocarbon gel, or ferrogel. Many types of porous hydrogels are known, such as those used in the wound dressing of U.S. Pat. No. 6,372,248, incorporated herein by reference in its entirety. Alternatively, the sample collector may include a synthetic or natural adsorbent material such as a proteoglycan or charged polymer like polylysine, of a type that promotes the adhesion of one or more fluid constituent, e.g. a cell or protein. Other materials may include semi-specific or non-specific adsorbers, such as silica ($SiO_2$) or alumina ($Al_2O_3$) gel or ion exchange resin, possibly as part of the matrix material. Further examples of materials for sample collection are disclosed in U.S. Pat. Nos. 6,861,001 and 6,475,639, which are incorporated herein by reference. Alternatively or in addition, the sample collector may include one or more recognition elements of a type able to recognize and/or specifically bind a constituent of the fluid. Such a recognition element might be a biologic, such as a staphylococcus protein A complex, which generally binds immunoglobulins; a binding peptide or protein like an immunoglobulin; a DNA binding protein and/or genetically engineered protein; a nucleic acid, perhaps an aptamer; a carbohydrate; a lipid; a conjugate; or a synthetic molecule like an artificial antibody or other mimetic. U.S. Pat. Nos. 6,255,361; 5,804,563; 6,797,522; and 5,831,012 and U.S. Patent Application 2004/0018508 provide examples of such mimetics and are incorporated herein by reference in their entirety.

Figure 12:
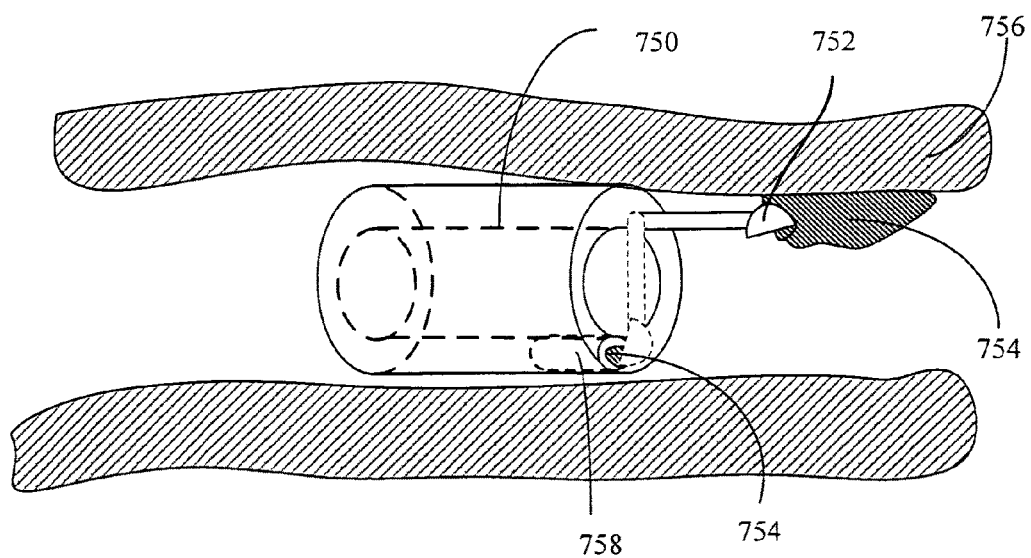
FIG. 12 is a depiction of a lumen-traveling device including a material collection structure.
Figure 13:
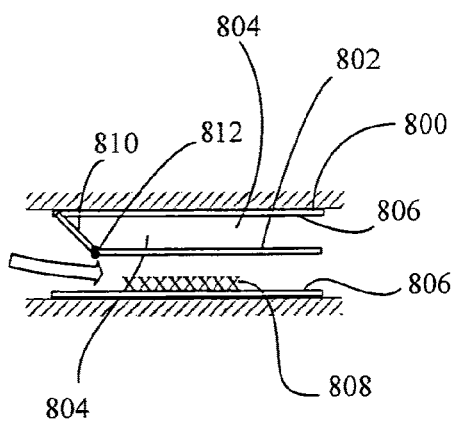
FIG. 13 illustrates an embodiment of an active portion of a lumen-traveling device.

FIG. 12 depicts lumen-traveling device 750 including a sample collection structure 752 capable of collecting a solid sample 754, e.g. for biopsy purposed and/or for removal of damaged, diseases, or otherwise unwanted tissue. In the example depicted in FIG. 12, solid sample 754 is a solid material found upon or immediately under the surface of the lumen-defining wall 756 (an arterial plaque, for example). Solid sample 754 placed in storage reservoir 758 by sample collection structure 752. In a related alternative embodiment, a lumen-traveling device may include a filter or selective binding region to remove materials from fluid moving past or through the lumen-traveling device.

In some embodiments, the active portion may include a catalytic portion operatively connected to the response initiation circuitry and configured to expose or activate a catalyst in response to receipt of the response initiation signal. Examples of catalysts include inorganic catalysts such as metal surfaces, and organic catalysts such as enzymes. A surface having catalytic properties (such as a metal) or having catalytic material adhered or bound thereto may be exposed or activated by directing the flow of fluid across, the surface, modifying a chemical property of the surface, or removing a covering from the surface. For example, as shown in cross-section in FIG. 13, a lumen-traveling device portion 800 may include a channel divider 802 separating two channels 804 and 806. Channel 806 includes catalytic material 808, which is capable of catalyzing a reaction with one or more component of fluid flowing through channel 806, as indicated by the arrow. A movable gate 810 on pivot 812 may block the flow of fluid into channel 804 while permitting the flow of fluid into channel 806 and across catalytic material 808, or it may be repositioned to block the flow of fluid into channel 806 while permitting the flow of fluid into channel 804. In some embodiments of a lumen-traveling device, the active portion may include a catalytic portion operatively connected to the response initiation circuitry and configured to expose a catalytic surface to the fluid in response to detection of the condition of interest. The catalytic surface may catalyze a reaction that modifies or destroys a material of interest, for example.

Figure 14:
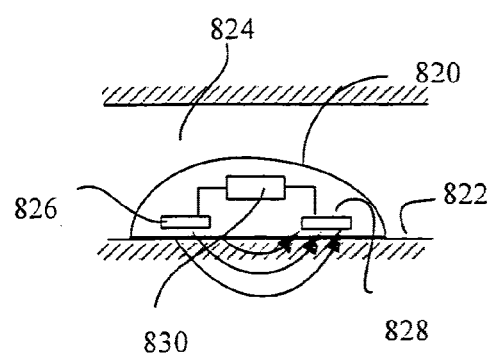
FIG. 14 illustrates an embodiment of an active portion of a lumen-traveling device.

The active portion may include an electric field source, as depicted in FIG. 14, operatively connected to the response initiation circuitry and configured to apply an electric field to the fluid and/or lumen wall or surrounding tissue in response to receipt of the response initiation signal. For example, a lumen-traveling device 820, here shown contacting wall 822 of lumen 824, may include a first contact 826 and second contact 828 connected to source 830. Source 830 may be a capacitor or other charge storing device, to generate a static electric field, or it may be current source capable of generating a dynamic electric field.

Figure 15:
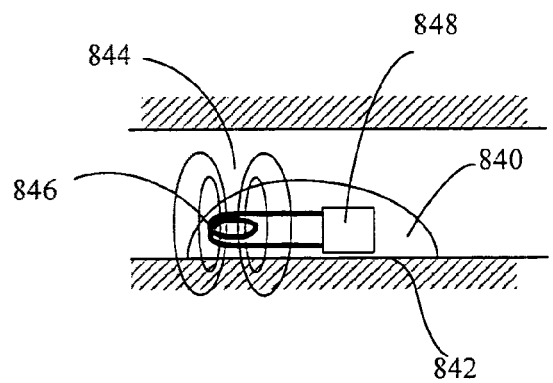
FIG. 15 illustrates an embodiment of an active portion of a lumen-traveling device.

Alternatively, as shown in FIG. 15, an active portion may include a magnetic field source operatively connected to the response initiation circuitry and configured to apply a magnetic field to the fluid and/or lumen wall or surrounding tissue in response to receipt of the response initiation signal. A lumen-traveling device 840 adjacent wall 842 of lumen 844 may include (for example) a coil 846 connected to current source 848. Current from current source 848 flowing through coil 846 will produce a magnetic field as indicated in FIG. 15. The magnetic field source need not include a coil; as known to those of skill in the art, a magnetic field may be generated by current flowing through various types of structures. Moreover, one or more fixed magnets may be included in a magnetic field source.

Figure 16:
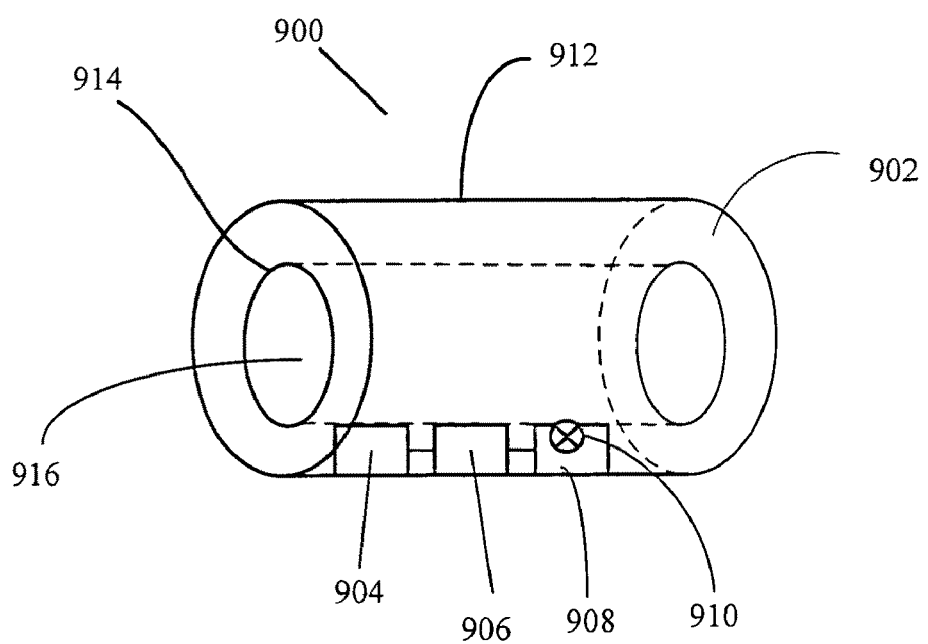
FIG. 16 is an illustration of a device including stored deliverable material.

In some embodiments, the active portion of a lumen-traveling device may include a material release structure operatively coupled to the response initiation circuitry and configured to release a material in response to receipt of the response initiation signal. FIG. 16 depicts a delivery device 900 including a structural element 902, sensor 904, control signal generation circuitry 906, and release structure 908 including release mechanism 910. Structural element 902 includes external surface 912, configured to fit within a body lumen, and internal surface 914 defining central opening 916, through which a fluid may flow. Upon sensing of a condition of interest in the fluid by sensor 904, control signal generation circuitry 906 may cause release of material from material release structure 908 by activating release mechanism 910. Release mechanism 910 may include a variety of different types of release mechanisms, including, for example, a controllable valve. Various types of valves and microvalves are known to those of skill in the art, and may be used to regulate the release of material from material release structure 908 in response to a control signal from control signal generation circuitry 906. Control signal generation circuitry 906 may activate release mechanism 910 by supplying a delivery control signal, which may be an electrical signal, for example. In some embodiments, other types of delivery control signals, including magnetic signals, optical signals, acoustic signals, or other types of signals may be used. Combinations of several types of signals may be used in some embodiments. In some embodiments, control signal generation circuitry 906 may cause release of material from material release structure in response to passage of a certain amount of time, as monitored, for example, by a timekeeping device. In some embodiments, material release structure 908 may include a pressurized reservoir of material. In still other embodiments, the material (or materials) to be released may be generated within the material release structure. In other embodiments, the material(s) may diffuse away from the release structure along a concentration gradient.

Figure 17:
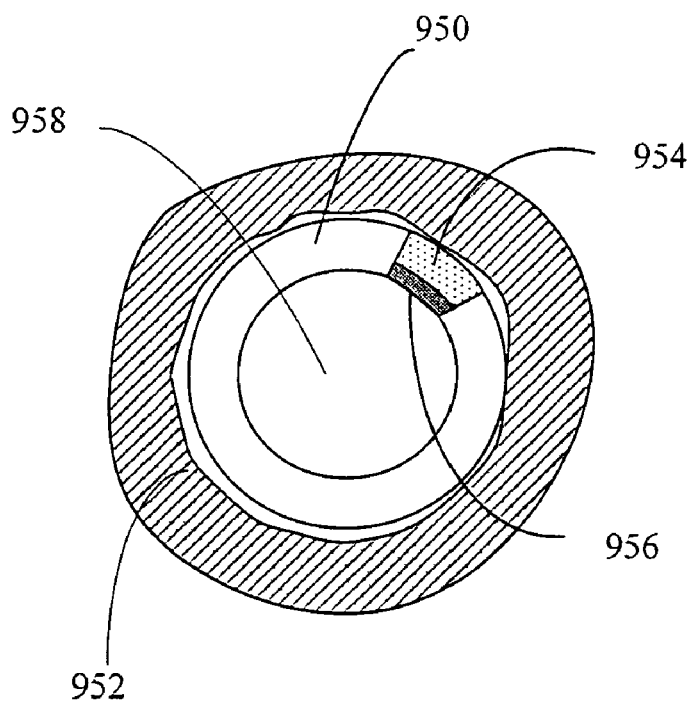
FIG. 17 is a cross-sectional view of an embodiment of a device including a stored deliverable material and a barrier release mechanism.

FIG. 17 illustrates, in cross sectional view, a structural element 950 of a lumen-traveling device positioned in a lumen-containing structure 952. A reservoir 954 contains stored deliverable material. Barrier 956 is a controllable barrier that control the release of the stored deliverable material into central opening 958, and thus into a fluid that fills and/or flows through lumen-containing structure 952.

Figure 18:
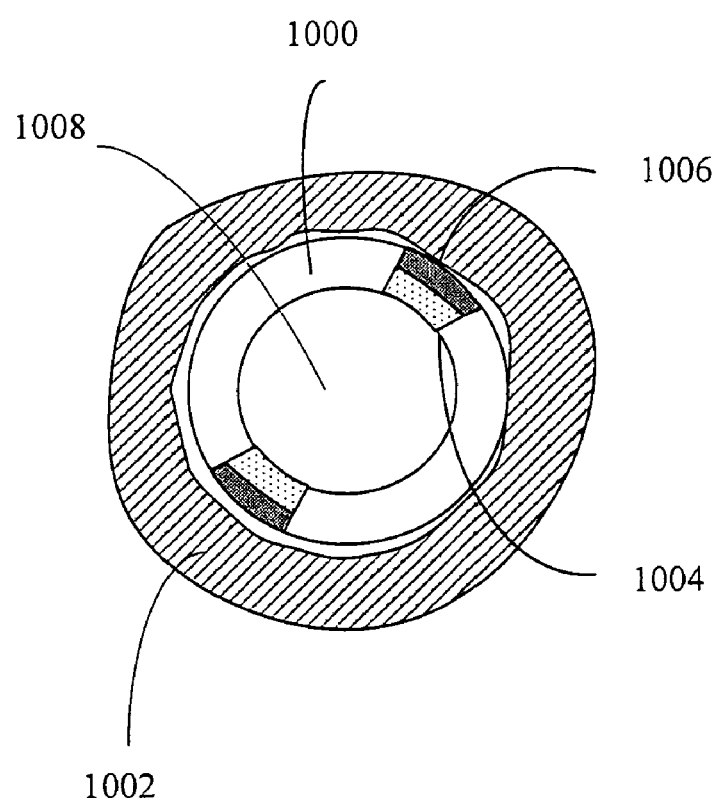
FIG. 18 is a cross-sectional view of another embodiment of a device including a stored deliverable material and a barrier release mechanism.

FIG. 18 illustrates an embodiment similar to that depicted in FIG. 20, including a structural element 1000 of a lumen-traveling device positioned in a lumen-containing structure 1002. A reservoir 1004 contains stored deliverable material. Barrier 1006 is a controllable barrier that controls the release of the stored deliverable material. In the embodiment of FIG. 18, activation of barrier 1006 causes release of the stored deliverable material toward the lumen wall of lumen-containing structure 1002, rather than into central opening 1008.

FIGS. 19A, 19B, 20A, 20B, 22A and 22B, illustrate several alternative embodiments of material release structures that include controllable barriers. In FIGS. 19A and 19B, release structure 1150 includes reservoir 1152 containing stored deliverable material 1154. As shown in FIG. 19A, while rupturable barrier 1156 is intact, stored deliverable material 1154 is contained within reservoir 1152. As shown in FIG. 19B, when rupturable barrier 1156 has been ruptured (as indicated by reference number 1156'), deliverable material 1154 may be released from reservoir 1152. Rupturable barrier 1156 may be ruptured by an increase of pressure in reservoir 1152 caused by heating, for example, which may be controlled by response initiation circuitry. In another alternative shown in FIGS. 20A and 20B, release structure 1200 includes reservoir 1202 containing stored deliverable material 1204. As shown in FIG. 20A, while degradable barrier 1206 is intact, stored deliverable material 1204 is contained within reservoir 1202. As shown in FIG. 20B, degradation of degradable barrier 1206 to degraded form 1206' causes stored deliverable material 1204 to be released from reservoir 1204. FIGS. 21A and 21B depict release structure 1250 including reservoir 1252 containing stored deliverable material 1254. FIG. 21A shows barrier 1256, which has a controllable permeability, in a first, impermeable state, while FIG. 21B shows barrier 1256 in a second, permeable state (indicated by reference number 1256'). Stored deliverable material 1254 passes through barrier 1256', when it is in its permeable state, and is released. Rupturable barriers as described above may be formed from a variety of materials, including, but not limited to, metals, polymers, crystalline materials, glasses, ceramics, semiconductors, etc. Release of materials through rupture or degradation of a barrier is also described in U.S. Pat. No. 6,773,429, and U.S. Patent Application 2004/0260391, which are incorporated herein by reference. Semipermable barriers having variable permeability are described, for example, in U.S. Pat. No. 6,669,683, which is incorporated herein by reference. Those of skill in the art will appreciate that barriers can be formed and operated reversibly through multiple release cycles, in addition to the single-release functionality available from a rupturable barrier.

Figure 22:
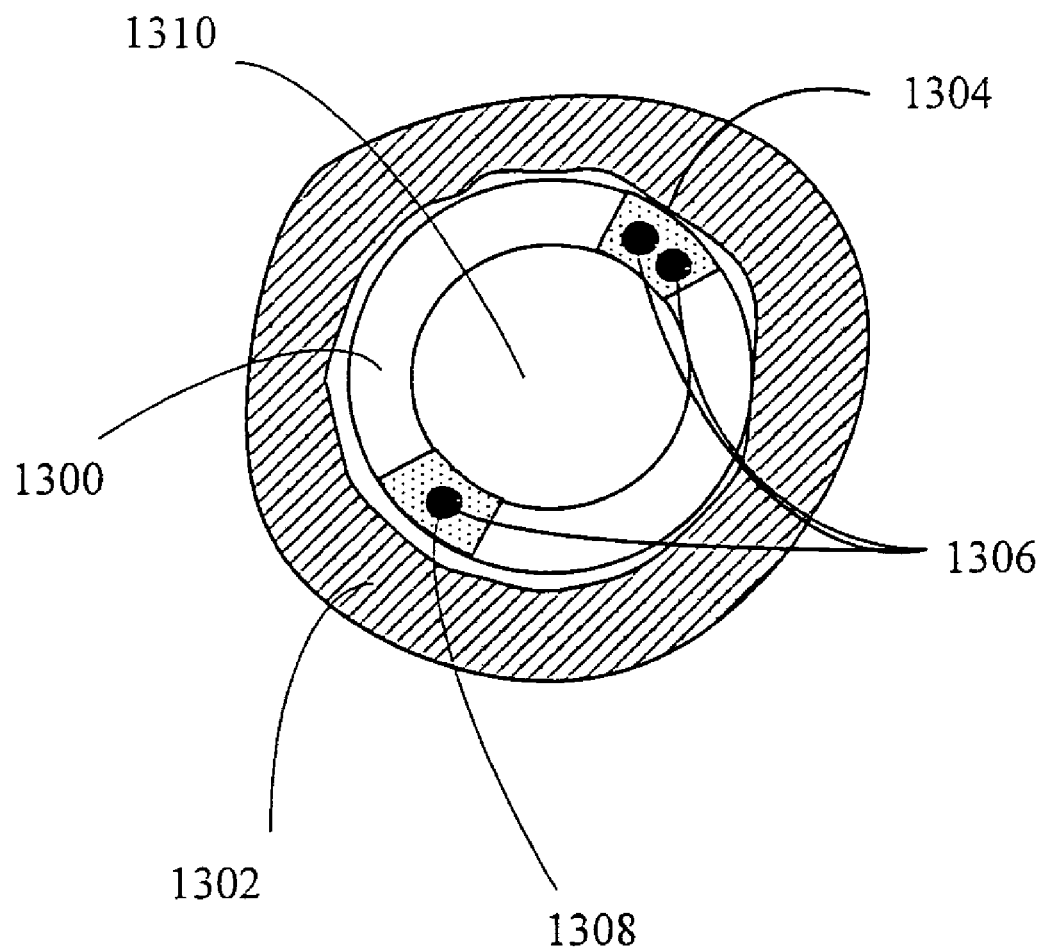
FIG. 22 is a cross-sectional view of another embodiment of a device including a stored deliverable material.

FIG. 22 depicts another embodiment of a structural element of a lumen-traveling device 1300 in a lumen containing structure 1302. Lumen-traveling device 1300 includes stored deliverable material 1304 dispersed in a carrier material 1306. Stored deliverable material 1304 may be released from carrier material 1306 by release mechanism 1308 upon activation of release mechanism 1308. Released deliverable material 1304 may be released into central opening 1310 of lumen-traveling device 1300 and/or into the area around the lumen-traveling device.

Figure 23A:
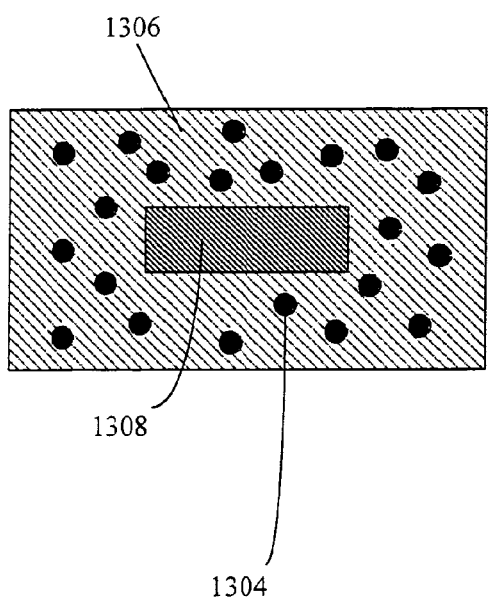
FIGS. 23A and 23B are depictions of the release of a stored deliverable material from a carrier material.
Figure 23B:
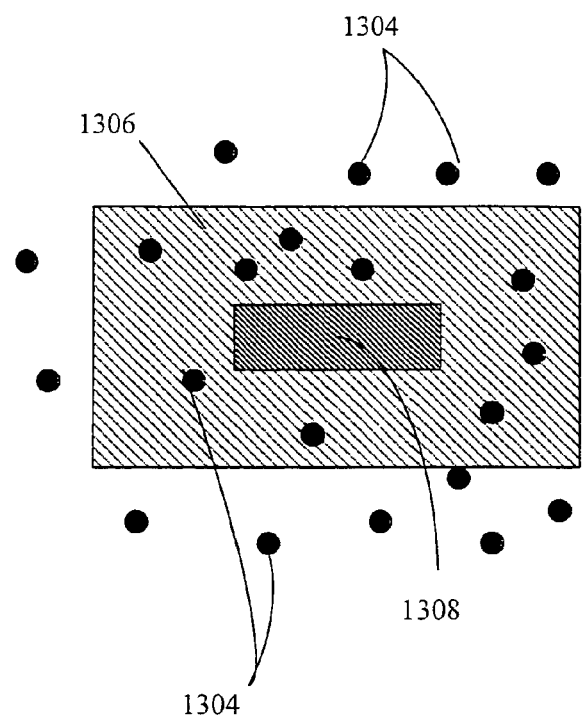

FIGS. 23A and 23B depict in greater detail the release of stored deliverable material from the carrier material. In FIG. 23A, deliverable material 1304 is stored in carrier material 1306. Carrier material 1306 may be, for example, a polymeric material such as a hydrogel, and deliverable material is dispersed or dissolved within carrier material 1306. Release mechanism 1308 may be a heating element, for example a resistive element connected directly to response initiation circuitry, or an electrically or magnetically responsive material that may be caused to move, vibrate or heat, by an externally applied electromagnetic field, which in turn causes release of deliverable material 1304 from carrier material 1306, as shown in FIG. 23B. See, for example, U.S. Pat. Nos. 5,019,372 and 5,830,207, which are incorporated herein by reference. In some embodiments, an electrically or magnetically active component may be heatable by an electromagnetic control signal, and heating of the electrically or magnetically active component may cause the polymer to undergo a change in configuration. An example of a magnetically responsive polymer is described, for example, in Neto, et al, "Optical, Magnetic and Dielectric Properties of Non-Liquid Crystalline Elastomers Doped with Magnetic Colloids"; Brazilian Journal of Physics; bearing a date of March 2005; pp. 184-189; Volume 35, Number 1, which is incorporated herein by reference. Other exemplary materials and structures are described in Agarwal et al., "Magnetically-driven temperature-controlled microfluidic actuators"; pp. 1-5; located at: http://www.unl.im.dendai.ac.jp/INSS2004/INSS2004_papers/OralPresentations/C2.pdf or in U.S. Pat. No. 6,607,553, both of which are incorporated herein by reference. In connection with the release of materials and/or detection of a local condition, in some embodiments the permeability of the lumen wall to the released material may be increased by the use of retractable protrusions that penetrate the lumen wall, as described in U.S. Pat. No. 6,991,617; by hollow microneedles capable of penetrating the lumen wall, as described in U.S. Pat. No. 6,743,211; by introduction of a magnetic or electromagnetic field (Physical and Chemical Permeation Enhancers in Transdermal Delivery of Terbutaline Sulphate, *AAPS Pharm Sci Tech*, 2001; 2 (1) 1-5; http://www.aapspharmscitech.org/view.asp?art=pt0201_tnl); by a chemical permeability enhancer as described in U.S. Pat. No. 6,673,363, which may be released from the lumen-traveling delivery device along with the material or from a separate reservoir or other source or which may be incorporated within a component of the device for example as a coating; or by an electrical permeability enhancer, such as a voltage source for producing electroporation and/or iontophoresis, as in U.S. Pat. Nos. 6,022,316, 6,219,577, 6,512,950; or by sonophoresis or phonophoresis, perhaps using techniques based on those in U.S. Pat. No. 6,322,532; all of which patents are incorporated herein by reference in their entirety. Chemical permeation enhancers may include, for example, isopropyl myristate, bile salts, surfactants, fatty acids and derivatives, chelators, cyclodextrins, or chitosan. Other technologies that might be useful for enhancing permeability may include iontophoresis, microdialysis, ultrafiltration, electromagnetic, osmotic, electroosmosis, sonophoresis, suction, electroporation, thermal poration, microporation, microfine cannulas, skin permeabilization, or a laser.

Figure 24:
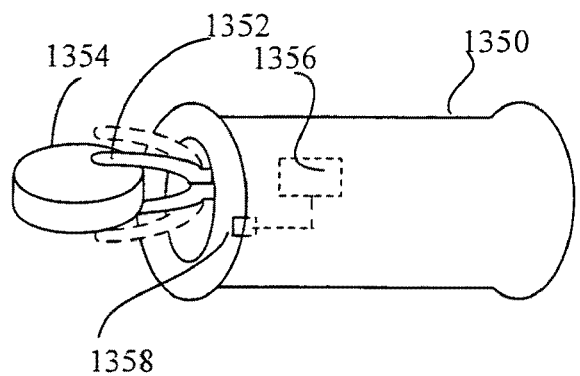
FIG. 24 illustrates a lumen-traveling device including a device release structure.

The active portion may include a device release structure operatively coupled to the response initiation circuitry and configured to release a device in response to receipt of the response initiation signal. For example, FIG. 24 illustrates a lumen-traveling device 1350 including device release structure 1352 (which in this example is a grasper type structure) holding a device 1354 that is to be released into a body lumen. Response initiation circuitry 1356 may receive a sense signal from sensor 1358, and generate a response initiation signal to cause device release structure 1352 to release device 1354. Device 1354 may be any type of device small enough to be carried by a lumen-traveling device. For example, device 1354 might be a sensor with a transmitter, a device that releases a drug or other compound, or an electromagnetic stimulation device. The device configuration illustrated in FIG. 24 is intended as an example only, and the device released by a device release structure of a lumen-traveling device may have various configurations. It will be appreciated that the device release structure may be designed to be compatible with a particular type of device, or may be suitable for use with a number of types of devices.

Figure 25A:
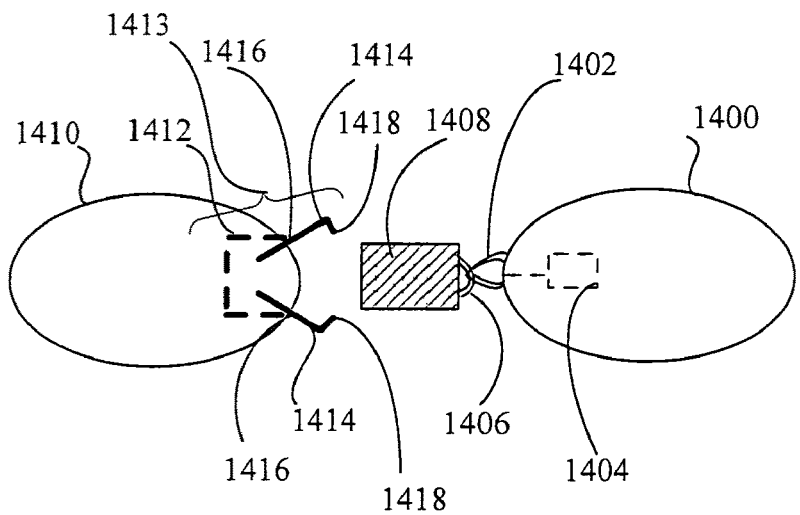
FIGS. 25A and 25B illustrate lumen-traveling devices including delivery and receiving structures.
Figure 25B:
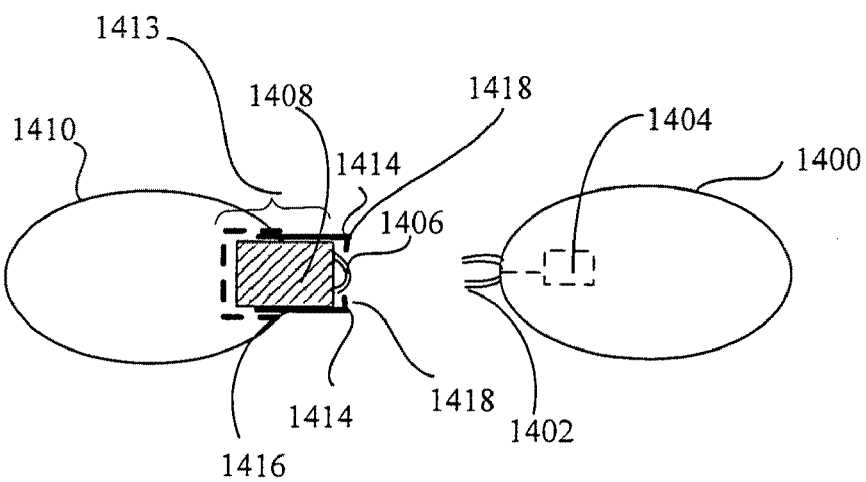

As illustrated in FIGS. 25A and 25B, the active portion of a lumen-traveling device 1400 may include a delivery structure 1402 operatively coupled to the response initiation circuitry 1404 and configured to deliver a material or structure 1408 to a receiving device in 1410 response to receipt of the response initiation signal. In FIG. 25A, lumen-traveling device 1400 includes delivery structure 1402, which is capable of attaching to connector 1406 on structure 1408, thus permitting structure 1408 to be carried by lumen-traveling device 1400. In use, lumen-traveling device 1400 may carry structure 1408 to receiving device 1410. A response initiation signal may be generated by response initiation circuitry 1404 when lumen-traveling device 1400 is close to receiving device 1410. Receiving device 1410 may include a receiving structure 1413 made up of recess 1412 and receiving arms 1414 mounted on pivots 1416. Receiving device 1410 may be a non-mobile device or structure that has been implanted or placed in the lumen, or, in some embodiments, receiving device 1410 may be a second lumen-traveling device. The second lumen-traveling device may include various features as described previously; the active portion may include a receiving structure (e.g., receiving structure 1413 in FIGS. 25A and 25B) operatively coupled to the response initiation circuitry and configured to receive a material or structure (e.g., structure 1408) from a delivering device 1400 in response to receipt of the response initiation signal. As structure 1408 is pushed into receiving recess 1412, receiving arms 1414 may be caused to move on pivots 1416 to allow structure 1408 to slide into recess 1412, where it may be retained by projections 1418, as illustrated in FIG. 25B.

The active portion may include a collecting structure operatively coupled to the response initiation circuitry and configured to collect a structure (including, but not limited to, a man-made structure) from the body lumen in response to receipt of the response initiation signal. The collecting structure may be comparable to a device release structure as depicted previously, and may collect a structure from the body lumen by attaching to a connector such as connector 1406. In related embodiments, the collecting structure may grasp the body of a device-to-be-collected, generally as depicted in FIG. 24. In other embodiments, a collecting structure may be large enough to receive the structure to be collected within the body of the lumen-traveling device.

The active portion of a lumen-traveling device may include an attachment structure operatively coupled to the response initiation circuitry and configured to attach to a structure (particularly a man-made structure) present in the body lumen in response to receipt of the response initiation signal. The attachment structure may be a grasper shown in FIG. 24 or the device release structure shown in FIGS. 25A and 25B. Other attachment mechanisms may include various other mechanical mechanisms, or be based on magnetic attraction, electrostatic forces, chemical bonding, surface interactions, etc. Microscale structures for gripping or grasping are described in U.S. Pat. No. 6,398,280, and "Zyvex NanoEffector Microgrippers"; Nanotechnology at Zyvex; printed on Dec. 7, 2006; pp. 1-2; located at http://www.zyvex.com/Products/Grippers_Features.html and "Zyvex NanoEffector Microgrippers"; Zyvex.com; bearing a date of 2006; pp. 1-2; Zyvex Corporation, all of which are incorporated herein by reference.

The active portion may include one or more tools, especially surgical tools, e.g., tools for cutting, as depicted in FIGS. 26A and 26B, scraping, as depicted in FIG. 27, suturing, or cauterizing. In FIG. 26A, a lumen-traveling device 1450 includes a cutting tool 1452 mounted on shaft 1454, which may be retracted into channel 1456, driven by translation motor 1458. In the embodiment depicted in FIG. 26A, lumen-traveling device 1450 includes main lumen 1460. A cross-section of lumen-traveling device 1450 taken at section line B-B, showing shaft 1454, channel 1456, and main lumen 1460 is illustrated in FIG. 26B. Channel 1456 and main lumen 1460 pass through core portion 1462 of lumen-traveling device 1450.

FIG. 27 depicts a lumen-traveling device 1500, generally similar to lumen-traveling device 1450 in FIGS. 26A and 26B, but including a scraping tool 1502. Scraping tool 1502 is mounted on shaft 1504 which may retract in channel 1506. Shaft 1504 may also rotate in channel 1506, both during use of scraping tool 1502, as illustrated with the double-headed arrow, and also to permit the scraping tool 1502 to be retracted into main lumen 1508 of the lumen-traveling device, to the position shown in dashed lines. An example of a scraping tool is presented in JP 2005-74229, which is incorporated herein by reference.

Various examples of suturing tools are disclosed and described in U.S. Pat. Nos. 7,131,979 and 5,964,773, both of which are incorporated herein by reference. A cauterizing tool may be a specialized form of a heating element, as depicted in FIG. 7A, or electromagnetic radiation source as depicted in FIG. 7C. Tools may be micro-scale tools formed by MEMS manufacturing techniques, e.g., as described in U.S. Pat. No. 5,728,089, which is incorporated herein by reference. It will be appreciated that various other active portions disclosed herein may also have surgical utility: for example, active portions for performing sample collection, material release, heating, cooling, etc. may all have surgical applications.

Figure 28:
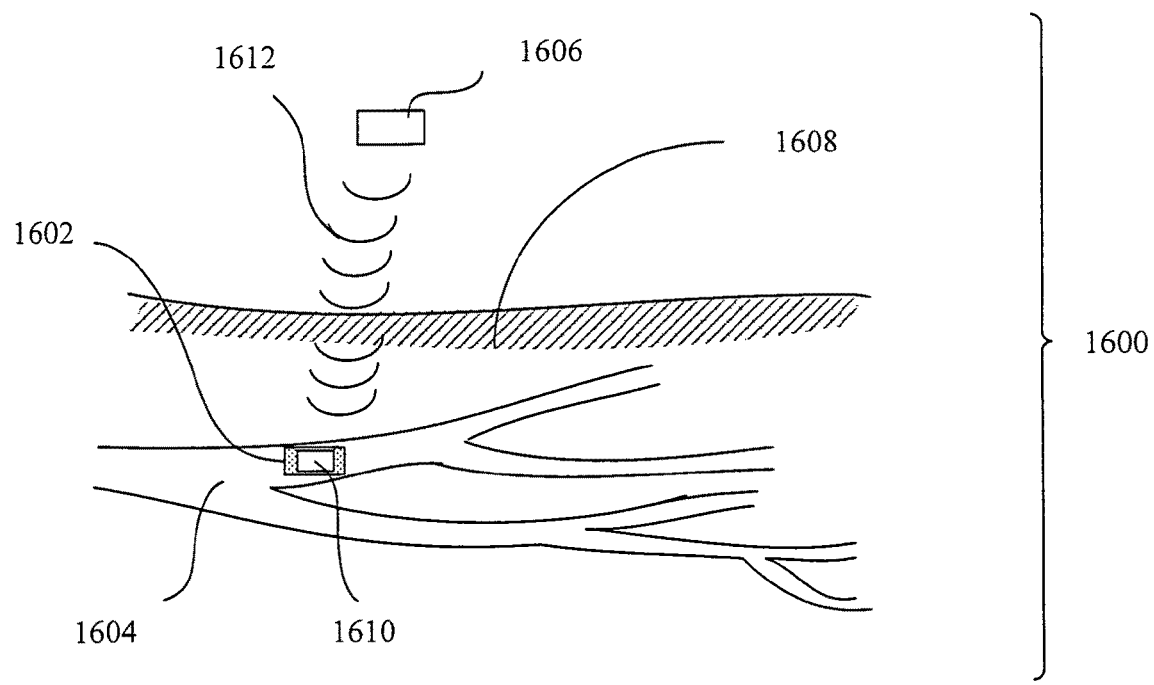
FIG. 28 is an illustration of a lumen-traveling system that includes an external control portion.

FIG. 28 depicts a system 1600 including a lumen-traveling device 1602 located in a body lumen 1604 (here, a portion of the circulatory system) and a remote portion 1606, which in this example is located outside body surface 1608. In some embodiments, a remote portion may be located inside the body at a distance from the lumen-traveling device. The active portion of a lumen-traveling device 1602 may include a transmitter 1610 operatively coupled to the response initiation circuitry and configured to transmit a detection signal 1612 to a remote location (e.g., remote portion 1606) in response to receipt of the response initiation signal. The detection signal may be used to inform a medical caregiver about a condition of the subject so that suitable treatment may be provided by the caregiver, or the detection signal may contain information usable by an automated system to control operation of the lumen-traveling device.

Various types of propelling mechanisms may be used to move the lumen-traveling device through the body lumen. Examples are provided in U.S. Pat. Nos. 5,337,732; 5,386, 741; 5,662,587; and 6,709,388; and KASSIM, IRWAN; PHEE, LOUIS; NG, WAN S.; GONG, FENG; DARIO, PAOLO; MOSSE, CHARLES A. ("Locomotion Techniques for Robotic Colonoscopy"; IEEE ENGINEERING IN MEDICINE AND BIOLOGY MAGAZINE; bearing dates of May/June 2006 and 2006; pp. 49-56; IEEE); CHRISTENSEN, BILL ("Musclebot: Microrobot with a Heart"; Technovelgy.com; pp. 1-2; bearing a date of Feb. 27, 2004; located at http://www.technovelgy.com/ct/Science-Fiction-News.asp?NewsNum=46; printed on Sep. 12, 2006); ANANTHASWAMY, ANIL ("First robot moved by muscle power"; bearing a date of Feb. 27, 2004; pp. 1-3; New Scientist; located at http://www.newscientist.com/article.ns?id=dn4714; printed on Sep. 12, 2006); and FREITAS JR., ROBERT A. ("8.2.1.2 Arteriovenous Microcirculation"; "9.4.3.5 Legged Ambulation"; "9.4.3.6 Tank-Tread Rolling"; "9.4.3.7 Amoeboid Locomotion"; "9.4.3.8 Inchworm Locomotion"; "Nanomedicine Volume I: Basic Capabilities"; bearing a date of 1999; pp. 211-214, pp. 316-318; Landes Bioscience; Georgetown, Tex., USA); all of which are incorporated herein by reference in their entirety. The propelling mechanism of the lumen-traveling device may include one or more cilium-like or flagellum-like structures, for example, as described in U.S. Patent Application 2004/0008853; MATHIEU, J-B.; MARTEL, S.; YAHIA, L'H.; SOULEZ, G.; BEAUDOIN, G. ("MRI Systems as a Mean of Propulsion for a Microdevice in Blood Vessels"; bearing a date of 2003; pp. 3419-3422; IEEE); LU, ZHAO; MARTEL, SYLVAIN ("Preliminary Investigation of Bio-carriers Using Magnetotactic Bacteria"; Proceedings of the 28th IEEE EMBS Annual International Conference; bearing dates of Aug. 30, 2006-Sep. 3, 2006 and 2006; pp. 3415-3418; IEEE), and MARTEL, SYLVAIN ("Towards MRI-Controlled Ferromagnetic and MC-1 Magnetotactic Bacterial Carriers for Targeted Therapies in Arteriolocapillar Networks Stimulated by Tumoral Angiogenesis"; Proceedings of the 28th IEEE EMBS Annual International Conference; bearing dates of Aug. 30, 2006-Sep. 3, 2006 and 2006; pp. 3399-3402; IEEE), all of which are incorporated herein by reference. The propelling mechanism may include rollers or wheel-like structures, as shown in U.S. Pat. No. 7,042,184 and U.S. Patent Application 2006/0119304, both of which are incorporated herein by reference; screw-like structures, as disclosed in IKEUCHI, K.; YOSHINAKA, K.; HASHIMOTO, S.; TOMITA, N. ("Locomotion of Medical Micro Robot with Spiral Ribs Using Mucus"; Seventh International Symposium on Micro Machine and Human Science; bearing a date of 1996; pp. 217-222; IEEE), which is incorporated herein by reference; appendages capable of walking motion, as described, for example, in U.S. Pat. No. 5,574,347; CHRISTENSEN, BILL ("Musclebot: Microrobot with a Heart"; Technovelgy.com; pp. 1-2; bearing a date of Feb. 27, 2004; located at http://www.technovelgy.com/ct/Science-Fiction-News.asp?NewsNum=46; printed on Sep. 12, 2006) and MARTEL, SYLVAIN ("Fundamentals of high-speed piezo-actuated three-legged motion for miniature robots designed for nanometer-scale operations"; pp. 1-8), incorporated herein by reference, and others. Appendage-like structures may intermittently engage the lumen wall and push the structural element with respect to the lumen wall with a walking-type motion, or may push against fluid within the lumen in a paddling or swimming motion. In some embodiments, the propelling mechanism may drive rotational movement of a lumen-wall-engaging structure with respect to the structural element, e.g., as in turning of a wheel or a screw element to propel the structural element through a lumen. Propelling mechanisms may include mechanical or micromechanical structures driven by at least one motor, micromotor, or molecular motor, or by expansion or change in configuration of a shape change polymer or metal. A molecular motor may be a biomolecular motor that runs on a biological chemical such as ATP, kinesin, RNA polymerase, myosin dynein, adenosinetriphosphate synthetase, rotaxanes, or a viral protein.

FIG. 1 depicts an example of a lumen-traveling device that includes a propelling mechanism which drives rotational movement of a lumen-wall-engaging structure. Lumen-traveling device 10 may include a structural element 12 configured to fit within at least a portion of a body lumen 14. The structural element 12 may include a lumen-wall-engaging portion 16. Lumen-traveling device 10 may also include a propelling mechanism 20 capable of producing movement of the structural element 12 through a body lumen 14 in which the structural element is deployed. Here, propelling mechanism 20 includes two rotating wheels, the outer rims of which form lumen-wall-engaging portions 16.

Figure 29A:
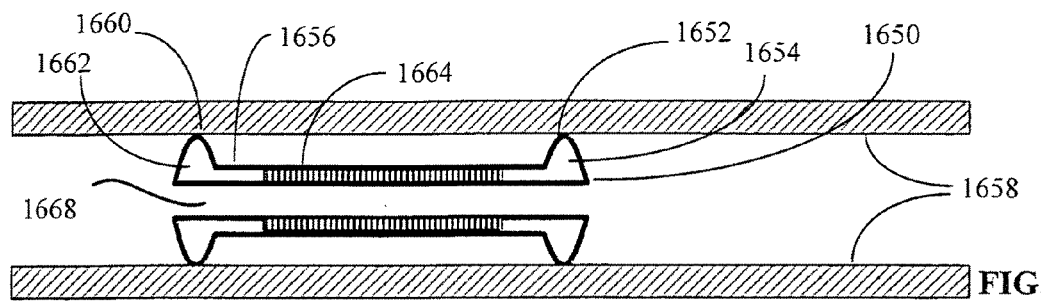
FIGS. 29A-29E illustrate a propelling mechanism of a lumen-traveling device.
Figure 29B:
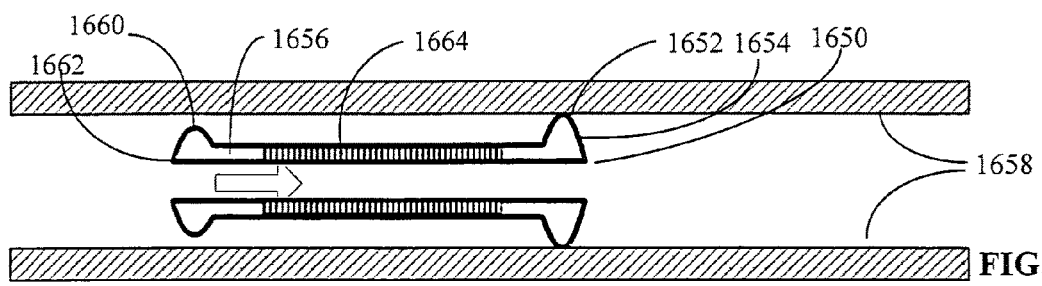
Figure 29C:
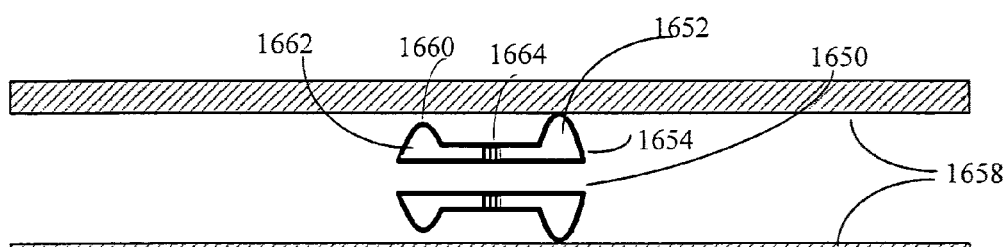
Figure 29D:
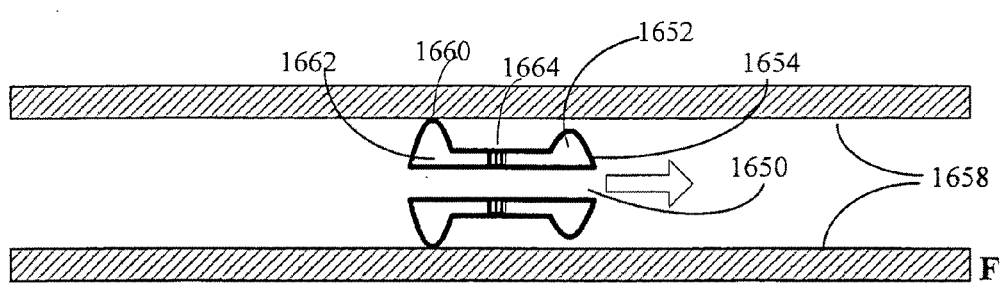
Figure 29E:
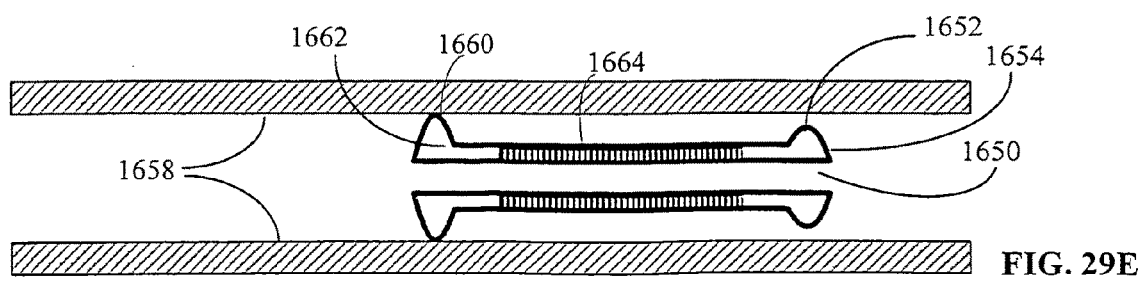

In several alternative approaches, two (or more) lumen-wall-engaging portions may engage the lumen walls intermittently. FIGS. 29A-29E depict (in cross-section) an embodiment of a lumen-traveling device 1650 which includes a motion-arresting portion including a first lumen-wall-engaging structure 1652 on first portion 1654 of the lumen-traveling device, capable of at least intermittently engaging an inner surface 1658 of body lumen in which the lumen-traveling device 1650 is deployed. The device may also include at least one second lumen-wall-engaging structure 1660 on second portion 1662 of the lumen-traveling device, wherein the propelling mechanism produces lengthening and shortening of the distance, between the first lumen-wall-engaging structure 1652 and the second lumen-wall-engaging structure 1660 in coordination with alternate engagement of the first lumen-wall-engaging structure 1652 and the second lumen-wall-engaging structure 1660 with the inner surface 1658 of the body lumen in which the lumen-traveling device is deployed. In the present example, the lengthening and shortening of the distance between the first and second lumen-wall-engaging structures may take place in region 1664, but in other embodiments, the distance between the first and second lumen-wall-engaging structures may change due to change in position of the lumen-wall-engaging structures, e.g., in limbs that move relative to each other to produce walking-type motion. Portions of the lumen-traveling device (e.g. end portion 1656) may not change in length, in order to provide a stable location for mounting of control circuitry (not shown). The alternate engagement and disengagement of the lumen wall by the first and second lumen-wall-engaging structures may produce inchworm-type propulsion of the device through the body lumen. Lumen-traveling device 1650 includes a propelling mechanism capable of producing relative extension and retraction of the at least two lumen-wall-engaging structures (1652 and 1660) with respect to each other in combination with alternate engagement and disengagement of the body lumen wall to produce inch-worm-like movement of the lumen-traveling stimulation device with respect to the body lumen wall. The embodiment of the lumen-traveling device depicted in FIGS. 29A-29E has a tubular structure with a central lumen 1668, to permit movement of fluid through the device. FIG. 29A depicts lumen-traveling device in which lumen-wall-engaging structures 1652 and 1660 are extended to engage with inner surface 1658. In FIG. 29B, second lumen-wall-engaging structure 1660 has been retracted, and region 1664 shortened to cause movement of second portion 1662 of lumen-traveling device 1650 in the direction indicated by the arrow, to attain the configuration shown in FIG. 29C. Second lumen-wall-engaging structure 1660 is then extended to engage inner surface 1658, and first lumen-wall-engaging structure 1652 is retracted, to attain the configuration shown in FIG. 29D. Then, as indicated in the arrow in FIG. 29D, region 1664 is extend to move first portion 1654 of lumen-traveling device 1650 in the direction indicated by the arrow in FIG. 29D. At the end of the movement cycle, lumen-traveling device 1650 has attained the configuration shown in FIG. 29E. First lumen-wall-engaging structure 1652 may then be extended to engage inner surface 1658, as depicted in FIG. 29A. It will be appreciated that by repeating the motion cycle illustrated in FIGS. 29A-29E, movement of the lumen-traveling device through the lumen may be accomplished. Various types of lumen-wall-engaging structures may be used in devices that produce inchworm-type motion, and in addition to lumen-wall-engaging structures that expand or extend, structures that engage the lumen wall through other mechanisms (for example, with suction mechanisms, adhesives, claws or hooks) may be used. Lumen-traveling devices that utilize an inchworm-type propulsion mechanism with suction mechanisms for engaging the surface of the heart are disclosed in PATRONIK, N. A.; OTA, T.; ZENATI, M. A.; RIVIERE, C. N. ("Improved Traction for a Mobile Robot Traveling on the Heart"; Proceedings of the 28$^{th}$ IEEE EMBS Annual International Conference; bearing dates of Aug. 30, 2006-Sep. 3, 2006 and 2006; pp. 339-342; IEEE); DARIO, P.; CARROZZA, M. C.; LENCIONI, L.; MAGNANI, B.; D'ATTANASIO, S. ("A Micro Robotic System for Colonoscopy"; Proceedings of the 1997 IEEE International Conference on Robotics and Automation; bearing dates of April 1997 and 1997; pp. 1567-1572; IEEE) and DONGXIANG, CHI; GUOZHENG, YAN ("An earthworm based miniature robot for intestinal inspection"; Proceedings of SPIE; bearing dates of Nov. 7, 2001-Nov. 9, 2001; pp. 396-400; Volume 4601; SPIE); all of which are incorporated herein by reference in their entirety.

Radially and longitudinally expanding or extending structures may be mechanical or micromechanical structures, expandable materials, inflatable structures, or shape-changing materials or structures. While reference is made to expandable and inflatable materials and structures here, and throughout the specification, it will be appreciated that structures that are specified as being expandable and inflatable may also be contractible or deflatable, and thus capable of reversible change in dimension. Reversible changes of dimension may be used in generating cyclical motions for propelling a lumen-traveling device. In some embodiments, expansion/contraction may force fluid out of the device to generate jet or vortex propulsion. Nevertheless, it is contemplated that, in some applications, materials and structures that change dimension in one direction (only expansion or only contraction) may be used.

Figure 30A:
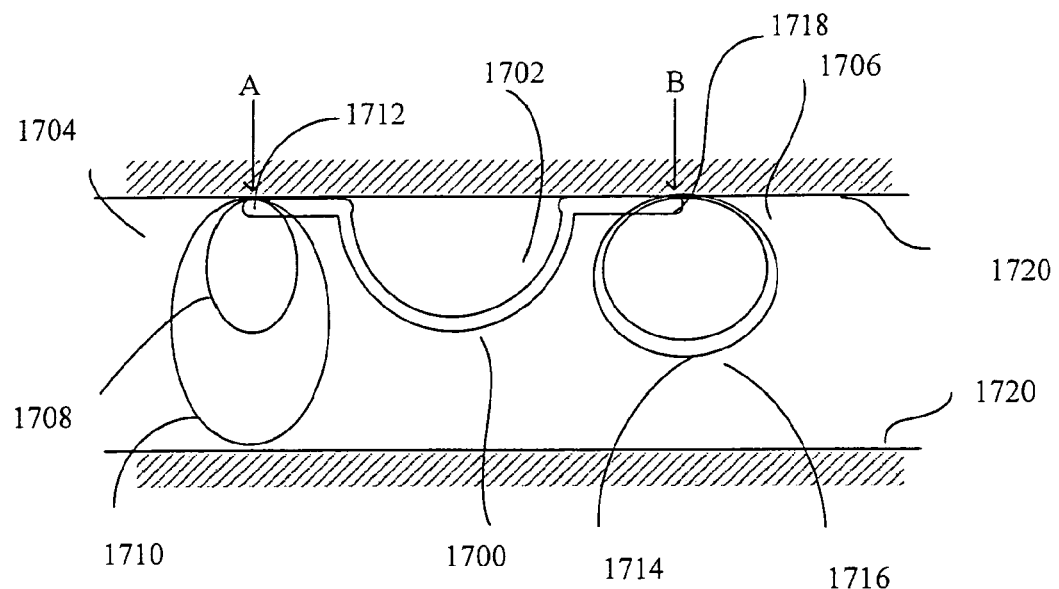
FIGS. 30A and 30B illustrate an example of a lumen-traveling device including expanding and extending structures.
Figure 30B:
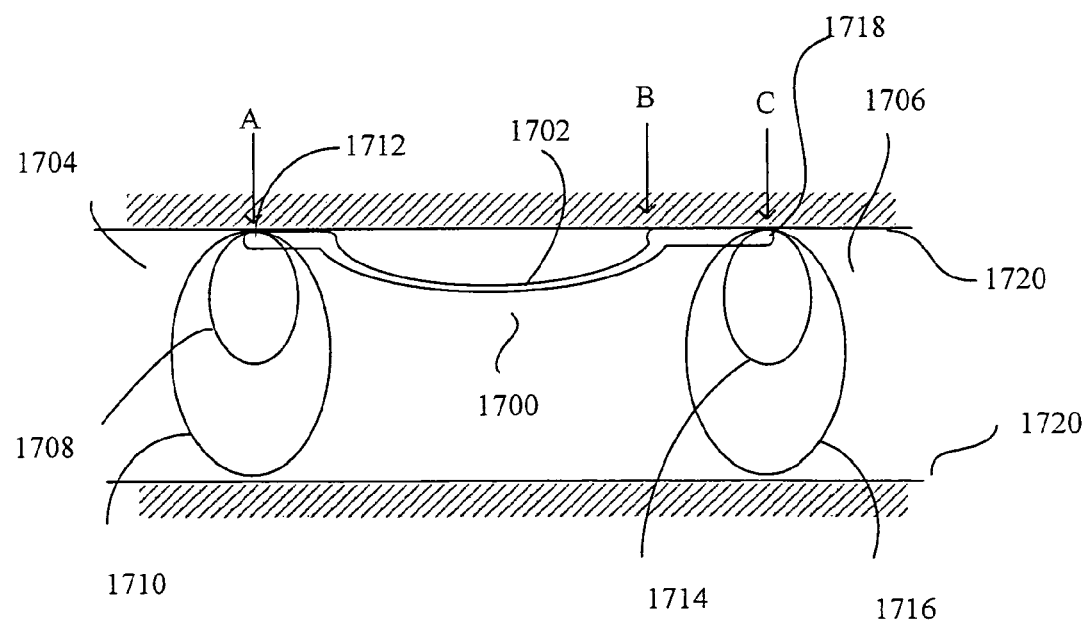

FIGS. 30A and 30B depict the use of shape-changing structure for engagement of a lumen wall and extension of a body structure of a lumen-traveling device. In FIG. 30A, lumen-traveling device 1700 includes shape-changing arc 1702, which may have a curved configuration, as shown in FIG. 30A, or an extended configuration as shown in FIG. 30B. Such a change in configuration may be produced by heating of a bimetallic strip, or by the use of a shape memory material having at least two configurations, and may be used to provide lengthening and shortening of lumen-traveling device 1700. Lumen-traveling device may include a first lumen-wall-engaging structure 1704 and second lumen-wall-engaging structure 1706. First lumen-wall-engaging structure 1704 is formed from a strip of material formed into first and second loops 1708 and 1710, respectively. In FIG. 30A, first loop 1708 is small, and second loop 1710 is large, so that it engages lumen walls 1720. Second lumen-wall-engaging structure 1706 is formed of first loop 1714 and second loop 1716, which in FIG. 30A are of medium size, so that neither engages lumen walls 1720. First lumen-wall-engaging structure 1704 is connected to lumen-traveling device 1700 at mounting point 1712, which includes a translational mechanism for moving first loop 1708 with respect to second loop 1712 to change the size of the two loops. Similarly, second lumen-wall-engaging structure 1706 is connected to lumen-traveling device 1700 at mounting point 1718, which includes a translational mechanism for moving first loop 1714 with respect to second loop 1716 to change the size of the two loops. In FIG. 30B, arc 1702 is extended, so that second lumen-wall-engaging structure 1706 has moved from point B (in FIG. 30A) to point C (in FIG. 30B). First loop 1714 of second lumen-wall-engaging structure 1706 has been reduced in size by a translational mechanism at mounting point 1718, while second loop 1716 has been increased in size to engage lumen walls 1720. Inchworm motion similar to that depicted in FIGS. 29A-29E can thus be produced by an embodiment of lumen-traveling device as depicted in FIGS. 30A and 30 B.

Figure 31:
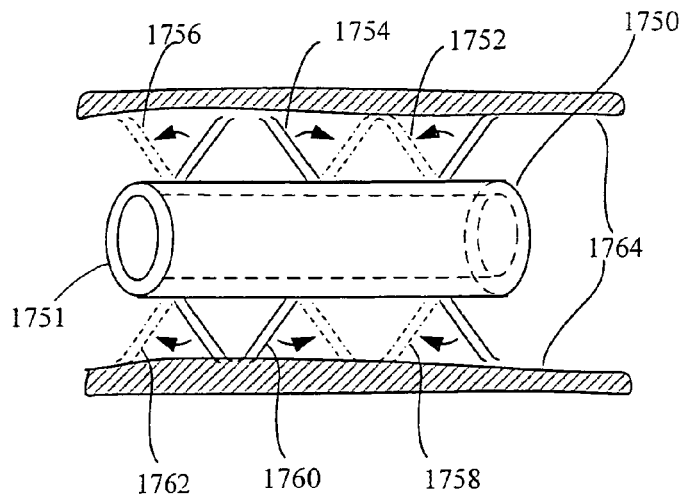
FIG. 31 illustrates a propelling mechanism of a lumen-traveling device.

FIG. 31 depicts a further embodiment of a lumen-traveling device adapted to travel through the body lumen with a propelling mechanism that produces walking-type motion. The lumen-traveling device may include two or more lumen-wall-engaging structures on a portion of the lumen-traveling device capable of at least intermittently engaging an inner surface of a body lumen in which the lumen-traveling device is deployed, wherein the propelling mechanism drives walking movement of the two or more lumen-wall-engaging structures with respect to inner surface of the body lumen. Lengthening and shortening of the distance between the lumen-wall-engaging structures is produced by change in leg configuration rather than by lengthening or shortening of the main structure (e.g. body structure) of the lumen-traveling device. Lumen-traveling device 1750 includes a structural element 1751 sized to fit within a body lumen; at least two lumen wall-engaging structures operable to alternately engage and disengage a wall of the body lumen (in FIG. 31, 6 lumen-wall-engaging structures 1752, 1754, 1756, 1758, 1760, and 1762 are shown); a propelling mechanism capable of producing relative extension and retraction of the at least two lumen-wall-engaging structures with respect to each other in combination with alternate engagement and disengagement of the body lumen wall 1764 to produce movement of the lumen-traveling stimulation device with respect to the body lumen wall. Lumen-traveling device 1750 may also include motion control circuitry carried at least in part by the lumen-traveling device and configured to control the propelling mechanism to control movement of the lumen-traveling device through the body lumen; a sensor capable of detecting a condition of interest in the body lumen; and an active portion carried by the structural element and configured to perform an action in response to detection of the condition of interest by the sensor, not shown in FIG. 31 but operating as described elsewhere herein. The at least two lumen-wall-engaging structures may include at least two appendages configured for walking motion. In the embodiment shown in FIG. 31, legs 1752 and 1754 extend and retract with respect to each other, for example, so that as one leg swings forward, the other swings back. Larger or smaller numbers of legs, distributed in various patterns about the structural element, may be used to propel the lumen-traveling device through the body lumen, and the embodiment depicted in FIG. 31 represents one possible example.

Leg structures for lumen-traveling devices may be formed of various materials and structures, including nanotubes and nanotube bundles, carbon fibers and carbon fiber bundles, silicon, metal, polymers, and other materials as described herein. Legs may be moved to produce walking motion may be actuated by various mechanisms. In some embodiments the legs formed from shape-changing material may be moved through change in configuration of the leg structure itself, while in other embodiments the leg may have a substantially rigid or fixed configuration that may be moved by separate actuation mechanism. Shape-changing materials that may be used in leg structures or actuators may be of various types, for example, stacked piezoelectric elements, electroactive polymers, heat sensitive polymers, magnetic field responsive polymers, and ferromagnetic materials, as described elsewhere herein. In some embodiments, motors and actuators may be used to drive leg motion, as known to those of skill in the art.

In another embodiment of a propelling mechanism, as depicted in FIGS. 32 and 32, multiple lumen-wall-engaging structures, operating in sequence to alternately engage and disengage the lumen wall, may be used to produce "peristaltic" motion of the lumen-traveling device. Examples of devices that produce this type of motion are described in U.S. Pat. No. 6,764,441; U.S. Patent Application 2006/0004395; MANGAN, ELIZABETH V.; KINGSLEY, DAN A.; QUINN, ROGER D.; CHIEL, HILLEL J.; "Development of a Peristaltic Endoscope"; IEEE International Conference on Robotics & Automation 2002; pp. 1-6; located at http://biorobots.cwru.edu/publications/ICRA02_Mangan_Endoscope.pdf; and MEIER, P.; OBERTHÜR, S.; LANG, M.; "Development of a compliant device for minimally invasive surgery"; Proceedings of the 28$^{th}$ IEEE EMBS Annual International Conference; bearing dates of Aug. 30, 2006-Sep. 3, 2006 and 2006; pp. 331-334; IEEE; all of which are incorporated herein by reference.

Figure 32A:
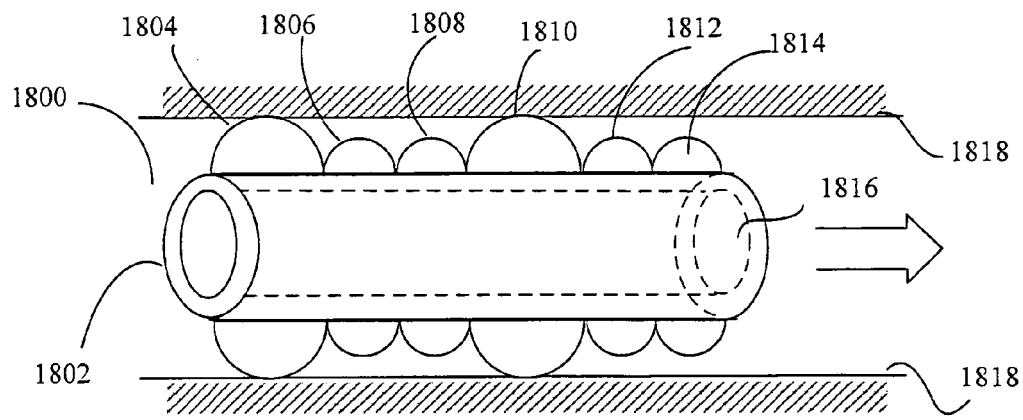
FIGS. 32A and 32B illustrate another embodiment of a propelling mechanism.
Figure 32B:
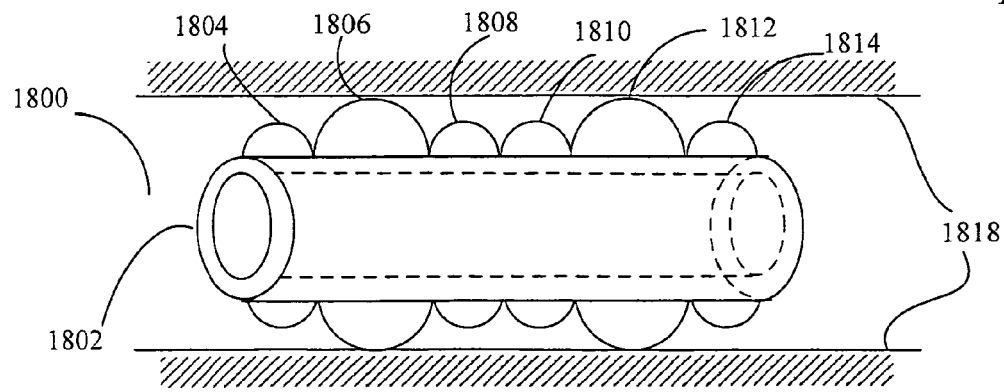

In FIGS. 32A and 32B, lumen-traveling device 1800 includes structural element 1802, which may be formed of a resilient material. Structural element 1802 may be a substantially tubular structure with a central lumen 1816, for example. A plurality of expanding or extending structures 1804, 1806, 1808, 1810, 1812, 1814, and 1818 may be positioned along the length of structural element 1802. Expanding or extending structures may expand in a lengthwise direction as well as expanding in a radially outward direction. For example, in FIG. 32A, expanding or extending structures 1804 and 1810 are shown in their expanded configurations, in which they are both wider and longer than in their contracted configurations as shown in FIG. 32B. Conversely, expanding or extending structures 1806, 1808, 1812, and 1814 are shown in the contracted configurations in FIG. 32A, and in their expanded configurations in FIG. 32B. By expanding and contracting the expanding or extending structures in sequence, as depicted in FIGS. 32A and 32B, movement of the lumen-traveling device through the body lumen may be accomplished.

Figure 33:
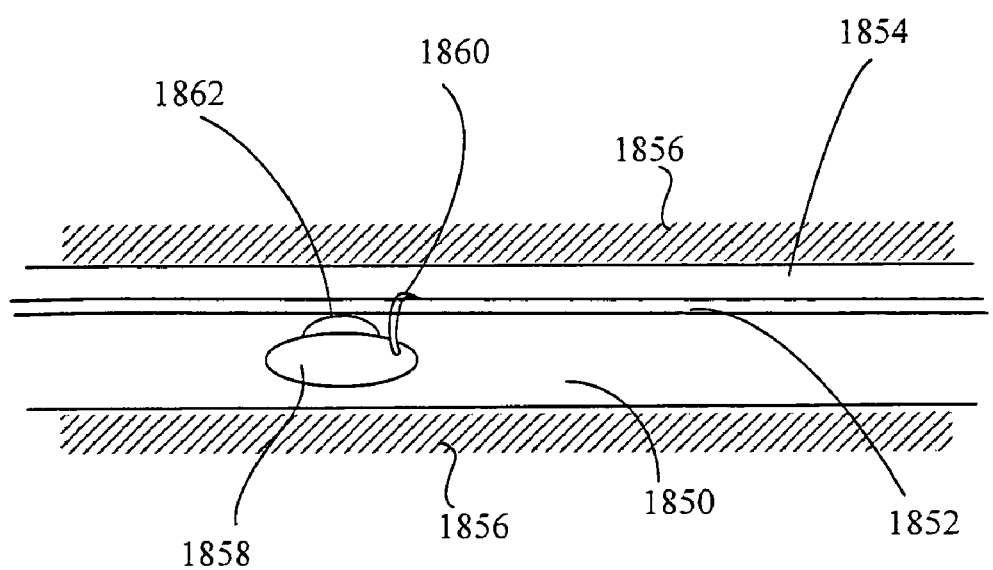
FIG. 33 illustrates another embodiment of a propelling mechanism.

In some embodiments, a propelling mechanism may be configured to drive movement of the lumen-traveling device along a wire, catheter, cannula, or tube within the body lumen. For example, as shown in FIG. 33, lumen-traveling device 1850 moves along elongated structure 1852 (which may be, for example, a wire, catheter, cannula, tube or other structure) located within body lumen 1854, surrounded by lumen walls 1856. Lumen-traveling device 1850 includes body structure 1858, retainer 1860, and propelling mechanism 1862. In the example depicted in FIG. 33, retainer 1860 is a hook-like structure that holds lumen-traveling device 1850 against elongated structure 1852 while allowing it to move along elongated structure 1852, while propelling mechanism 1862 causes lumen-traveling device 1850 to move along elongated structure 1852. In the embodiment of FIG. 33, propelling mechanism 1862 is a rotating wheel that moves lumen-traveling device 1850 along elongated structure 1852, but in other embodiment, other propelling mechanisms may be used to move a lumen-traveling device along an elongated structure.

Finally, as noted elsewhere herein, in some embodiments, the lumen-traveling device may be propelled through the body lumen by one or more paddles, propellers, vortex generators, jets, flagellum-like structures, or the like, which push against fluid contained within the lumen rather than engaging the wall of the body lumen, e.g. as described in U.S. Pat. No. 6,240,312 or in BEHKAM, BAHAREH; SITTI, METIN; "TOWARDS HYBRID SWIMMING MICROROBOTS: BACTERIA ASSISTED PROPULSION OF POLYSTYRENE BEADS"; Proceedings of the 28$^{th}$ IEEE EMBS Annual International Conference; bearing dates of Aug. 30, 2006-Sep. 3, 2006 and 2006; pp. 2421-2424; IEEE; CHRISTENSEN, BILL; "Propulsion System for 'Fantastic Voyage' Robot", bearing a date of Nov. 10, 2006, printed on Jan. 4, 2007, located at http://technovelgy.com/ct/Science-Fiction-News.asp?NewsNum=811; or "Researchers: Squid-Inspired Vortex Generators Could Mean Better Propulsion for Unmanned Underwater Vehicles"; UnderwaterTimes.com; Dec. 12, 2006; pp. 1-2; printed on Jan. 4, 2007; located at http://www.underwatertimes.com/print.php?article_id=51030782641; or MOHSENI, KAMRAN; "Biomimemetic & Bio-Inspired Aerial and Underwater Vehicles"; bearing a date of Sep. 23, 2006; pp. 1-100 printed on Jan. 4, 2007, located at http://enstrophy.colorado.edu/~mohseni/MicroVehicles1.html#UUV1#UUV1 all of which are incorporated herein by reference.

The direction of movement produced by the various propelling mechanisms described herein may be reversed by simply reversing the operation of the propelling mechanisms.

In various embodiments as described herein, a lumen-traveling device may include a power source configured to provide power to at least one of the propelling mechanism, the motion control circuitry, the sensor, the response initiation circuitry, or the active portion. The power source may be a battery or microbattery, a fuel cell or biofuel cell, or a nuclear battery. One or more power sources of the same or different types may be included in the lumen-traveling device, without limitation. Batteries may be located on the lumen-traveling device, possibly a microbattery like those available from Quallion LLC (http://www.quallion.com) or designed as a film (U.S. Pat. Nos. 5,338,625 and 5,705,293), which are incorporated herein by reference. Alternatively, the power source could be one or more fuel cell such as an enzymatic, microbial, or photosynthetic fuel cell or other biofuel cell (US2003/0152823A1; WO03/106966A2; or Chen T et al. J. Am. Chem. Soc. 2001, 123, 8630-8631, A Miniature Biofuel Cell, all of which are incorporated herein by reference), and could be of any size, including the micro- or nano-scale. In some embodiments, the power source may be a nuclear battery. The power source may be an energy-scavenging device such as a pressure-rectifying mechanism that utilizes pulsatile changes in blood pressure, for example, or an acceleration-rectifying mechanism as used in self-winding watches, or other types of flow-rectifying mechanism capable of deriving energy from other flow parameters. In some embodiments, the power source may be an electrical power source located remote from the structural element and connected to the structural element by a wire, or an optical power source located remote from the structural element and connected to the structural element by a fiber-optic line or cable. In some embodiments, the power source may be a power receiver capable of receiving power from an external source, for example, an acoustic source or electromagnetic source (e.g., infrared energy, or inductively coupled, as described in U.S. Pat. No. 6,170,485 or U.S. Patent Application No. 2005/0228259, which are incorporated herein by reference). In some embodiments, the power source may include an electrical power source located remote from the lumen-traveling device and connected to the lumen-traveling device by a wire, or an optical power source located remote from the lumen-traveling device and connected to the lumen-traveling device by an optical fiber.

In some embodiments, the lumen-traveling device may include a power transmitter capable of transmitting power from the lumen-traveling device to a secondary location. The power transmitter may be capable of transmitting at least one of acoustic power, electrical power, or optical power. The secondary location may be, for example, another device within the body, either in a body lumen or elsewhere, that includes a power receiver and structures for using, storing and/or re-transmitting the received power.

Figure 34:
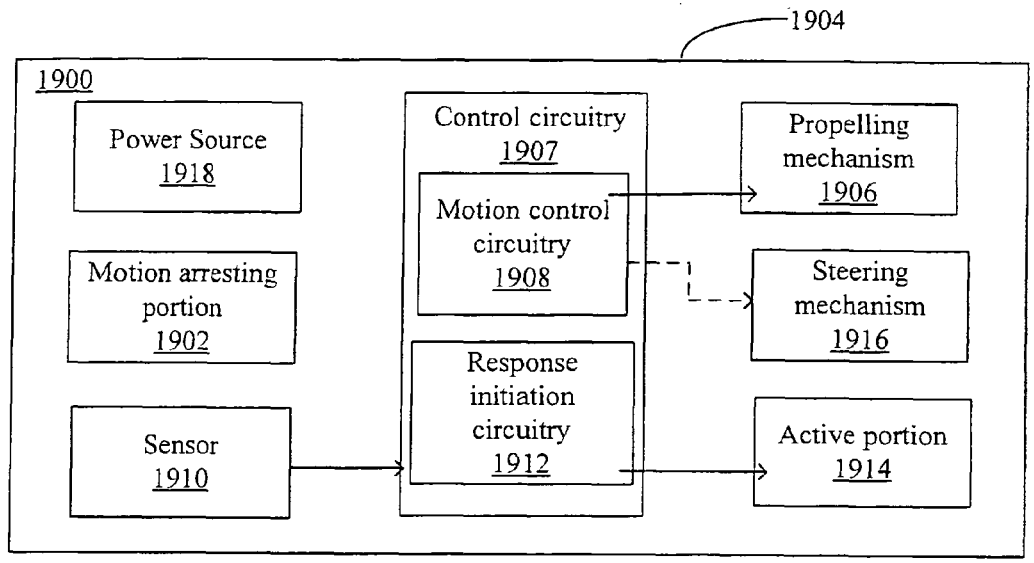
FIG. 34 is a schematic diagram of a lumen-traveling device.

FIG. 34 is a block diagram depicting a further embodiment of a lumen-traveling device 1900, which includes a motion-arresting portion 1902; a fluid-contacting portion 1904 configured to contact fluid within the body lumen and to at least intermittently permit flow of fluid through the body lumen; a propelling mechanism 1906 capable of producing movement of the lumen-traveling device through a body lumen in which the lumen-traveling device is deployed; motion control circuitry 1908 carried at least in part by said lumen-traveling device and configured to control propelling mechanism 1906 to control movement of the lumen-traveling device through the body lumen; a sensor 1910 capable of detecting a condition of interest in the body lumen and generating a sense signal indicating detection of the condition of interest; response initiation circuitry 1912 operatively connected to sensor 1910 and configured to generate a response initiation signal upon receipt of the sense signal indicating detection of a condition of interest in the body lumen; and an active portion 1914 operatively connected to response initiation circuitry 1912 and capable of producing a response upon receipt of the response initiation signal. Motion control circuitry 1908 and response initiation circuitry 1912 make up part of control circuitry 1907, which may also include other components not specifically described herein. The embodiment of FIG. 34 also includes a steering mechanism 1916 capable of modifying the direction of movement of the lumen-traveling device; wherein the motion control circuitry 1908 may be configured to control the steering mechanism 1916 to control movement of the lumen-traveling device through the body lumen. The embodiment of FIG. 34 may include power source 1918 configured to provide power to at least one of propelling mechanism 1906, steering mechanism 1916, motion control circuitry 1908, sensor 1910, response initiation circuitry 1912 or active portion 1914. Components of the embodiment of FIG. 34 may be generally as described elsewhere herein. Steering mechanism 1916 may be any of various structures, depending on the type of propelling mechanism used. If the propelling mechanism is a paddle or propeller that causes the lumen-traveling device to move in the fluid in the lumen, the steering mechanism may be a rudder. If the propelling mechanism includes multiple wheels or limb-like structures, they may be activated differentially on different sides of the lumen-traveling device to steer it in one direction or another. In embodiments in which the lumen-traveling device contacts the lumen walls on all sides of the device, the steering mechanism may be used only in the cases that the lumen-traveling device encounters a branch point in the lumen, and once the front portion of the device (defined by the direction of travel) is steered to cause the device to enter a selected branch, the back portion of the device will follow without the need for additional steering.

Various embodiments of the lumen-traveling device may include a marker or tag. The marker or tag may be an imaging marker or tag detectable by a remote imaging system to indicate the position of the lumen-traveling device within the body of a subject (for example, a radio-opaque marker for x-ray imaging). Alternatively, the marker or tag may be detectable by a sensing device or structure within the body of the subject.

Figure 35:
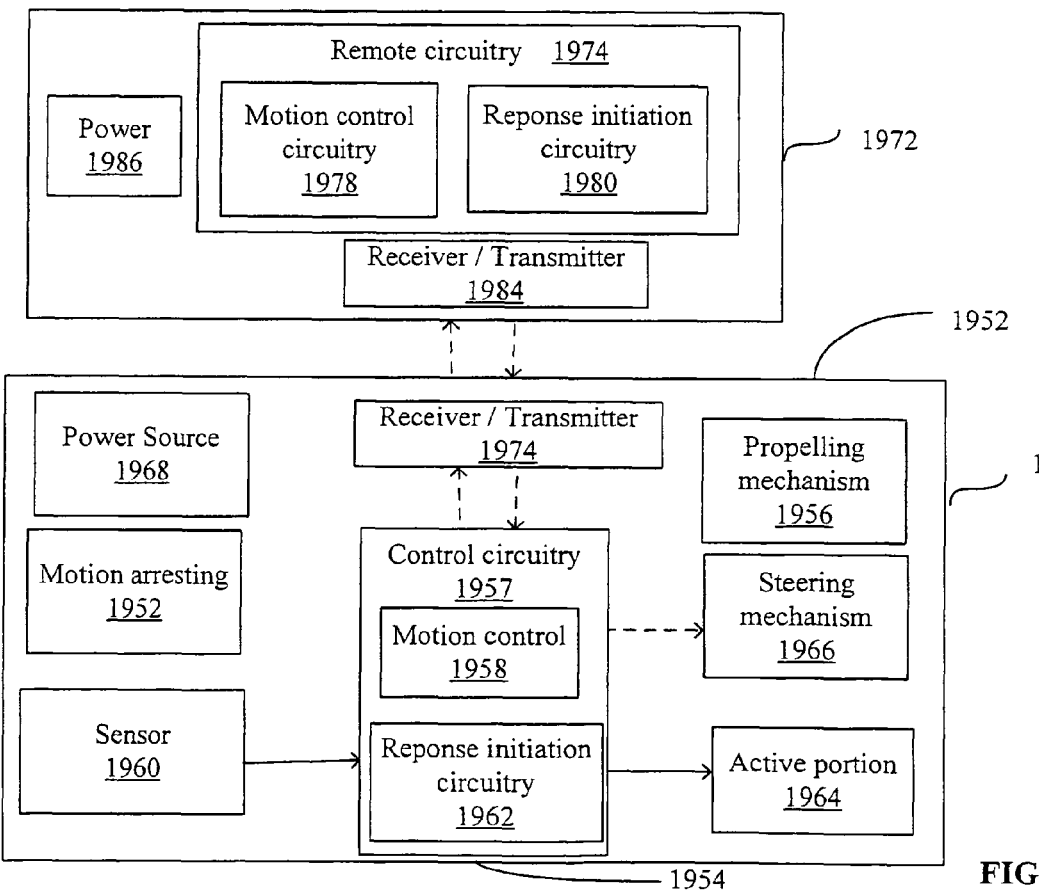
FIG. 35 is a schematic diagram of a lumen-traveling device including a remote portion.

In some embodiments, as depicted in FIG. 35, at least a portion of the circuitry that controls the operation of the lumen-traveling device 1950 may be located remote from the lumen-traveling device in remote portion 1972, outside the body of the subject as shown in FIG. 28, or at a location within the body of the subject at a distance from the lumen-traveling device. In the embodiment of FIG. 35, lumen-traveling device 1950 includes a motion-arresting portion 1952; a fluid-contacting portion 1954 configured to contact fluid within the body lumen and to at least intermittently permit flow of fluid through the body lumen; a propelling mechanism 1956 capable of producing movement of the lumen-traveling device through a body lumen in which the lumen-traveling device is deployed; motion control circuitry 1958 carried at least in part by said lumen-traveling device and configured to control propelling mechanism 1956 to control movement of the lumen-traveling device through the body lumen; a sensor 1960 capable of detecting a condition of interest in the body lumen and generating a sense signal indicating detection of the condition of interest; response initiation circuitry 1962 operatively connected to sensor 1960 and configured to generate a response initiation signal upon receipt of the sense signal indicating detection of a condition of interest in the body lumen; and an active portion 1964 operatively connected to response initiation circuitry 1962 and capable of producing a response upon receipt of the response initiation signal. The embodiment of FIG. 35 includes a steering mechanism 1966 capable of modifying the direction of movement of the lumen-traveling device; wherein the motion control circuitry 1958 may be configured to control the steering mechanism 1966 to control movement of the lumen-traveling device through the body lumen. At least a portion of the control circuitry for lumen-traveling device 1950, remote circuitry 1974, may be located remote from lumen-traveling device 1950 in remote portion 1972. Remote circuitry 1974 may include a remote portion of the motion control circuitry 1978 and remote portion of the response initiation circuitry 1980. Lumen-traveling device 1950 may include receiver/transceiver 1984 that may include data reception and/or transmission circuitry configured to receive a wireless control signal from the remote portion of the motion control circuitry 1978, transmitted from transceiver 1984. Data may be transmitted from lumen-traveling device 1950 to remote portion 1972. Remote portion 1972 may include a power source 1986. Alternatively, the motion control circuitry may be located in or on the lumen-traveling device. The embodiment of FIG. 35 may include power source 1968 configured to provide power to at least one of propelling mechanism 1956, steering mechanism 1966, motion control circuitry 1958, sensor 1960, response initiation circuitry 1962 or active portion 1964. Components of the embodiment of FIG. 35 may be generally as described elsewhere herein. Steering mechanism 1966 may be as described above in connection with FIG. 34. In some embodiments, power may be transmitted to lumen-traveling device 1950 from remote portion 1972.

The motion control circuitry may be operatively connected to the sensor, and configured to control at least one of steering mechanism or propelling mechanism to control the movement of the lumen-traveling device at least in part in response to receipt of the sense signal indicating detection of the condition of interest in the body lumen. Similarly, the response initiation circuitry may be located in or on the lumen-traveling device in some embodiments, while in other embodiments at least a portion of the response initiation circuitry may be located remote from the lumen-traveling device, wherein the lumen-traveling device may include data transmission and reception circuitry configured for communicating with the at least a portion of the response initiation circuitry located remote from the lumen-traveling device.

The control circuitry for the lumen-traveling device, located either on the lumen-traveling device or in a remote portion, and including response initiation circuitry and/or motion control circuitry, may include a microprocessor, and/or at least one of hardware, software, or firmware. Examples of devices and/or systems for communicating within devices in the body are provided in U.S. Pat. No. 5,843,139; 6,409,674; or 7,125,382; U.S. Patent Application 2002/0198604, and RICE, MIKE; "Implantable Neurostimulation Device Market Poised for Explosive Growth"; Future Fab International; Jan. 7, 2006; pp. 1-4; printed on Oct. 6, 2006; located at http://www.future-fab.com/documents.asp?d_ID=3725, all of which are incorporated herein by reference in their entirety.

Various embodiments of lumen-traveling devices as depicted and described herein may include a lumen-wall-engaging portion; a fluid-contacting portion configured to contact fluid within the body lumen and to at least intermittently permit flow of fluid through the body lumen; a propelling mechanism capable of producing movement of the lumen-traveling device through a body lumen in which the lumen-traveling device may be deployed; at least one sensor capable of detecting a condition of interest in the body lumen and generating a sense signal indicating detection of the condition of interest; motion control circuitry carried at least in part on said lumen-traveling device and configured to control the propelling mechanism at least in part based upon the sense signal; response initiation circuitry operatively connected to the sensor and configured to generate a response initiation signal upon receipt of the sense signal indicating detection of a condition of interest in the body lumen; and an active portion operatively connected to the response initiation circuitry and capable of producing a response upon receipt of the response initiation signal. A fluid contacting portion configured to contact fluid within the body lumen and at least intermittently permit flow of fluid through the body lumen is though to be a useful feature for lumen-traveling device used in lumens through which fluid travel, such as, for example, blood vessels, portions of the respiratory tract, digestive tract or CSF space. In some cases, blockage of flow may cause serious problems. Thus, lumen-traveling devices which are configured to permit the flow of fluid at least a portion of the time may be of value. For example, fluid may flow through a channel or lumen passing through the lumen-traveling device (e.g., as depicted in FIG. 1, 29, or 32), or past a lumen-traveling device that has an cross section that does not fill the cross-section of the lumen, as in FIG. 5A, 5E, 30A, 30B, or 33, for example.

As shown in various of the figures, a lumen-traveling device may include a power source configured to provide power to at least one of the propelling mechanism, the motion control circuitry, the sensor, the response initiation circuitry, or the active portion. The power source may be located on the lumen-traveling device, or (at least in part) on a remote portion as illustrated in FIG. 35, with power being transmitted to the lumen-traveling device.

A lumen-traveling device may include various types of sensing or information gathering devices or structures. A lumen-traveling device may include one or multiple sensors of the same or different types, which may include but are not limited to, pressure sensors, temperature sensors, flow sensors, viscosity sensors, shear sensors (e.g., for measuring the effective shear modulus of the fluid at a frequency or strain-rate), pH sensors, chemical sensors for determining the concentration of a chemical compound or species, optical sensors, acoustic sensors, biosensors, electrical sensors, magnetic sensors, clocks or timers. Examples of a variety of sensor which may be used in embodiments as described herein are provided in U.S. Pat. Nos. 5,522,394; 5,873,835; 6,053,837; 6,409,674; 6,111,520; 6,278,379; 6,475,639; 6,855,115, and U.S. Patent Applications 2005/0277839 and 2005/0149170, all of which are incorporated herein by reference. U.S. Pat. No. 6,802,811, which is included herein by reference, provides additional examples of sensing and/or monitoring. In some embodiments, an imaging device (e.g., a CCD array) may be operatively connected to lumen-traveling device, e.g. connected to the structural element.

An optical sensor may be configured to measure the optical absorption, optical emission, fluorescence, or phosphorescence of at least a portion of the fluid, for example. Such optical properties may be inherent optical properties of all or a portion of the fluid or tissue, or may be optical properties of materials added or introduced to the fluid, such as tags or markers for materials of interest. Optical sensing of materials in blood is described, for example, in KRUEGER, CURTIS; "New light on blood testing"; Oct. 20, 2006; pp. 1-2; St. Petersburg Times; printed on Dec. 24, 2006; located at http://www.sptimes.com/2006/10/20news_pf/Tampabav/New_light_on_blood_te.shtml, which is incorporated herein by reference.

A biosensor may detect materials including, but not limited to, a biological marker, an antibody, an antigen, a peptide, a polypeptide, a protein, a complex, a nucleic acid, a cell (and, in some cases, a cell of a particular type, e.g. by methods used in flow cytometry), a cell fragment, a cellular component, a platelet, an organelle, a gamete, a pathogen, a lipid, a lipoprotein, an alcohol, an acid, an ion, an immunomodulator, a sterol, a carbohydrate, a polysaccharide, a glycoprotein, a metal, an electrolyte, a metabolite, an organic compound, an organophosphate, a drug, a therapeutic, a gas, a pollutant, or a tag. A biosensor may include an antibody or other binding molecule such as a receptor or ligand. As used herein a sensor may include a single sensor or an array of sensors, and is not limited to a particular number or type of sensors. A sensor might comprise, in part or whole, a gas sensor such as an acoustic wave, chemiresistant, or piezoelectric sensor, or perhaps an electronic nose. A sensor may be very small, comprising a sensor or array that is a chemical sensor ("Chemical Detection with a Single-Walled Carbon Nanotube Capacitor," Snow, E. S. et al., Science, Vol. 307, pp. 1942-1945, 2005), a gas sensor ("Smart single-chip gas sensor microsystem," Hagleitner, C. et al., Nature, Vol. 414, pp. 293-296, 2001), an electronic nose, a nuclear magnetic resonance imager ("Controlled multiple quantum coherences of nuclear spins in a nanometre-scale device", Go Yusa, 2005, Vol. 343: pp. 1001-1005, Nature). The foregoing references are incorporated herein by reference. Further examples of sensors are provided in The Biomedical Engineering Handbook, Second Edition, Volume I, J. D. Bronzino, Ed., Copyright 2000, CRC Press LLC, pp. V-1-51-9, and U.S. Pat. No. 6,802,811, both of which are incorporated herein by reference.

A sensor may be configured to measure various parameters, including, but not limited to, the electrical resistivity of fluid, tissue, or other material, the density or sound speed of a material, the pH, the osmolality, or the index of refraction of the fluid at least one wavelength. The selection of a suitable sensor for a particular application or use site is considered to be within the capability of a person having skill in the art. In some embodiments, a sensor may include some signal processing or pre-processing capability integrated therewith.

The condition of interest detected by the sensor may include an anatomical feature (for example, a branching point) that indicates proximity to a treatment target, or indicates the presence of the treatment target itself. The condition of interest may include a man-made structure, such as an implantable device of some sort, potentially including another lumen-traveling device. Alternatively, the condition of interest may include one or more of an electrical field, magnetic field, temperature, flow condition, time, location, pressure, pH, presence or concentration of a chemical compound or species.

A sensor may sense a wide variety of physical or chemical properties. In some embodiments, detecting a condition of interest may include detecting the presence (or absence) of a material or structure of interest.

In some applications, detecting a condition of interest in the fluid within the body lumen may include detecting the presence of a material of interest in the fluid within the body lumen. A material of interest in a fluid may include, for example, an object such as a blood clot, a thrombus, an embolus, a plaque, a lipid, a kidney stone, a dust particle, a pollen particle, an aggregate, a cell, a specific type of cell, a cell fragment, a cellular component, a platelet, an organelle, a collection or aggregation of cells or components thereof a gamete, a pathogen, or a parasite.

Lumen-traveling devices may be used in a number of different ways. In some embodiments, a lumen-traveling device may travel through the lumen performing an action at selected locations that are identified as the device travels through the lumen. A device may move through the body lumen performing "surveillance" for periods of time ranging from a few minutes, to hours, days, weeks, or years. When the lumen-traveling device identifies a location of interest (e.g., a location where some sort of medical treatment is needed), it may perform an action, which may include delivering a medical treatment, transmitting a signal indicating the need for medical treatment to a monitoring system, or recording information about the location of interest, for example. A lumen-traveling device performing surveillance in a body lumen may perform an action "on the fly" as it moves past the location of interest, or it may pause or cease moving at or near a location of interest in order to perform an action.

Sensors in combination with logic circuitry (hardware, firmware, and/or software) may be used to detect a condition of interest in or on the wall of the body lumen, in the tissue that forms or surrounds the body lumen, or in the fluid within the body lumen. A location of interest in a body lumen may include a location of anatomical interest (e.g., a branching point), a location near an organ, a tumor, an injury, etc, a diseased or damaged region (e.g. a fistula or aneurysm), area of scar tissue, a polyp, a blockage or constriction formed by a bacterial plaque, blood clot, or vasospasm, for example. Locations of interest may be detected by the detection of chemical markers or fingerprints, by altered mechanical, optical, thermal, electrical or acoustic properties, by imaging, and by other detection methods as known to those of skill in the art. The lumen-traveling device may perform one or more actions with an active portion in response to detection of a location of interest. Tissue condition can be detected with the use of pressure pulses, as described in U.S. Pat. No. 6,170,488 and U.S. Patent Applications 2003/0220556 and 2004/0225325, all of which are incorporated herein by reference.

In some embodiments, a lumen-traveling device may perform an action continuously or intermittently as it moves through a body lumen. Performance of the action may not necessarily always be associated with detection of a region of interest within a body lumen.

In some embodiments, a lumen-traveling device may move through a body lumen until it reaches a particular location and then cease traveling in order to reside, either temporarily or substantially permanently, at the location. At the location, it may perform an action on the local tissue forming the lumen or perform an action on fluid within the lumen, which may be flowing or moving in some other manner, either continuously or intermittently, or may be substantially unmoving. The location at which a lumen-traveling device stops and resides may be pre-selected, in which case the device may be targeted to the location. Alternatively, the location may be selected as the device is traveling through the lumen, based on one or more features of the location, which may be sensed by the device. Features of the location may include, but are not limited to, indicators of injuries, pathologies or disease conditions to be treated by the device, or anatomical characteristics (size, proximity to an organ or other structure, etc.) that make the location a suitable site for the device to be positioned. Features of locations of interest may include chemical, thermal, mechanical, optical, or other properties as may be sensed with various types of sensors as described elsewhere herein. A parameter may be measured at a single point in time/space or may be measured over multiple dimensions (spatial, temporal, or other—e.g. frequency) to generate an image of a region that may include features of interest. Signal processing to perform analysis of the signal or image may be used to detect features/locations of interest from signal or image.

In one application, a lumen-traveling device traveling within the male reproductive tract may detect pH, flow, or viscosity of semen, for example, and based upon the value of the detected parameter, may perform an action to alter it to either enhance fertility or provide contraception.

In some embodiments, the lumen-traveling device may be used to deliver treatment to a location that is relatively inaccessible by other means. For example, a lumen-traveling device may move through vasculature within the brain in order to access brain regions for delivery of drugs, therapeutics, chemotherapy agents, chemical mechanical, optical, electrical or magnetic stimuli, etc.

Figure 36:
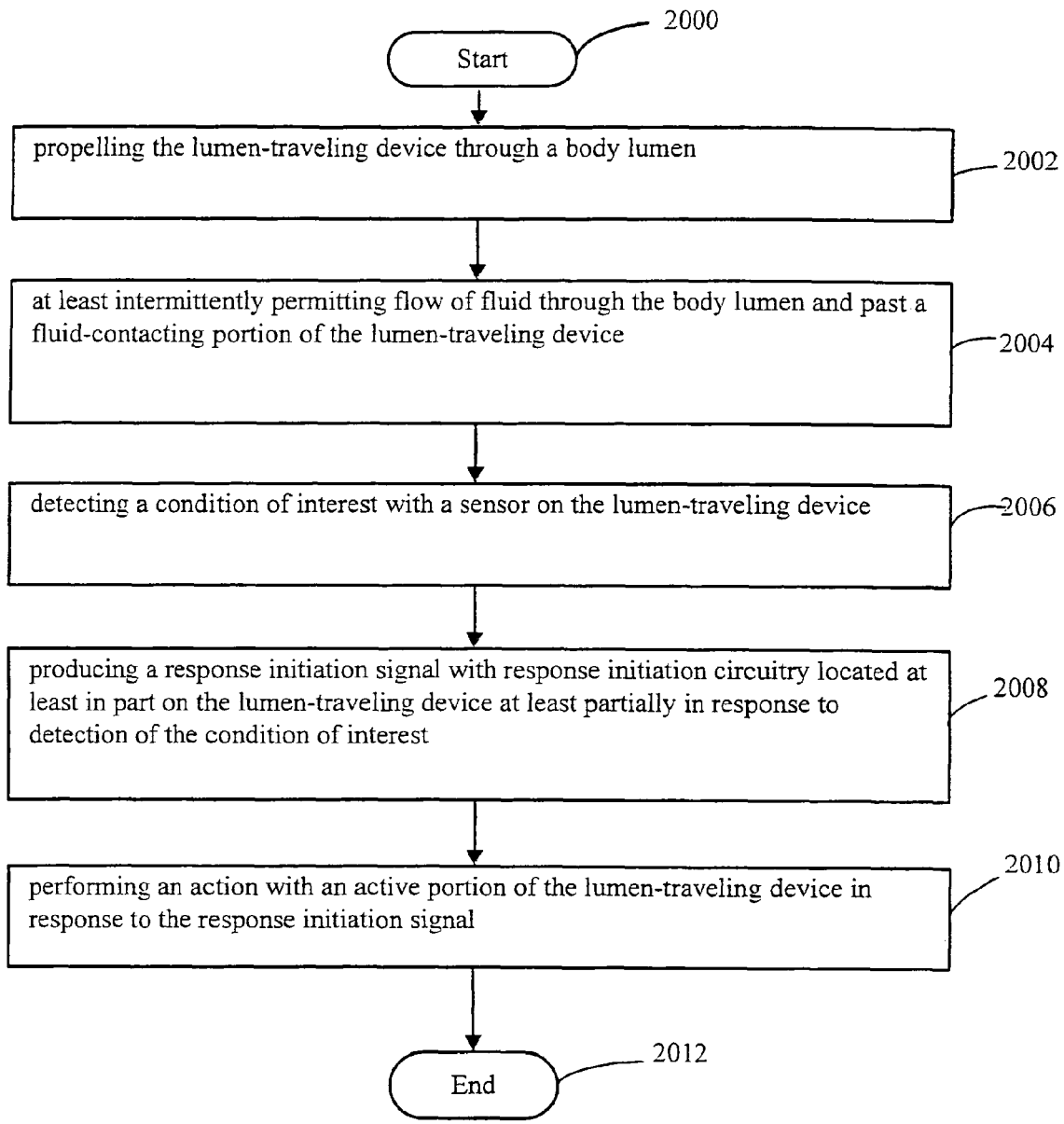
FIG. 36 is flow diagram of a method implemented with a lumen-traveling device.

FIG. 36 shows steps of a method implemented with a lumen-traveling device. The method steps include propelling the lumen-traveling device through a body lumen at step 2002; at least intermittently permitting flow of fluid through the body lumen and past a fluid-contacting portion of the lumen-traveling device at step 2004; detecting a condition of interest with a sensor on the lumen-traveling device at step 2006; producing a response initiation signal with response initiation circuitry located at least in part on the lumen-traveling device at least partially in response to detection of the condition of interest at step 2008; and performing an action with an active portion of the lumen-traveling device in response to the response initiation signal at step 2010.

Figure 37:
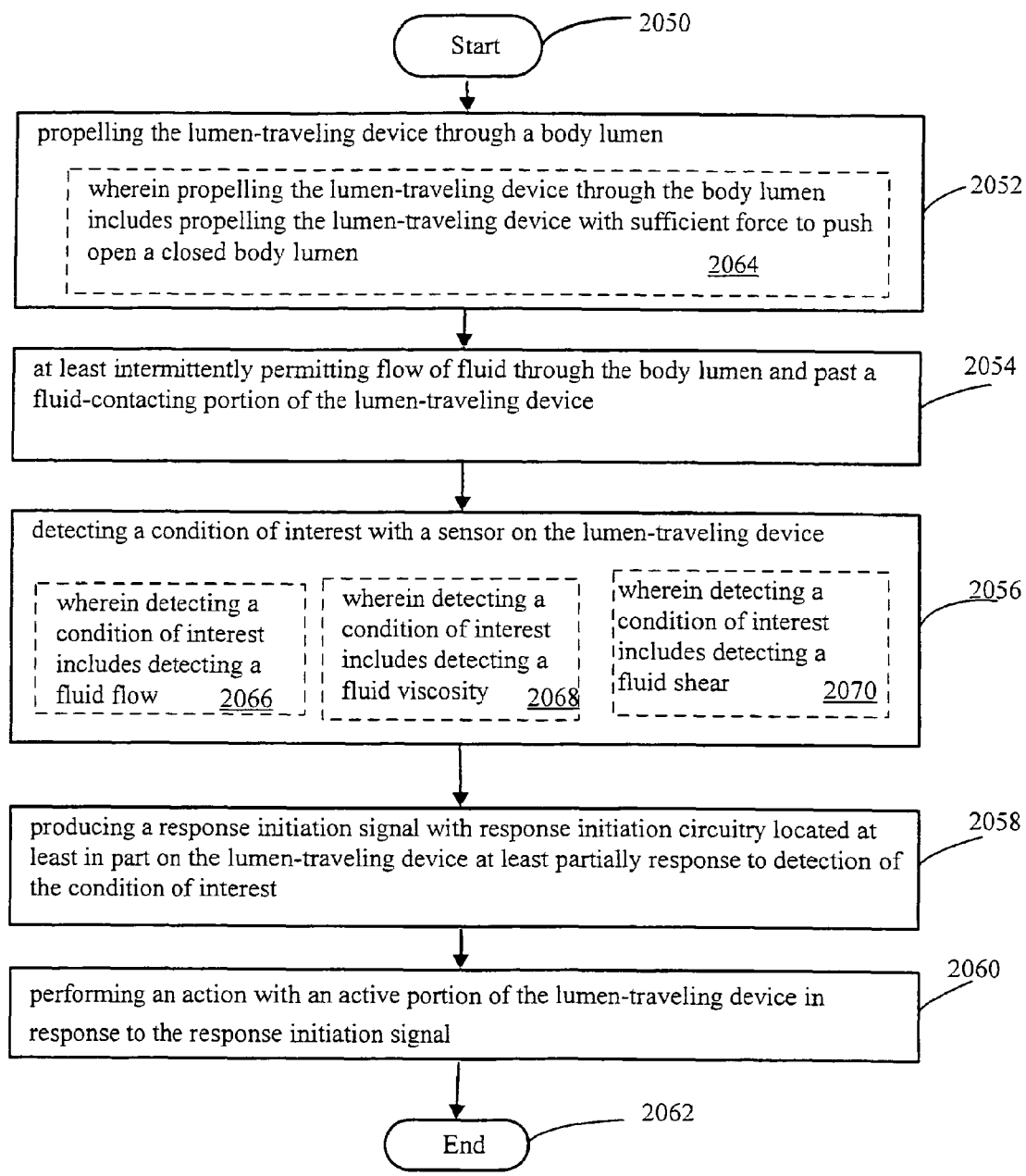
FIG. 37 is flow diagram of a further method implemented with a lumen-traveling device.

FIG. 37 shows further variants of the method of FIG. 36. The method may include propelling the lumen-traveling device through a body lumen at step 2052; at least intermittently permitting flow of fluid through the body lumen and past a fluid-contacting portion of the lumen-traveling device at step 2054; detecting a condition of interest with a sensor on the lumen-traveling device at step 2056; producing a response initiation signal with response initiation circuitry located at least in part on the lumen-traveling device at least partially in response to detection of the condition of interest at step 2058; and performing an action with an active portion of the lumen-traveling device in response to the response initiation signal at step 2060. In addition, propelling the lumen-traveling device through the body lumen may include propelling the lumen-traveling device with sufficient force to push open a closed body lumen, as shown in step 2064. The step of detecting a condition of interest may include detecting a fluid flow, as shown in step 2066, detecting fluid viscosity as shown in step 2068, or detecting a fluid shear, as shown in step 2070.

Figure 38:
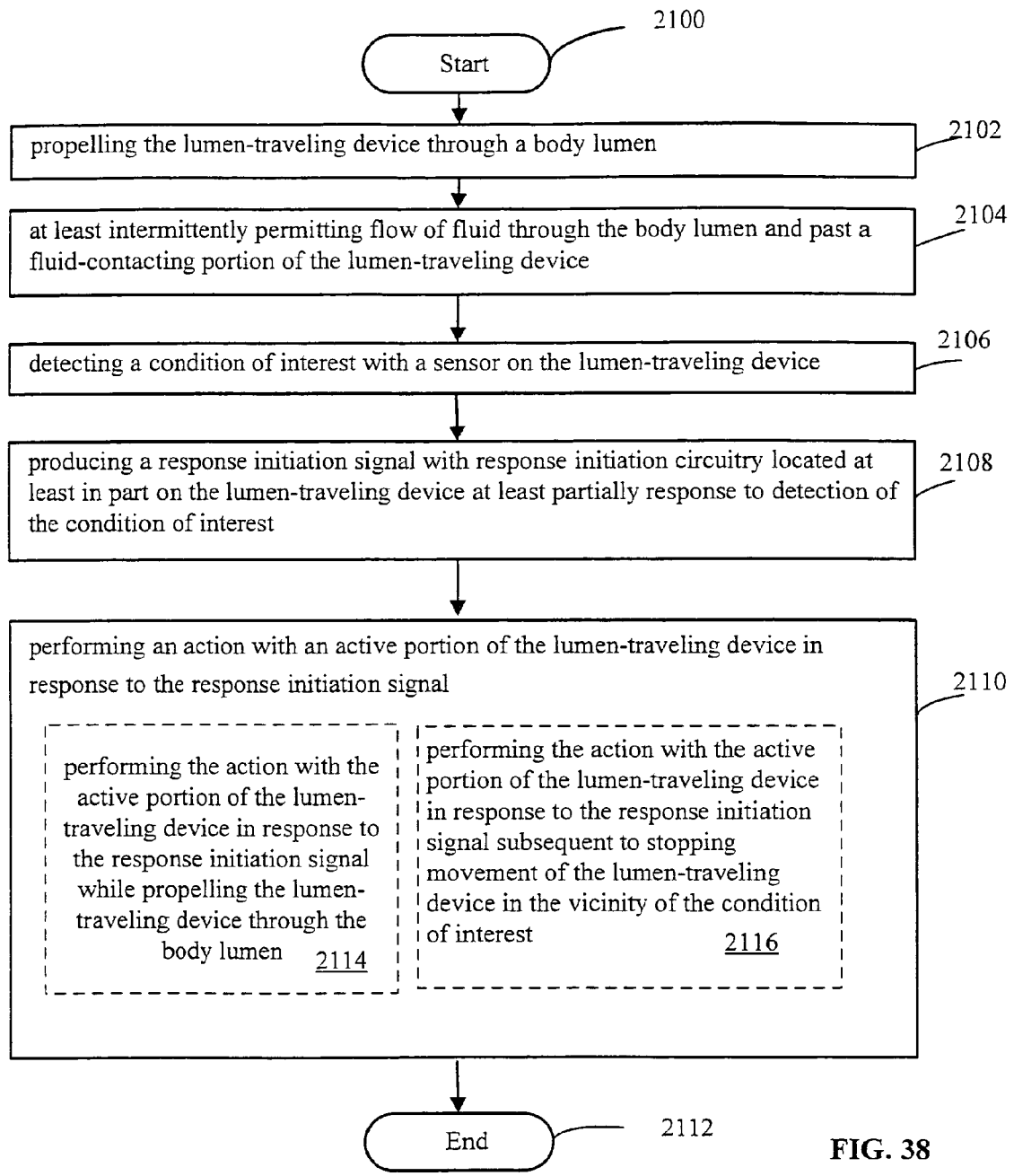
FIG. 38 is flow diagram of a further method implemented with a lumen-traveling device.

FIG. 38 shows further variants of the method of FIG. 36. Again, the method may include propelling the lumen-traveling device through a body lumen at step 2102; at least intermittently permitting flow of fluid through the body lumen and past a fluid-contacting portion of the lumen-traveling device at step 2104; detecting a condition of interest with a sensor on the lumen-traveling device at step 2106; producing a response initiation signal with response initiation circuitry located at least in part on the lumen-traveling device at least partially in response to detection of the condition of interest at step 2108; and performing an action with an active portion of the lumen-traveling device in response to the response initiation signal at step 2110. In addition, the method may include performing the action with the active portion of the lumen-traveling device in response to the response initiation signal while propelling the lumen-traveling device through the body lumen, as shown in step 2114. Alternatively, the method may include performing the action with the active portion of the lumen-traveling device in response to the response initiation signal subsequent to stopping movement of the lumen-traveling device in the vicinity of the condition of interest, as shown in step 2116.

Figure 39A:
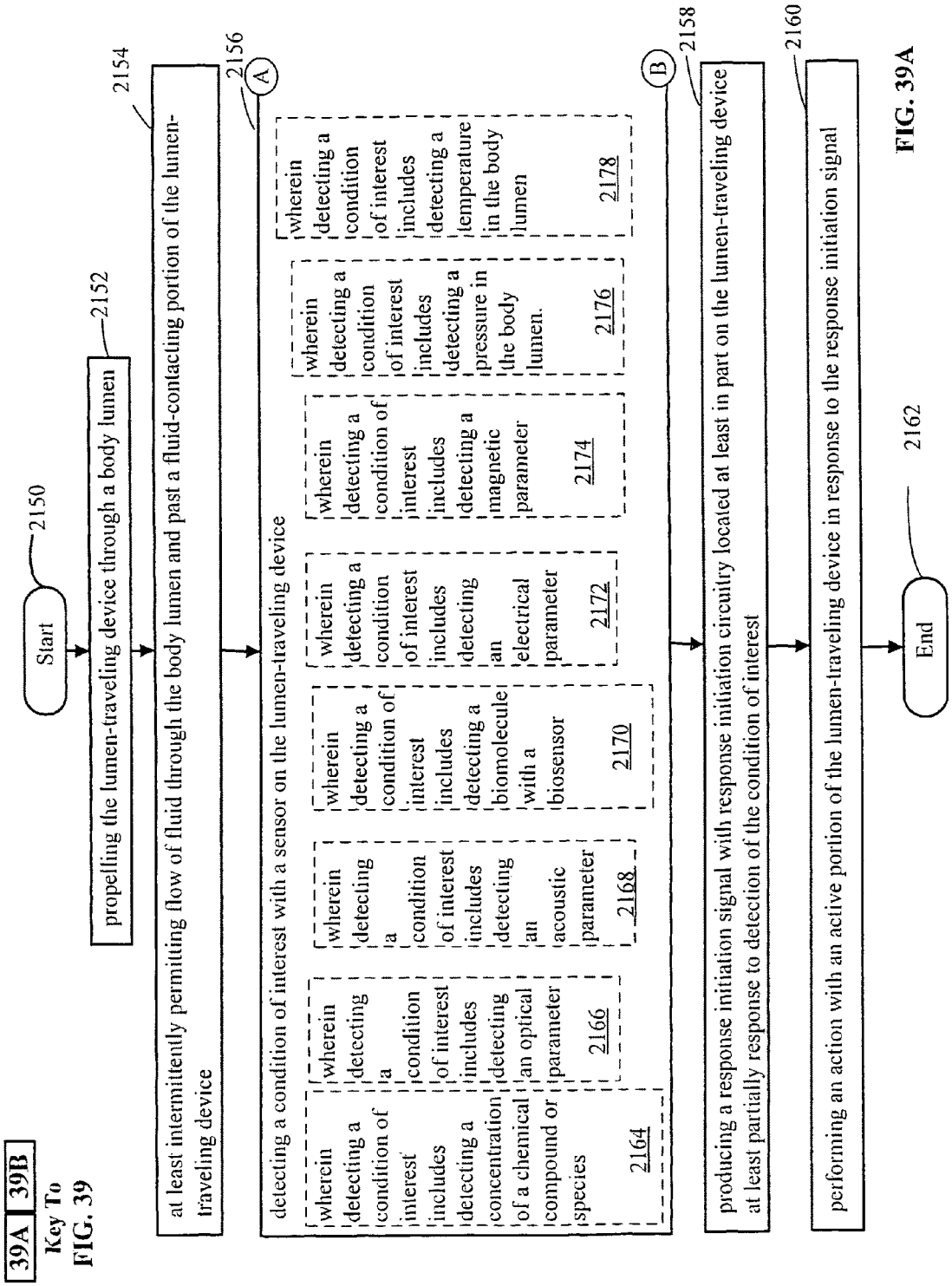

FIGS. 39A and 39B show further variations of the method of FIG. 36. The basic steps of the method include propelling the lumen-traveling device through a body lumen at step 2152; at least intermittently permitting flow of fluid through the body lumen and past a fluid-contacting portion of the lumen-traveling device at step 2154; detecting a condition of interest with a sensor on the lumen-traveling device at step 2156; producing a response initiation signal with response initiation circuitry located at least in part on the lumen-traveling device at least partially in response to detection of the condition of interest at step 2158; and performing an action with an active portion of the lumen-traveling device in response to the response initiation signal at step 2160. Detecting a condition of interest with a sensor on the lumen-traveling device may include detecting a concentration of a chemical compound or species (at step 2164), detecting an optical parameter (at step 2166), detecting an acoustic parameter (at step 2168), detecting a biomolecule with a biosensor (at step 2170), detecting an electrical parameter (at step 2172), detecting a magnetic parameter (at step 2174), detecting a pressure in the body lumen (at step 2176), or detecting a temperature in the body lumen (at step 2178), as shown in FIG. 39A, or, as shown in FIG. 39B, detecting a pH in the body lumen (at step 2180), detecting an anatomic feature (at step 2182), detecting a location (at step 2184), detecting a man-made structure (at step 2186), or detecting a time (at step 2188). If a man-made structure is detected, as at step 2186, the method may include the steps of delivering a material or structure to the man-made structure (at step 2190), receiving a material or structure from the man-made structure (at step 2192), or collecting the man-made structure (at step 2194). This may, for example, involve connecting to the man-made structure so that it can be pushed or pulled by the lumen-traveling device, or may involve taking up the man-made structure to be contained in or carried within the lumen-traveling device.

Steps 40A-40E show further variants of a method as described generally in FIG. 36. Again, the method may include propelling the lumen-traveling device through a body lumen at step 2252; at least intermittently permitting flow of fluid through the body lumen and past a fluid-contacting portion of the lumen-traveling device at step 2254; detecting a condition of interest with a sensor on the lumen-traveling device at step 2256; producing a response initiation signal with response initiation circuitry located at least in part on the lumen-traveling device at least partially in response to detection of the condition of interest at step 2258; and performing an action with an active portion of the lumen-traveling device in response to the response initiation signal at step 2260. As shown in FIG. 40A, the step of performing an action with the active portion (at step 2260) may include transmitting a signal to a remote location (at 2264), releasing a material (at step 2266), which may be, for example, at least one of an adhesive, a filler, a hydrogel, an antibiotic, a pharmaceutical compound, a nutrient, a hormone, a growth factor, a medication, a therapeutic compound, an enzyme, a protein, a genetic material, a cell, a fraction of a cell, a vaccine, a vitamin, a neurotransmitter, a neurotropic agent, a neuroactive material, a cytokine, a cell-signaling material, a pro-apoptotic agent, an anti-apoptotic agent, an immunological mediator, an anti-inflammatory agent, a salt, an ion, an antioxidant, an imaging agent, a labeling agent, a diagnostic compound, a nanomaterial, an inhibitor, or a blocker (as indicated at step 2268). Alternatively, as shown in FIG. 40B, performing an action with the active portion may include collecting a material from the body lumen (as shown in step 2270), which may include collecting a sample from a fluid within the body lumen (as shown in step 2272), or collecting a sample from a wall region of the body lumen (as shown in step 2274). Alternatively, the method may include collecting a sample from beyond the wall region of the body lumen, e.g., with the use of a needle to penetrate the body lumen wall and/or utilizing a permeation enhancer.

In some versions of the method, as shown in FIG. 40B, performing an action with the active portion may include producing heating or cooling, as shown in steps 2276 and 2282, respectively. Heating may be used in a variety of locations, for a variety of purposes. In one example, the method may include propelling the lumen-traveling device through the body lumen to a location in the vicinity of the preoptic area, wherein performing an action with the active portion may include producing heating in the vicinity of the preoptic area, as shown in step 2278. In another example, heating may be used in the male reproductive system to destroy gametes, as shown in step 2280. In another example (not shown), heating may be used for ablation of tissue. In addition, or alternatively, performing an action with the active portion may include securing the lumen-traveling device into position within the body lumen as shown in step 2284, e.g., by using various positioning or lumen-wall-engaging structures.

Figure 40C:
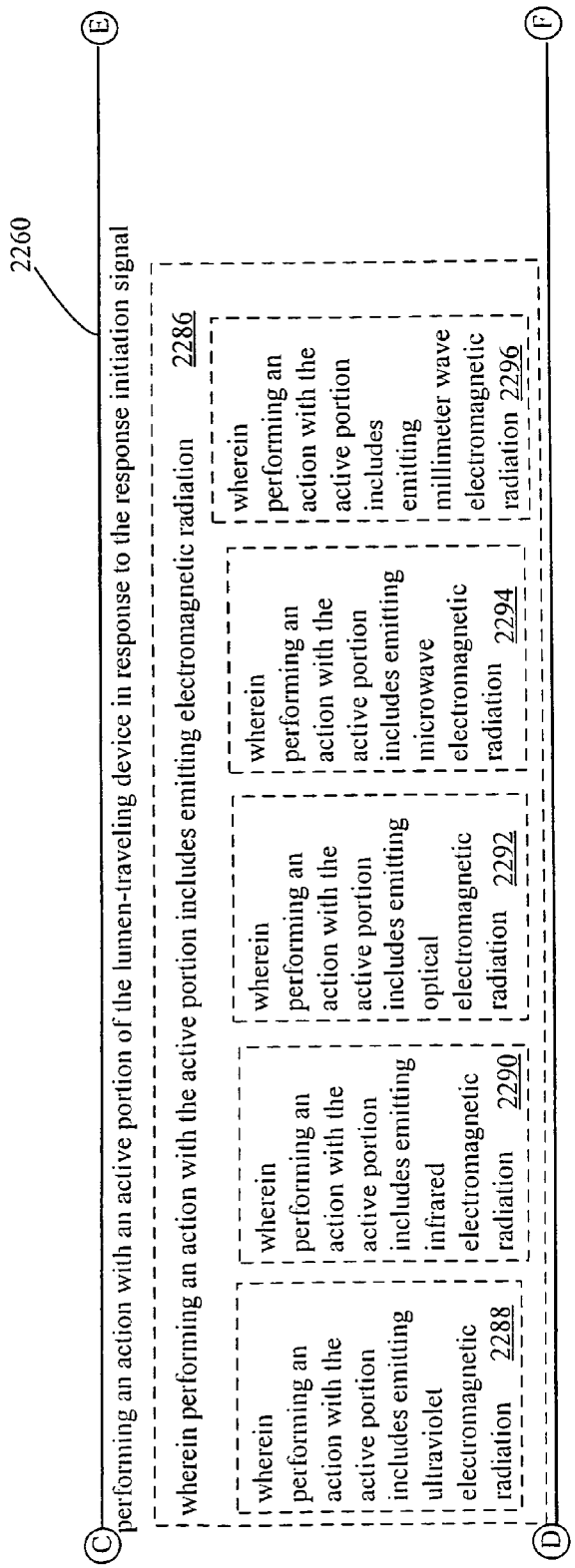
Figure 40D:
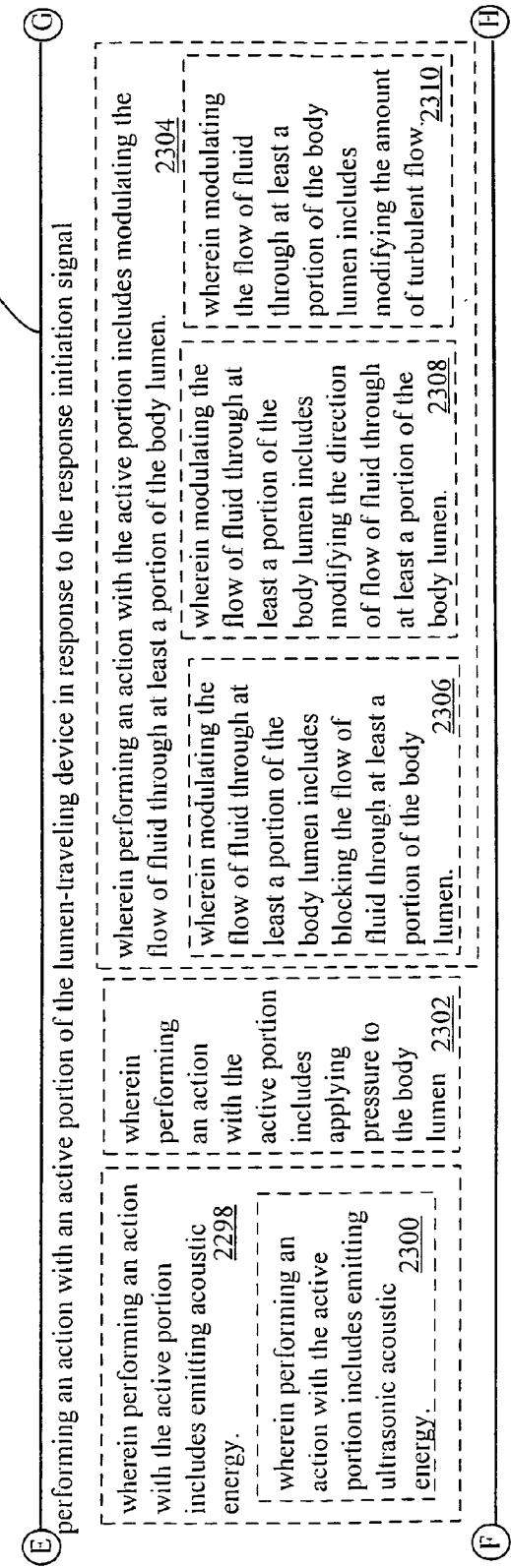

As shown in FIG. 40C, in some embodiments, performing an action with the active portion may include emitting electromagnetic radiation, as shown at step 2286. The action may include emitting ultraviolet, infrared, optical, microwave, or millimeter wave electromagnetic radiation, as indicated at steps 2288, 2290, 2292, 2294, and 2296, respectively. Alternatively, as shown in step 2298 of FIG. 40D, performing an action with the active portion may include emitting acoustic energy, including, but not limited to, ultrasonic acoustic energy, as indicated in step 2300. As shown in FIG. 40D, performing an action with the active portion may include applying pressure to the body lumen (step 2302), by expansion of the active portion, or by release of a gas or fluid. In other embodiments, performing an action with the active portion may include modulating the flow of fluid through at least a portion of the body lumen, as shown at step 2304, for example by blocking the flow of fluid through at least a portion of the body lumen (step 2306), modifying the direction of flow of fluid through at least a portion of the body lumen (2308), or modifying the amount of turbulent flow (step 2310). Modifying the direction of flow of fluid may include directing flow, toward a particular region and/or into a particular branch of a branching lumen, for example, with the use of various flow-directing structures as disclosed herein. Modifying the direction of flow of fluid may also include reversing the direction of flow, which may be accomplished, for example, by modifying the pressure within the lumen, as described herein.

Figure 40E:
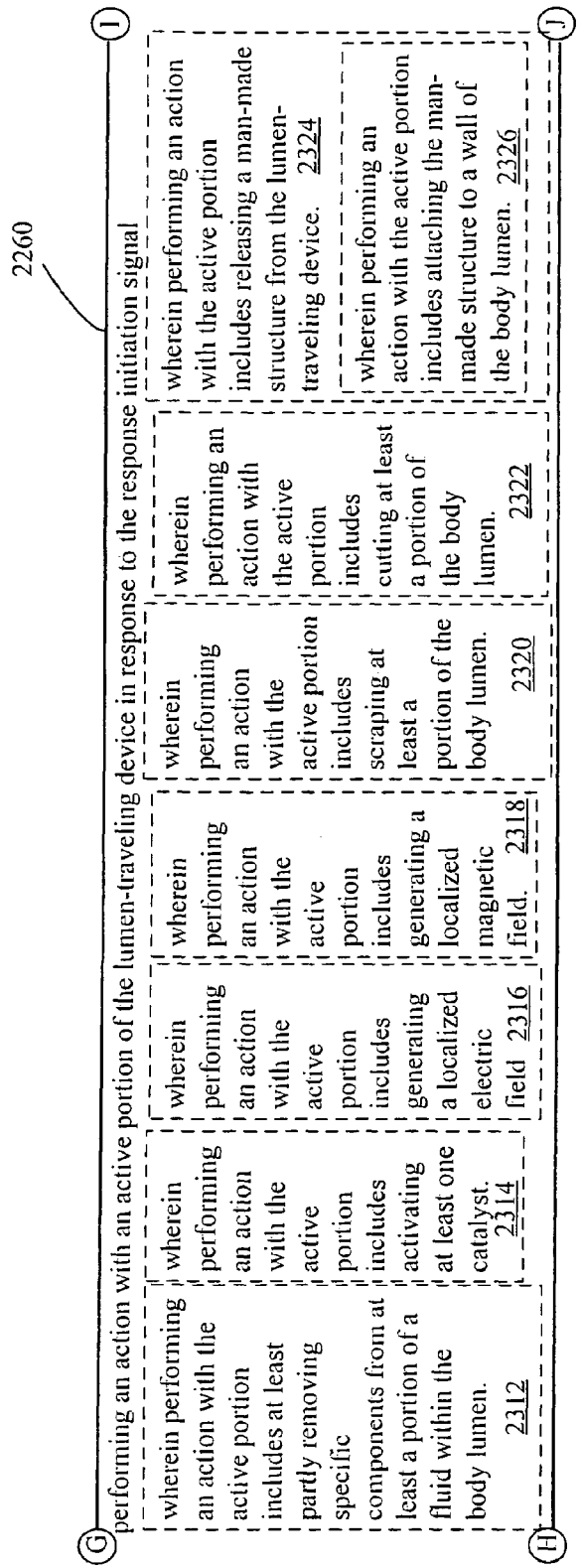
Figure 40F:
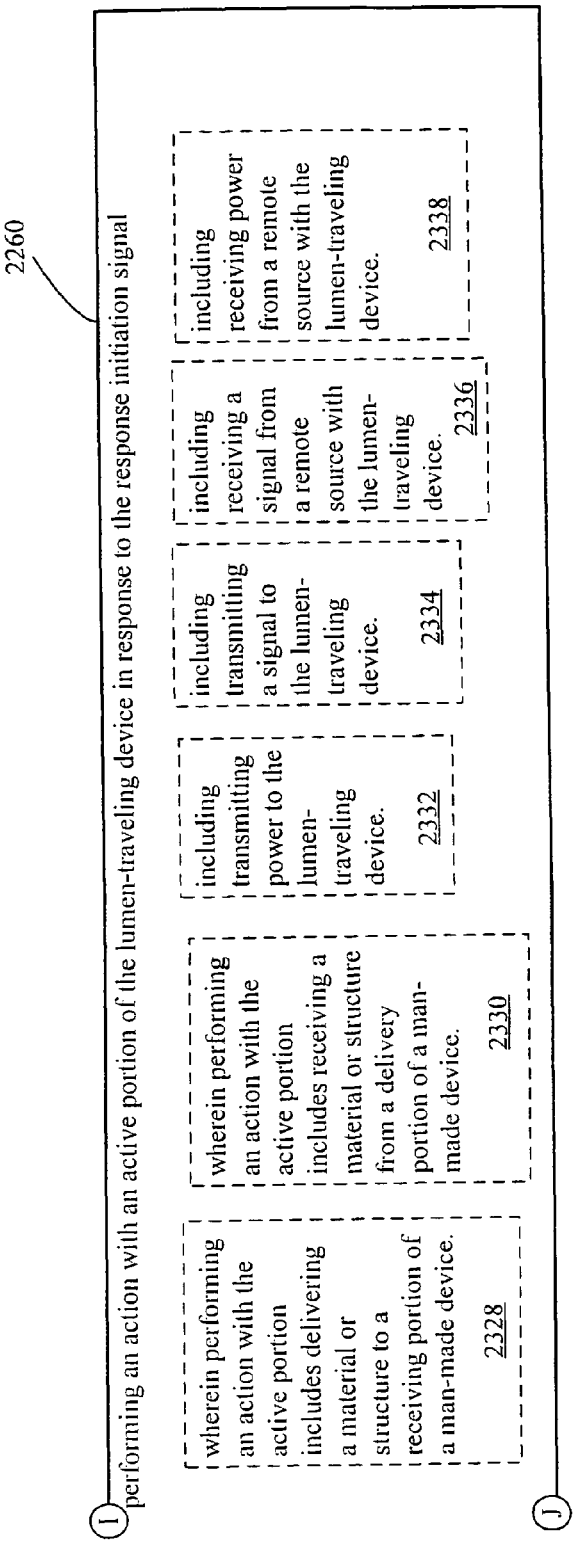

As shown in FIG. 40E, in some embodiments, performing an action with the active portion at step 2260 may include at least partly removing specific components from at least a portion of a fluid within the body lumen, as shown at step 2312, or activating at least one catalyst, as shown at step 2314. In still other embodiments, performing an action with the active portion may include generating an electric field, as shown at step 2316, generating a magnetic field, as shown at step 2318, or scraping or cutting at least a portion of the body lumen, as indicated at steps 2320 and 2322, respectively. Performing an action with the active portion may include releasing a man-made structure from the lumen-traveling device, as shown at step 2324, and, in some embodiments, attaching the man-made structure to a wall of the body lumen, as shown at step 2326. As shown in FIG. 40F, performing an action with the active portion at step 2260 may include delivering a material or structure to a receiving portion of a man-made device, as shown at 2328, receiving a material or structure from a delivery portion of a man-made device, as shown at 2330. Finally, the method may include one or more of transmitting power to the lumen-traveling device, as shown in step 2332, transmitting a signal to the lumen-traveling device, as shown in step 2334, receiving a signal from a remote source with the lumen-traveling device, as shown in step 2336, or receiving power from a remote source with the lumen-traveling device, as shown in step 2338.

A lumen-traveling device as described herein may include control circuitry for controlling various aspects of the operation of the device. Lumen-traveling devices and systems as described herein may be operated under the control of control circuitry, which may include hardware, software, firmware, or a combination thereof.

Figure 41:
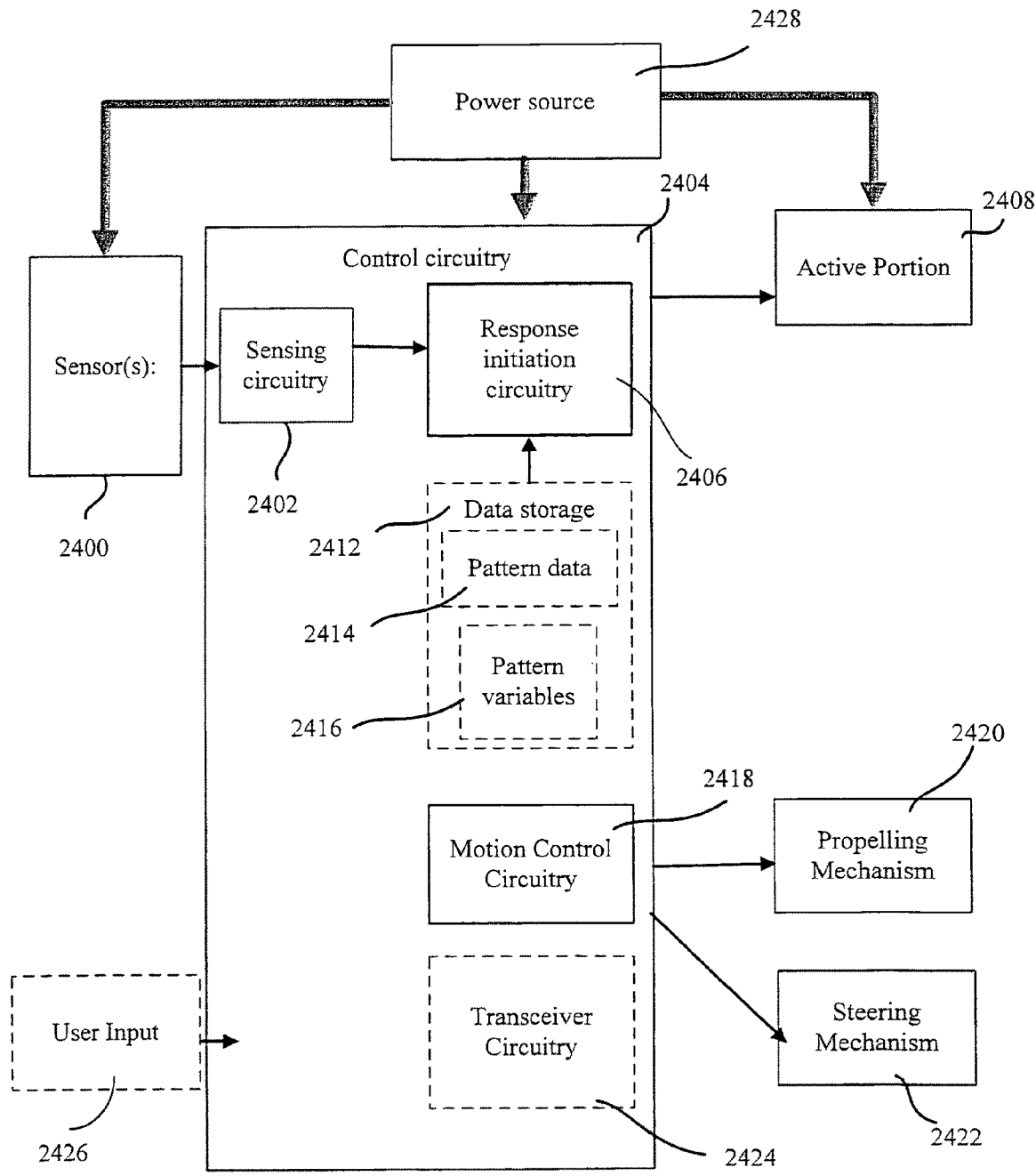
FIG. 41 is a block diagram of a lumen-traveling device system.

FIG. 41 is a block diagram illustrating in greater detail various circuitry components of a lumen-traveling system. As discussed elsewhere herein, the circuitry components may be located entirely on the structural element of a lumen-traveling device, or may be distributed between the lumen-traveling device and a remote portion. The lumen-traveling system may include one or more sensors 2400 for measuring or detecting a condition of interest. Sensing circuitry 2402 may be associated with sensors 2400. The lumen-traveling system may include various control circuitry 2404, including response initiation circuitry 2406. Response initiation circuitry 2406 may provide a response initiation signal to active portion 2408. Control circuitry 2404 may also include data storage portion 2412, which may, for example, be used to store pattern data 2414 or pattern variables 2416 for determining an activation pattern of active portion 2408. Data storage portion 2412 may also store positional information, including, for example, the current device position or the position of one or more target locations or landmarks, or a map of some or all of the relevant body lumen(s) of the subjects. In some embodiments, control circuitry 2404 may include motion control circuitry 2418 for controlling propelling mechanism 2420, and optionally steering mechanism 2422. Control circuitry may include transceiver circuitry 2424, which provides for the transmission and reception of data and/or power signals between the lumen-traveling device and one or more remote portion or external devices (e.g., monitoring or recording equipment). A user input portion 2426 may provide for the input of user instructions, parameter, etc. to control circuitry 2404. Finally, one or more power source 2428 may provide power to electrical components of the lumen-traveling system. Some components of the lumen-traveling device may be operated in whole or in part under software control, and control circuitry 2404 may include hardware, software, hardware, or various combinations thereof. The lumen-traveling device may include components that may be primarily hardware-based, e.g., sensor 2400, active portion 2408, propelling mechanism 2420, steering mechanism 2422, and, optionally, user input device 2426. Hardware-based devices may include components that are electrical, mechanical, chemical, optical, electromechanical, electrochemical, electro-optical, and are not limited to the specific examples presented herein. As described elsewhere, in some embodiments, portions of the control circuitry, including, for example, the response initiation circuitry, may be located in or on the structural element, while in other embodiments the response initiation circuitry may be at a location remote from the structural element.

Figure 42:
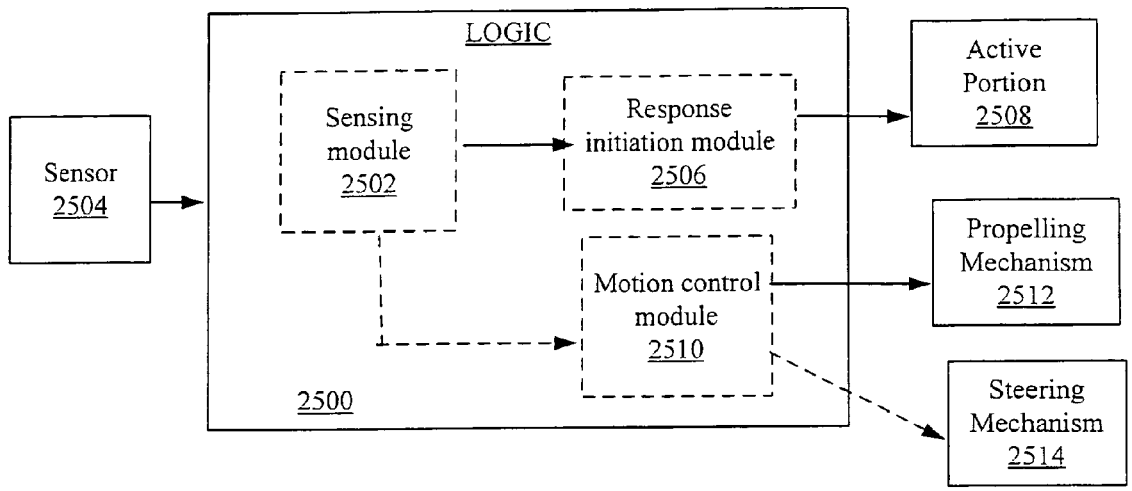
FIG. 42 is block diagram of an embodiment of logic for controlling a lumen-traveling device.
Figure 43:
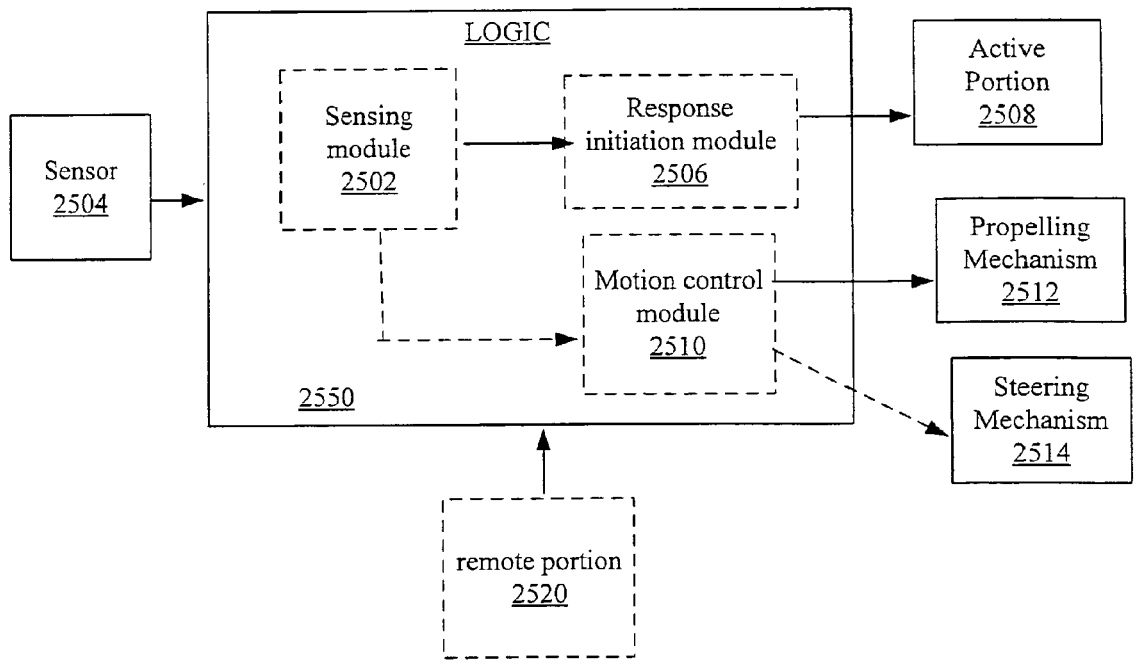
FIG. 43 is a block diagram of a further embodiment of logic for controlling a lumen-traveling device.

In many embodiments, the control circuitry as depicted in FIG. 41 may be implemented in the form of logic, for example software or digital logic circuitry. FIG. 42 depicts modules of logic (which may be software or hardware) which may be used in the control of lumen-traveling devices as described herein. As shown in FIG. 42, logic 2500 for controlling a lumen-traveling device, may include, for example, a sensing module 2502 capable of processing an input from a sensor 2504 on the lumen-traveling device to generate a sense signal indicating detection of a condition of interest in a body lumen of an organism; a response initiation module 2506 capable of receiving the sense signal from the sensing module 2502 and based at least in part upon the sense signal generating a response initiation signal configured for causing an action to be performed in the body lumen by an active portion 2508 of the lumen-traveling device; and a motion control module 2510 capable of controlling at least one of a propelling mechanism 2512 or a steering mechanism 2514 on the lumen-traveling device to control direction or rate of movement of the lumen-traveling device through the body lumen. The logic may be implemented in digital circuitry, analog circuitry, software, or combinations thereof. The motion control module 2510 may be capable of receiving the sense signal from the sensing module 2502 and controlling at least one of the propelling mechanism 2512 or the steering mechanism 2514 on the lumen-traveling device based at least in part upon the sense signal. In one alternative embodiment, as shown in FIG. 43, the motion control 2510 module may be capable of controlling at least one of the propelling mechanism 2512 or steering mechanism 2514 on the lumen-traveling device based at least in part upon a motion control signal from a remote portion 2520. Otherwise, the logic 2550 is like that shown in FIG. 42, including sensing module 2502 capable of processing an input from a sensor 2504 on the lumen-traveling device to generate a sense signal indicating detection of a condition of interest in a body lumen of an organism; a response initiation module 2506 capable of receiving the sense signal from the sensing module 2502 and based at least in part upon the sense signal generating a response initiation signal configured for causing an action to be performed in the body lumen by an active portion 2508 of the lumen-traveling device; and a motion control module 2510 capable of controlling at least one of a propelling mechanism 2512 or a steering mechanism 2514 on the lumen-traveling device to control direction or rate of movement of the lumen-traveling device through the body lumen. In another related embodiment, motion control module 2510 may be capable of controlling at least one of propelling mechanism 2512 or the steering mechanism 2514 on the lumen-traveling device based at least in part upon a pre-programmed motion pattern, for example a motion pattern stored in a data storage location 2412 as data storage location 2412 in FIG. 41. In some embodiments, sensing module 2502 may be capable of generating a sense signal indicating the presence or absence of the condition of interest, wherein response initiation module 2506 may be capable of generating a response initiation signal configured for initiating the performance of the action in the body lumen by active portion 2508 of the lumen-traveling device. Response initiation module 2506 may include control logic that uses a pre-programmed pattern which may be stored in a memory location on the lumen-traveling device (again, like data storage location 2412 in FIG. 41).

In some embodiments, sensing module 2502 may be capable of generating a sense signal indicating the presence or absence of the condition of interest, and response initiation module 2506 may be capable of generating a response initiation signal configured for controlling the performance of the action in the body lumen by the active portion of the lumen-traveling device in a pre-programmed pattern. In some embodiments, the sensing module may be capable of generating a sense signal indicating a parameter value of the condition of interest, wherein the response initiation module may be capable of generating a response initiation signal configured for initiating the performance of the action in the body lumen by the active portion 2508 of the lumen-traveling device as a function of the parameter value of the condition of interest. In addition, response initiation module 2506 may in some embodiments be capable of generating a response initiation signal configured for controlling the action by the active portion 2508 of the lumen-traveling device for a period of time as a function of the parameter value of the condition of interest. In some embodiments, sensing module 2502 may be capable of generating a time-varying sense signal indicating a time-varying parameter value of the condition of interest, wherein the response initiation module 2506 may be capable of generating a response initiation signal configured for controlling active portion 2508 of the lumen-traveling device as a function of the time-varying sense signal.

Figure 44:
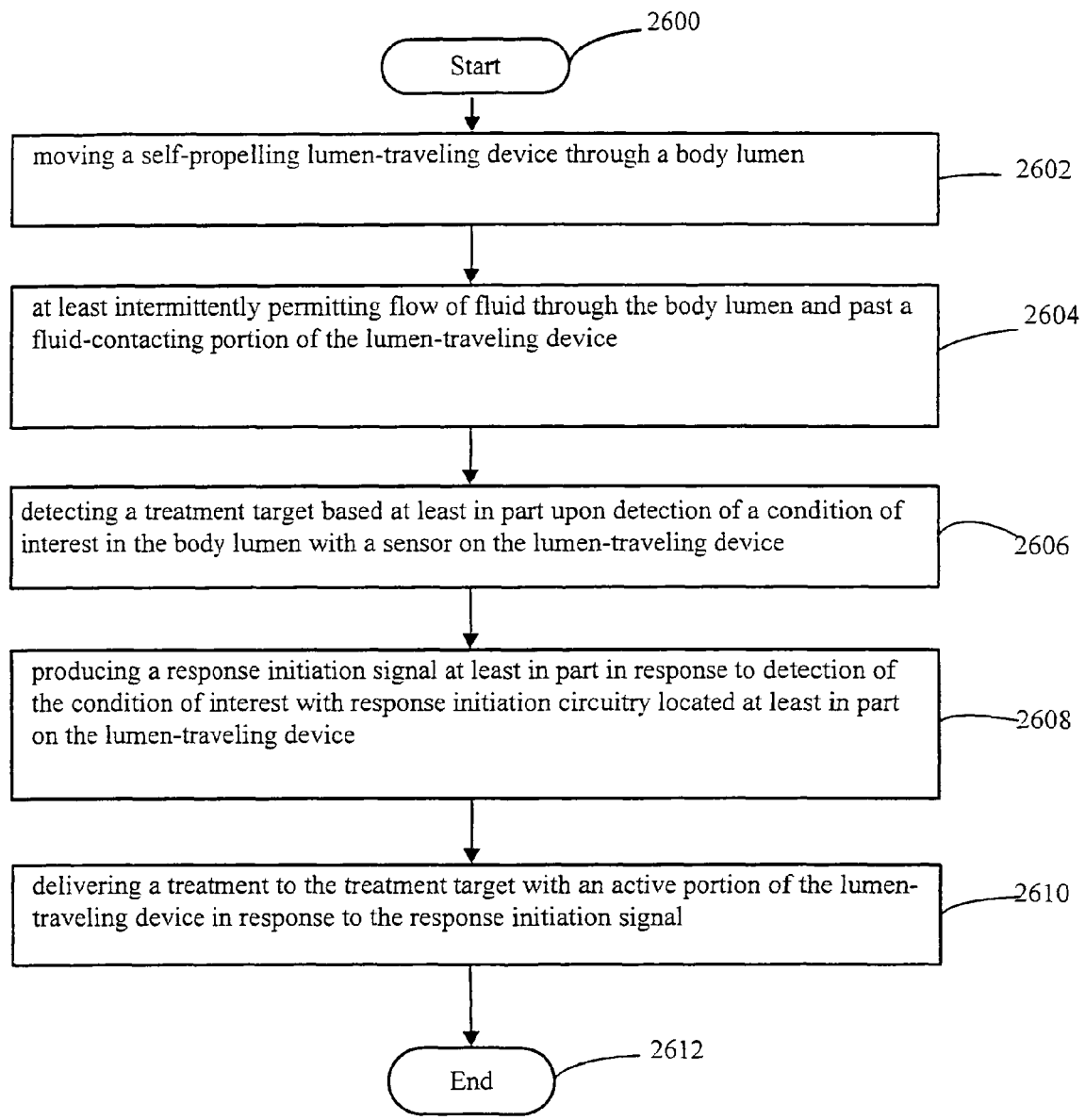
FIG. 44 is flow diagram of a method of using a lumen-traveling device.

FIG. 44 illustrates a method of using a lumen-traveling device, which includes moving a self-propelling lumen-traveling device through a body lumen at step 2602; at least intermittently permitting flow of fluid through the body lumen and past a fluid-contacting portion of the lumen-traveling device at step 2604; detecting a treatment target based at least in part upon detection of a condition of interest in the body lumen with a sensor on the lumen-traveling device at step 2606; producing a response initiation signal at least in part in response to detection of the condition of interest with response initiation circuitry located at least in part on the lumen-traveling device at step 2608; and delivering a treatment to the treatment target with an active portion of the lumen-traveling device in response to the response initiation signal at step 2610.

Figure 45:
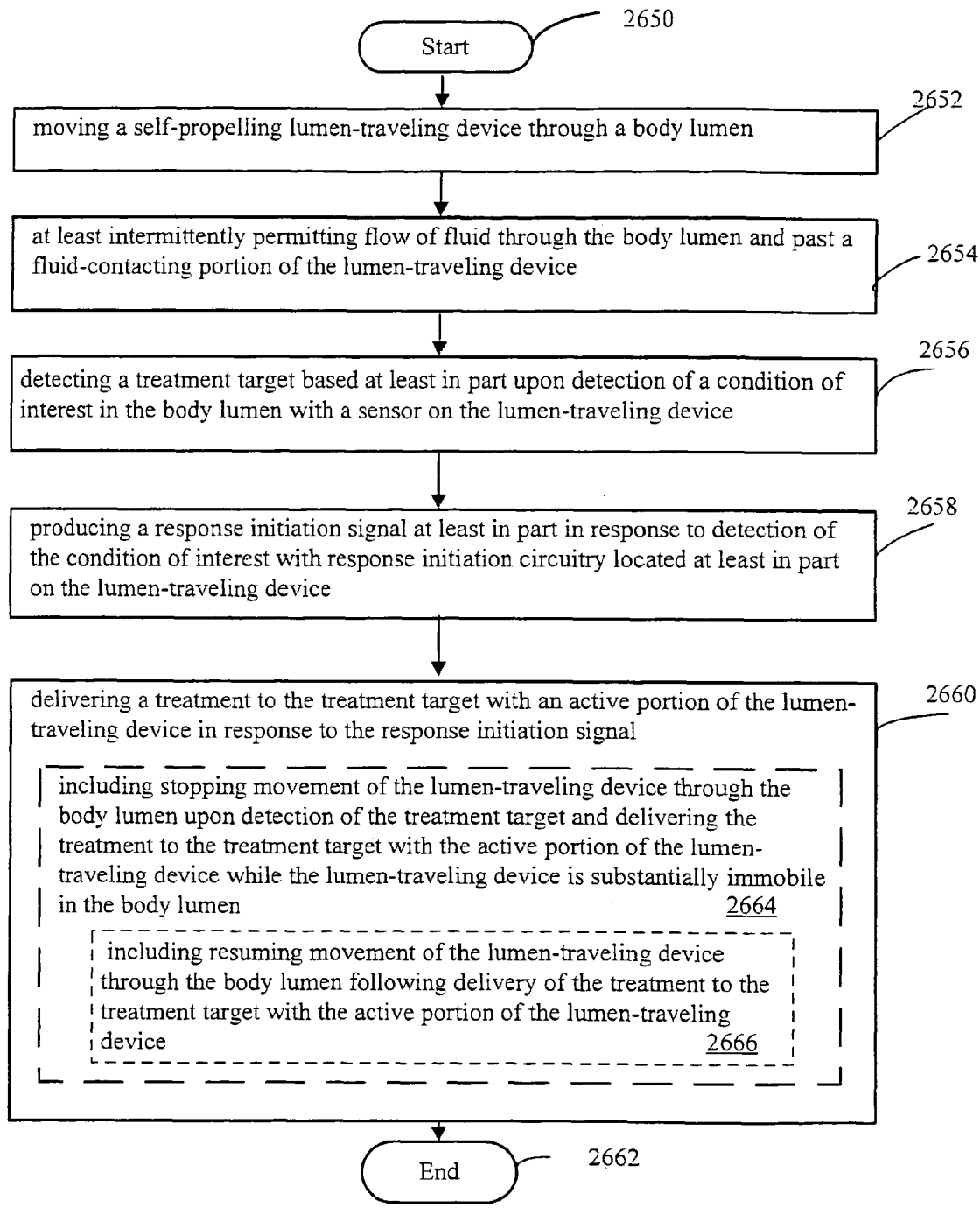
FIG. 45 is a flow diagram of a method of using a lumen-traveling device.

FIG. 45 shows an expanded version of the method of FIG. 44, including the steps of moving a self-propelling lumen-traveling device through a body lumen at step 2652; at least intermittently permitting flow of fluid through the body lumen and past a fluid-contacting portion of the lumen-traveling device at step 2654; detecting a treatment target based at least in part upon detection of a condition of interest in the body lumen with a sensor on the lumen-traveling device at step 2656; producing a response initiation signal at least in part in response to detection of the condition of interest with response initiation circuitry located at least in part on the lumen-traveling device at step 2658; and delivering a treatment to the treatment target with an active portion of the lumen-traveling device in response to the response initiation signal at step 2660, and also including a further step 2664 of stopping movement of the lumen-traveling device through the body lumen upon detection of the treatment target and delivering the treatment to the treatment target with the active portion of the lumen-traveling device while the lumen-traveling device may be substantially immobile in the body lumen. A further method step 2666 may include resuming movement of the lumen-traveling device through the body lumen following delivery of the treatment to the treatment target with the active portion of the lumen-traveling device.

Figure 46:
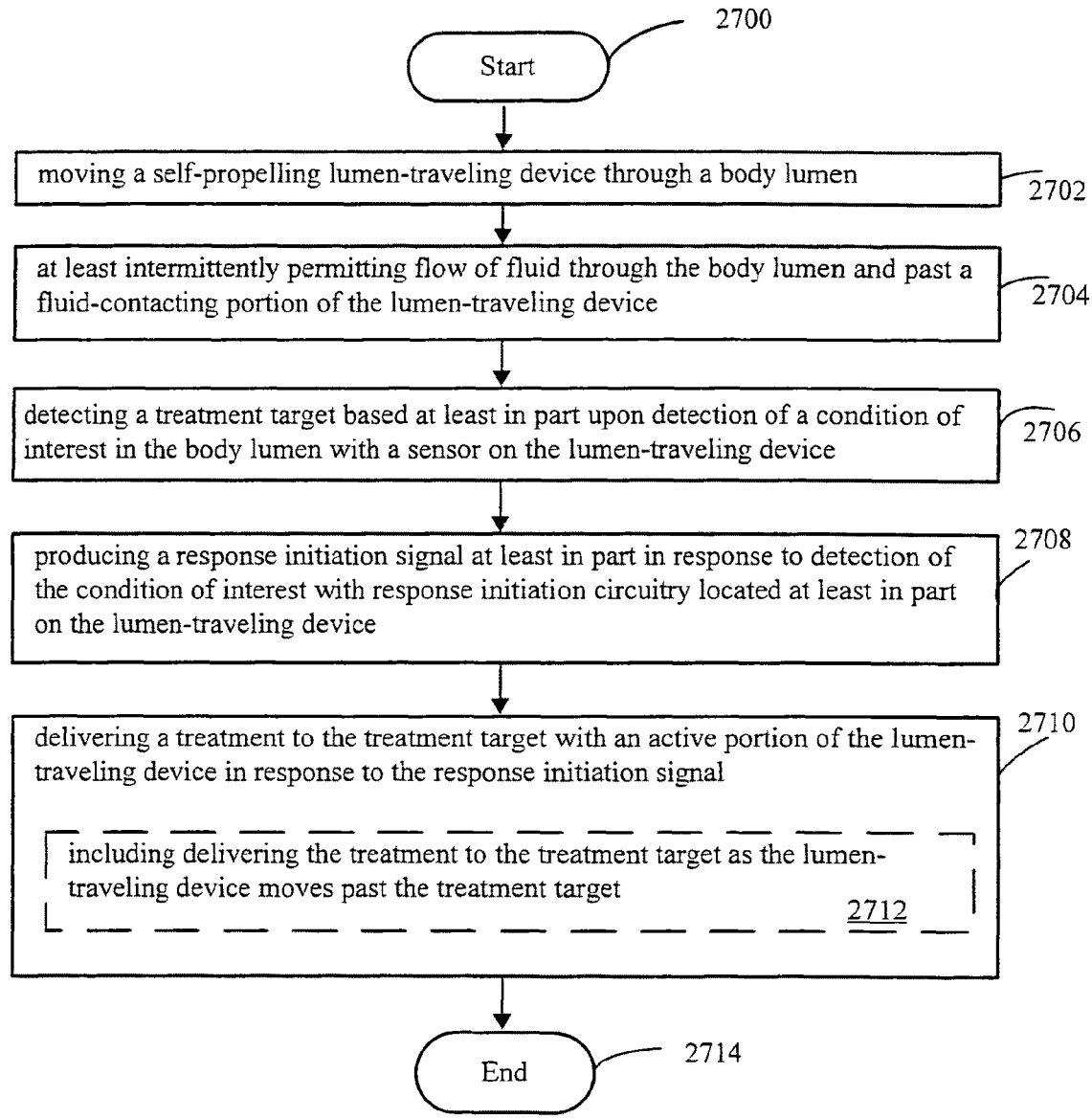
FIG. 46 is a flow diagram of a method of using a lumen-traveling device.

FIG. 46 shows a further variation of the method of FIG. 44, including moving a self-propelling lumen-traveling device through a body lumen at step 2702; at least intermittently permitting flow of fluid through the body lumen and past a fluid-contacting portion of the lumen-traveling device at step 2704; detecting a treatment target based at least in part upon detection of a condition of interest in the body lumen with a sensor on the lumen-traveling device at step 2706; producing a response initiation signal at least in part in response to detection of the condition of interest with response initiation circuitry located at least in part on the lumen-traveling device at step 2708; and delivering a treatment to the treatment target with an active portion of the lumen-traveling device in response to the response initiation signal at step 2710, where delivering the treatment to the treatment target may include delivering the treatment to the treatment target as the lumen-traveling device moves past the treatment target, as shown in step 2712.

In some embodiments of methods as illustrated in FIGS. 44, 45, and 46, a method of using a lumen-traveling device may include delivering the treatment to the treatment target with an active portion of the lumen-traveling device, wherein the treatment may be determined based at least in part upon at least one sensed parameter of the treatment target. In other embodiments, the treatment may be determined at least in part by a treatment pattern stored in the lumen-traveling device.

In some cases, the treatment target may include at least a portion of a wall of the body lumen, or in some cases, the treatment target may lie beyond the wall of the body lumen, so that delivering a treatment to the treatment target with an active portion of the lumen-traveling device in response to the response initiation signal may include delivering a treatment to the treatment target through a wall of the body lumen. In some cases, the treatment target may include at least a portion of the contents of the body lumen.

Figure 47:
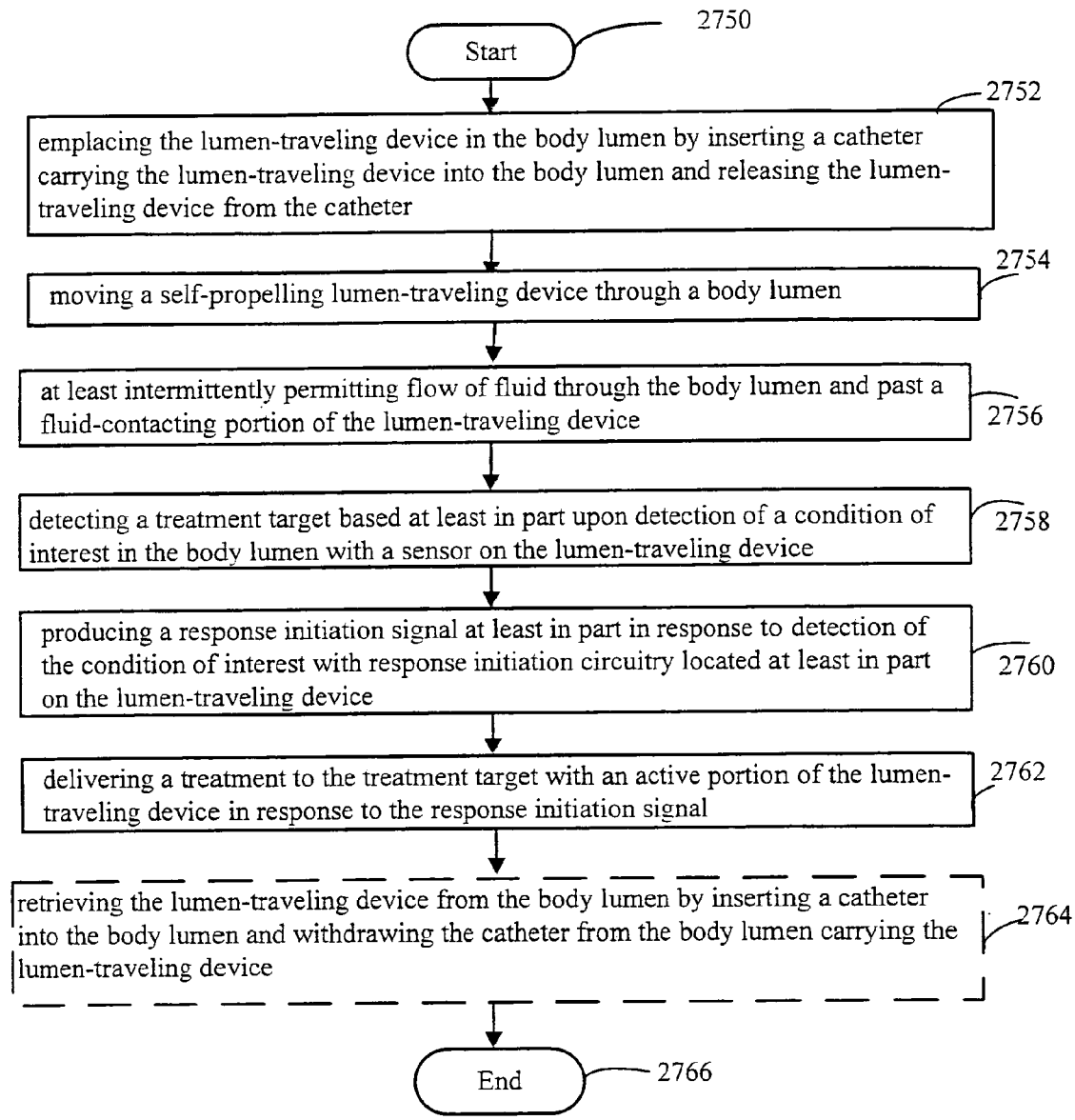
FIG. 47 is a flow diagram of a method of using a lumen-traveling device.

A further method of using a lumen-traveling device, as outlined in FIG. 47, may also include emplacing the lumen-traveling device in the body lumen by inserting a catheter carrying the lumen-traveling device into the body lumen and releasing the lumen-traveling device from the catheter, at step 2752, followed by the steps of moving a self-propelling lumen-traveling device through a body lumen at step 2754; at least intermittently permitting flow of fluid through the body lumen and past a fluid-contacting portion of the lumen-traveling device at step 2756; detecting a treatment target based at least in part upon detection of a condition of interest in the body lumen with a sensor on the lumen-traveling device at step 2758; producing a response initiation signal at least in part in response to detection of the condition of interest with response initiation circuitry located at least in part on the lumen-traveling device at step 2760; and delivering a treatment to the treatment target with an active portion of the lumen-traveling device in response to the response initiation signal at step 2762. A method of using a lumen-traveling device may optionally include retrieving the lumen-traveling device from the body lumen by inserting a catheter into the body lumen and withdrawing the catheter from the body lumen carrying the lumen-traveling device, for example as shown in step 2764 of FIG. 47.

Figure 48A:
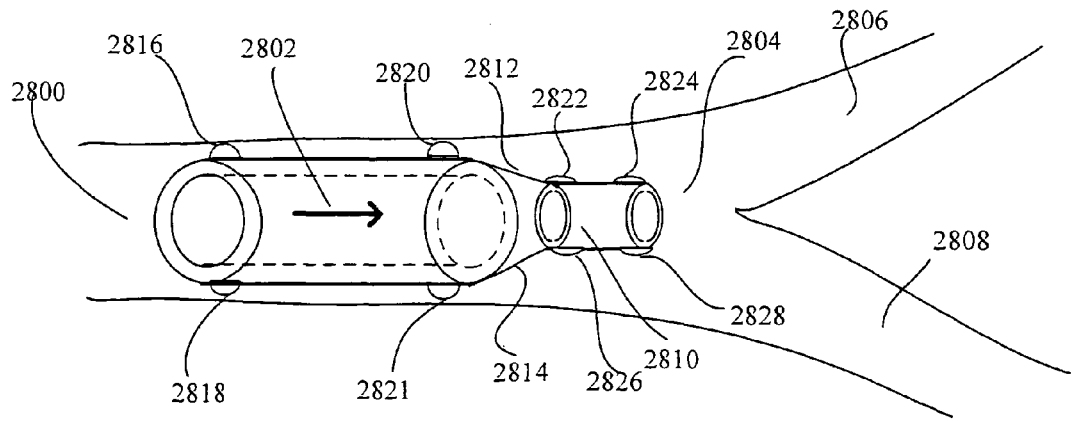
FIGS. 48A-48C illustrate an embodiment of a system including two lumen-traveling devices.
Figure 48B:
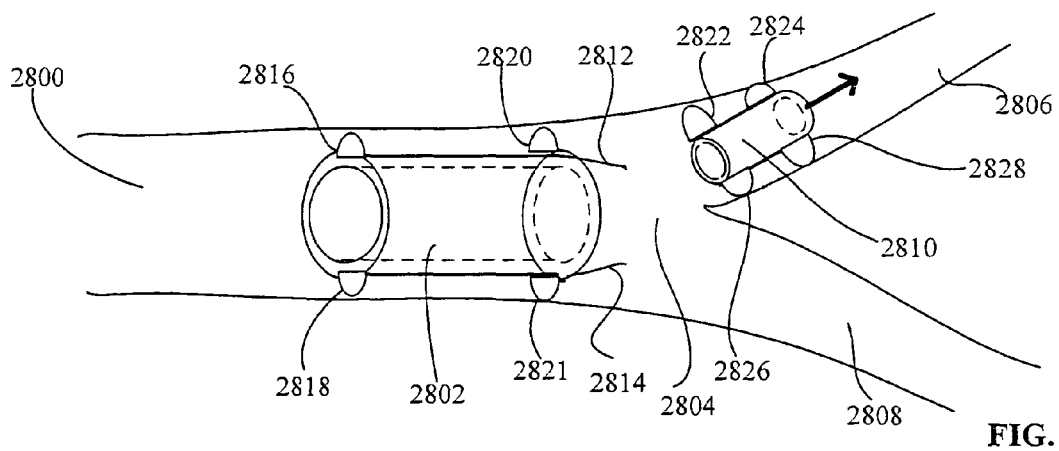
Figure 48C:
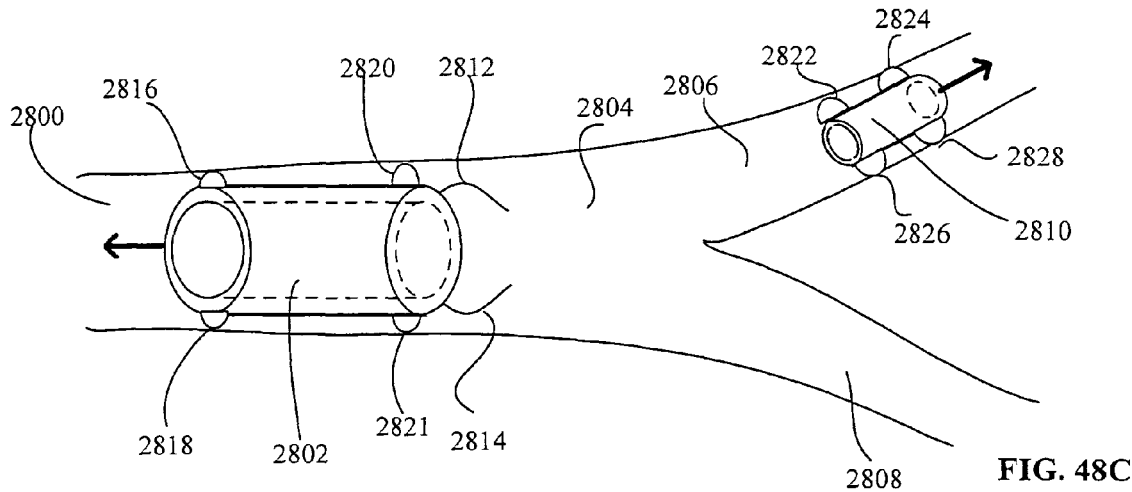

In some embodiments of a method of using a lumen-traveling device, as shown in FIGS. 48A-48C, a primary lumen-traveling device 2802 and a secondary lumen-traveling device 2810 may be used. In some embodiments of a method, e.g., as outlined in FIG. 44, the self-propelling lumen-traveling device may be a secondary lumen-traveling device 2810, and the method may include emplacing secondary lumen-traveling device 2810 in the body lumen by releasing the secondary lumen-traveling device 2810 from a primary lumen-traveling device 2802. In FIG. 48A, primary lumen-traveling device 2802 is located in body lumen 2800 near branch point 2804, where body lumen 2800 branches into smaller branch lumens 2806 and 2808. Secondary lumen-traveling device 1820 is carried by primary lumen-traveling device 2802, attached by retaining portions 2812 and 2814. Primary lumen-traveling device 2802 is propelled through body lumen 2800 (in this example, with lumen-wall-engaging structures 2816, 2818, 2820, and 2821). As shown in FIG. 48B, when primary lumen-traveling device 2802 reaches branch point 2804, it may stop and release secondary lumen-traveling device 2810. Secondary lumen-traveling device 2810 may be smaller than the primary lumen-traveling device 2802, for example to permit it to travel into a smaller body lumen than the primary lumen-traveling device will fit into, such as branch lumen 2806. Secondary lumen-traveling device 2810 may include lumen-wall-engaging structures 2822, 2824, 2826, and 2828, which operate to propel it down branch lumen 2806 and away from primary lumen-traveling device 2802. As illustrated in FIG. 48C, primary lumen-traveling device may leave branch point 2804 after releasing secondary lumen-traveling device 2810.

Primary lumen-traveling device 2802 and secondary lumen-traveling device 2810 may be substantially similar in design, but of different sizes, as depicted in FIGS. 48A-48C. In some embodiments of a method as outlined in FIG. 44, a self-propelling lumen-traveling device (as recited in the method of FIG. 44) may be a primary lumen-traveling device as depicted in FIG. 48, and the method may include emplacing a secondary lumen-traveling device in the body lumen by releasing the secondary lumen-traveling device from the primary lumen-traveling device. As depicted in FIG. 48, the secondary lumen-traveling device may be smaller than the primary lumen-traveling device.

Figure 49:
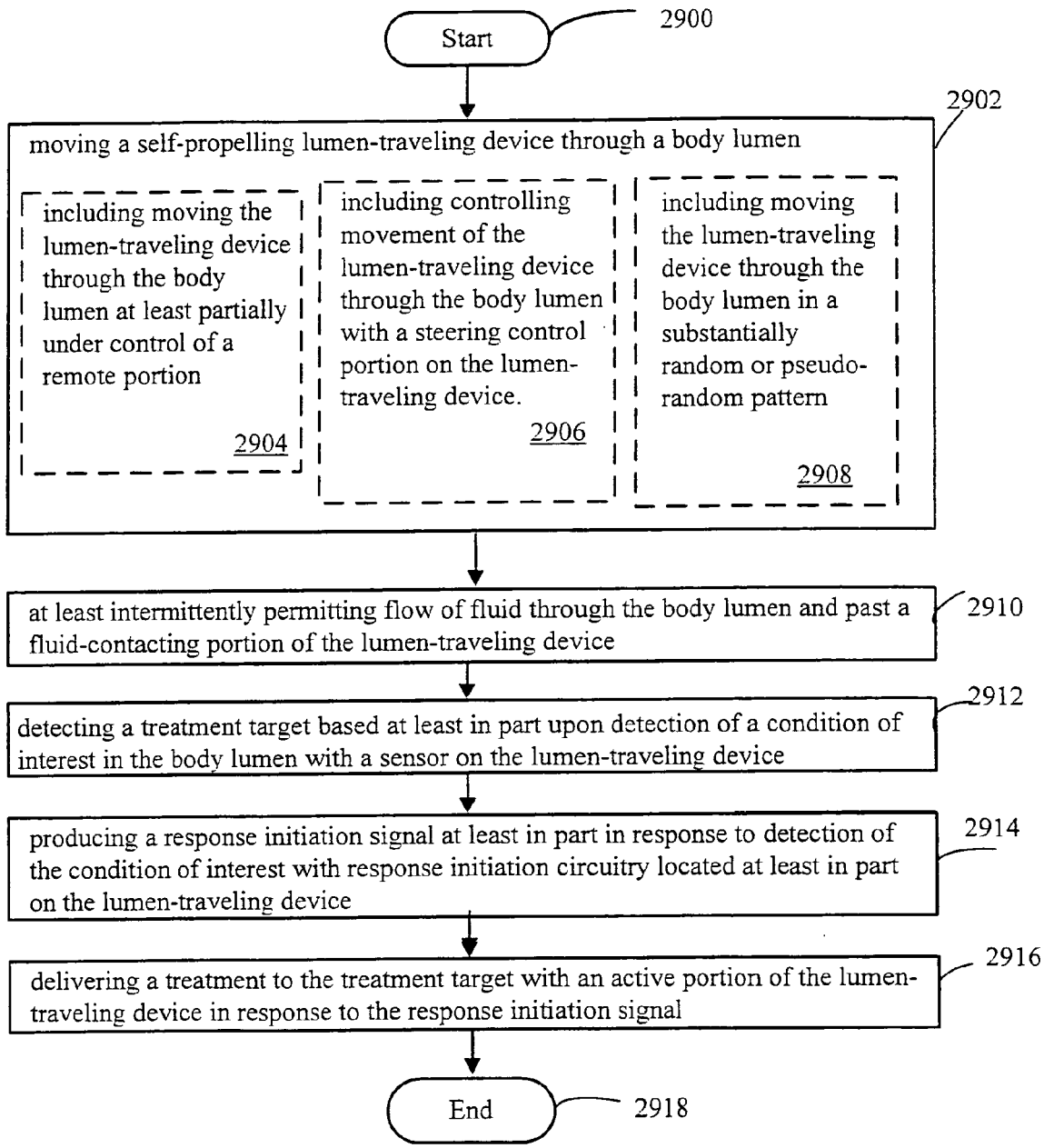
FIG. 49 is a flow diagram of a method of using a lumen-traveling device.

FIG. 49 shows a method which includes moving a self-propelling lumen-traveling device through a body lumen at step 2902; at least intermittently permitting flow of fluid through the body lumen and past a fluid-contacting portion of the lumen-traveling device at step 2910; detecting a treatment target based at least in part upon detection of a condition of interest in the body lumen with a sensor on the lumen-traveling device at step 2912; producing a response initiation signal at least in part in response to detection of the condition of interest with response initiation circuitry located at least in part on the lumen-traveling device at step 2914; and delivering a treatment to the treatment target with an active portion of the lumen-traveling device in response to the response initiation signal at step 2916. In addition, the method of FIG. 49 may include moving the lumen-traveling device through the body lumen at least partially under control of a remote portion, e.g., of the type illustrated in FIG. 35, as indicated at step 2904. For example, a motion control signal may be transmitted to the lumen-traveling device with the remote portion. The motion control signal may be generated with the remote portion. The motion control signal may be received from a remote portion with a signal receiver in the lumen-traveling device. The method may also include transmitting a signal indicative of detection of a condition of interest from the lumen-traveling device to a remote location, or transmitting a signal indicative of performance of an action by the lumen-traveling device to a remote location.

Alternatively, as shown in FIG. 49, step 2906, a method of using a lumen-traveling device may include controlling movement of the lumen-traveling device through the body lumen with a steering control portion on the lumen-traveling device. It should be noted that in some embodiments, propulsion may be provided without steering. In some embodiments, movement of the lumen-traveling device through the body lumen may be controlled based at least in part upon a detected condition of interest in the body lumen, controlled based at least in part on the use of logic circuitry included in the lumen-traveling device, and/or controlled based at least in part on a movement pattern stored in the lumen-traveling device. In another alternative, the lumen-traveling device may be moved through the body lumen in a substantially random or pseudo-random pattern, as indicated in FIG. 49, step 2908.

In this and other embodiments of methods disclosed herein, detecting a condition of interest may include detecting a variety of conditions, including but not limited to, an embolism, a plaque, a thrombus, an aneurysm, a stenosis, a puncture, a perforation, a rupture, a dissection, a tear, or a branching point in the body lumen, the branching point including at least two branches of the body lumen. The term "condition", as used herein, may refer to normally occurring anatomic features, man-made or other foreign structures, features, or conditions, disease states or injuries that may be present in a lumen by chance or purpose, and various detectable or measurable characteristics or parameters that indicate the presence of such conditions or features. In some embodiments, the method may include detecting a branching point in the body lumen, the branching point including at least two branches of the body lumen; the method may then also include steering the lumen-traveling device into a selected one of the at least two branches of the body lumen.

Several additional examples of embodiments of lumen-traveling devices are now provided, to further illustrate use of lumen-traveling devices as described herein.

Figure 50A:
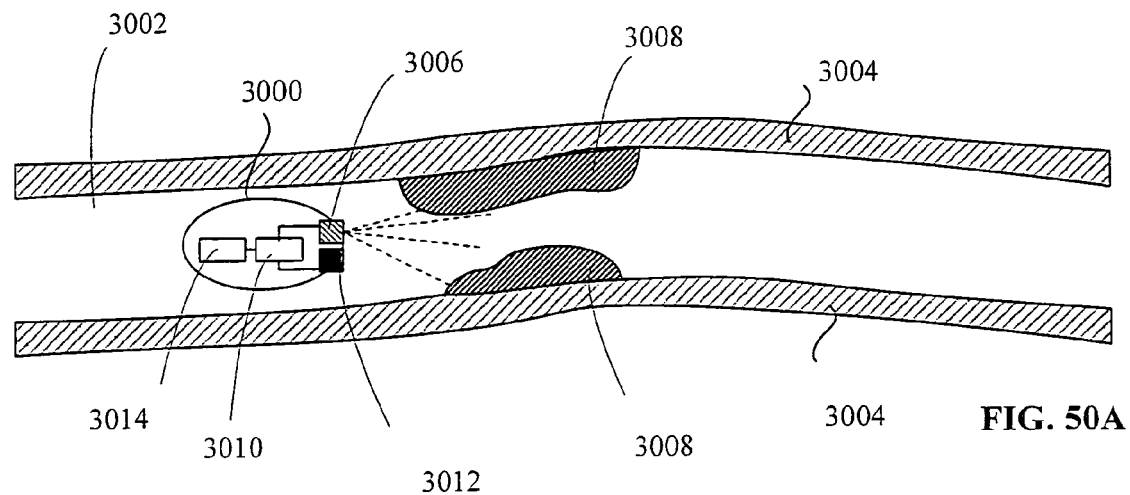
FIGS. 50A and 50B are longitudinal cross-sectional views of an example of the operation of a lumen-traveling device in a body lumen.
Figure 50B:
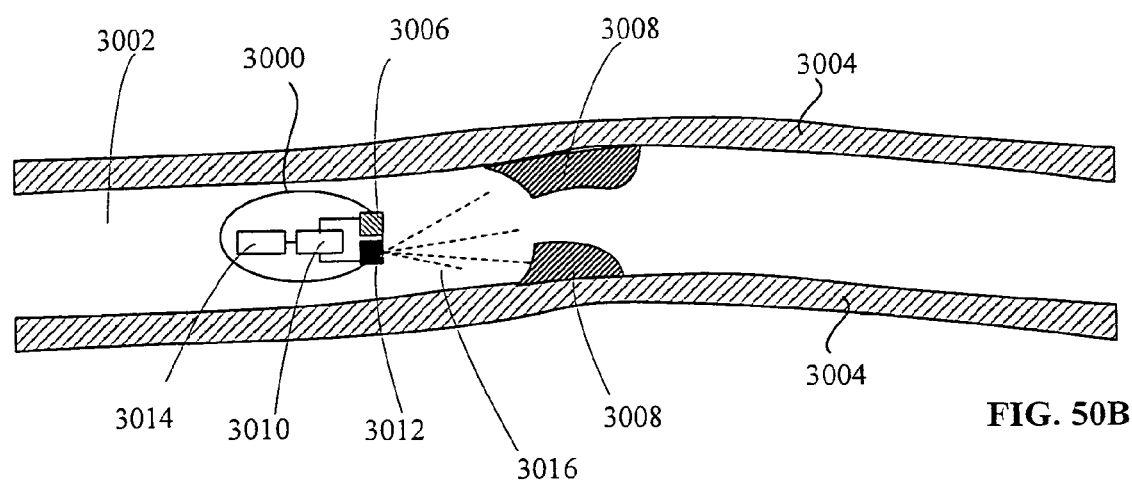

FIGS. 50A and 50B depict lumen-traveling device 3000 moving through a body lumen 3002. Lumen-traveling device 3000 includes sensor 3006, response initiation circuitry 3010, and active portion 3012. Lumen-traveling device 3000 also includes motion control circuitry 3014. As shown in FIG. 50A, sensor 3000 detects a location of interest—in this case, material 3008 on the wall 3004 of body lumen 3002. Material 3008 may be, for example, a plaque on the wall of an artery. Sensor 3006 may be an optical sensor, an imaging device, or various other types of sensors, as are known to those of skill in the art. Upon detection of material 3008, active portion 3012 may be an activated, as shown in FIG. 50B. In this example active portion 3012 performs ablation of material 3008; for example, active portion 3012 may be an optical device which generates light to perform, for example, laser ablation of a plaque, or it may be an acoustic device for performing ultrasonic ablation of a plaque.

Figure 51A:
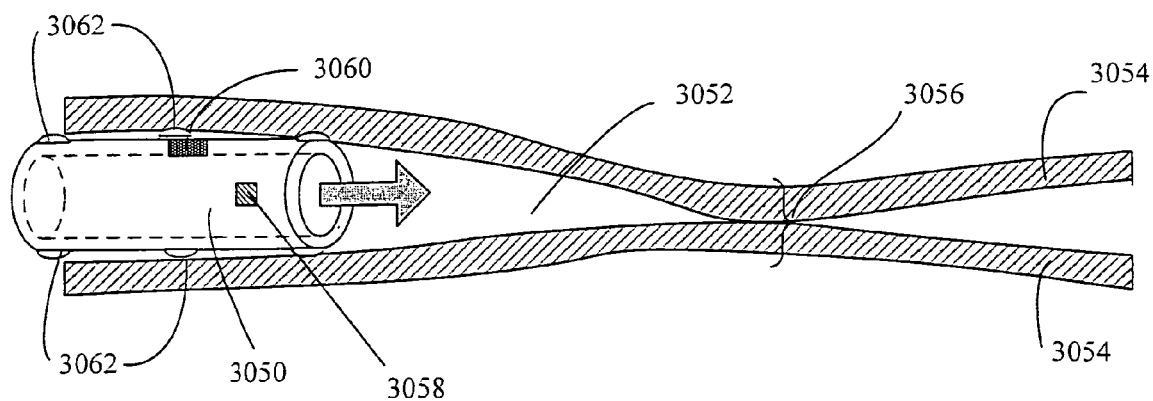
FIGS. 51A and 51B are longitudinal cross-sectional views of an example of the operation of a lumen-traveling device in a body lumen.
Figure 51B:
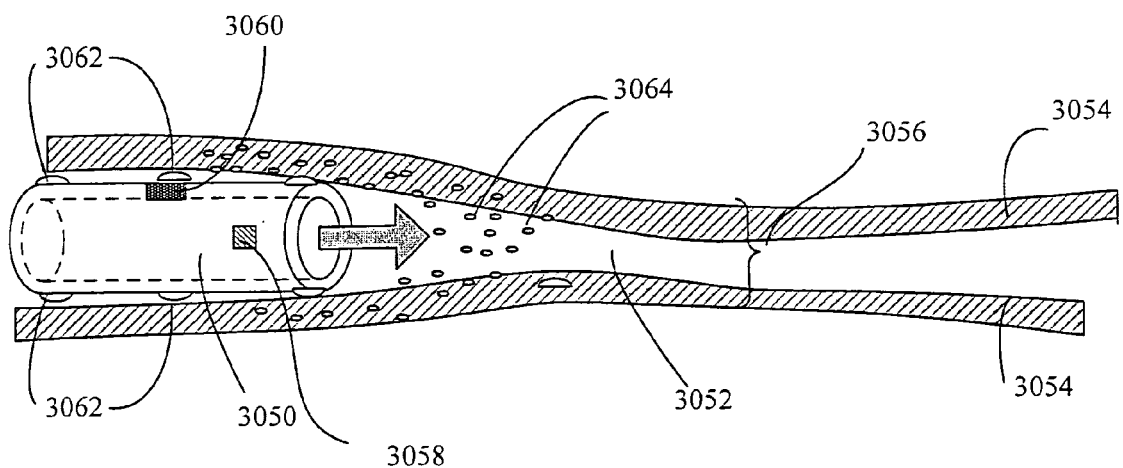

FIGS. 51A and 51B depict a lumen-traveling device 3050 moving through a lumen 3052 that is constricted, e.g. by a vasospasm. Lumen 3052 is defined by lumen walls 3054, which at vasospasm 3056 are constricted, blocking the flow of fluid through the lumen. Lumen-traveling device 3050 includes sensor 3058, which detects the presence of the vasospasm, for example, by detecting reduced flow of fluid through the body lumen. Lumen-traveling device 3050 also includes material release structure 3060, which may be activated in response to detection of vasospasm 3056, to release a vasoactive substance 3064 to produce relaxation of the vasospasm, as illustrated in FIG. 51B. Lumen-traveling device 3050 may also include propelling mechanism 3062, as well as other components not depicted in FIGS. 51A and 51B, but as described elsewhere herein.

Figure 52B:
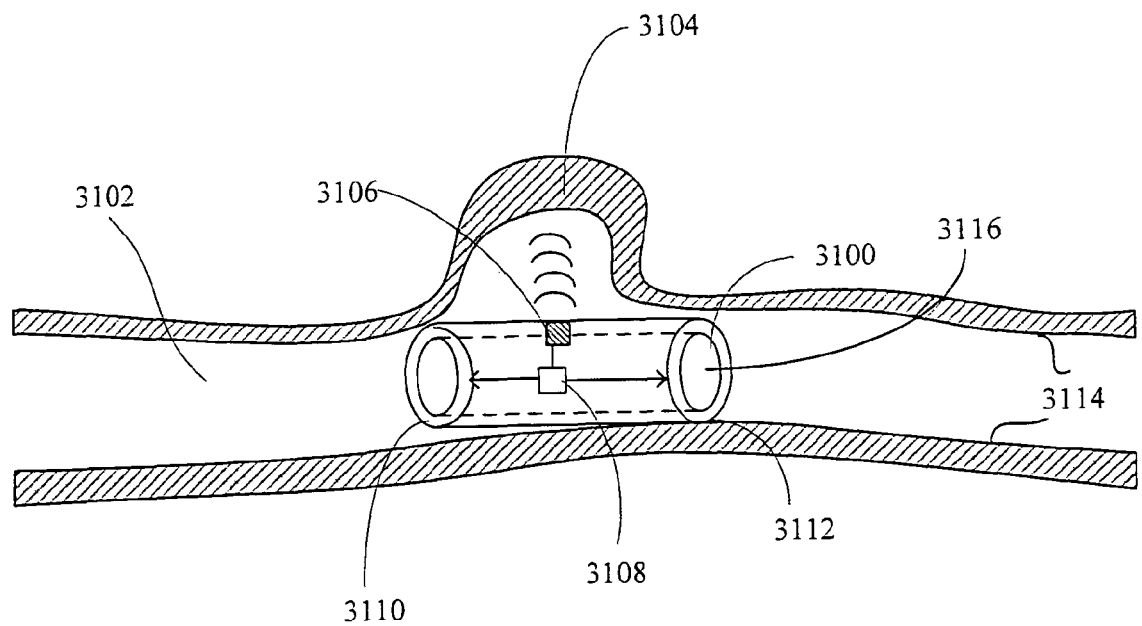
FIGS. 52A and 52B are longitudinal cross-sectional views of an example of the operation of a lumen-traveling device in a body lumen.
Figure 52A:
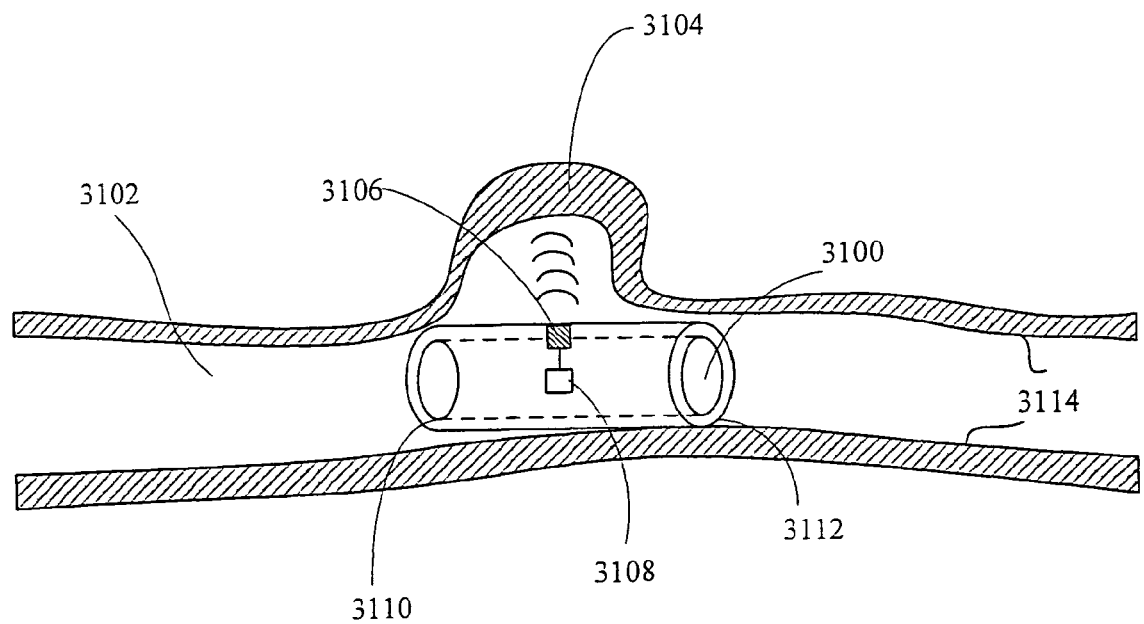

FIGS. 52A and 52B illustrate a further example of a lumen-traveling device 3100 traveling through a body lumen 3102. Body lumen 3102 includes an aneurysm 3104, which may be detected by sensor 3106 on lumen-traveling device 3100. A sense signal generated by sensor 3106 causes response initiation circuitry 3108 to cause activation of active portions 3110 and 3112 to engage walls 3114 of body lumen 3102 to seal off aneurysm 3104 and cause fluid to flow through central lumen 3116 of lumen-traveling device 3100, rather than into aneurysm 3104.

Figure 53A:
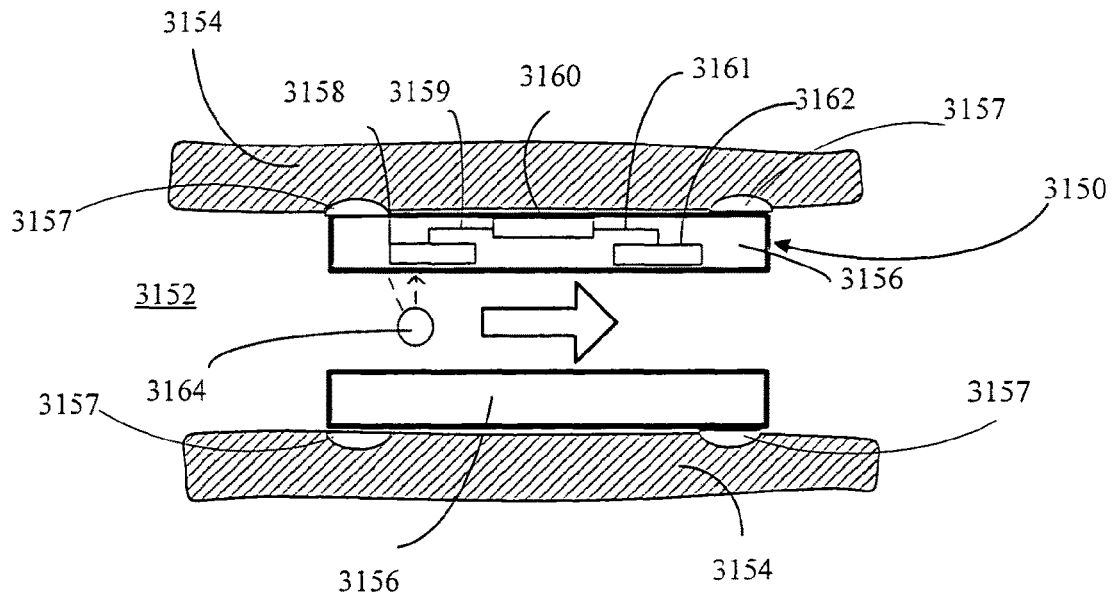
FIGS. 53A and 53B are longitudinal cross-sectional views of an example of the operation of a lumen-traveling device in a body lumen.
Figure 53B:
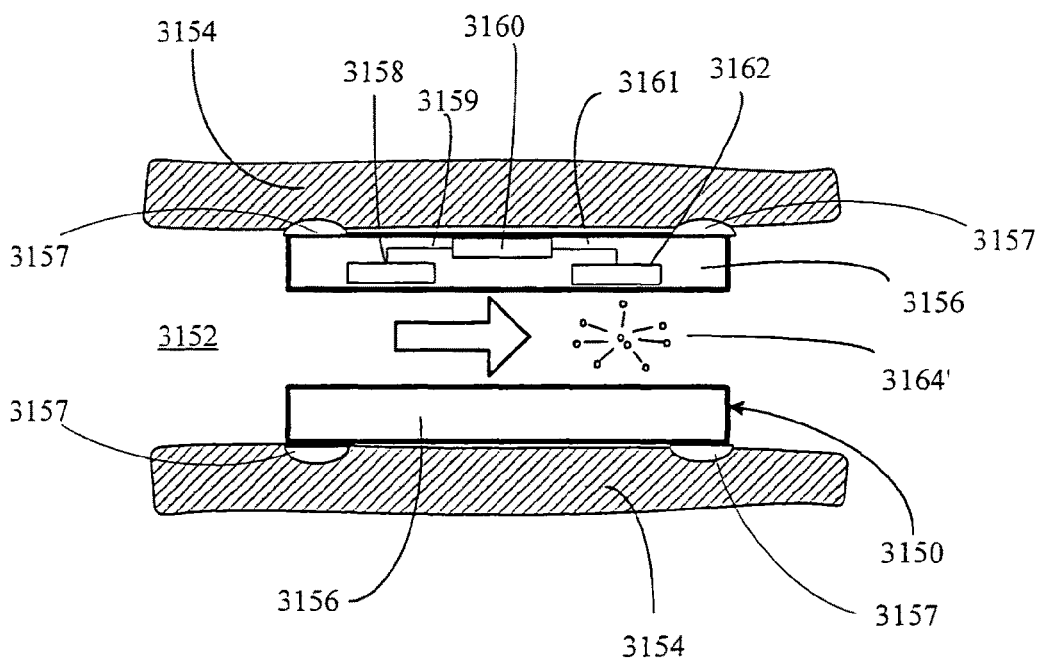

FIGS. 53A and 53B illustrate the treatment of a fluid flowing through a lumen-traveling device 3150 positioned in a body lumen 3152. The lumen-traveling device 3150 may move to a location of interest through the use of propelling mechanism 3157, for example, and then engage the lumen walls to remain in the location of interest and treat fluid moving through it. Alternatively, lumen-traveling device 3150 may treat fluid as it moves through body lumen 3152, including fluid residing in or flowing through the lumen-traveling device. Body lumen 3152 is defined by wall portions 3154. In FIG. 53A, component 3164 of fluid flowing through body lumen 3152 is detected by sensor 3158 in structural element 3156 of lumen-traveling device 3150. Upon detection of component 3164 by sensor 3158, a sense signal 3159 is sent to response initiation circuitry 3160, which generates a response initiation signal 3161. Response initiation signal 3161 is sent to active portion 3162. As shown in FIG. 53B, upon receipt of response initiation signal 3161, active portion 3162 produces a response or action, which in this example is a pulse of energy (e.g. acoustic energy) to destroy component 3164 (indicated following destruction by reference number 3164'). For example, a pulse of acoustic energy may be used to modify a kidney stone in the urinary tract, or to modify another object in another body fluid.

In connection with detection of the presence of a material, location, or other condition(s) of interest within or near the body lumen or the lumen contents, the active portion of the lumen-traveling device or system may be capable of removing, modifying, or destroying a material of interest or treating a location of interest. Modification or destruction of the material of interest may be accomplished by the release of a suitable material (e.g. an anti-coagulant for destroying a blood clot, complement to coat a parasite for recognition by the immune system, or by the release of an anti-inflammatory, biomimetic or biologic to bind to and inactivate an inflammatory mediator such as TNFα, by the delivery of suitable energy (e.g., acoustic energy for modifying a kidney stone, electromagnetic energy such as light to cause a photoreaction, break bonds in a molecule, produce heating, vaporization, ablation, etc., or by delivery of heat or cold or other chemophysical change (e.g. ambient pressure, pH, osmolality, toxic material introduction/generation) for tissue modification, as in ablation of circulating tumor cells or plaque or temperature-induced modification of sperm as it passes through the vas deferens.

In some embodiments of lumen-traveling devices or systems, a lumen-traveling device may be a self-contained device that includes all functionalities necessary for operation of the device. In other embodiments, as illustrated in FIG. 28, 35 or 43, a lumen-traveling system may include a lumen-traveling device that may be placed in a body lumen, and a remote portion that includes a portion of the functionalities of the lumen-traveling system. In some embodiments, all functionalities essential for the operation of the lumen-traveling device may be located on the lumen-traveling device, but certain auxiliary functions may be located in the remote portion. For example, the remote portion may provide monitoring of the operation of the lumen-traveling device or data collection or analysis. The remote portion may be located within the body of the subject at a distance from the lumen-traveling device, or outside the body of the subject, as depicted in FIG. 28. The remote portion may be located near the subject (e.g., carried or worn on the subject's body or placed on a table near the subject) or distant from the subject (e.g. in a different room or building, or in a different city, state or country). Data and/or power signals may be transmitted between lumen-traveling device and remote portion with the use of electromagnetic or acoustic signals, or, in some embodiments, may be carried over electrical or optical links. Various types and/or combinations of types of communications methods and devices may be used, as are known to those of skill in the art. In some embodiments, transmission of information between the lumen-traveling device and one or more remote portions may be via multiple communication channels, in series or in parallel. In general, the remote portion may be placed in a location where there is more space available than within the body lumen, or that is more readily accessible than the body lumen. It is contemplated that a portion of the electrical circuitry portion of the lumen-traveling system (which may include hardware, firmware, software, or any combination thereof) may be located in a remote portion.

Methods of distributing functionalities of a system between hardware, firmware, and software located at two or more sites are well known to those of skill in the art. An electrical circuitry portion of the lumen-traveling system may include, but is not limited to, electrical circuitry associated with the sensor, response initiation circuitry, and electronics associated with the active portion. While the response initiation circuitry has been discussed within the context of electrical circuitry, it will be appreciated that in some embodiments other types of logic/circuitry may be used in place of or in addition to electrical circuitry, and the response initiation circuitry and other circuitry described herein is not limited to electrical circuitry. For example, fluid circuitry, chemo-mechanical circuitry, and other types of logic/circuitry may provide equivalent functionality and may be used in certain embodiments.

In some embodiments, the lumen-traveling device may include an external steering system capable of transmitting a wireless control signal to the structural element. In some embodiments, the lumen-traveling device may include a steering control portion in or on the structural element. Either the steering control portion in or on the structural element or an external steering system may be operated in a number of ways.

A lumen-traveling device may include an imaging marker or tag, and the remote portion may include an external imaging system or be capable of receiving information from an external imaging system. The position of the lumen-traveling device may be correlated with a pre-existing map of the body of the subject, or used to construct a map of the body of the subject. Movement of the lumen-traveling device may be controlled based at least in part upon the location of the lumen-traveling device within the body of the subject. In some embodiments, the lumen-traveling device may include a data storage location in which a map of the body of the subject may be stored. A pre-existing map may be stored in the data storage location before the lumen-traveling device is introduced into the body lumen of the subject. Alternatively, a map may be generated, either with the use of logic on the device or in a remote system, on the basis of information gathered as the device travels through the body of the subject, and the map thus generated may be stored in a memory location on the lumen-traveling device or elsewhere. In some embodiments, rather than storing a map, other positional or locational information may be stored that may be used to control the route taken through the body by the lumen-traveling device. In some embodiments, it may be desired that the device covers some statistical distribution of lumen sizes or locations during its travels, but it may not be necessary that it travel a specific route through the body, and size and location information for already-visited sites may be stored and used in selection of the route to be taken by the device.

Figure 54:
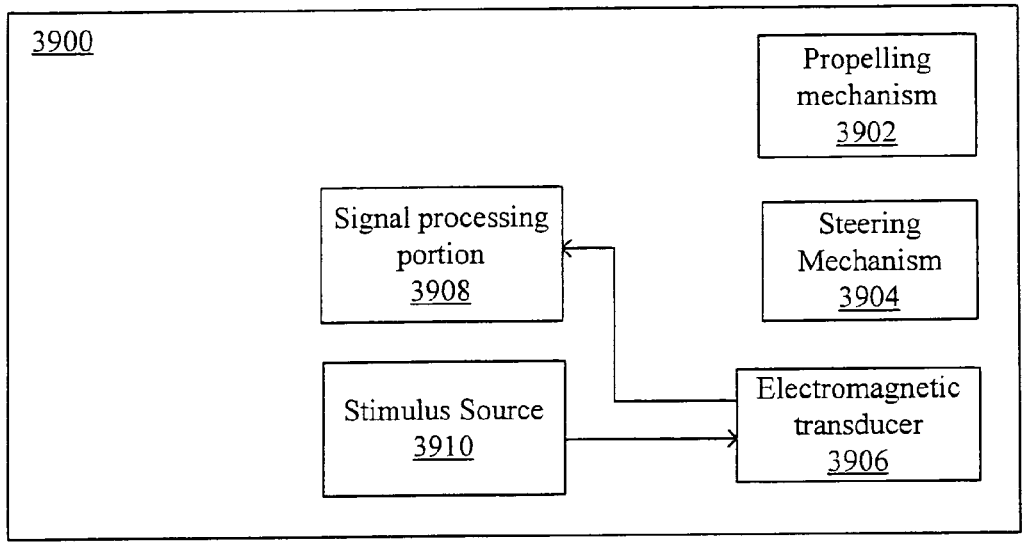
FIG. 54 is a schematic diagram of an embodiment of a lumen-traveling device.

FIG. 54 illustrates an embodiment of a lumen-traveling device 3900 that includes a propelling mechanism 3902 capable of producing directional movement of the lumen-traveling device 3900 through a body lumen; a steering mechanism 3904 capable of modifying a direction of movement of the lumen-traveling device; at least one electromagnetic transducer 3906 configured for at least one of producing an output signal representative of a bioelectromagnetic signal sensed from a target tissue or delivering an electromagnetic stimulus to the target tissue; and at least one of a signal processing portion 3908 capable of processing the output signal from the electromagnetic transducer or a stimulus source 3910 capable of producing an electromagnetic stimulus for delivery to the target tissue with the at least one electromagnetic transducer. As used herein, the term "bioelectromagnetic signal" refers to a signal that is an electrical, magnetic, and/or electromagnetic signal (or combination thereof) that is biological in original, for example as may be detected from neural tissue, cardiac tissue, and various other body tissues, as is known by those of skill in the art. Bioelectromagnetic signals are considered to include electrical and ionic currents, potentials, and/or charges, magnetic fields, fluxes, static and quasi-static electromagnetic fields, for example. A biological signal source may generate both electric and magnetic fields, either or both of which may be detected, and which may in some cases may be related. See J. Malmivuo and R. Plonsey, *Bioelectromagnetism: Principles and Applications of Bioelectric and Biomagnetic Fields*, Oxford University Press, NY, 1995 (Web Version), http://butler.cc.tut.fi/~malmivuo/bem/bembook/, which is incorporated by reference in its entirety; in particular, chapters 11 and 12 discuss the theory underlying bioelectric and biomagnetic measurements, respectively, chapters 13 and 14 discuss electric and magnetic measurements of electric activity of neural tissue, and chapters 15-20 discuss electric and magnetic measurements of the electric activity of the heart.

The lumen-traveling device may include at least one wall-engaging structure capable of engaging a wall of the body lumen to secure the lumen-traveling stimulation device with respect to the wall of the body lumen in the vicinity of a target tissue. A wall-engaging structure may be, for example, an expanding or extending structure, or a structure that engages the lumen wall through other mechanisms, such as suction mechanisms, adhesives, claws or hooks, as described elsewhere herein.

The lumen-traveling device may include a structural element configured to at least intermittently permit the movement of fluid through the body lumen past the lumen-traveling device. In some cases the structural element may permit continuous or near continuous flow of fluid past the lumen-traveling devices, while in others the device may permit fluid movement at some times and obstruct fluid movement at other times, in a controlled and/or predictable manner. The structural element may be a described herein in connection with FIGS. 2A-2D, 3A-3C, and elsewhere herein.

Figure 55:
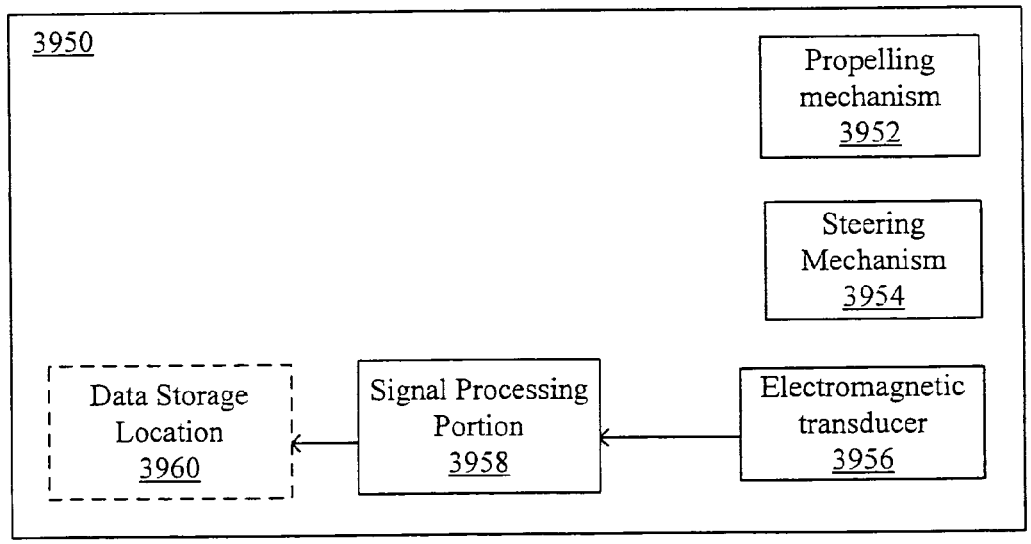
FIG. 55 is a schematic diagram of an embodiment of a lumen-traveling device.

In some embodiments, as illustrated in FIG. 55, the lumen-traveling device 3950 may be configured for recording, and this in addition to a propelling mechanism 3952 capable of producing directional movement of the lumen-traveling device 3950 through a body lumen; a steering mechanism 3954 capable of modifying a direction of movement of the lumen-traveling device, which may include at least one electromagnetic transducer 3956 configured for producing an output signal representative of a bioelectromagnetic signal sensed from a target tissue, and at least one signal processing portion 3958 capable of processing the bioelectromagnetic signal recorded from the target tissue with the at least one electromagnetic transducer. Lumen-traveling device 3950 may also include a data storage location 3960, or other structure for storing the sensed signal. Alternatively, lumen-traveling device 3950 may include a transmitter for transmitting the sensed signal to a remote location.

Figure 56:
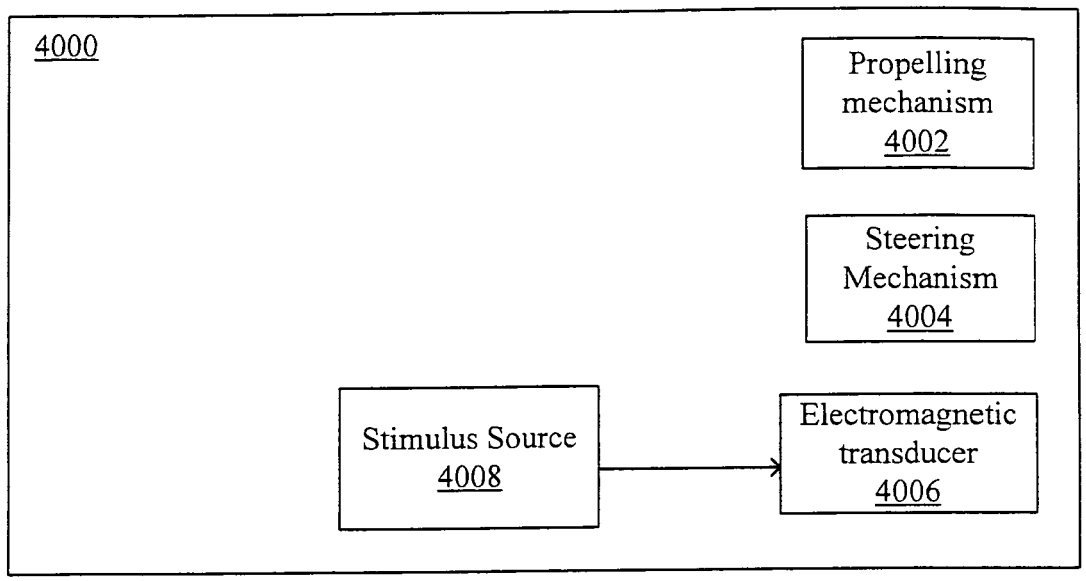
FIG. 56 is a schematic diagram of an embodiment of a lumen-traveling device.

In other embodiments, as illustrated in FIG. 56, the lumen-traveling device 4000 may be configured for stimulation, including a propelling mechanism 4002, steering mechanism 4004, at least one electromagnetic transducer 4006 configured for delivering an electromagnetic stimulus to the target tissue, and at least one stimulus source 4008 capable of producing an electromagnetic stimulus for delivery to the target tissue with the at least one electromagnetic transducer.

Figure 57:
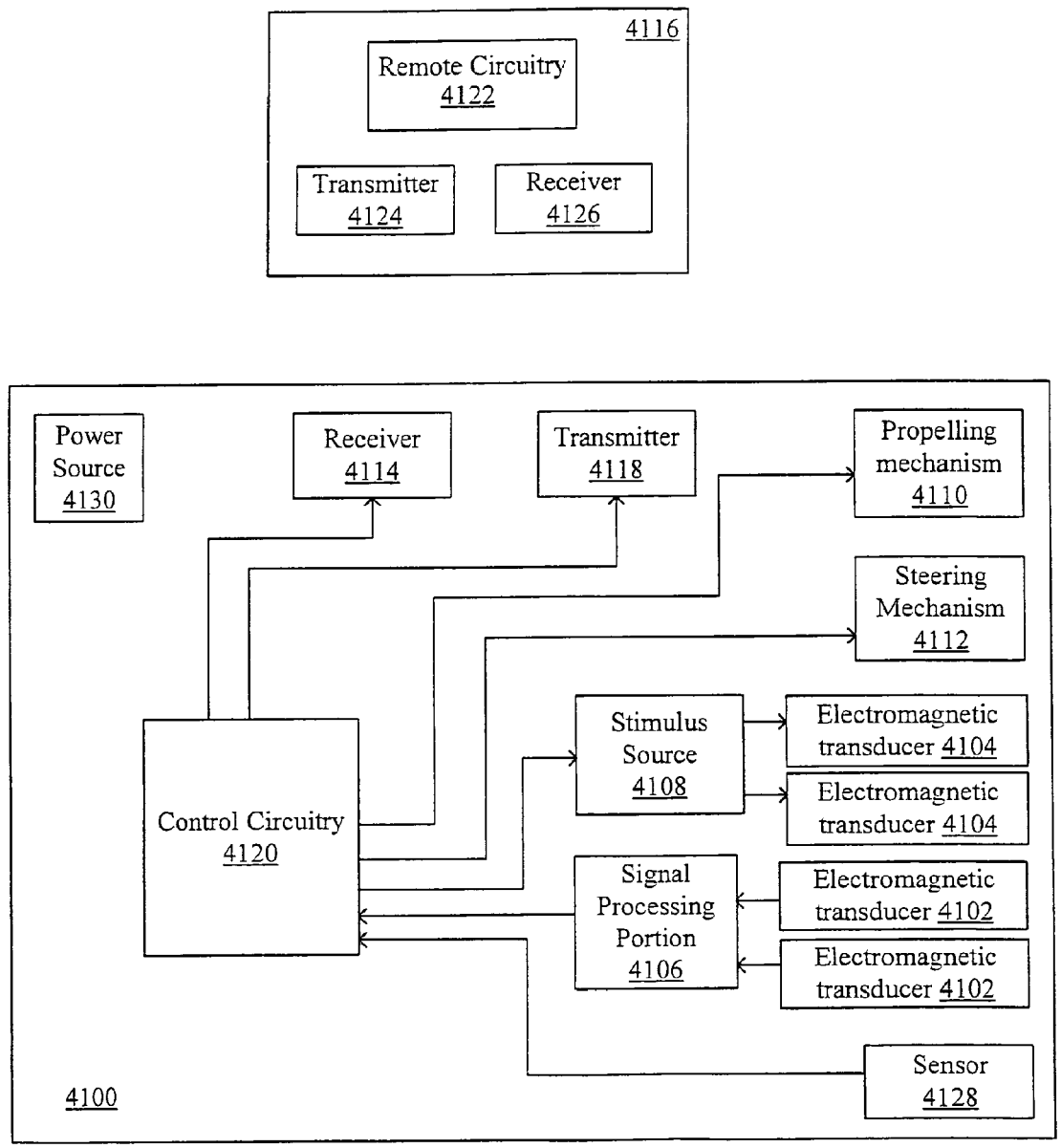
FIG. 57 is a schematic diagram of an embodiment of a lumen-traveling device including a remote portion.

FIG. 57 depicts a version of a lumen-traveling device 4100 that is configured to perform both stimulation and recording. FIG. 57 also depicts and describes additional components that may be included in various embodiments of lumen-traveling biological interface devices that perform only stimulation or only recording, for example as depicted in simplified schematic form in FIGS. 54, 55, and 56. Lumen-traveling device 4100 may include at least one electromagnetic transducer 4102 configured for producing an output signal representative of a bioelectromagnetic signal sensed from a target tissue (in this example two electromagnetic transducers 4102 are depicted, but one or larger numbers of electromagnetic transducers may be used for sensing), at least one electromagnetic transducer 4104 configured for delivering an electromagnetic stimulus to the target tissue (again, in this example two electromagnetic transducers for delivering stimuli are depicted, but one or a larger number of electromagnetic transducers for stimulation may be used), at least one signal processing portion 4106 capable of processing the output signal from the electromagnetic transducer 4102, and at least one stimulus source 4108 capable of producing an electromagnetic stimulus for delivery to the target tissue with the at least one electromagnetic transducer 4104. In some embodiments, the lumen-traveling device 4100 may include at least one electromagnetic transducer that is configured for both producing an output signal representative of a bioelectromagnetic signal sensed from a target tissue and delivering an electromagnetic stimulus to the target tissue; i.e. a single electromagnetic transducer may perform both recording or stimulating functions. In other embodiments, separate structures are used for recording and stimulating. Separate structures may be of the same or different types. Although FIG. 57 illustrates two transducers for recording and two transducers for stimulating, it is contemplated that a single lumen-traveling device may include larger numbers of electromagnetic transducers, which may be used for one or both of recording or stimulation. Naturally, the electronic circuitry associated with the transducers may be modified appropriately; for example, various multiplexing schemes, as known to those of skill in the art, may be used for handling input to and output from multiple transducers. As described previously, lumen-traveling device 4100 may include a propelling mechanism 4110 and steering mechanism 4112. A lumen-traveling device 4100 may also include a receiver 4114 configured to receive a signal from a remote portion 4116. Lumen-traveling device 4100 may include a transmitter 4118 configured to transmit a signal to a remote device. The remote device may be a controller (e.g. remote portion 4116 shown in FIG. 57) or any device that detects, records, and/or re-transmits data from lumen-traveling device 4100. Remote portion 4116 may include remote circuitry 4122, transmitter 4124, and receiver 4126, and may include other components, for example as depicted in connection with FIG. 34. Control circuitry 4120 on lumen-traveling device 4100 may also include additional components, as described generally elsewhere herein, e.g. in connection with FIG. 34.

The lumen-traveling device may include a sensor 4128 capable of sensing a parameter indicative of proximity to the target tissue and generating a sense signal, which may be, for example, an optical sensor, an imaging device, a thermal sensor, a chemical sensor, an electrical or a magnetic sensor or other sensors as described elsewhere herein. The sensor may be used for sensing an anatomical feature, which may be, for example, a branching point. In addition, the lumen-traveling device may include a power source 4130 such as a battery or microbattery, a fuel cell, a bio fuel cell, an inductively driven power receiving structure driven by a remotely applied electromagnetic field, or an energy scavenging device capable of transducing blood flow, heart motion, gastrointestinal tract motion, pulmonary motion, or muscle motion, for example. A lumen-traveling device may be sized to fit within various body lumens, in order to travel to a location in proximity to a stimulation target or source of a biological signal of interest. For example, a lumen-traveling device may be sized to fit within a blood vessel in the brain in order to gain access to stimulation targets or signal source in regions of the brain, or sized to fit within a chamber of the heart for delivering a cardiac pacing stimulus or recording electromagnetic activity from the heart.

In some embodiments the lumen-traveling device may include at least one stimulus source capable of generating a stimulus adapted for controlling or modifying heart activity. In other embodiments the lumen-traveling device may include at least one stimulus source capable of generating a neural stimulus.

Electromagnetic transducers may include electrodes for delivering electrical stimuli and/or sensing electrical or electrochemical signals, coils for generating or sensing magnetic fields, other magnetic field sensing devices such as Hall effect sensors, antennae for delivering or sensing electromagnetic fields, and other types of electromagnetic devices for delivering or sensing electromagnetic fields or energy, including but not limited to ion-sensitive capacitive or electroactive devices, laser diodes, lasers, light emitting diodes, photodiodes, or photodetectors. Some types of electromagnetic transducers may be used for both delivery of electromagnetic stimuli and sensing of bioelectromagnetic signals, while other types of electromagnetic transducers may be suitable for stimulation or sensing, but not both. Various types of electrodes for delivering electrical stimuli and coils for delivering magnetic stimuli and associated signal generation and processing circuitry are known in the art. See for example, BUCHER, VOLKER; GRAF, MICHAEL; STELZLE, MARTIN; NISCH, WILFRIED; "Low-Impedance Thin-Film Polycrystalline Silicon Microelectrodes for Extracellular Stimulation and Recording"; Biosensors and Bioelectronics; bearing a date of 1999; pp. 639-649; Vol. 14; Elsevier Science S.A.; located at: www.elsevier.com/locate/bios; CUI, XINYAN; HETKE, JAMILLE F.; WILER, JAMES A.; ANDERSON, DAVID J.; MARTIN, DAVID C.; "Electrochemical Deposition and Characterization of Conducting Polymer Polypyrrole/PPS on Multichannel Neural Probes"; Sensors and Actuators A Physical; bearing a date of 2001; pp. 8-18; Vol. 93; Elsevier Science B.V.; located at: www.elsevier.com/locate/sna; FIACCABRINO, G. C.; TANG, X.-M.; SKINNER, N.; DE ROOIJ, N. F.; KOUDELKA-HEP, M.; "Electrochemical Characterization of Thin-Film Carbon Interdigitated Electrode Arrays"; Analytica Chimica Acta; bearing a date of 1996; pp. 155-160; Vol. 326; Elsevier Science B.V.; GITTER, ALFRED H.; FROMM, MICHAEL; SCHULZKE, JÖRG-DIETER; "Impedance Analysis for the Determination of Epithelial and Subepithelial Resistance in Intestinal Tissues"; Journal of Biochemical and Biophysical Methods, bearing a date of 1998; pp. 35-46; Vol. 37; Elsevier Science B.V.; JANDERS, M.; EGERT, U.; STELZE, M.; NISCH, W.; "Novel Thin Film Titanium Nitride Micro-Electrodes with Excellent Charge Transfer Capability for Cell Stimulation and Sensing Applications"; IEEE Engineering in Medicine and Biology Society; bearing a date of 1996; pp. 245-247; IEEE; LOEB, G. E.; PECK, R. A.; MARTYNIUK, J.; "Toward the Ultimate Metal Microelectrode"; Journal of Neuroscience Methods; bearing a date of 1995; pp. 175-183; Vol. 63; Elsevier Science B.V.; RIEDMÜLLER, J.; BOLZ, A.; REBLING, H.; SCHALDACH, M.; "Improvement of Stimulation and Sensing Performance of Bipolar Pacemaker Leads"; IEEE Eng. Med. Biol. Soc.; 1992; pp. 2364-2365; IEEE; ROUSCHE, PATRICK J.; PELLINEN, DAVID S.; PIVIN, DAVID P.; WILLIAMS, JUSTIN C.; VETTER, RIO J.; KIPKE, DARYL R.; "Flexible Polyimide-Based Intracortical Electrode Arrays with Bioactive Capability"; IEEE Transactions on Biomedical Engineering; bearing a date March 2001; pp. 361-371; Vol. 48, No. 3; IEEE; RUTTEN, WIM; MOUVEROUX, JEAN-MARIE; BUITENWEG, JAN; HEIDA, CISKA; RUARDIJ, TEUN; MARANI, ENRICO; LAKKE, EGBERT; "Neuroelectronic Interfacing with Cultured Multielectrode Arrays Toward a Cultured Probe"; Proceedings of the IEEE; bearing a date of July 2001; pp. 1013-1029; Vol. 89, No. 7; IEEE; ROBINSON, DAVID A.; "The Electrical Properties of Metal Microelectrodes"; Proceedings of the IEEE; bearing a date of June 1968; pp. 1065-1071; Vol. 56, No. 6, all of which are incorporated herein by reference, for examples of electrodes for use in the central nervous system, peripheral nervous system, gut, or cardiac pacing.

Electrical circuitry and software/firmware for use in the acquisition and processing of bioelectromagnetic signals are described in various references, including the following examples which are incorporated herein by reference: DILLIER, NORBERT; LAI, WAI KONG; ALMQVIST, BENGT; FROHNE, CAROLIN; MÜLLER-DEILE, JOACHIM; STECKER, MATTHIAS; VON WALLENBERG, ERNST; "Measurement of the Electrically Evoked Compound Action Potential Via a Neural Response Telemetry System"; Annals Of Otology Rhinology and Laryngology; bearing a date of May 2002; pp. 407-414; Vol. 111, No. 5; Annals Publishing Company; DONOGHUE, JOHN P.; "Review: Connecting Cortex to Machines: Recent Advances in Brain Interfaces"; Nature Neuroscience Supplement; bearing a date on November 2002; pp. 1085-1088; Vol. 5; Nature Publishing Group; located at: http://www.nature.com/natureneuroscience; GOZANI, SHAI N.; MILLER, JOHN P.; "Optimal Discrimination and Classification of Neuronal Action Potential Waveforms from Multiunit, Multichannel Recordings Using Software-Based Linear Filters"; IEEE Transactions on Biomedical Engineering; bearing a date of April 1994; pp. 358-372; Vol. 41, No. 4; IEEE; GRAY, CHARLES M.; MALDONADO, PEDRO E.; WILSON, MATHEW; MCNAUGHTON, BRUCE; "Tetrodes Markedly Improve the Reliability and Yield of Multiple Single-Unit Isolation from Multi-Unit Recordings in Cat Striate Cortex"; Journal of Neuroscience Methods; bearing a date of 1995; pp. 43-54; Vol. 63; Elsevier Science B.V.; HOFMANN, U. G.; FOLKERS, A.; MÖSCH, F.; HÖHL, D.; KINDLUNDH, M.; NORLIN, P.; "A 64(128)-Channel Multisite Neuronal Recording System"; bearing a date of 2002; pp. 1-4; JI, JIN; NAJAFI, KHALIL, WISE, KENSALL D.; "A Low-Noise Demultiplexing System for Active Multichannel Microelectrode Arrays"; IEEE Transactions of Biomedical Engineering; bearing a date of January 1991; pp. 77-81; Vol. 38, No. 1; IEEE; OLSSON III, R. H.; GULARI, M. N.; WISE, K. D.; "Poster 114: Silicon Neural Recording Arrays with On-Chip Electronics for In-Vivo Data Acquisition"; Microtechnologies in Medicine and Biology; bearing dates of May 2, 2002-May 4, 2002; pp. 237-240; IEEE; and SCHOONHOVEN, R.; STEGEMAN, D. F.; "Models and Analysis of Compound Nerve Action Potentials"; Critical Reviews in Biomedical Engineering; bearing a date of 1991; pp. 47-111; Vol. 19, No. 1; CRC Press, Inc. An example of electronic circuitry for control of stimulation with an implanted electrode system is provided, for example, in LOEB, GERALD E.; PECK, RAYMOND A.; MOORE, WILLIAM H.; HOOD, KEVIN; "BION System for Distributed Neural Prosthetic Interfaces"; Medical Engineering and Physics; bearing a date of 2001; pp. 9-18; Vol. 23; Elsevier Science Ltd.; located at: www.elsevier.com/locate/medengphy which is incorporated herein by reference.

Various references discuss the theoretical basis for electromagnetic sensing and stimulation. Examples (all of which are included herein by reference) include: HODGKIN, A. L.; HUXLEY, A. F.; "A Quantitative Description of Membrane Current and its Application to Conduction and Excitation in Nerve"; Journal of Physiology; bearing a date of 1952; pp. 500-544; Vol. 117; MARKS, WILLIAM B.; LOEB, GERALD E.; "Action Currents, Internodal Potentials, and Extracellular Records of Myelinated Mammalian Nerve Fibers Derived from Node Potentials"; Biophysical Journal; 1976; pp. 655-668; Vol. 16; MCNEAL, DONALD R.; "Analysis of a Model for Excitation of Myelinated Nerve"; IEEE Transactions on Biomedical Engineering; bearing a date of July 1976; pp. 329-337; Vol. BME-23, No. 4; RATTAY, FRANK; "Analysis of Models for Extracellular Fiber Stimulation"; IEEE Transactions on Biomedical Engineering; bearing a date of July 1989; pp. 676-682; Vol. 36, No. 7; IEEE; RATTAY, FRANK, ABERHAM, MATTHIAS; "Modeling Axon Membranes from Functional Electrical Stimulation"; IEEE Transactions on Biomedical Engineering; bearing a date of December 1993; pp. 1201-1209; Vol. 40, No. 12; IEEE; and STRUIJK, JOHANNES JAN; "The Extracellular Potential of a Myelinated Nerve Fiber in an Unbounded Medium and in Nerve Cuff Models"; Biophysical Journal; bearing a date of June 1997; pp. 2457-2469; Vol. 72; Biophysical Society. Related methods and devices, as well as underlying theory, are also described in various texts, for example, K. W. Horch and G. S. Dhillon, Editors, *Neuroprosthetics: Theory and Practice* (Series on Bioengineering and Biomedical Engineering—Vol. 2), World Scientific Publishing Co. Pte. Ltd, Singapore, 2004, and J. Malmivuo and R. Plonsey, *Bioelectromagnetism: Principles and Applications of Bioelectric and Biomagnetic Fields*, Oxford University Press, NY, 1995, http://butler.cc.tut.fi/~malmivuo/bem/bembook/, which is incorporated herein by reference. As used herein, the term "coil" refers to various structures used to generate magnetic fields for use in magnetic stimulation. In some embodiments, a coil may include multiple current-carrying loops and in other embodiments a coil may include a single full or partial loop; while coils may often include generally rounded or circular loops (full or partial) coils are not limited to any particular configuration of loops. Optical stimulation may be performed by methods as described in U.S. Pat. No. 6,921,413, which is incorporated herein by reference.

In various embodiments, the stimulus source may be capable of generating a depolarizing stimulus sufficient to produce depolarization of at least a portion of the target tissue, or a hyperpolarizing stimulus sufficient to produce hyperpolarization of at least a portion of the target tissue. In some embodiments, the stimulus source may be capable of generating a stimulus sufficient to produce functional inhibition of activity of the target tissue, while in other embodiments the stimulus source may be capable of generating a stimulus sufficient to produce functional promotion of activity of the target tissue. Stimuli sufficient to produce functional inhibition or promotion of activity in a target tissue or portion thereof may be determined experimentally or selected based upon information and knowledge available to a person of skill in the art. In some embodiments, the stimulus source may be capable of generating a pre-programmed stimulation pattern. In some embodiments, the stimulus source may be capable of generating a stimulus in response to the sense signal from a sensor, which may be an electrical sensor, a magnetic sensor, or a chemical sensor.

The at least one stimulus source may be capable of generating a stimulus in response to the signal from the remote portion.

The lumen-traveling device of may include at least one signal processing portion capable of processing the output signal from the electromagnetic transducer, for example by amplifying the output signal recorded from the target tissue with the at least one electromagnetic transducer. The signal processing portion may process the output signal by various signal processing methods, including, for example, filtering or performing feature detection/pattern recognition on the output signal.

As illustrated in FIG. 57, in some embodiments, the lumen-traveling device may include at least one signal processing portion capable of processing the output signal from the electromagnetic transducer; and at least one transmitter configured to transmit an output of the at least one signal processing portion to a remote location. Alternatively, or in addition, a transmitter may be configure to transmit information relating to the status, location, or position of the lumen-traveling device or relating to an action taken by the lumen-traveling device (e.g., delivery of an electromagnetic stimulus to a target tissue) to a remote location.

Or, referring back to FIG. 55, the lumen-traveling device may include at least one signal processing portion capable of processing the output signal from the electromagnetic transducer; and at least one data storage location configured for storing an output of the at least one signal processing portion of the lumen-traveling device.

Figure 58:
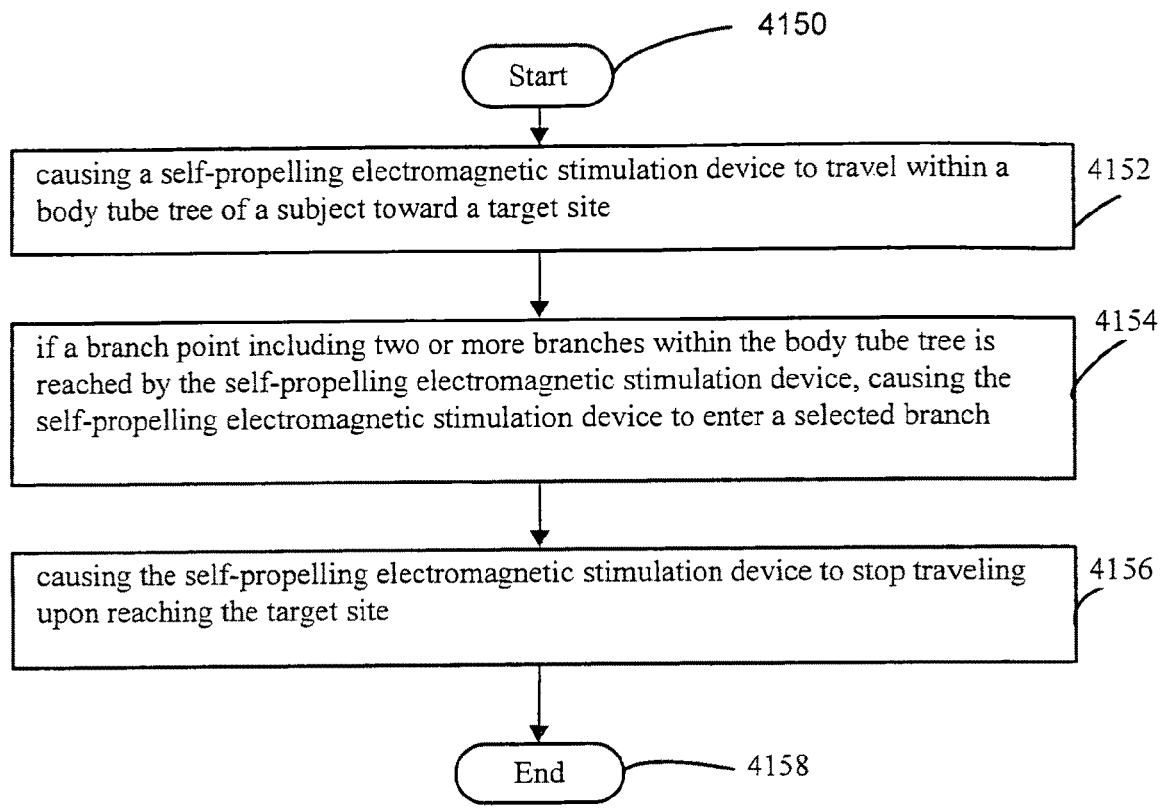
FIG. 58 is a flow diagram of a method of emplacing an electrical stimulation device.

FIG. 58 shows a method of emplacing an electromagnetic stimulation device. The method includes the steps of causing a self-propelling electromagnetic stimulation device to travel within a body tube tree of a subject toward a target site (step 4152); if a branch point including two or more branches within the body tube tree is reached by the self-propelling electromagnetic stimulation device, causing the self-propelling electromagnetic stimulation device to enter a selected branch (step 4154); and causing the self-propelling electromagnetic stimulation device to stop traveling upon reaching the target site (step 4156).

As used herein, the term "self-propelling" refers to a device having an on-board propelling mechanism for generating a propulsion force. The power source for the propelling mechanism may be located on-board the device, or, in some embodiments, power may be beamed or transmitted to the device from an external source. Control circuitry for controlling operation of the propelling mechanism may be on-board the device, or, in some embodiments, located at least in part in a remote portion. For example, causing a self-propelling electromagnetic stimulation device to travel within a body tube tree is considered to include causing the generation of control or driving signal with electronic circuitry on-board or at least in part off-board the device, but is not considered to include the application of an external force to cause movement of the electromagnetic stimulation device.

Figure 59:
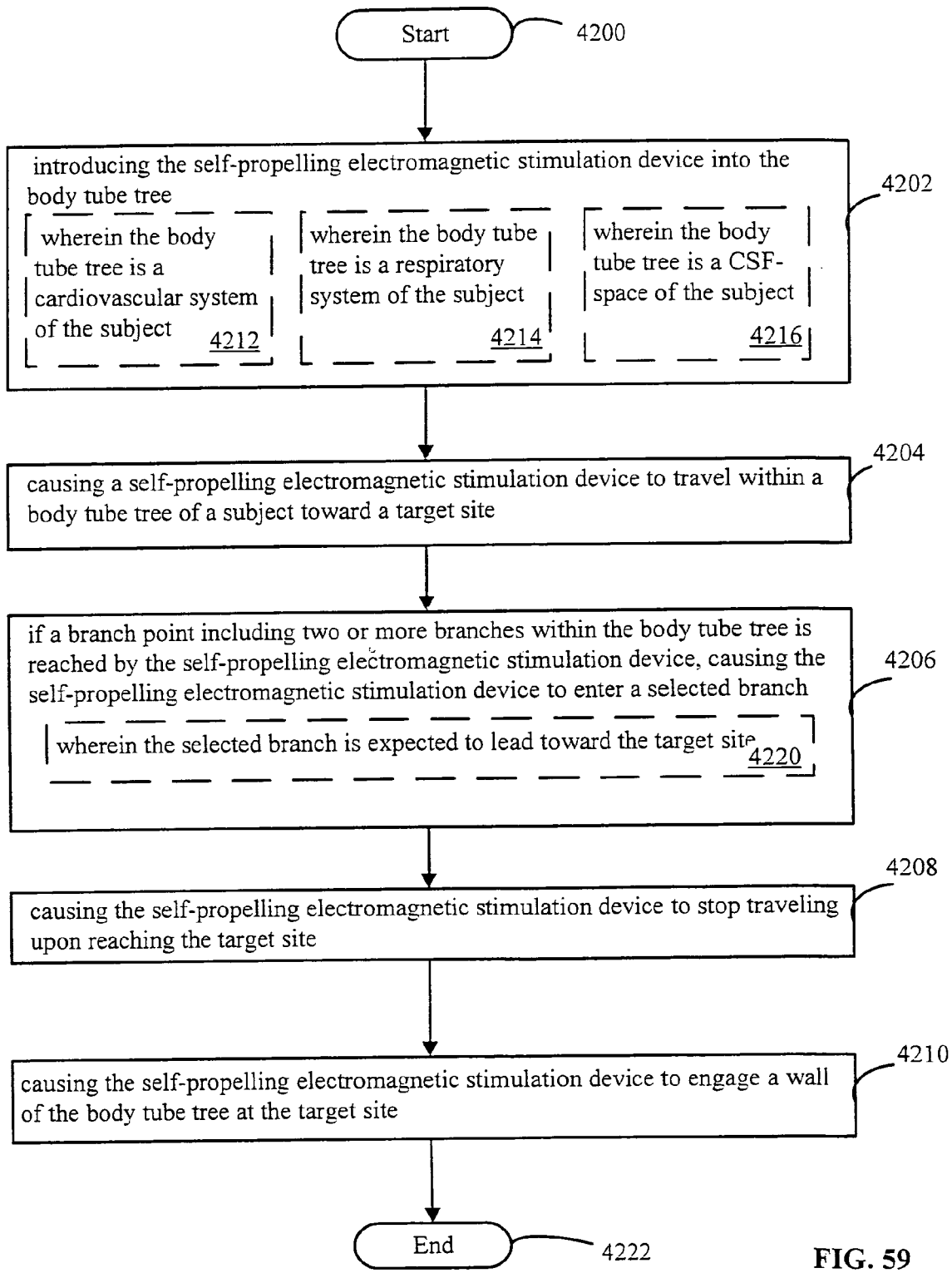
FIG. 59 is a flow diagram showing variations of the method of FIG. 58.

FIG. 59 illustrates possible expansions of the method shown in FIG. 58, in which the method may include a step of introducing the self-propelling electromagnetic stimulation device into the body tube tree at 4202; causing a self-propelling electromagnetic stimulation device to travel within a body tube tree of a subject toward a target site (step 4204); if a branch point including two or more branches within the body tube tree is reached by the self-propelling electromagnetic stimulation device, causing the self-propelling electromagnetic stimulation device to enter a selected branch (step 4206); and causing the self-propelling electromagnetic stimulation device to stop traveling upon reaching the target site (step 4208). The method may also include causing the self-propelling electromagnetic stimulation device to engage the wall of the body tube tree at the target site, as shown at step 4210. The body tube tree into which the self-propelling electromagnetic stimulation device is introduced may be the cardiovascular system of the subject, as indicated at 4212, the respiratory system of the subject, as indicated at 4214, or CSF-space of the subject, as indicated at 4216. The branch which the self-propelling electromagnetic stimulation device enters at step 4206 may be selected because it is expected to lead toward the target site, as indicated at 4220; or the branch may be selected on some other basis (e.g., size, orientation, direction of fluid flow through the branch, etc.).

Figure 60:
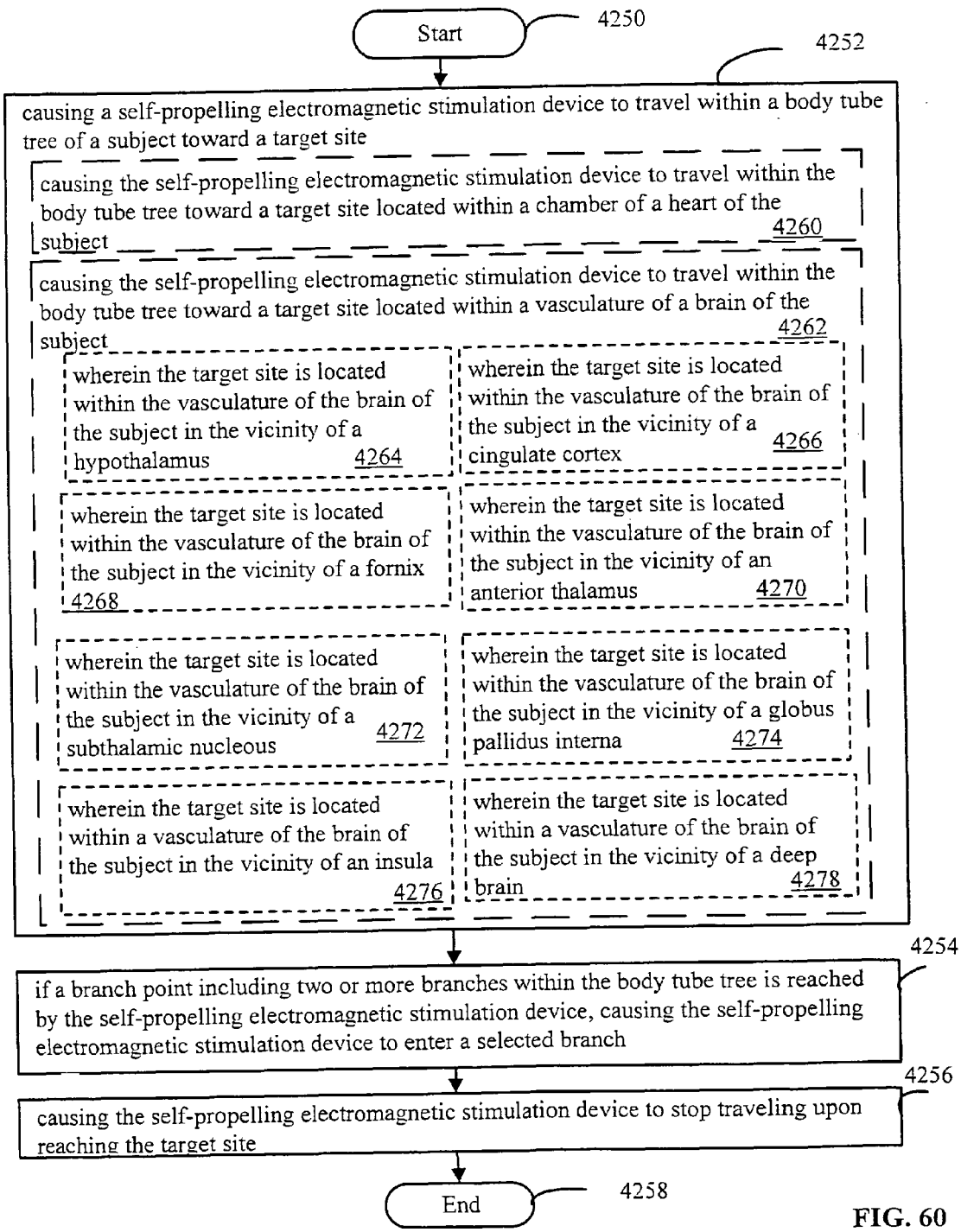
FIG. 60 is a flow diagram showing variations of the method of FIG. 58.

FIG. 60 shows a method of emplacing a self-propelling electromagnetic stimulation device generally as shown in FIG. 58, which includes causing a self-propelling electromagnetic stimulation device to travel within a body tube tree of a subject toward a target site (step 4252); if a branch point including two or more branches within the body tube tree is reached by the self-propelling electromagnetic stimulation device, causing the self-propelling electromagnetic stimulation device to enter a selected branch (step 4254); and causing the self-propelling electromagnetic stimulation device to stop traveling upon reaching the target site (step 4256). As indicated in dashed box 4260, the method may include causing the self-propelling electromagnetic stimulation device to travel within the body tube tree toward a target site located within a chamber of the heart of the subject. Alternatively, as shown in dashed box 4262, the method may include causing the self-propelling electromagnetic stimulation device to travel within the body tube tree toward a target site located within the vasculature of the brain of the subject. Here and elsewhere, dashed boxes are used to indicate optional and/or alternative steps in a flow diagram. The target site may be located within the vasculature of the brain in the vicinity of a stimulation target including tissue responsive to electromagnetic stimulation—examples of which include the hypothalamus (as indicated at 4264), cingulate cortex (as indicated at 4266), fornix (as indicated at 4268), anterior thalamus (as indicated at 4270), subthalamic nucleus (as indicated at 4272), globus pallidus interna (as indicated at 4274), insula (as indicated at 4276), or deep brain (as indicated at 4278).

A large number of brain areas may be suitable sites for stimulation, including but not limited to the myelencephalon or hindbrain, including the medulla oblongata (medullary pyramids, or nuclei including arcuate nucleaus of medulla, solitary nucleus, hypoglossal nucleus, nucleus ambiguus, olivary body, inferior olivary nucleus, cuneate nucleus, accessory cuneate neucleus, gracile nucleus, inferior salivatory nucleus, raphe nuclei [obscurus, magnus, and pallidus], area postrema, posterior nucleus of vagus nerve); the metencephalon, including the pons (pontine tegmentum, superior salivary nucleus, trapezoid body, pontine nuclei [superior olivary nucleus, trigeminal nerve nuclei, abducens nucleus, facial motor nucleus, cochlear nuclei vestibular nuclei], locus ceruleus, paramedian pontine reticular formation, nucleus centralis superior) and the cerebellum (cerebellar vermis, cerebellar hemispheres [anterior lobe, posterior lobe, flocculonodular lobe], cerebellar nuclei, fastigial nucleus, globose nucleus, emboliform nucleus, dentate nucleus); the mesencephalon or midbrain, including the tectum (inferior colliculi and superior colliculi), the cerebral peduncle, the midbrain tegmentum (ventral tegmental area, Red Nucleus, substantia nigra, and crus cerebri), and the pretectum; the diencephalon, including epithalamus (pineal body, habenular nuclei stria medullares, and tenia thalami), the thalamus including the anterior nuclear group (anteroventral nucleus, anterodorsal nucleus, anteromedial nucleus), medial nuclear group (dorsomedial nucleus, midline nuclear group, paratenial nucleus, paraventricular nucleus, reniens nucleus, rhomboidal nucleus), intralaminar nuclear group (centromedial nucleus, parafascicular nucleus, paracentral nucleus, central lateral nucleus, central medial nucleus), lateral nuclear group (lateral dorsal nucleus, lateral posterior nucleus, pulvinar), ventral nuclear group (ventral anterior nucleus, ventral lateral nucleus, ventral posterior nucleus), metathalamus (medial geniculate body, lateral geniculate body) and thalamic reticular nucleus, the hypothalamus (optic chiasm, arcuate nucleus, subformical organ, preoptic area, suprachiasmatic nucleus, supraoptic nucleus, periventricular nucleus, paraventricular nucleus, ventromedial nucleus, dorsomedial nucleus, lateral hypothalamus, infundibulum, tuber cinereum, tuberal region, mammillary bodies, mammillary nucleus), the subthalamus (thalamic nucleus, zona incerta), and the pituitary gland (neurohypophysis, intermediate pituitary, adenohypophysis); the Telencephalon or cerebrum including the cerebral hemispheres, which include the white matter (corona radiata, internal capsule, external capsule, extreme capsule, arcuate fasciculus, uncinate fasciculus), subcortical structures (amygdala, including central nucleus, medial nucleus, cortical and basomedial nuclei, and lateral and basolateral nuclei hippocampus, including dentate gyrus and cornu ammonis; and basal ganglia including striatum, nucleus lentiformis, globus pallidus, medial pallidum (GPi), lateral pallidum (GPe), putamen, nucleus caudatus, claustrum, corpus amygdaloideum), Rhinencephalon (olfactory bulb, piriform cortex, anterior olfactory nucleus, olfactory tract, anterior commissure), cerebral cortex (frontal lobe including primary motor cortex and Brodmann area 4, prefrontal cortex, supplementary motor cortex, premotor cortex) and Brodmann areas 6, 8, 9, 10, 11, 24, 25, 32, 33, 44, 45, 46, 47), temporal lobe including primary auditory cortex-A1, A2, inferior temporal cortex, posterior inferior temporal cortex, and Brodmann areas 9, 20, 21, 22, 27, 34, 35, 36, 37, 38, 41, 42), parietal lobe including primary somatosensory cortex-S1, S2, posterior parietal cortex, precuneus, Brodmann areas 1, 2, 3, 5, 7, 23, 26, 29, 31, 39, 40, occipital lobe including primary visual cortex (V1), V2, cuneus and Brodmann areas 17, 18, and 19, insula, cingulate cortex (anterior cingulate, posterior cingulate, Brodmann areas 23, 24, 26, 29, 30, 31 and 32); and the limbic system, including the amygdala, cingulate gyrus, fornicate gyrus, hippocampus, hypothalamus, mammillary body, nucleus accumbens, orbitofrontal cortex, and parahippocampal gyrus. In addition to brain structures, other portions of the nervous system, both central (e.g. spinal canal, retina, brain, etc.) and peripheral may be responsive to electrical, magnetic and/or other forms of stimulation. In addition, central and peripheral portion of the nervous system may also be sources of bioelectric activity that may be detected with a lumen-traveling biological interface device. Other tissues (including smooth, skeletal, and cardiac muscles) may also be sources of bioelectric/biomagnetic signals and may also be responsive to electrical, magnetic, chemical or other stimuli.

Figure 61:
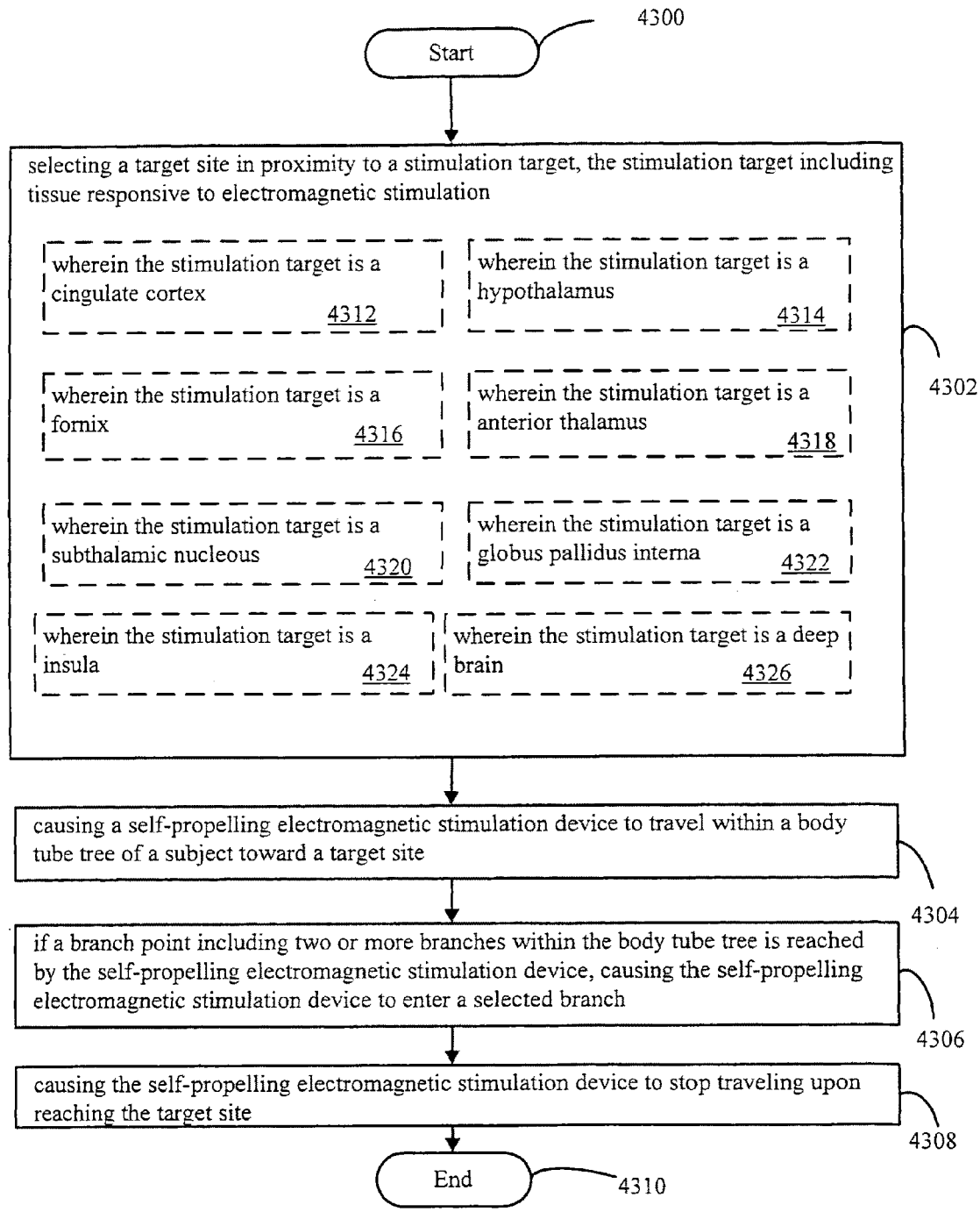
FIG. 61 is a flow diagram showing variations of the method of FIG. 58.

FIG. 61, shows a method of emplacing a self-propelling electromagnetic stimulation device that is an expansion of the method shown in FIG. 58, and includes selecting a target site in proximity to a stimulation target, the stimulation target including tissue responsive to electromagnetic stimulation (at 4302); causing a self-propelling electromagnetic stimulation device to travel within a body tube tree of a subject toward a target site (step 4304); if a branch point including two or more branches within the body tube tree is reached by the self-propelling electromagnetic stimulation device, causing the self-propelling electromagnetic stimulation device to enter a selected branch (step 4306); and causing the self-propelling electromagnetic stimulation device to stop traveling upon reaching the target site (step 4308). For example the stimulation target may be the cingulate cortex, as indicated at 4312, the hypothalamus, as indicated at 4314, the fornix, as indicated at 4316, the anterior thalamus, as indicated at 4318, the subthalamic nucleus as indicated at 4320, the globus pallidus interna, as indicated at 4322, the insula, as indicated at 4324, or the deep brain, as indicated at 4326.

Activity in certain brain regions is associated with certain moods, feelings, sensations, or behaviors, and stimulation in these brain areas (which may be excitatory/promoting or inhibitory) may be used to up- or down-regulate these moods or behaviors. For example, stimulation of the hypothalamus is thought to produce a sensation of satiety, which may reduce overeating leading to obesity (see for example U.S. Pat. No. 5,782,798; also see U.S. Pat. No. 6,950,707 relating to stimulation to treat obesity, which are incorporated herein by reference; stimulation of the cingulate cortex or vagus nerve may reduce depression; injury to the insula may diminish addictive behaviors such as smoking, suggesting that stimulation in this area could influence addictive behaviors (see N. H. Naqvi et al., "Damage to the Insula Disrupts Addiction to Cigarette Smoking," Science Vol. 315, pp. 531-534, 2007, doi:10.1126/science.1135926, incorporated herein by reference); stimulation of the fornix and anterior thalamus (thalamic nucleus) may be used in the treatment of epilepsy (see U.S. Pat. Nos. 7,003,352; 6,597,954; 6,134,474; and 6,337,997 regarding stimulation of various brain areas to treat epilepsy, all of which are incorporated herein by reference), stimulation of the subthalamic nucleus may reduce Parkinson's, and stimulation of the globus pallidus interna may suppress tremor. Stimulation of various areas may reduce schizophrenia or bipolar disorder. A number of patents, all of which are incorporated herein by reference, describe methods of electrically, magnetically and/or chemically stimulating various tissues to treat various problems, including stimulating various brain areas to treat neurological disorders (U.S. Pat. Nos. 6,128,538 and 6,016,449) or sleep disorders (U.S. Pat. No. 5,335,657); stimulating vagus nerve to treat dementia (U.S. Pat. No. 5,269,303); stimulating deep brain or other areas to treat pain and/or headaches (U.S. Pat. Nos. 7,013,177; 6,735,475; and 6,402,678); stimulating deep brain to treat Parkinsons disease (U.S. Pat. No. 6,920,359); stimulating deep brain or motor cortex to suppress essential tremor (U.S. Pat. No. 6,959,215); and stimulating stomach and/or small intestine to treat gastrointestinal disorders (U.S. Pat. No. 6,591,137).

Many stimulation/recording targets may be accessed via one or more body lumens. For example, the hippocampus may be accessed via the temporal horn of the lateral ventricles. Deep brain structures (e.g. the hypothalamus) may be accessed via the third ventricle, or via various blood vessels. Basal ganglia may be accessed via the lenticulostriate artery or thalamostriate vessels. Regions of the heart may be accessed through the chambers of the heart. Selection of suitable body lumens for use as target sites for providing access to a stimulation/recording target may be based upon anatomical considerations. One consideration may be proximity of the body lumen (or a region thereof) to the stimulation/recording target. Proximity may be determined simply on the basis of physical distance, or may take into account tissue properties that influence the transmission of stimuli/signals between the target site and the stimulation/recording target (e.g., electrical conductivity or capacitance, magnetic permittivity or permeability, etc.). Another consideration may be the ability to position the lumen-traveling device in the body lumen without producing unwanted effects; for example, it may be undesirable to block the supply of blood or other fluid to a tissue region or to prevent drainage of a fluid (blood, CSF, etc.) from a tissue region, so a body lumen that is small enough that the presence of a lumen-traveling device would significantly diminish fluid movement in the body lumen may be a less desirable target site, as might be a body lumen that is the single source/drainage for a tissue region. Conversely, a body lumen that is large relative to the lumen-traveling device, or that is one of multiple body lumens supplying or draining a tissue region may be a more desirable target site.

Figure 62:
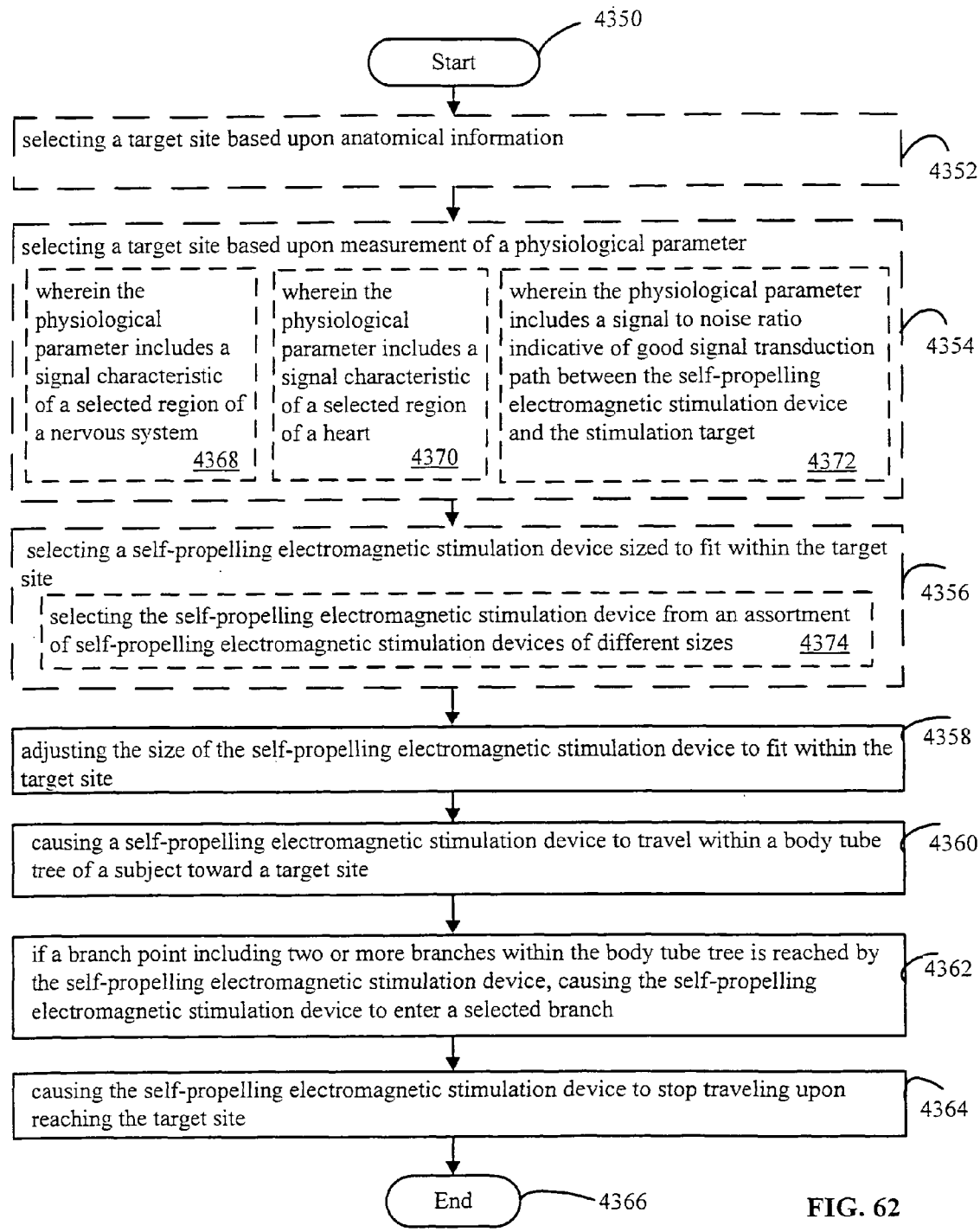
FIG. 62 is a diagram showing variations of the method of FIG. 58.

As shown in FIG. 62, a method of emplacing an self-propelling electromagnetic stimulation device may include selecting a target site based upon anatomical information as indicated at step 4352 (e.g., position within a particular blood vessel or cerebral ventricle known to be close to a particular brain structure may be detected by imaging) or selecting a target site based upon measurement of a physiological parameter, as indicated at step 4354. The physiological parameter may include a signal characteristic of a selected region of the nervous system (as shown at 4368) or a signal characteristic of a selected region of the heart (as shown at 4370), or the physiological parameter may include a signal-to-noise ratio indicative of good signal transduction path between the self-propelling electromagnetic stimulation device and the stimulation target (as shown at 4372).

As indicated at step 4356, the method may include selecting a self-propelling electromagnetic stimulation device sized to fit within the target site, for example by selecting the self-propelling electromagnetic stimulation device from an assortment of self-propelling electromagnetic stimulation devices of different sizes as indicated at step 4374. Alternatively, in some cases, as indicated step 4358, the size of the self-propelling electromagnetic stimulation device may be adjusted to fit within the target site. Further steps of causing a self-propelling electromagnetic stimulation device to travel within the body tube tree of a subject toward a target site, at step 4360; if a branch point including two or more branches within the body tube tree is reached by the self-propelling electromagnetic stimulation device, causing the stimulation device to enter a selected branch (step 4362); and causing the self-propelling electromagnetic stimulation device to stop traveling upon reaching the target site (step 4364) are as described elsewhere herein.

Figure 63:
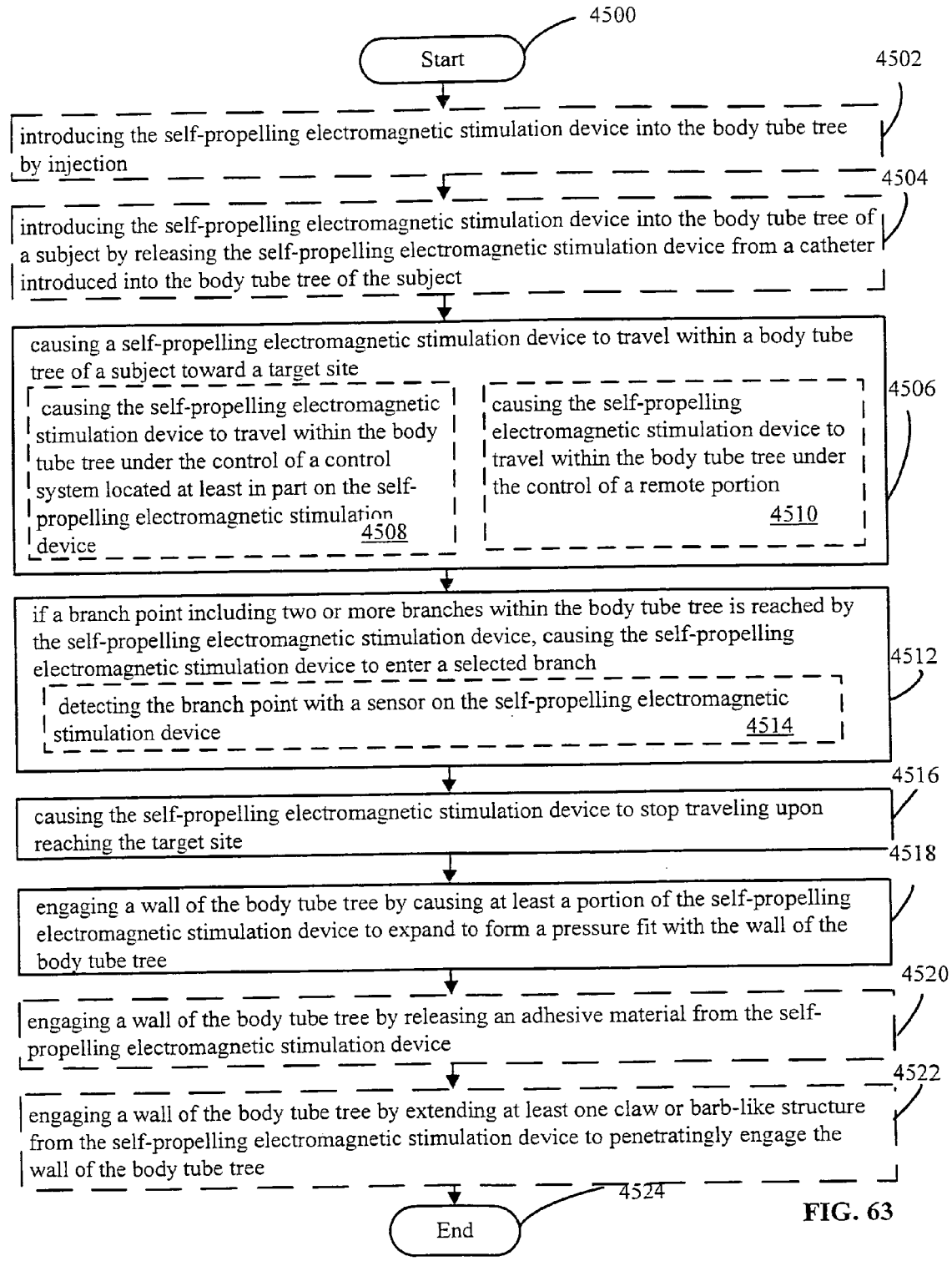
FIG. 63 is a diagram showing variations of the method of FIG. 58.

FIG. 63 depicts a further variant of the basic method depicted in FIG. 58, showing several additional possible steps. For example, the method may include the step of introducing the self-propelling electromagnetic stimulation device into the body tube tree by injection, as shown at 4502, or, alternatively, releasing the self-propelling electromagnetic stimulation device from a catheter introduced into the body tube tree of the subject, as shown at 4504.

As shown at step 4506, the method may include causing the self-propelling electromagnetic stimulation device to travel within the body tube tree of a subject toward a target site, which may be performed under the control of a remote portion, as shown at 4508, or alternatively, under the control of a control system located at least in part on the self-propelling electromagnetic stimulation device, as shown at 4510. As shown at 4512, if a branch point including two or more branches within the body tube tree is reached by the self-propelling electromagnetic stimulation device, the method may include causing the self-propelling electromagnetic stimulation device to enter a selected branch. For example, the method may include detecting the branch point with a sensor on the self-propelling electromagnetic stimulation device, as indicated at 4514. As shown in previous figures, the method may include causing the self-propelling electromagnetic stimulation device to stop traveling upon reaching the target site, as shown at 4516. The method may include engaging a wall of the body tube tree by several possible alternative methods: the method may include engaging a wall of the body tube tree by causing at least a portion of the self-propelling electromagnetic stimulation device to expand to form a pressure fit with the wall of the body tube tree (step 4518), by releasing an adhesive material from the self-propelling electromagnetic stimulation device (step 4520), or extending at least one claw or barb-like structure from the self-propelling electromagnetic stimulation device to penetratingly engage the wall of the body tube tree (step 4522).

Figure 64:
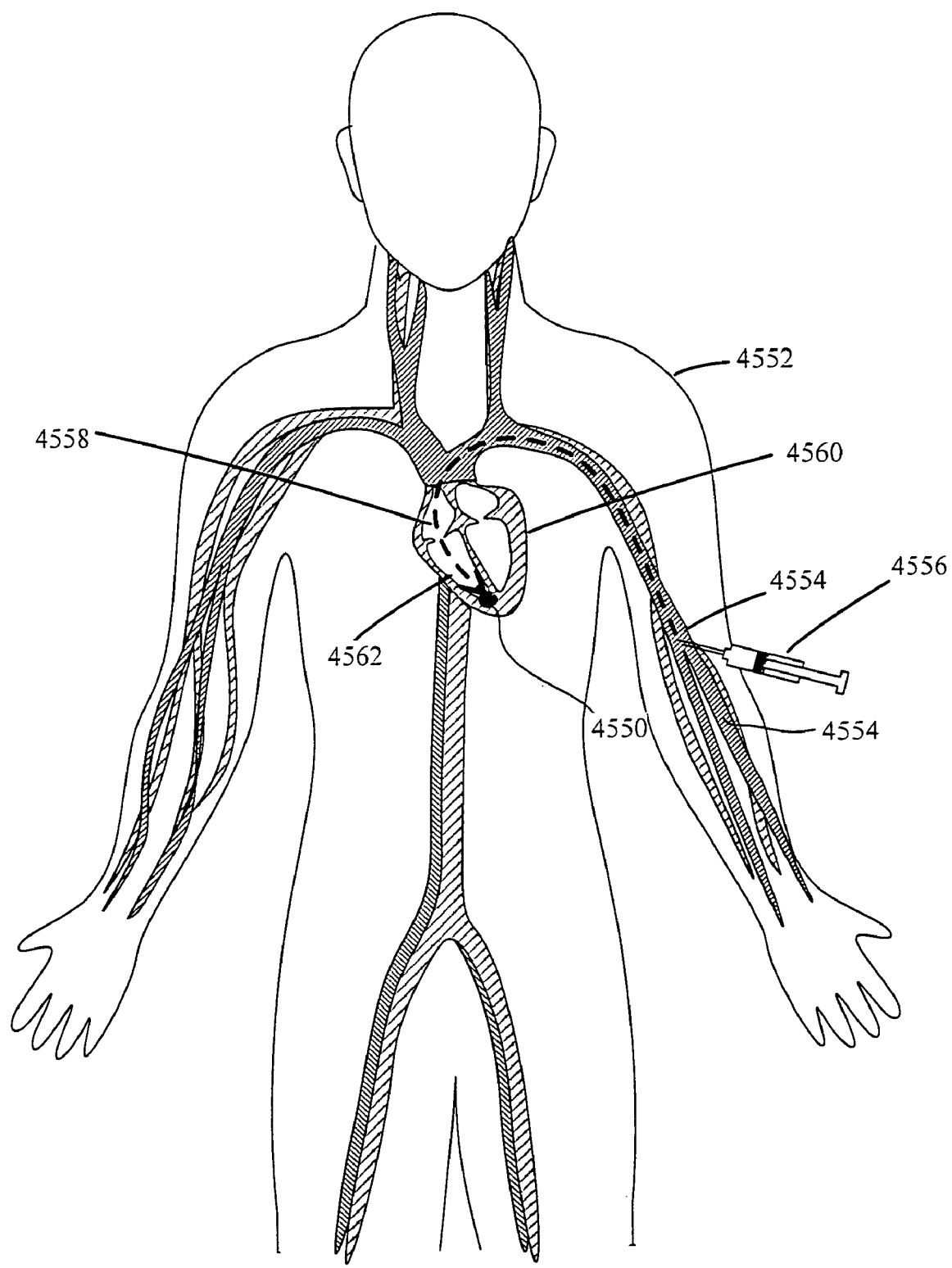
FIG. 64 illustrates the delivery of a lumen-traveling device into the body by injection.

FIG. 64 illustrates the introduction of a self-propelling electromagnetic stimulation device 4550 into the body 4552 of a subject by injection. In the example depicted in FIG. 64, the self-propelling electromagnetic stimulation device 4550 is a cardiac stimulation device (e.g. a portion of a pacemaker). Self-propelling electromagnetic stimulation device 4550 is injected into arm vein 4554 (e.g. the cephalic vein) with hypodermic needle 4556, and travels in the direction of the blood flow to right atrium 4558 of heart 4560, along the route indicated by the dashed arrow. From right atrium 4558, the self-propelling electromagnetic stimulation device travels may travel to the base of right ventricle 4562, where it may reside and deliver cardiac pacing stimuli.

Figure 65:
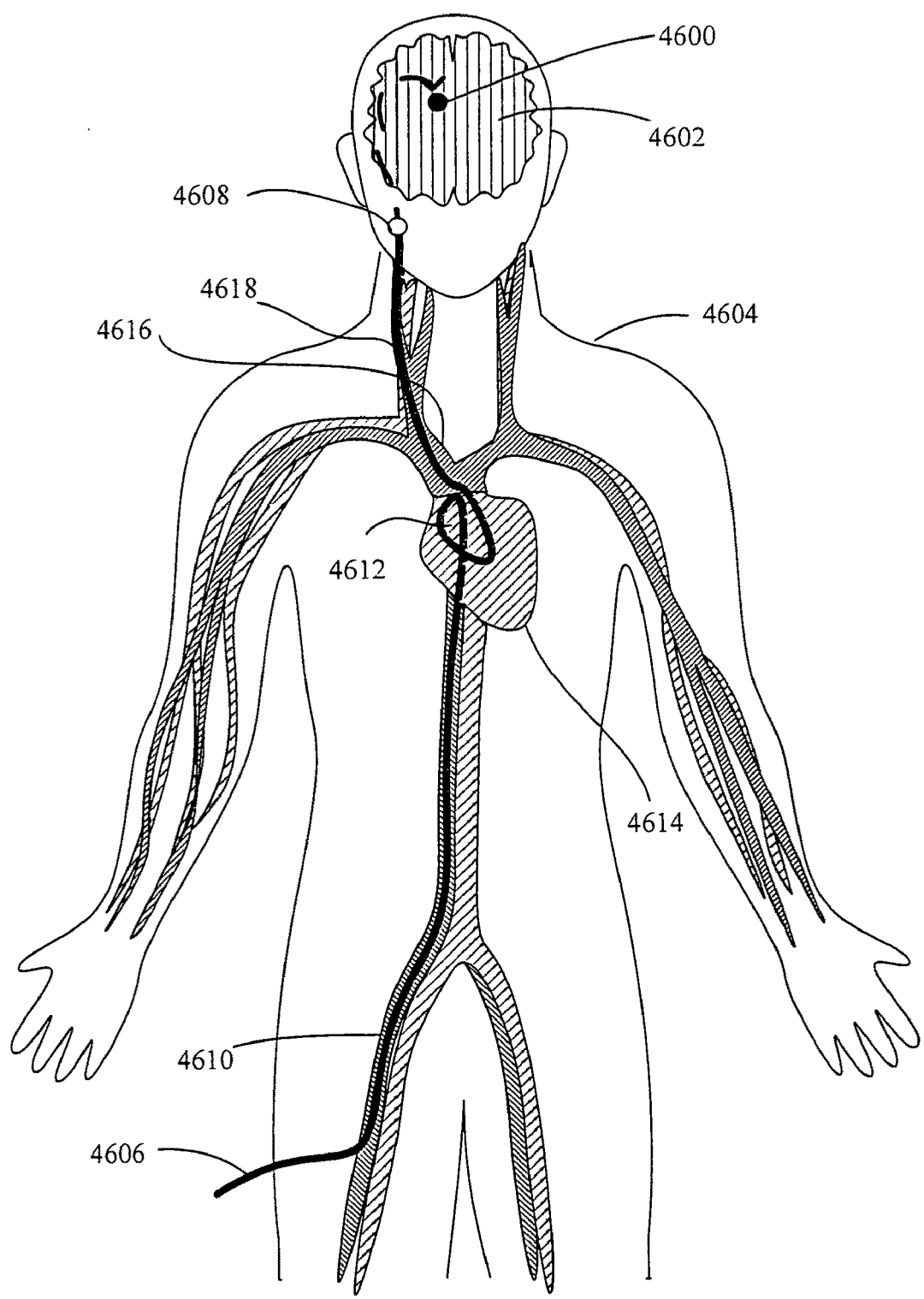
FIG. 65 illustrates the release of a lumen-traveling device from a catheter.

FIG. 65 illustrates the introduction of a lumen-traveling biological interface device 4600 (e.g. a neural stimulation and/or sensing device) into the brain 4602 of a subject 4604 with a catheter 4606. Catheter 4606, carrying lumen-traveling biological interface device (the position of the lumen-traveling biological interface device on the catheter is indicated by an open circle 4608), is introduced into a vein (e.g. femoral 4610 as depicted in FIG. 65, or alternatively an arm vein as shown in FIG. 64). Catheter 4606 is advanced into the right atrium 4612 of the heart 4614, through heart 4614, and out via aorta 4616, and into carotid artery 4618. Lumen-traveling biological interface device 4600 may then be released from catheter 4606 and may travel through the brain vasculature (e.g. on the route indicated by the dashed line) until it reaches a target site within the brain. Catheter and device configuration may be modified in some embodiments to carry more than one device on the catheter in order to accomplish delivery of two or more devices at one time with a catheter.

Figure 66:
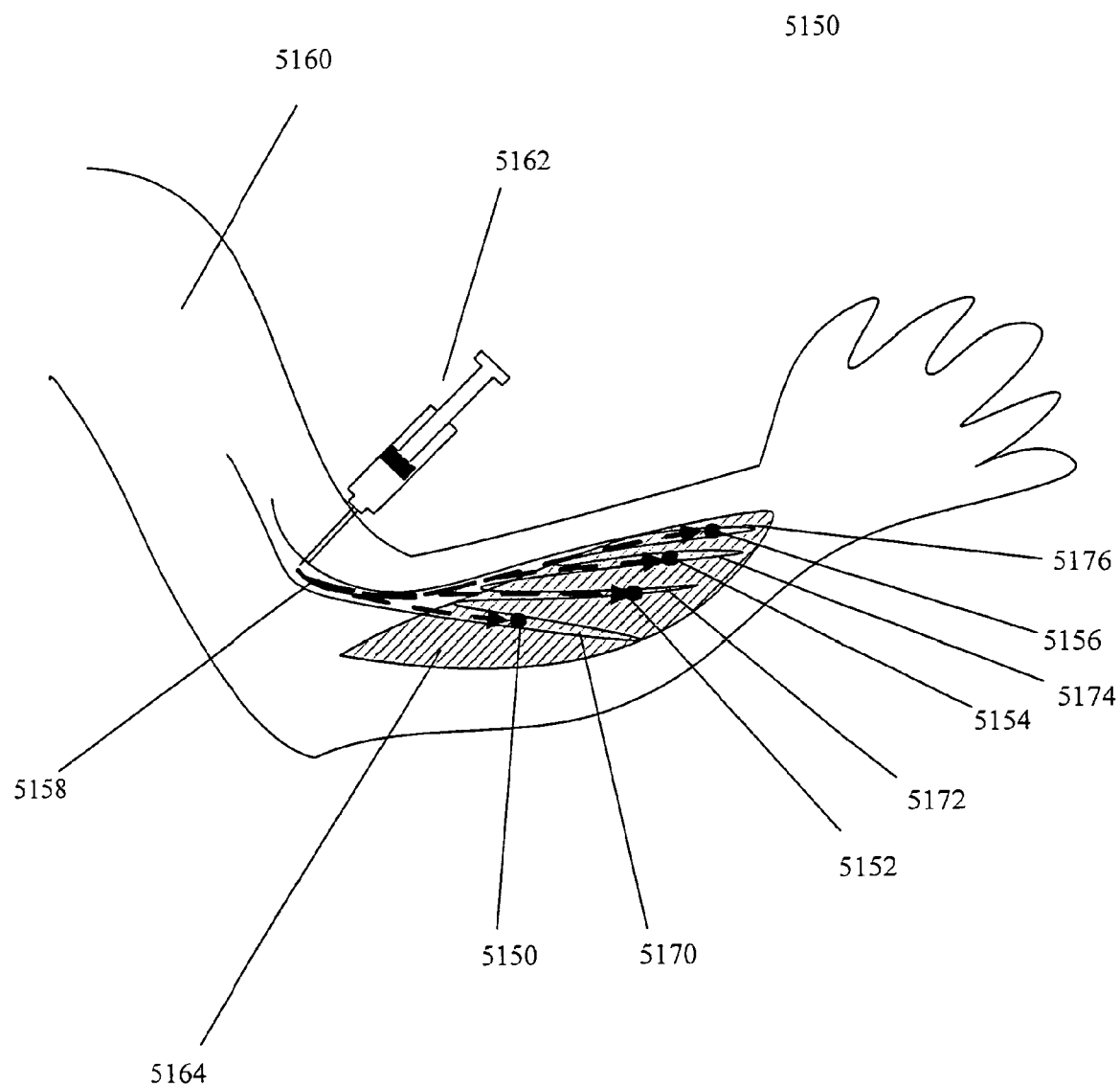
FIG. 66 illustrates the delivery of multiple lumen-traveling devices by injection.

FIG. 66 illustrates the introduction of lumen-traveling stimulation devices to muscle. In FIG. 66, lumen-traveling devices 5150, 5152, 5154, and 5156 are injected into vein 5158 of arm 5160 of a subject with syringe 5162, for example, where, as indicated by the dashed arrows, they may travel toward the muscle 5164 drained by the vein 5158, against the flow of blood, into capillaries 5170, 5172, 5174, and 5176 in muscle 5164, where they will reside in order to perform electromagnetic stimulation of the muscle 5164, e.g. for performing functional electromagnetic stimulation. In FIG. 66, lumen-traveling devices are not drawn to scale, but are indicated by black circles for purposed of illustration. Stimulation parameters suitable for use in stimulation of muscle with multiple, distributed, implanted microelectrodes are described in LOEB, GERALD E.; PECK, RAYMOND A.; MOORE, WILLIAM H.; HOOD, KEVIN; "BION System for Distributed Neural Prosthetic Interfaces"; Medical Engineering and Physics; bearing a date of 2001; pp. 9-18; Vol. 23; Elsevier Science Ltd.; located at: www.elsevier.com/locate/medengphy, which is incorporated herein by reference.

Figure 67A:
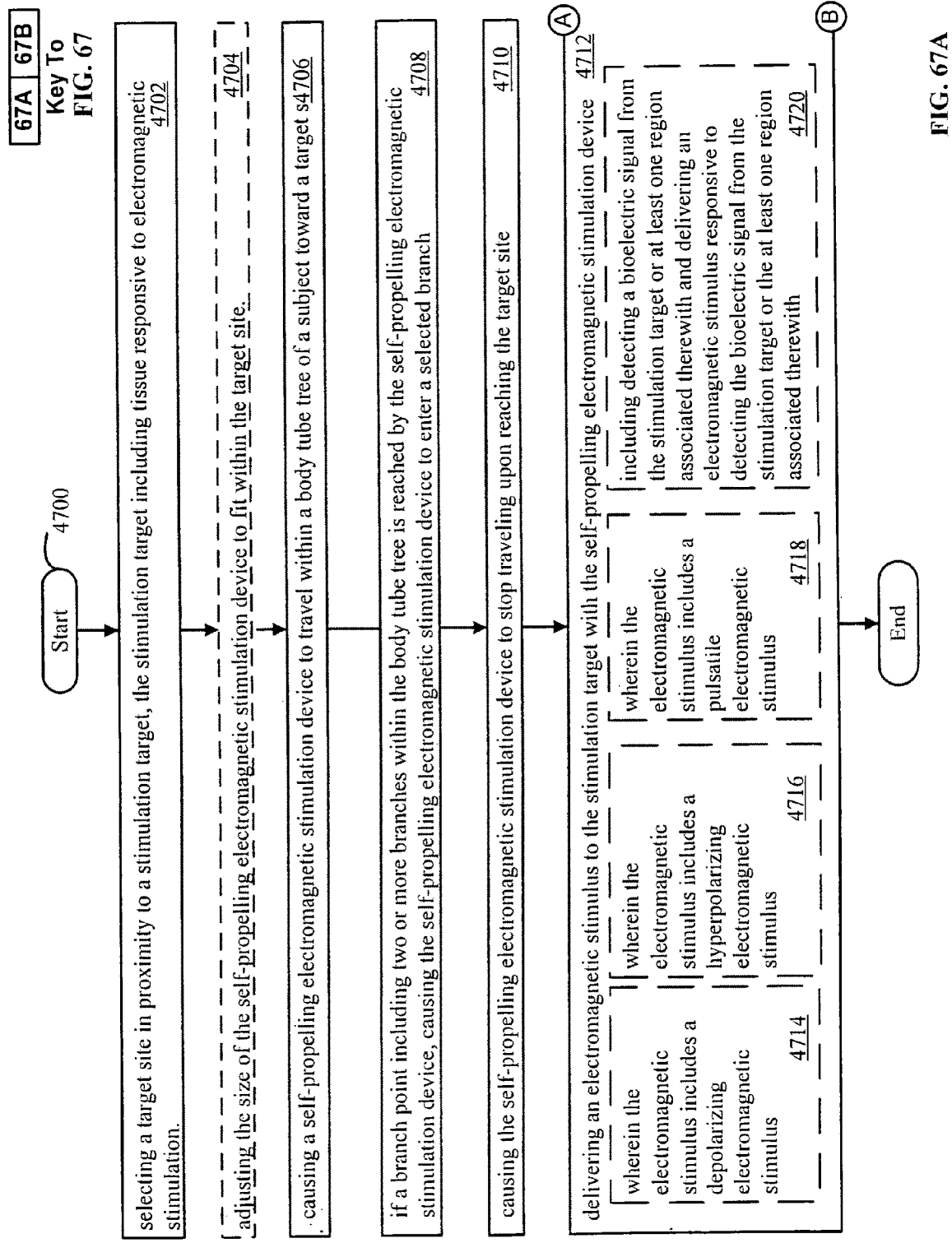
FIGS. 67A and 67B contain a flow diagram showing still further variations of the method of FIG. 58.
Figure 67B:
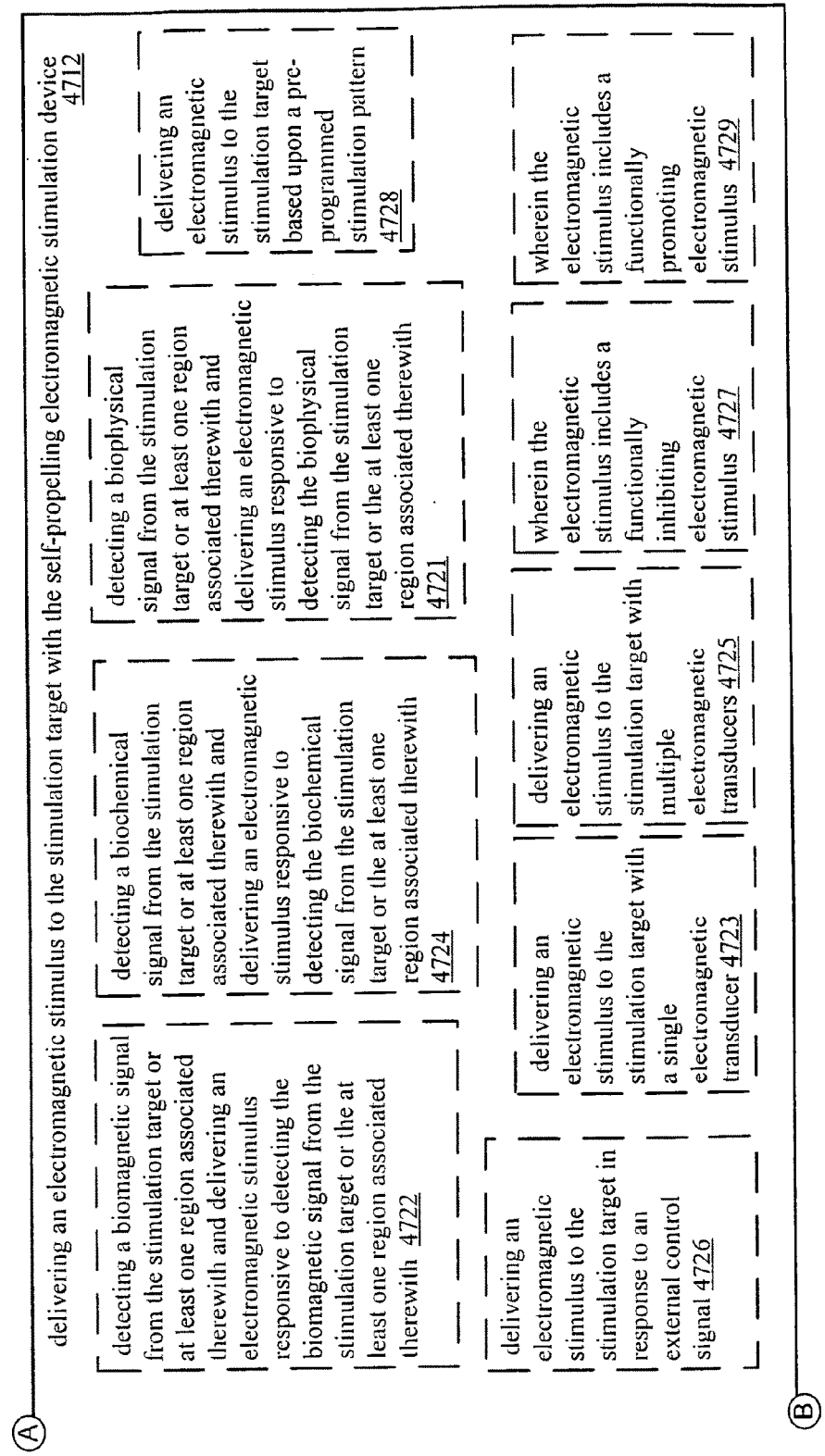

FIGS. 67A and 67B show further variations of the method shown in FIG. 58. The method may include selecting a target site in proximity to a stimulation target, the stimulation target including tissue responsive to electromagnetic stimulation, in step 4702. In some embodiments, the method may also include adjusting the size of the self-propelling electromagnetic stimulation device to fit within the target site, as shown at step 4704. As shown in FIG. 58, the method may include causing a self-propelling electromagnetic stimulation device to travel within a body tube tree of a subject toward a target site at 4706, and, at step 4708, if a branch point including two or more branches within the body tube tree is reached by the self-propelling electromagnetic stimulation device, causing the self-propelling electromagnetic stimulation device to enter a selected branch. At step 4710, the method includes the step of causing the self-propelling electromagnetic stimulation device to stop traveling upon reaching the target site. At step 4712, the method includes delivering an electromagnetic stimulus to the stimulation target with the self-propelling electromagnetic stimulation device. Various types of stimuli may be applied as shown in 4712 in FIG. 67A and in 4714, 4716, 4418, 4720, 4722, 4724, 4726, and 4728 in FIG. 67B (which is a continuation of FIG. 67A at connection points A and B). For example, the electromagnetic stimulus may include one or more of a depolarizing electromagnetic stimulus, as shown at 4714, a hyperpolarizing electromagnetic stimulus as shown at 4716, or a pulsatile electromagnetic stimulus, as shown at 4718. In some embodiments, the electromagnetic stimulus may be a functionally inhibiting stimulus (i.e., a stimulus sufficient to produce functional inhibition of activity of the target tissue or a portion thereof) as indicated at 4727 or a functionally promoting stimulus (i.e., a stimulus sufficient to produce functional promotion of activity of target tissue or a portion thereof), as indicated at 4729 in FIG. 67B. Various types of electrical and magnetic stimuli are well known to those of skill in the art, as exemplified by P. H. Peckham and J. S. Knutson, "Functional Electrical Stimulation for Neuromuscular Applications," Annu. Rev. Biomed. Eng., Vol. 7, 2005, pp. 327-60, Published online Mar. 23, 2005; doi:10.1146/annurev.bioeng.6.040803.140103, copyright 2005; KOBETIC, RUDI; TRIOLO, RONALD J.; UHLIR, JAMES P.; BIERI, CAROLE; WIBOWO, MICHAEL; POLANDO, GORDIE; MARSOLAIS, E. BYRON; DAVIS JR., JOHN A.; FERGUSON, KATHLEEN A.; SHARMA, MUKUT; "Implanted Functional Electrical Stimulation System for Mobility in Paraplegia: A Follow-Up Case Report"; IEEE Transactions on Rehabilitation Engineering; bearing a date of December 1999; pp. 390-398; Vol. 7, No. 4; IEEE; INMANN, ANDREAS; HAUGLAND, MORTEN; HAASE, JENS; BIERING-SØRENSEN, FIN; SINKJAER, THOMAS; "NeuroReport: Signals from Skin Mechanoreceptors used in Control of a Hand Grasp Neuroprosthesis"; Motor Systems; bearing a date of Sep. 17, 2001; pp. 2817-2819; Vol. 12, No. 13; Lippincott Williams & Wilkins; C. R. Butson and C. C. McIntyre, "Role of electrode design on the volume of tissue activated during deep brain stimulation," J. Neural Eng., Vol. 3, 2006, pp. 1-8, Published Online 19 Dec. 2005, doi:10.1088/1741-2560/3/1/001; and FANG, ZI-PING; MORTIMER, J. THOMAS; "Selective Activation of Small Motor Axons by Quasitrapezoidal Current Pulses"; IEEE Transactions on Biomedical Engineering; bearing a date of February 1991; pp. 168-174; Vol. 38, No. 2; IEEE; which are incorporated herein by reference.

In some embodiments, as shown at step 4720, the method may include detecting a bioelectric signal from the stimulation target or at least one region associated therewith and delivering an electromagnetic stimulus responsive to detecting the bioelectric signal from the stimulation target or the at least one region associated therewith. Alternatively, in some embodiments, as shown at step 4722, the method may include detecting a biomagnetic signal from the stimulation target or at least one region associated therewith and delivering an electromagnetic stimulus responsive to detecting the biomagnetic signal from the stimulation target or the at least one region associated therewith. In some embodiments, as shown at step 4724, the method may include detecting a biochemical signal from the stimulation target or at least one region associated therewith and delivering an electromagnetic stimulus responsive to detecting the biochemical signal from the stimulation target or the at least one region associated therewith. Biochemical signals may be detected using various sensors as described herein, including biosensors of various types, immunosensors, pH sensors, etc. In still other embodiments, as shown at step 4721, the method may include detecting a biophysical signal from the stimulation target or at least one region associated therewith and delivering an electromagnetic stimulus responsive to detecting the biophysical signal from the stimulation target or the at least one region associated therewith. A biophysical signal may include, for example, a pressure or flow condition, e.g. a pressure or flow signal associated with blood in the heart or other portion of the circulatory system. Delivery of an electromagnetic stimulus to the stimulation target may be performed with a single electromagnetic transducer, as indicated in 4723, or with multiple electromagnetic transducers 4725.

In various embodiments, stimuli delivered in response to a detected signal may be used to amplify naturally occurring activity, or to produce an effect that is complementary to naturally occurring activity. Alternatively, stimuli delivered in response to a detected signal may be used to diminish or damp naturally occurring activity, or produce an effect that counters naturally occurring activity. In some embodiments, sensed activity may be used to indicate proximity to a stimulation target. In some embodiments, stimulation may be correlated temporally, but not spatially, with the detected signal. The method may also include delivering an electromagnetic stimulus to the stimulation target in response to a remote control signal, as indicated at 4726, or in response to a pre-programmed stimulation pattern, as indicated at 4728.

Methods of detecting and analyzing bioelectric and/or biomagnetic signals are well known to those of skill in the art, as exemplified by K. W. Horch and G. S. Dhillon, Editors, *Neuroprosthetics: Theory and Practice* (Series on Bioengineering and Biomedical Engineering—Vol. 2), World Scientific Publishing Co. Pte. Ltd, Singapore, 2004, in particular, chapters 2.2, 2.4, 4.3 and 5.2, and J. Malmivuo and R. Plonsey, *Bioelectromagnetism: Principles and Applications of Bioelectric and Biomagnetic Fields*, Oxford University Press, NY, 1995, http://butler.cc.tut.fi/~malmivuo/bem/bembook/, which are incorporated herein by reference.

Figure 68:
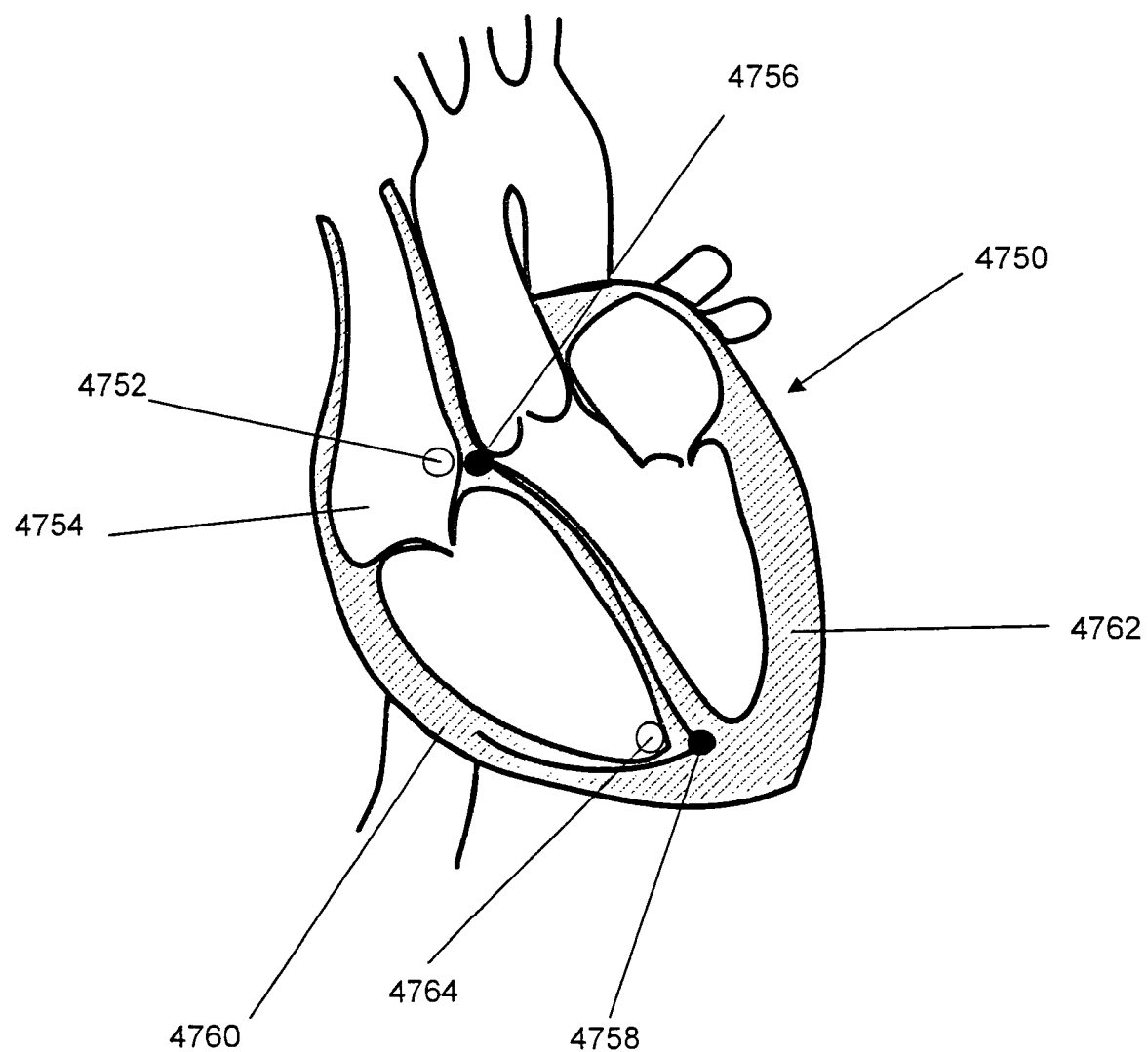
FIG. 68 illustrates delivery of a stimulus by a lumen-traveling device based upon a sensed signal.

FIG. 68 depicts an example of detection of a bioelectric signal and delivery of a stimulation in response to the detected signal is illustrated in FIG. 68. A heart 4750 of a subject is depicted in FIG. 68. A lumen-traveling device 4752 located in right atrium 4754 may sense naturally occurring bioelectrical activity generated by the sinoatrial 4756 node of heart 4750, for example, indicating the need to initiate a heartbeat. In the case of a conduction block between sinoatrial node 4756 and atrioventricular node 4758, the signal will not be transmitted normally and contraction of the ventricles 4760 and 4762 will not be initiated properly. In order to compensate for this defect, lumen-traveling device 4752 may transmit a signal to second lumen-traveling stimulation device 4764 located in right ventricle 4760, which may then deliver an electrical pacing signal to cause contraction of ventricles 4760 and 4762.

Figure 69:
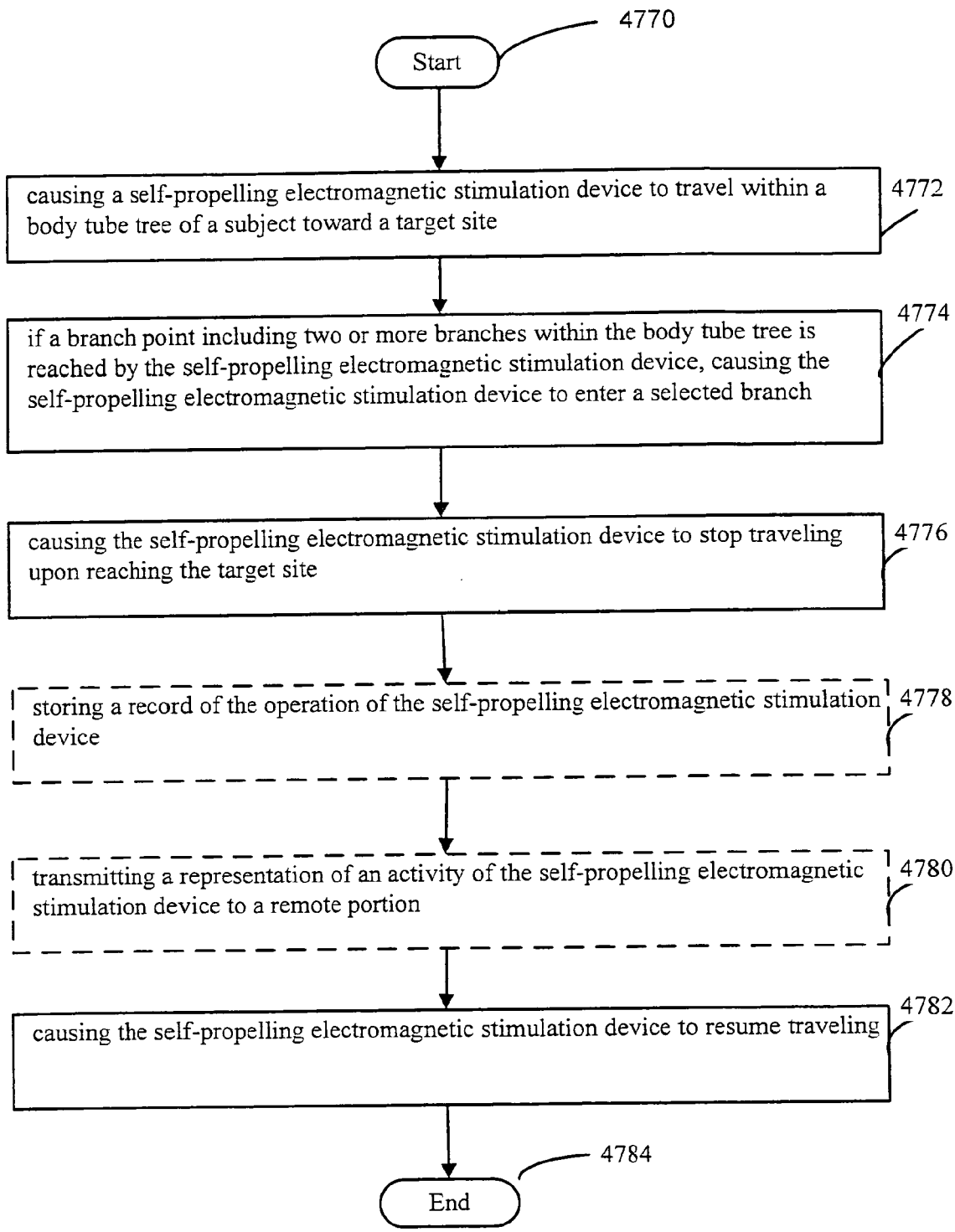
FIG. 69 is a flow diagram of a further variation of the method of FIG. 58.

FIG. 69 is a flow diagram of a further variation of the method shown in FIG. 58. The method of FIG. 69 includes causing a self-propelling electromagnetic stimulation device to travel within a body tube tree of a subject toward a target site at step 4772, if a branch point including two or more branches within the body tube tree is reached by the self-propelling electromagnetic stimulation device, causing the self-propelling electromagnetic stimulation device to enter a selected branch at step 4774, and causing the self-propelling electromagnetic stimulation device to stop traveling upon reaching the target site at 4776 as shown in previously described embodiments. Additional steps may include storing a record of the operation of the self-propelling electromagnetic stimulation device as indicated at 4778 and/or transmitting a representation of an activity of the self-propelling electromagnetic stimulation device to a remote portion as indicated at 4780. The method may also include causing the self-propelling electromagnetic stimulation device to resume traveling, as indicated at 4782. Although the steps of storing a record of the operation of the self-propelling electromagnetic stimulation device and transmitting a representation of an activity of the self-propelling electromagnetic stimulation device are presented in a particular order in the flow diagram of FIG. 69, in practice these steps may be performed at various times during the operation of the device, and in some cases may be performed prior to the device stopping traveling or after the device resumes traveling (or independent of starting or stopping of the device, in that the device may not necessarily stop or start, but may instead move continuously).

Figure 70:
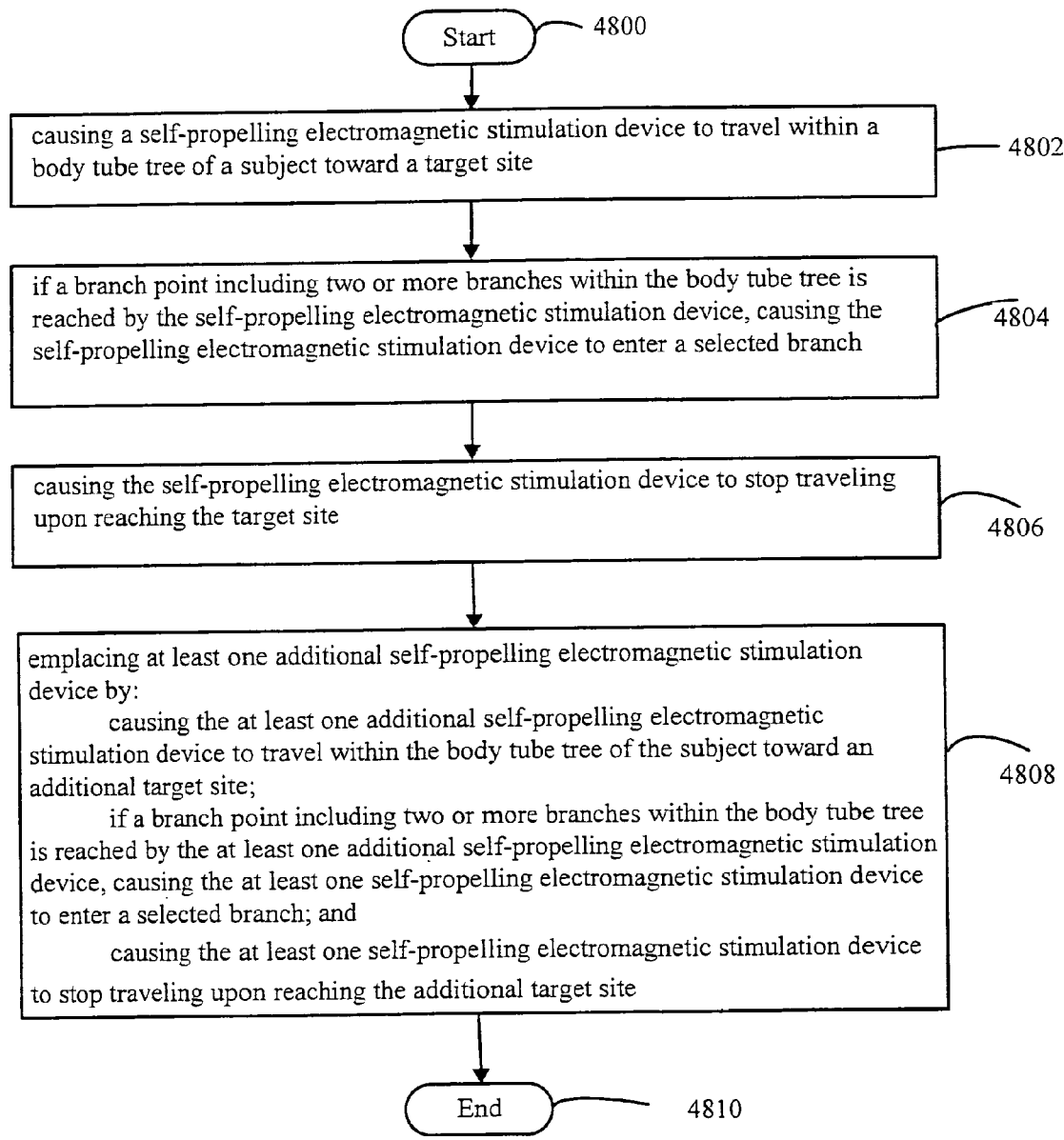
FIG. 70 is a flow diagram of an extension of the method of FIG. 58 to include emplacement of at least one additional self-propelling electromagnetic stimulation device.

FIG. 70 is a flow diagram of a method of emplacing an self-propelling electromagnetic stimulation device as shown in FIG. 58, including the steps of causing a self-propelling electromagnetic stimulation device to travel within a body tube tree of a subject toward a target site (step 4802); if a branch point including two or more branches within the body tube tree is reached by the self-propelling electromagnetic stimulation device, causing the self-propelling electromagnetic stimulation device to enter a selected branch (step 4804); and causing the self-propelling electromagnetic stimulation device to stop traveling upon reaching the target site (step 4806). At 4808, the method further includes emplacing at least one additional self-propelling electromagnetic stimulation device by causing the at least one additional self-propelling electromagnetic stimulation device to travel within the body tube tree of the subject toward an additional target site; wherein if a branch point including two or more branches within the body tube tree is reached by the at least one additional self-propelling electromagnetic stimulation device, causing the at least one self-propelling electromagnetic stimulation device to enter a selected branch; and causing the at least one self-propelling electromagnetic stimulation device to stop traveling upon reaching the additional target site.

Figure 71:
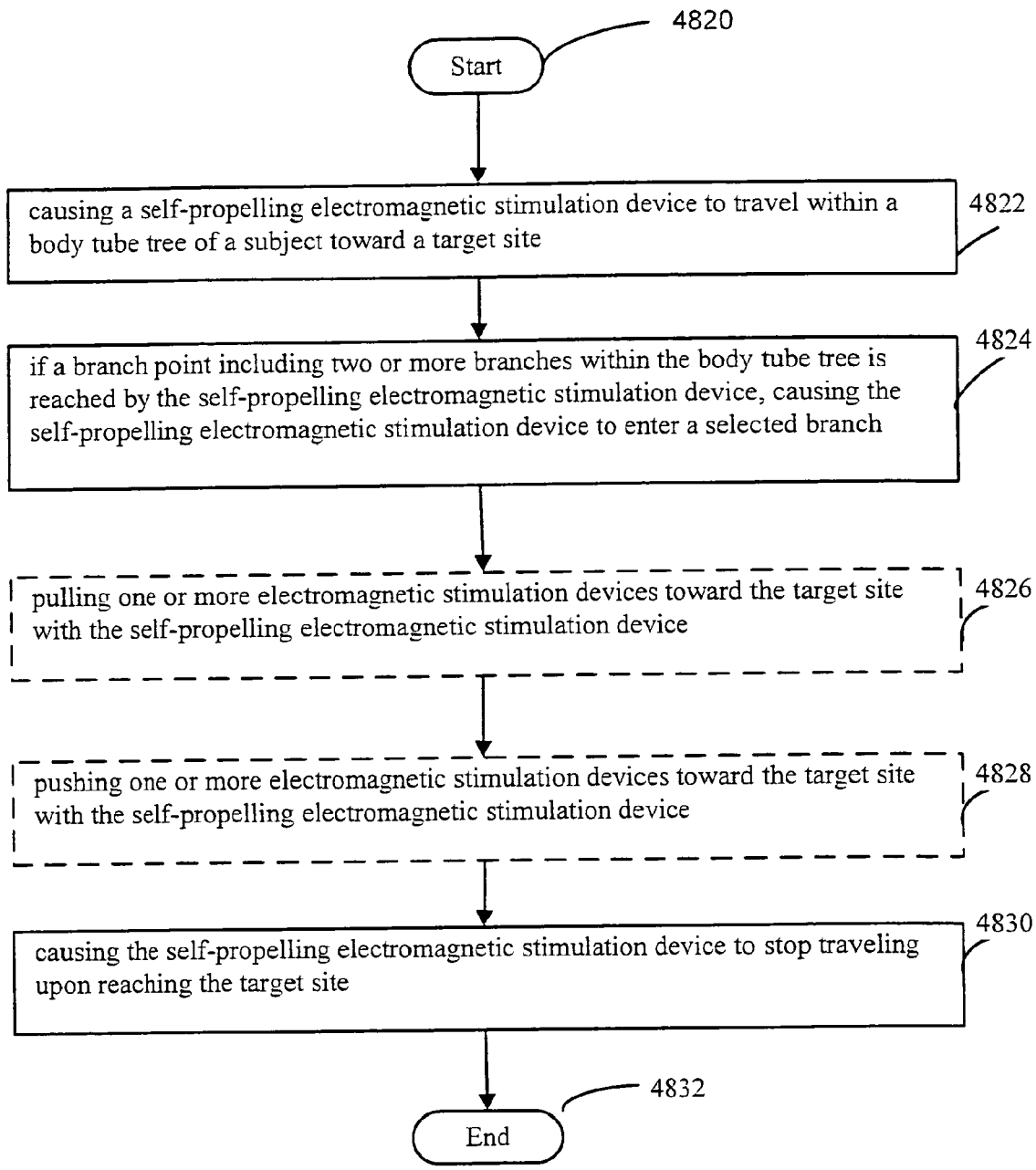
FIG. 71 is a flow diagram of an extension of the method of FIG. 58.

FIG. 71 is a flow diagram of a further extension of the method of FIG. 58, which includes the steps of causing a self-propelling electromagnetic stimulation device to travel within a body tube tree of a subject toward a target site at 4822, and if a branch point including two or more branches within the body tube tree is reached by the self-propelling electromagnetic stimulation device, causing the self-propelling electromagnetic stimulation device to enter a selected branch at step 4824. In some embodiments may include the variants specified in steps 4826 and 4828. As indicated in 4826, the method may include pulling one or more electromagnetic stimulation devices toward the target site with the self-propelling electromagnetic stimulation device. Alternatively, or in addition, the method may include pushing one or more electromagnetic stimulation devices toward the target site with the self-propelling electromagnetic stimulation device, as indicated at 4828. And, as shown in previous figures, the method may include causing the self-propelling electromagnetic stimulation device to stop traveling upon reaching the target site, as indicated at 4830.

Figure 72:
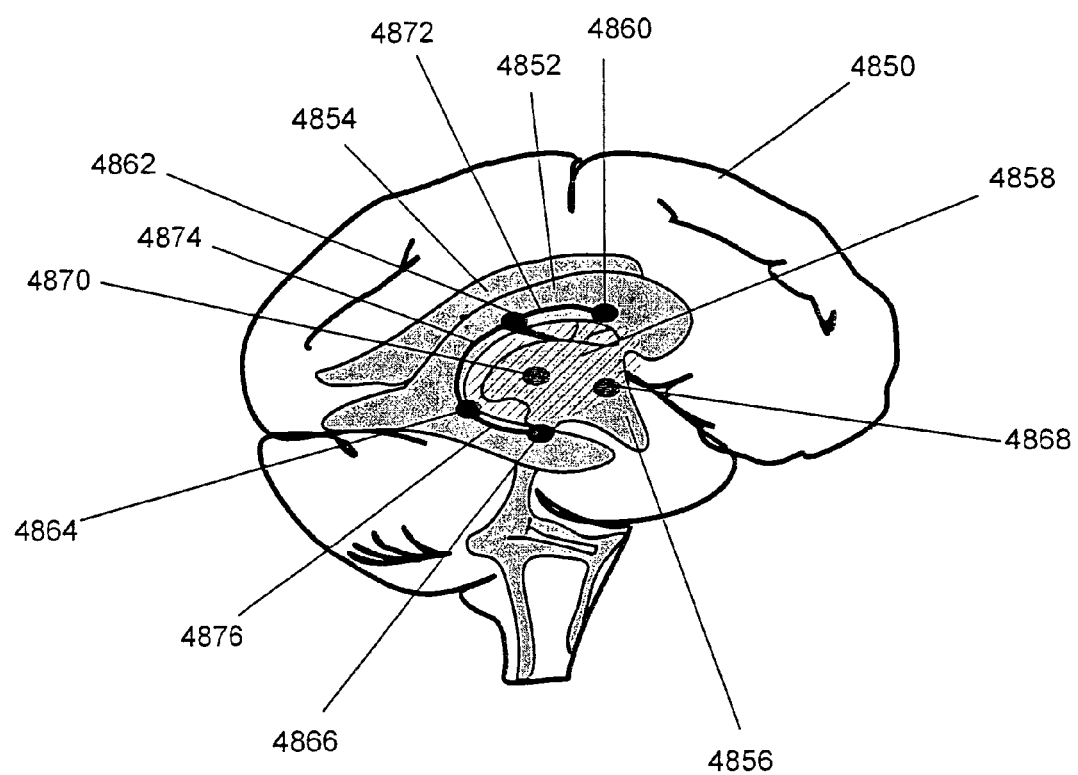
FIG. 72 illustrates the use of multiple stimulation or recording devices positioned around a target tissue.
Figure 73A:
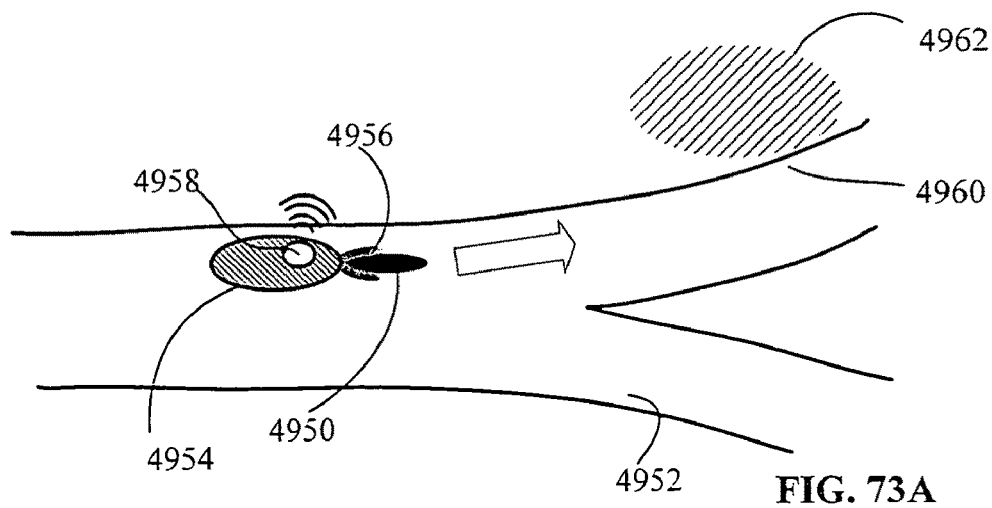
FIGS. 73A, 73B and 73C illustrate the emplacement of a bioelectromagnetic interface device at a target site in a body lumen with a lumen-traveling device.
Figure 73B:
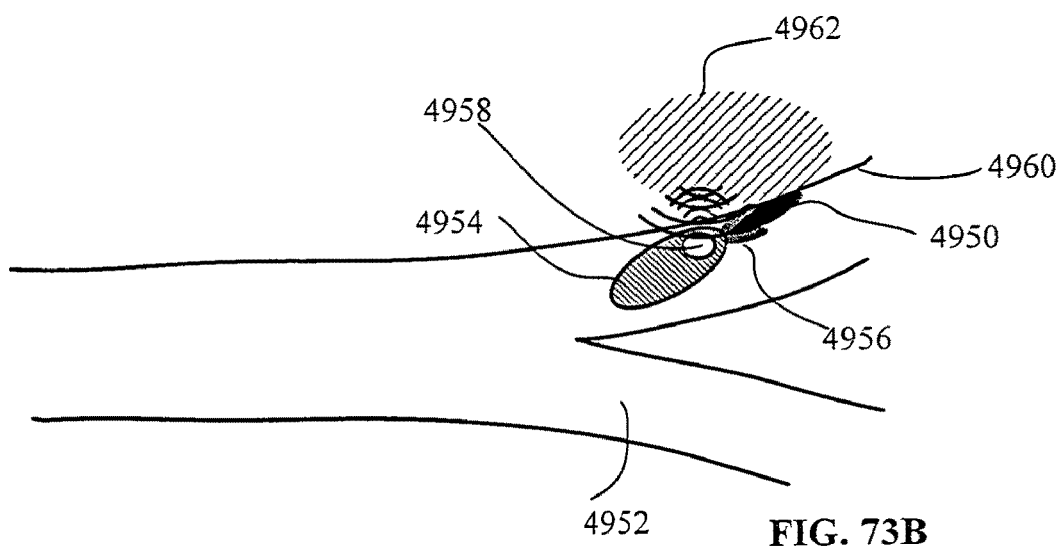
Figure 73C:
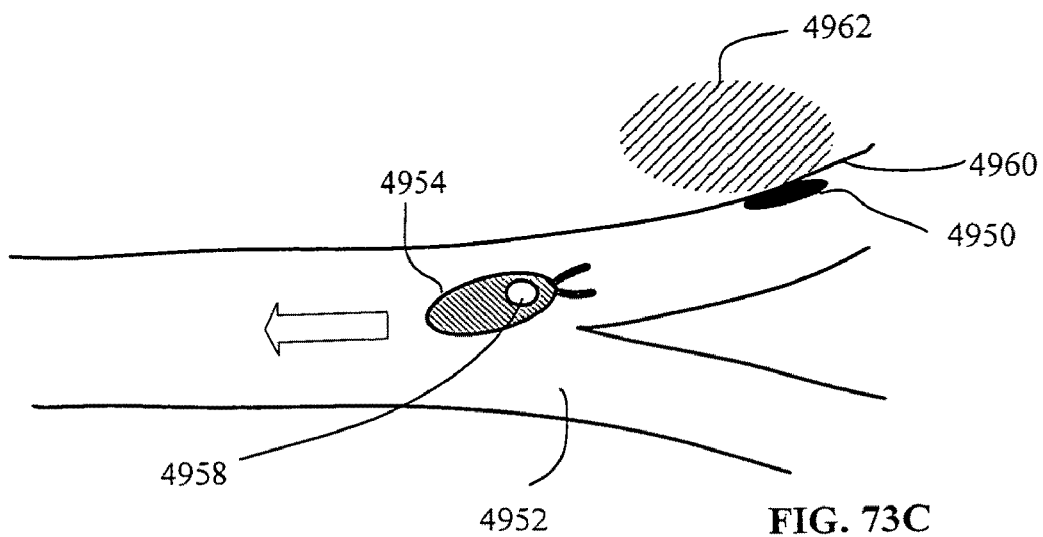

The use of multiple stimulation devices is depicted in FIG. 72. FIG. 72 illustrates brain 4850 of a subject, including lateral ventricals 4852 and 4854, third ventricle 4856, and thalamus 4858 (indicated generally as the striped region in FIG. 72). Stimulation devices 4860, 4862, 4864, and 4866 are positioned in lateral ventricle 4852, stimulation devices 4868 and 4870 are positioned in third ventricle 4856. The stimulation devices are thus distributed around thalamus 4858 and may be used to selectively stimulate thalamus 4858 (or portions thereof). For example, relatively low stimuli delivered through multiple stimulation devices may overlap to activate restricted regions of the thalamus. In another example, by activating multiple stimulation devices in appropriately selected patterns, spatially and/or temporally complex stimulation patterns may be produced. Stimulation devices 4860, 4862, 4864, and 4866 are linked by tethers 4872, 4874, and 4876, which may be formed of suture material, wire, cable, or fiber, for example. By forming a linked group of stimulation devices, the relative spacing between the stimulation devices may be controlled, and positioning of the stimulation devices relative to anatomical structures may be facilitated. A linked group of stimulation devices may be used in the practice of the method steps 4826 and 4828 of FIG. 71; a relatively flexible tether may be used if electromagnetic stimulation devices are to be pulled by a self-propelling electromagnetic stimulation device, while a more rigid linkage may be used if electromagnetic stimulation devices are to be pushed by a self-propelling electromagnetic stimulation device In some embodiments, a method may include using a lumen-traveling device to carry a bioelectromagnetic interface device to a target site. This approach is illustrated in FIG. 73A-73C. In FIG. 73A, bioelectromagnetic interface device 4950 is carried through body tube tree 4952 by self-propelling lumen-traveling device 4954, which may be of the type depicted generally in FIGS. 24 and 25A-25B. For example, self-propelling lumen-traveling device 4954 may include grasper 4956 for carrying bioelectromagnetic interface device 4950. Self-propelling lumen-traveling device 4954 may include sensor 4958, which is configured to detect the arrival of the bioelectromagnetic interface device at the target site 4960, near stimulation target 4962. Sensor 4958 may be any of various types of sensors, as described herein. In FIG. 73A, the self-propelling lumen-traveling device 4954, carrying bioelectromagnetic interface device 4950, travels through body tube tree 4952 in the direction indicated by the arrow. In FIG. 73B, the arrival of bioelectromagnetic interface device 4950 at target site 4960 is detected by sensor 4958. Bioelectromagnetic interface device 4950 may then be released from self-propelling lumen-traveling device 4954, and self-propelling lumen-traveling device may move away from target site 4960, leaving the bioelectromagnetic interface device at target site 4960.

Figure 74:
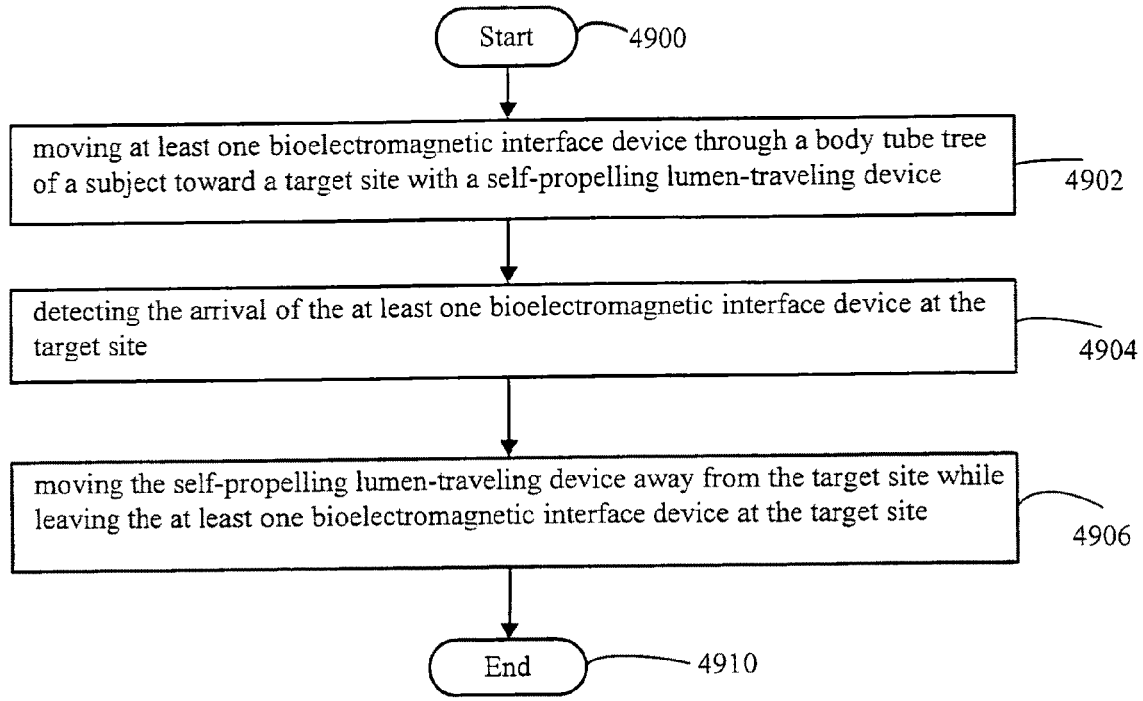
FIG. 74 is a flow diagram of a method of configuring a bioelectromagnetic interface system.

FIG. 74 is a flow diagram of a method of configuring a bioelectromagnetic interface system, including moving a at least one bioelectromagnetic interface device through a body tube tree of a subject toward a target site with a self-propelling lumen-traveling device (at step 4902); detecting the arrival of the at least one bioelectromagnetic interface device at the target site (at step 4904); and moving the self-propelling lumen-traveling device away from the target site while leaving the at least one bioelectromagnetic interface device at the target site (at step 4906).

Figure 75:
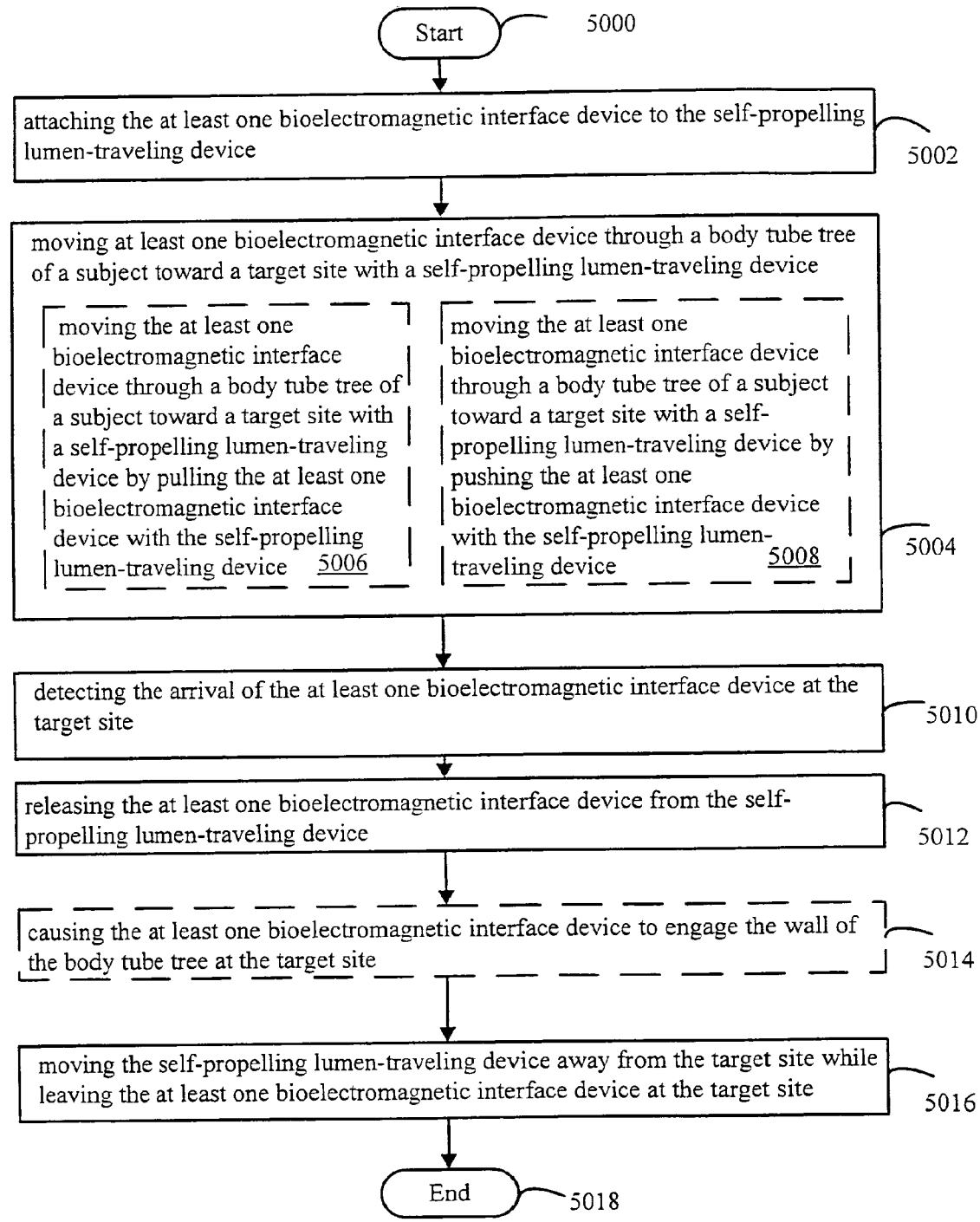
FIG. 75 is a flow diagram showing variations of the method of FIG. 74.

FIG. 75 is a flow diagram of an expansion of the method of FIG. 74, showing additional details of the method. In some embodiments, the method may include a preliminary step 5002 of attaching the at least one bioelectromagnetic interface device to the self-propelling lumen-traveling device. The method may include moving at least one bioelectromagnetic interface device through a body tube tree of a subject toward a target site with a self-propelling lumen-traveling device (at step 5004). In some embodiments, the method may include moving the at least one bioelectromagnetic interface device through a body tube tree of a subject toward a target site with a self-propelling lumen-traveling device by pulling the at least one bioelectromagnetic interface device with the self-propelling lumen-traveling device as shown at 5006, while in other embodiments the method may include moving the at least one bioelectromagnetic interface device through a body tube tree of a subject toward a target site with a self-propelling lumen-traveling device by pushing the at least one bioelectromagnetic interface device with the self-propelling lumen-traveling device, as shown at 5008. The method may include detecting the arrival of the at least one bioelectromagnetic interface device at the target site (at step 5010) and releasing the at least one bioelectromagnetic interface device from the self-propelling lumen-traveling device (at step 5012). In some cases the method may include causing the at least one bioelectromagnetic interface device to engage the wall of the body tube tree at the target site (as shown at 5014), and moving the self-propelling lumen-traveling device away from the target site while leaving the at least one bioelectromagnetic interface device at the target site (at step 5016).

Figure 76:
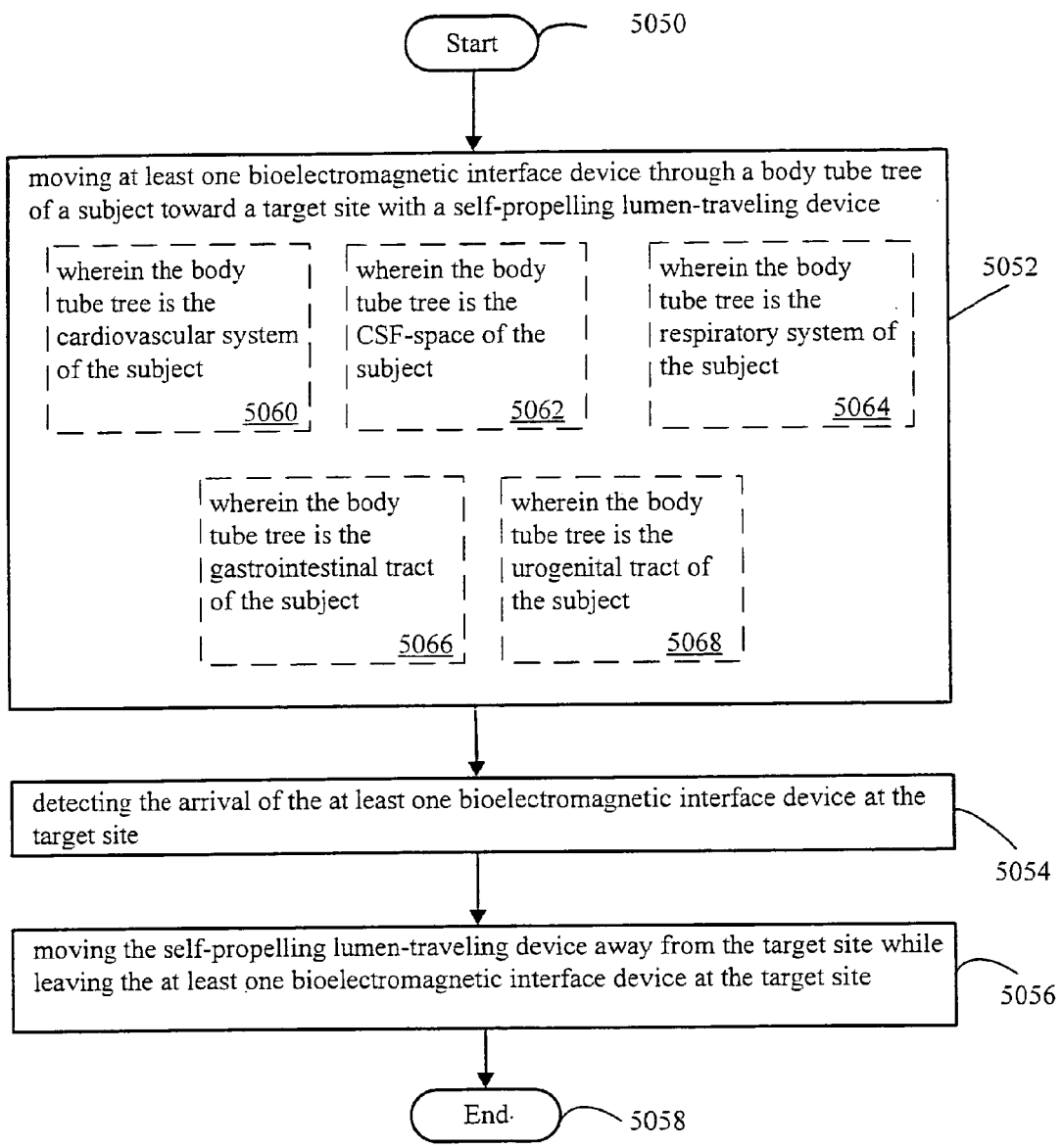
FIG. 76 is a flow diagram showing variations of the method of FIG. 74.

FIG. 76 is a flow diagram showing further details of the method of FIG. 74. The method includes moving at least one bioelectromagnetic interface device through a body tube tree of a subject toward a target site with a self-propelling lumen-traveling device (at step 5052); detecting the arrival of the at least one bioelectromagnetic interface device at the target site (at step 5054); and moving the self-propelling lumen-traveling device away from the target site while leaving the at least one bioelectromagnetic interface device at the target site (at step 5056). The body tube tree may be the cardiovascular system, as indicated at 5060, the CSF-space, as indicated at 5062, the respiratory system of the subject, as indicated at 5064, the gastrointestinal tract of the subject, as indicated at 5066, of the urogenital tract of the subject, as indicated at 5068, or various other body lumens that may provide access to a stimulation target.

Figure 77:
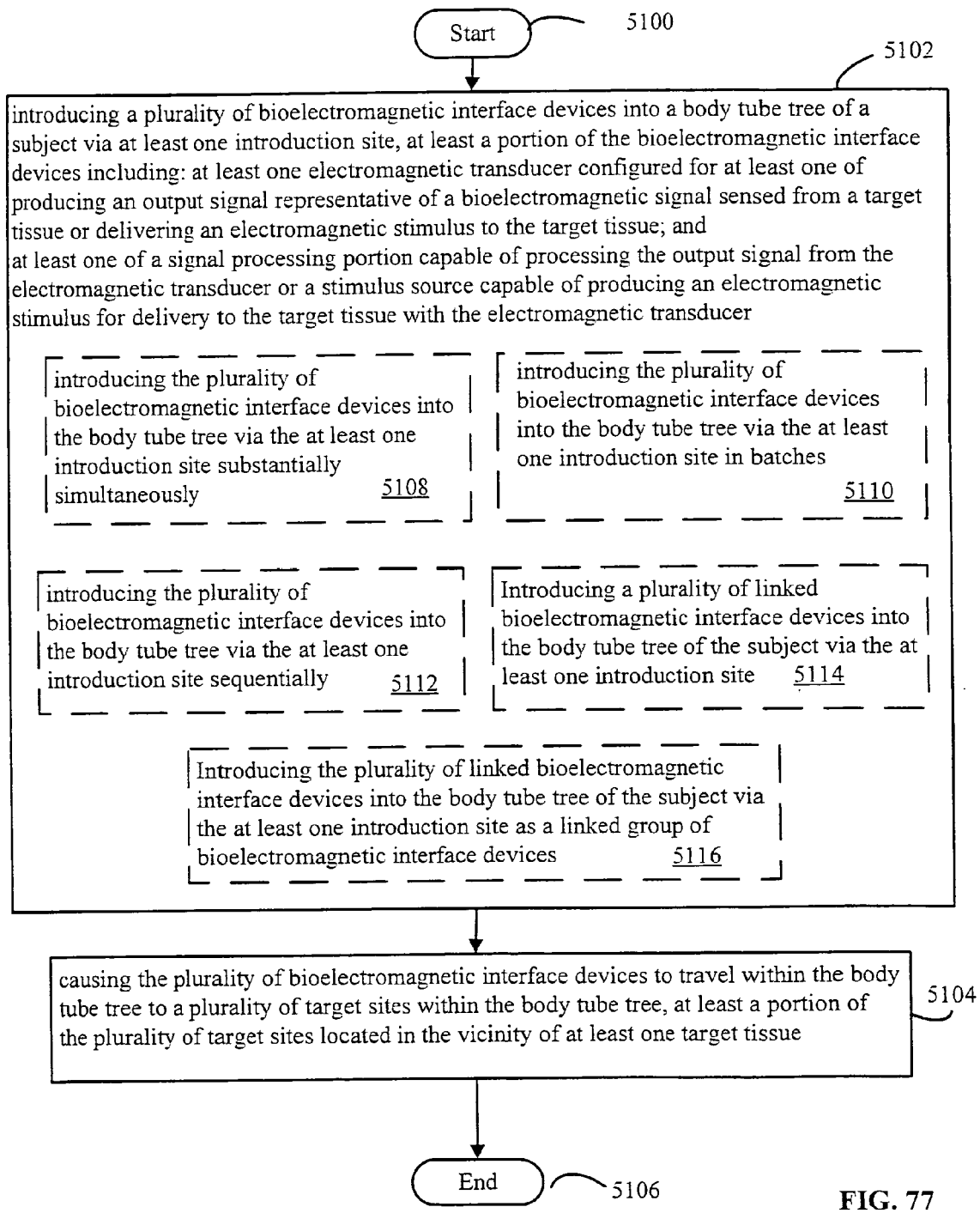
FIG. 77 is a flow diagram of a method of emplacing a bioelectromagnetic interface system.

FIG. 77 is a flow diagram of a method of emplacing a bioelectromagnetic interface system including: introducing a plurality of bioelectromagnetic interface devices into a body tube tree of a subject via at least one introduction site at step 5102, at least a portion of the bioelectromagnetic interface devices including at least one electromagnetic transducer configured for at least one of producing an output signal representative of a bioelectromagnetic signal sensed from a target tissue or delivering an electromagnetic stimulus to the target tissue and at least one of a signal processing portion capable of processing the output signal from the electromagnetic transducer or a stimulus source capable of producing an electromagnetic stimulus for delivery to the target tissue with the at least one electromagnetic transducer; and causing the plurality of bioelectromagnetic interface devices to travel within the body tube tree to a plurality of target sites within the body tube tree, at least a portion of the plurality of target sites located in the vicinity of at least one target tissue (step 5104).

The method may including introducing the plurality of bioelectromagnetic interface devices into the body tube tree via the at least one introduction site substantially simultaneously, as indicated at 5108. Alternatively, the method may include introducing the plurality of bioelectromagnetic interface devices into the body tube tree via the at least one introduction site in batches, as indicated at 5110. A batch is a group of devices that are introduced substantially simultaneously at a single location. In another alternative, the method may include introducing the plurality of bioelectromagnetic interface devices into the body tube tree via the at least one introduction site sequentially, as indicated at 5112. In another alternative, the method may include introducing the plurality of bioelectromagnetic interface devices into the body tube tree of the subject via the at least one introduction site as a linked group of bioelectromagnetic interface devices. For example, the bioelectromagnetic interface devices may be linked to each other end-to-end in a chain with connectors or graspers of the type depicted in FIGS. 25A and 25B, or each interface device may be attached, either permanently or temporarily, to one or more other interface devices in a chain or other configuration by suture material, wire, cable, fiber, etc., for example as depicted in FIG. 72.

Figure 78A:
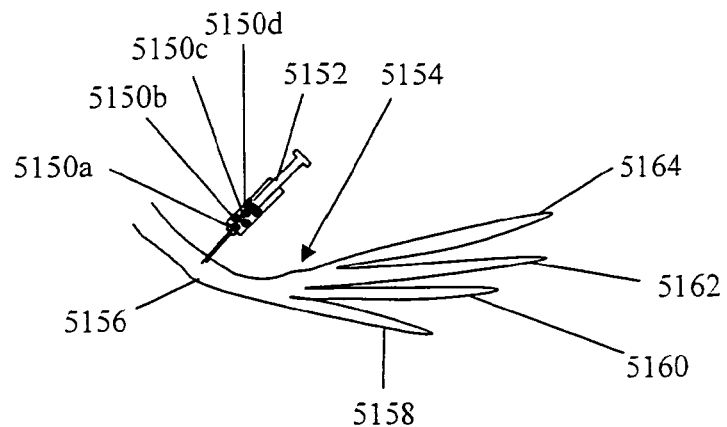
FIGS. 78A-78C illustrate the introduction of a plurality of bioelectromagnetic interface devices simultaneously.
Figure 78B:
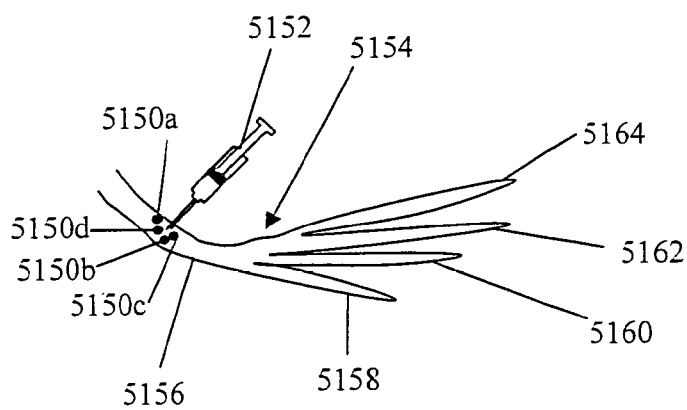
Figure 78C:
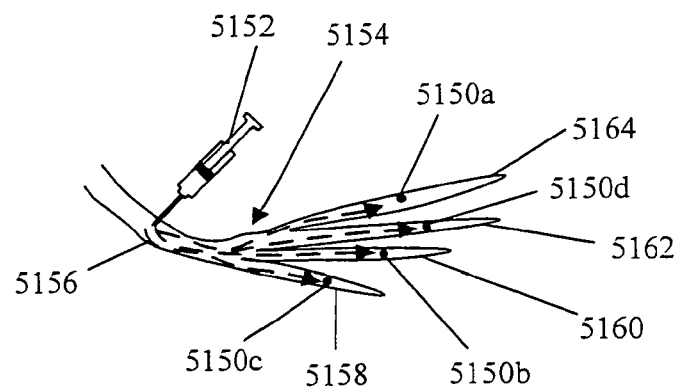

The introduction of a single bioelectromagnetic interface device is depicted in FIG. 64. The introduction of a batch of multiple bioelectromagnetic interface devices into the body tube tree at a single introduction site is illustrated in FIG. 66. FIGS. 78A-78B depict the introduction of a batch of multiple bioelectromagnetic interface devices into a body tube tree, showing greater detail. In FIG. 78A, a batch of multiple bioelectromagnetic interface devices including bioelectromagnetic interface devices 5150*a*, 5150*b*, 5150*c* and 5150*d* is contained in syringe 5152 prior to delivery into body tube tree 5154. Body tube tree 5154 includes first region 5156 and branches 5158, 5160, 5162, and 5164. As shown in FIG. 78B, bioelectromagnetic interface devices 5150*a*, 5150*b*, 5150*c* and 5150*d* are introduced into first region 5156 of body tube tree 5154 as a group, substantially simultaneously. As shown in FIG. 78C, bioelectromagnetic interface devices 5150*a*, 5150*b*, 5150*c* and 5150*d* travel along the routes indicated by the dashed arrows to reach branches 5164, 5160, 5158, and 5162, respectively. The same procedure can be carried out at multiple locations in the body, either simultaneously (by using multiple syringes or equivalents) or in sequence, to deliver multiple batches of bioelectromagnetic interface devices to the body.

Figure 79:
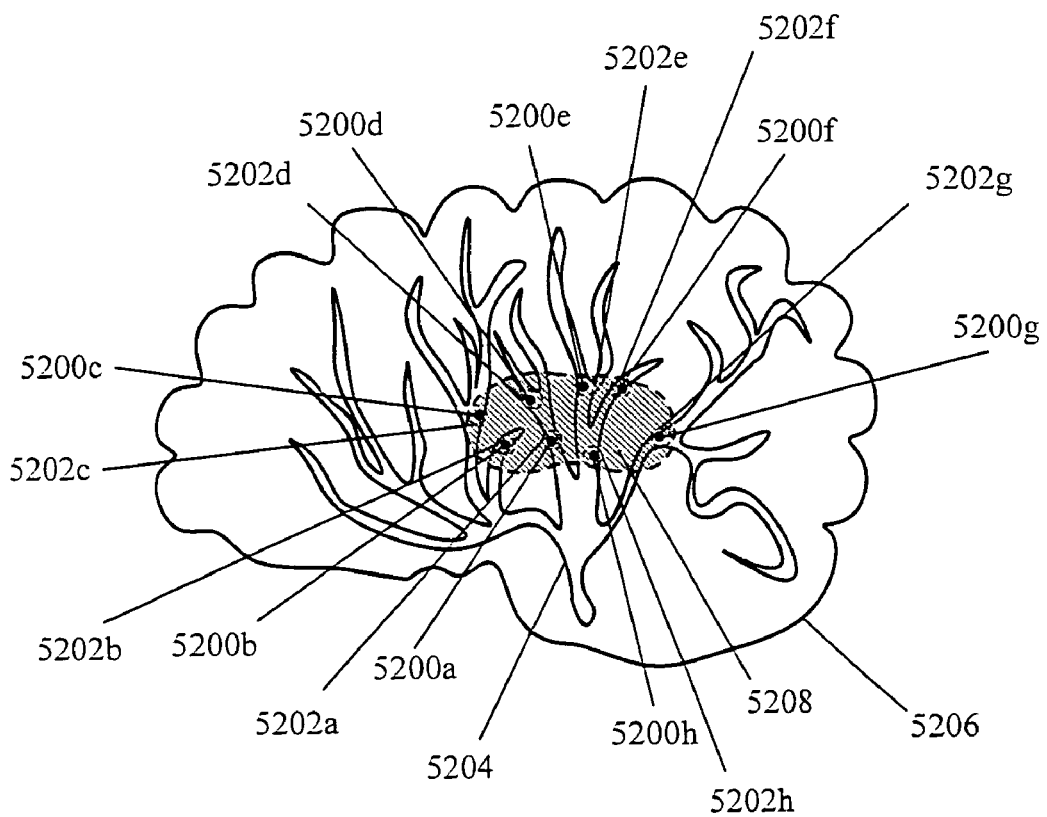
FIG. 79 illustrates the use of multiple stimulation or recording devices positioned within a target tissue.

FIG. 79 illustrates a plurality of bioelectromagnetic interface devices 5200*a*, 5200*b*, 5200*c*, 5200*d*, 5200*e*, 5200*f*, 5200*g*, 5200*h*, located at a plurality of target sites 5202*a*, 5202*b*, 5202*c*, 5202*d*, 5202*e*, 5202*f*, 5202*g*, 5202*h*, within vasculature 5204 of brain 5206. The target sites 5202*a*, 5202*b*, 5202*c*, 5202*d*, 5202*e*, 5202*f*, 5202*g*, 5202*h* (indicated by dashed circles) are distributed through out brain region 5208. Multiple bioelectromagnetic interface devices may be used to record activity from multiple locations, to record multiple signals from a single general area, to stimulate multiple areas, to generate complex electromagnetic fields for stimulation, or to perform both recording and stimulation, simultaneously or in a desired temporal sequence. Stimulation of a plurality of areas may include stimulation of spatially proximate areas, e.g., adjacent brain regions, or spatially separated regions of a body.

Figure 80:
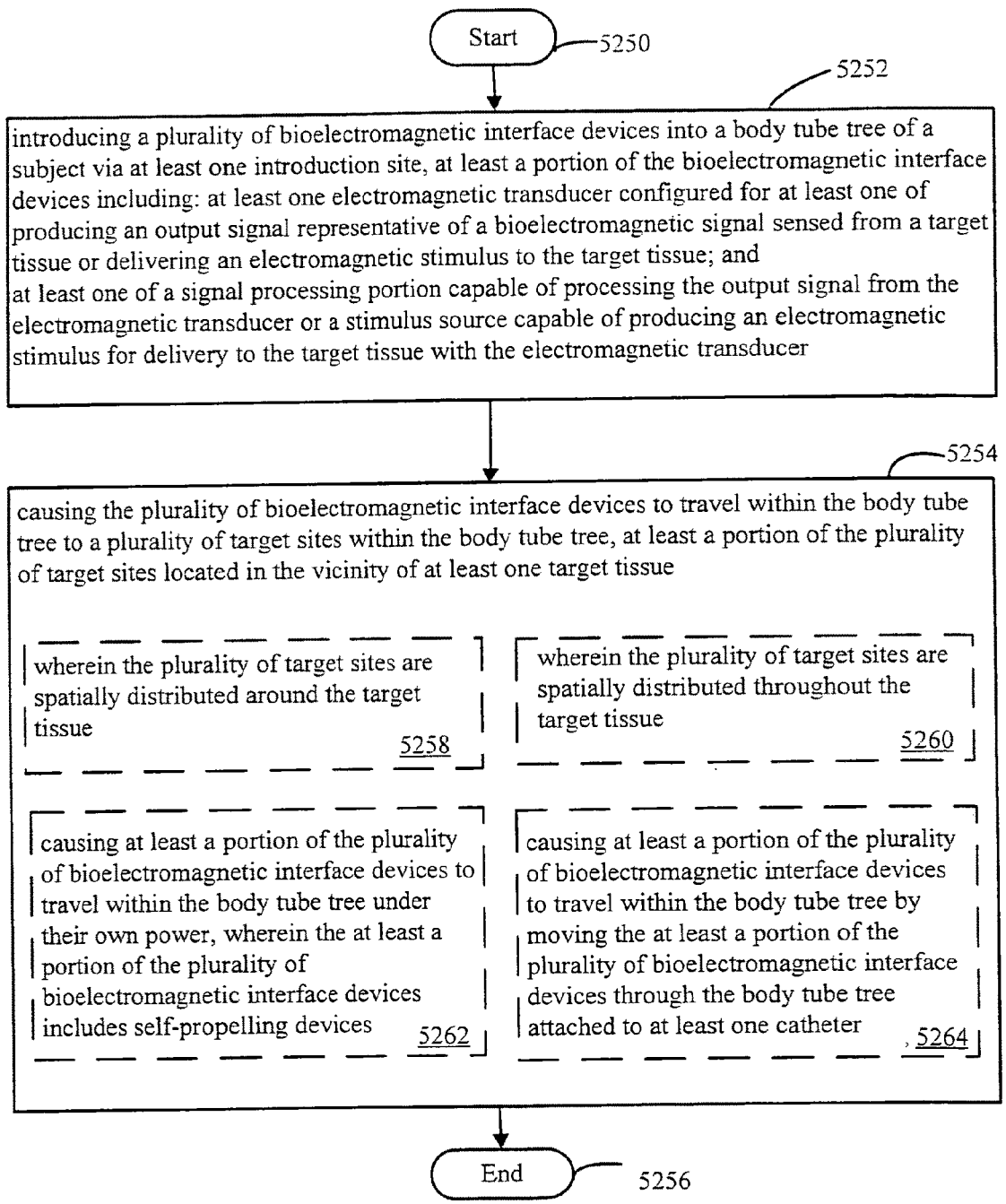
FIG. 80 is a flow diagram showing variants of the method of FIG. 77.

FIG. 80 is a flow diagram of a method of emplacing a bioelectromagnetic interface system as shown in FIG. 77, which includes: introducing a plurality of bioelectromagnetic interface devices into a body tube tree of a subject via at least one introduction site, at least a portion of the bioelectromagnetic interface devices including at least one electromagnetic transducer configured for at least one of producing an output signal representative of a bioelectromagnetic signal sensed from a target tissue or delivering an electromagnetic stimulus to the target tissue and at least one of a signal processing portion capable of processing the output signal from the electromagnetic transducer or a stimulus source capable of producing an electromagnetic stimulus for delivery to the target tissue with the at least one electromagnetic transducer (step 5252); and causing the plurality of bioelectromagnetic interface devices to travel within the body tube tree to a plurality of target sites within the body tube tree, at least a portion of the plurality of target sites located in the vicinity of at least one target tissue (step 5254). The plurality of target sites may spatially distributed around the target tissue, as indicated at 5258 in FIG. 80, and illustrated in FIG. 72, or spatially distributed throughout the target tissue as indicated at 5260 in FIG. 80, and as illustrated in FIG. 79.

As further shown in FIG. 80, the method may include causing at least a portion of the plurality of bioelectromagnetic interface devices to travel within the body tube tree under their own power, wherein the at least a portion of the plurality of bioelectromagnetic interface devices includes self-propelling devices, as shown at 5262. In some embodiments, the method may include causing at least a portion of the plurality of bioelectromagnetic interface devices to travel within the body tube tree by moving the at least a portion of the plurality of bioelectromagnetic interface devices through the body tube tree attached to at least one catheter, as indicated at 5264. An example of emplacement of a bioelectromagnetic interface device with a catheter is depicted in FIG. 65. Introduction of a device with a catheter is illustrated in FIG. 65. In some embodiments, following placement of a bioelectromagnetic interface device in the body tube tree with a catheter, the bioelectromagnetic interface device may travel from the initial placement site to a final destination under its own power.

Figure 81:
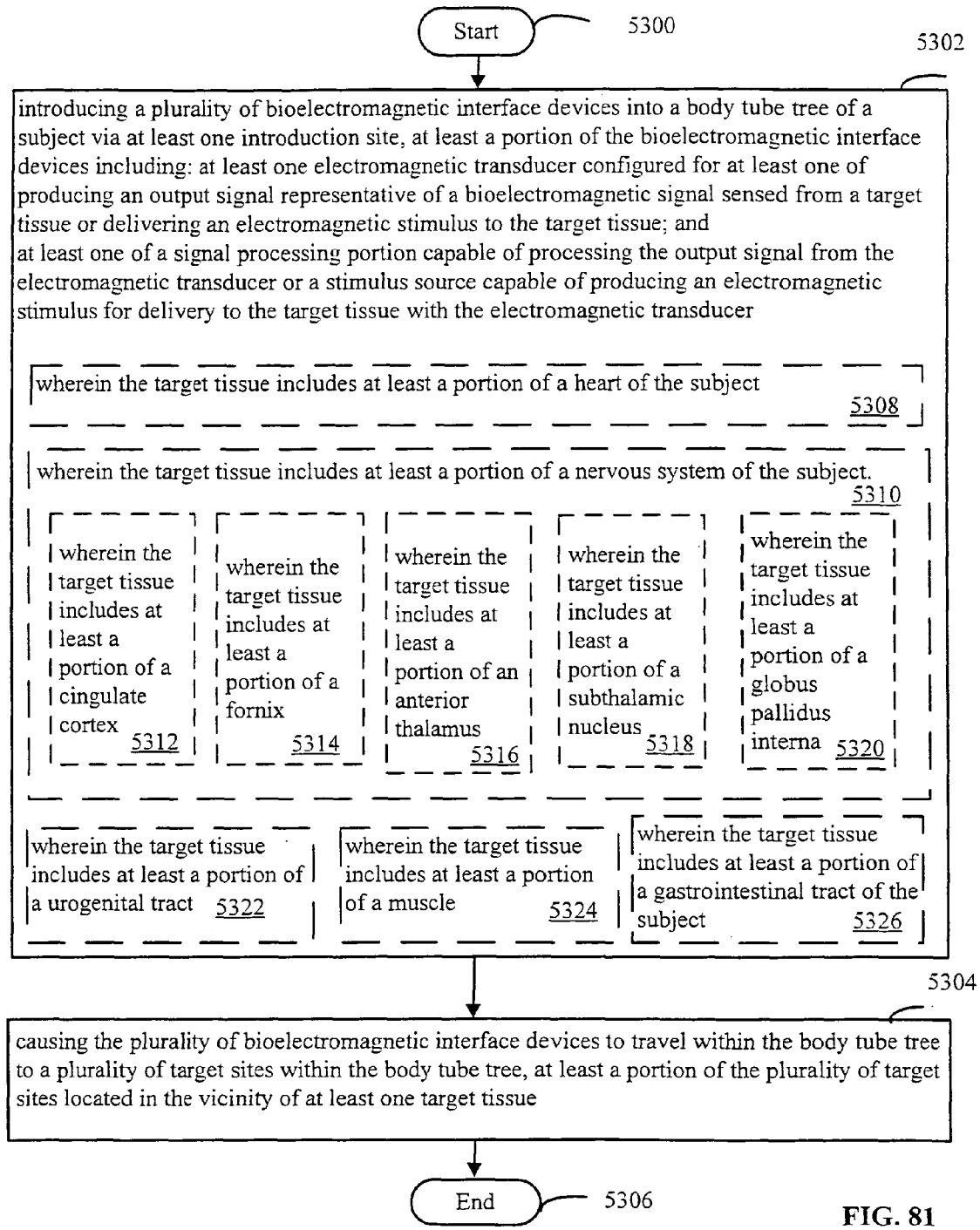
FIG. 81 is a flow diagram showing further variants of the method of FIG. 77.

FIG. 81 is a flow diagram of a method of emplacing a bioelectromagnetic interface system as shown in FIG. 77, which includes: introducing a plurality of bioelectromagnetic interface devices into a body tube tree of a subject via at least one introduction site, at least a portion of the bioelectromagnetic interface devices including at least one electromagnetic transducer configured for at least one of producing an output signal representative of a bioelectromagnetic signal sensed from a target tissue or delivering an electromagnetic stimulus to the target tissue and at least one of a signal processing portion capable of processing the output signal from the electromagnetic transducer or a stimulus source capable of producing an electromagnetic stimulus for delivery to the target tissue with the at least one electromagnetic transducer (step 5302); and causing the plurality of bioelectromagnetic interface devices to travel within the body tube tree to a plurality of target sites within the body tube tree, at least a portion of the plurality of target sites located in the vicinity of at least one target tissue (step 5304). As indicated at 5308, in some embodiments the target tissue may include at least a portion of the heart of the subject. In some embodiments, as indicated at 5310, the target tissue may include at least a portion of the nervous system of the subject, including but not limited to, the cingulate cortex as indicated in 5312, the fornix as indicated in 5314, the anterior thalamus as indicated in 5316, the subthalamic nucleus as indicated in 5318, the or the globus pallidus interna as indicated in 5320. In other embodiments, the target tissue may include at least a portion of a urogenital tract, as indicated at 5322, at least a portion of a muscle, as indicated at 5324, or at least a portion of a gastrointestinal tract, as indicated at 5326.

Figure 82:
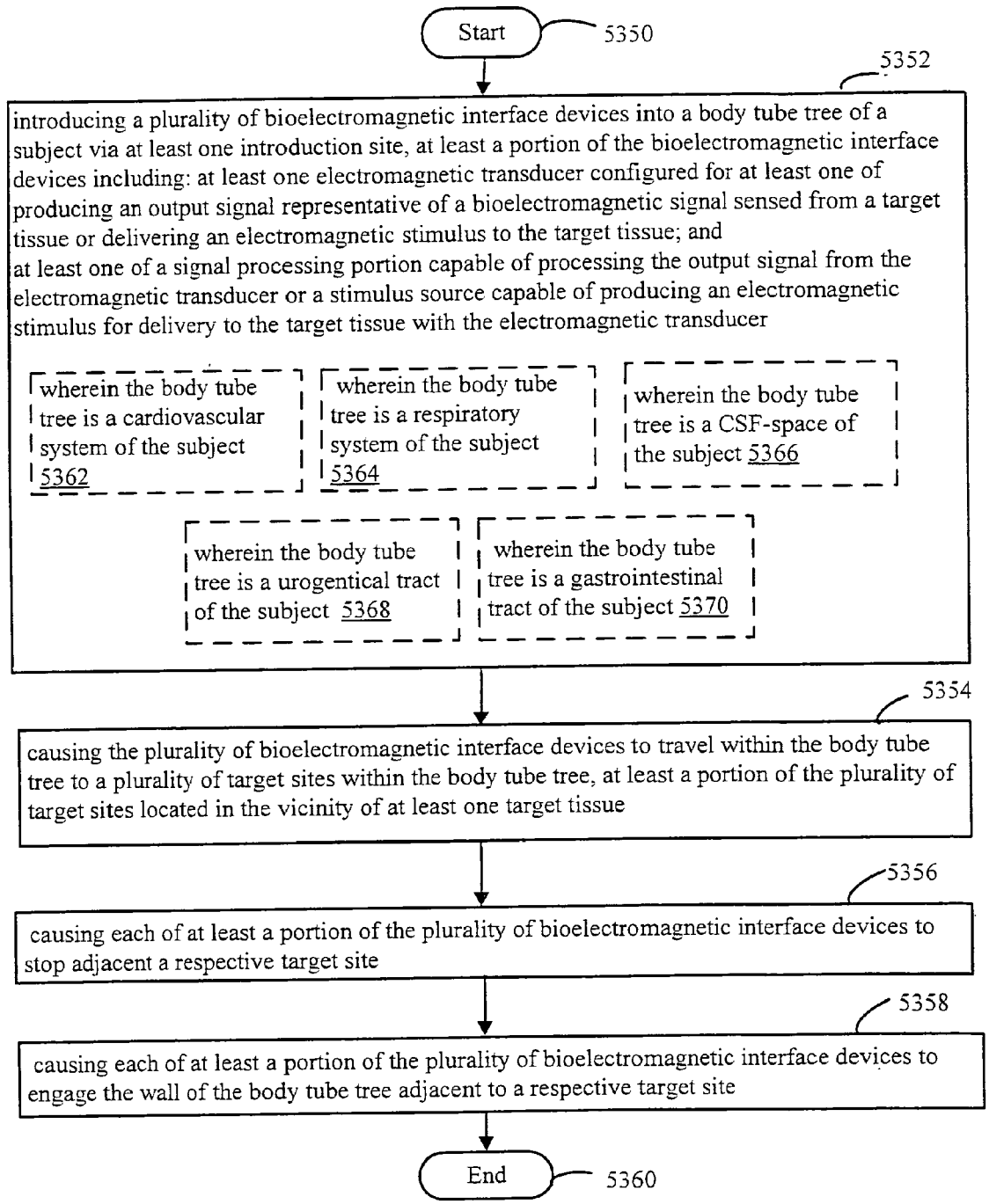
FIG. 82 is a flow diagram showing further variants of the method of FIG. 77.

FIG. 82 is a flow diagram of an expansion the method of emplacing a bioelectromagnetic interface system shown in FIG. 77, which includes: introducing a plurality of bioelectromagnetic interface devices into a body tube tree of a subject via at least one introduction site, at least a portion of the bioelectromagnetic interface devices including at least one electromagnetic transducer configured for at least one of producing an output signal representative of a bioelectromagnetic signal sensed from a target tissue or delivering an electromagnetic stimulus to the target tissue and at least one of a signal processing portion capable of processing the output signal from the electromagnetic transducer or a stimulus source capable of producing an electromagnetic stimulus for delivery to the target tissue with the at least one electromagnetic transducer (step 5352); causing the plurality of bioelectromagnetic interface devices to travel within the body tube tree to a plurality of target sites within the body tube tree, at least a portion of the plurality of target sites located in the vicinity of at least one target tissue (step 5354), causing each of at least a portion of the plurality of bioelectromagnetic interface devices to stop adjacent a respective target site (step 5356), and, optionally, causing each of at least a portion of the plurality of bioelectromagnetic interface devices to engage the wall of the body tube tree adjacent to a respective target site (step 5358). In some embodiments, as indicated at 5362, the body tube tree may be the cardiovascular system of the subject. In other embodiments, as indicated at 5364, the body tube tree may be the respiratory system of the subject. In still other embodiments, the body tube tree may be the CSF-space of the subject, as indicated at 5366, the urogenital tract of the subject, as indicated at 5368, or the gastrointestinal tract of the subject, as indicated at 5370.

Figure 83:
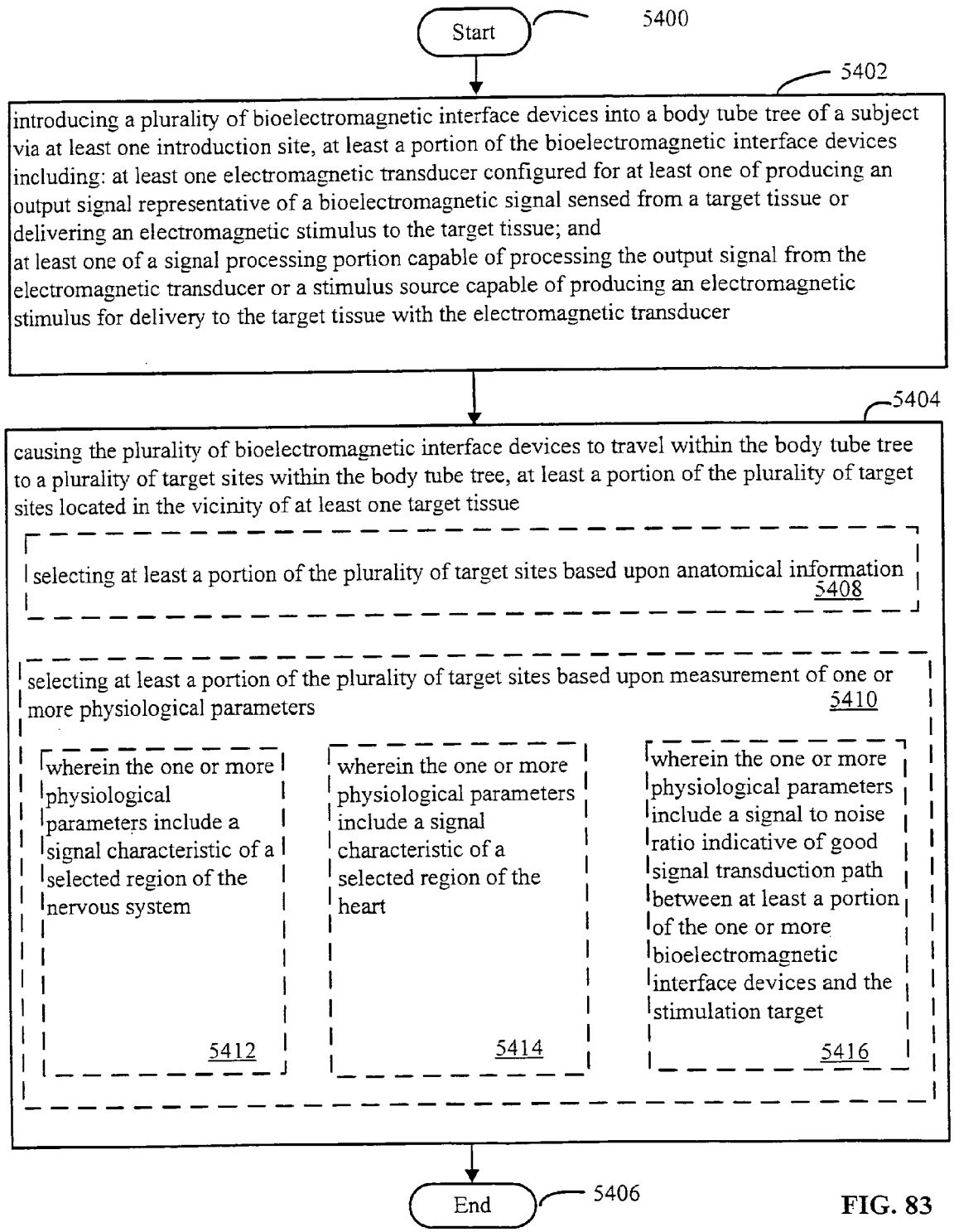

FIG. 83 is a flow diagram showing further variations of the method of emplacing a bioelectromagnetic interface system shown generally in FIG. 77. The method includes: introducing a plurality of bioelectromagnetic interface devices into a body tube tree of a subject via at least one introduction site, at least a portion of the bioelectromagnetic interface devices including at least one electromagnetic transducer configured for at least one of producing an output signal representative of a bioelectromagnetic signal sensed from a target tissue or delivering an electromagnetic stimulus to the target tissue and at least one of a signal processing portion capable of processing the bioelectromagnetic signal recorded from the target tissue with the at least one electromagnetic transducer or a stimulus source capable of producing an electromagnetic stimulus for delivery to the target tissue with the at least one electromagnetic transducer (step 5402); causing the plurality of bioelectromagnetic interface devices to travel within the body tube tree to a plurality of target sites within the body tube tree, at least a portion of the plurality of target sites located in the vicinity of at least one target tissue (step 5404). In some embodiments, as shown at 5408, the method may include selecting at least a portion of the plurality of target sites based upon anatomical information. In some embodiments, as shown at 5410, the method may include selecting at least a portion of the plurality of target sites based upon measurement of one or more physiological parameters, which might be, for example, a signal characteristic of a selected region of the nervous system, as shown at 5412, or a selected region of the heart, as shown at 5414. In some embodiments, as shown at 5416, the one or more physiological parameters may include a signal-to-noise ratio indicative of good signal transduction path between at least a portion of the one or more bioelectromagnetic interface devices and the stimulation target.

Figure 84:
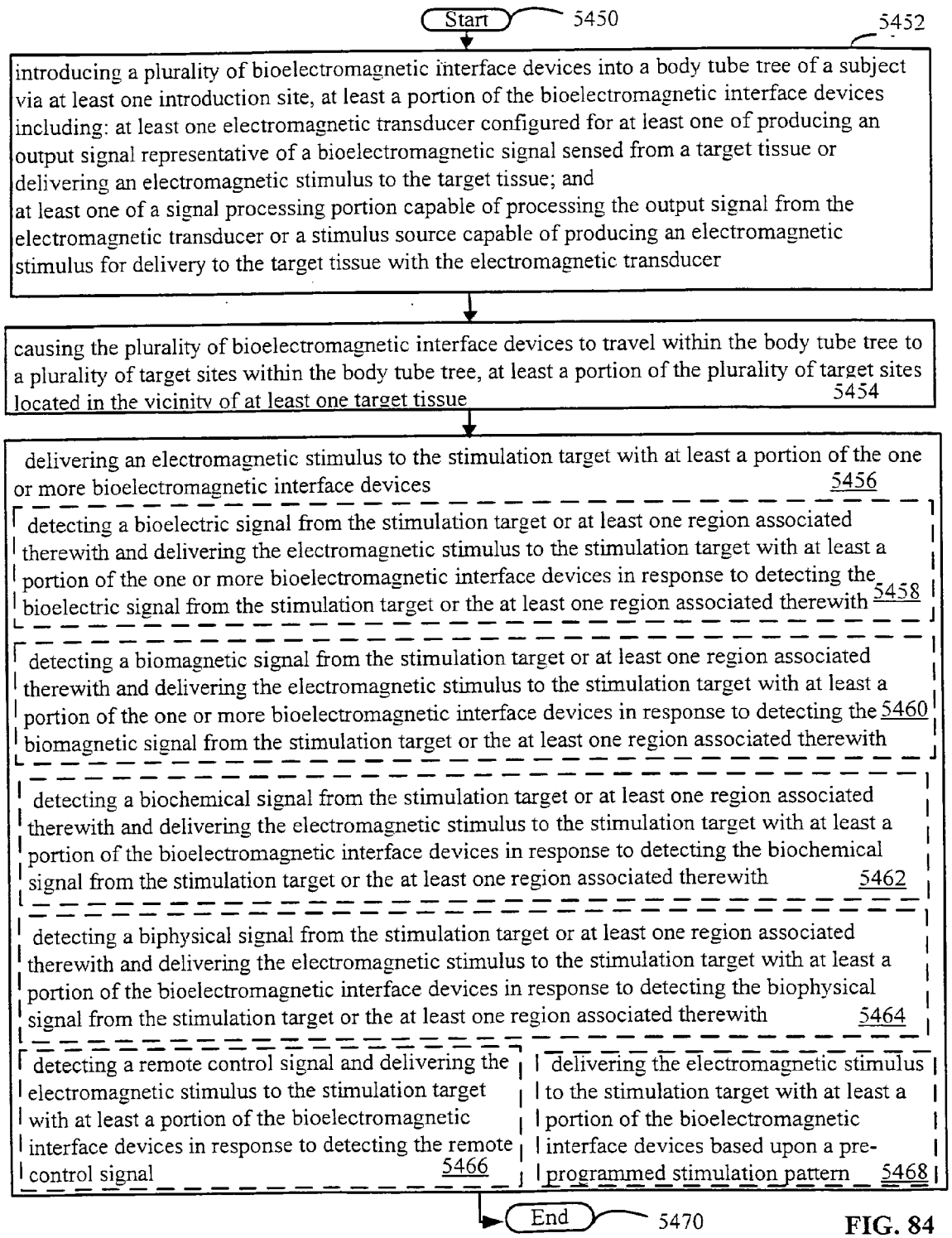
FIG. 84 is a flow diagram showing further variants of the method of FIG. 77.

FIG. 84 is a flow diagram including further variations of the method of emplacing a bioelectromagnetic interface system shown generally in FIG. 77. The method includes: introducing a plurality of bioelectromagnetic interface devices into a body tube tree of a subject via at least one introduction site, at least a portion of the bioelectromagnetic interface devices including at least one configured for at least one of producing an output signal representative of a bioelectromagnetic signal sensed from a target tissue or delivering an electromagnetic stimulus to the target tissue and at least one of a signal processing portion capable of processing the bioelectromagnetic signal recorded from the target tissue with the at least one electromagnetic transducer or a stimulus source capable of producing an electromagnetic stimulus for delivery to the target tissue with the at least one electromagnetic transducer (step 5452); causing the plurality of bioelectromagnetic interface devices to travel within the body tube tree to a plurality of target sites within the body tube tree, at least a portion of the plurality of target sites located in the vicinity of at least one target tissue (step 5454). In addition, the method may include delivering an electromagnetic stimulus to the stimulation target with at least a portion of the one or more bioelectromagnetic interface devices, at 5456.

As shown at 5458 of FIG. 84, the method may include detecting a bioelectric signal from the stimulation target or at least one region associated therewith and delivering the electromagnetic stimulus to the stimulation target with at least a portion of the one or more bioelectromagnetic interface devices in response to detecting the bioelectric signal from the stimulation target or the at least one region associated therewith. Alternatively, or in addition, the method may include detecting a biomagnetic signal from the stimulation target or at least one region associated therewith and delivering the electromagnetic stimulus to the stimulation target with at least a portion of the one or more bioelectromagnetic interface devices in response to detecting the biomagnetic signal from the stimulation target or the at least one region associated therewith, as shown at 5460. In another alternative, the method may include detecting a biochemical signal from the stimulation target or at least one region associated therewith and delivering the electromagnetic stimulus to the stimulation target with at least a portion of the one or more bioelectromagnetic interface devices in response to detecting the biochemical signal from the stimulation target or the at least one region associated therewith, as shown at 5462. Biochemical signals may include signals from various types of biosensors, indicating concentration of neurotransmitters, direct or indirect indicators of metabolic activity, pH, cell-signaling materials, and other biochemical signals indicating a condition of the stimulation target and/or indication for delivery of stimulation to the stimulation target.

In another alternative, the method may include detecting a biophysical signal from the stimulation target or at least one region associated therewith and delivering the electromagnetic stimulus to the stimulation target with at least a portion of the one or more bioelectromagnetic interface devices in response to detecting the biophysical signal from the stimulation target or the at least one region associated therewith, as shown at 5464.

In some embodiments, one or more remote portions may be used, and the method may include detecting a remote control signal and delivering the electromagnetic stimulus to the stimulation target with at least a portion of the bioelectromagnetic interface devices in response to detecting the remote control signal, as a shown at 5466. In other embodiments, the method may include delivering the electromagnetic stimulus to the stimulation target with at least a portion of the bioelectromagnetic interface devices based upon a pre-programmed stimulation pattern, as shown at 5468.

Figure 85:
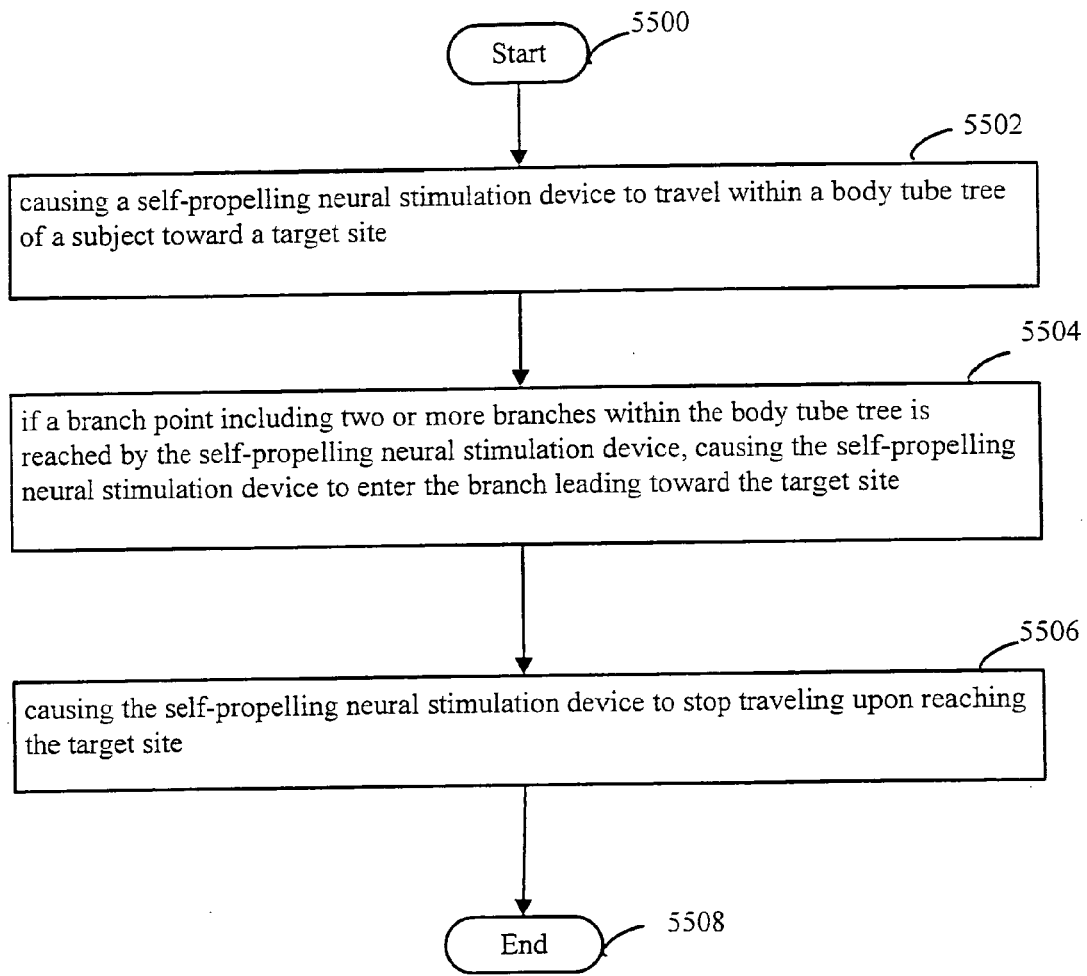
FIG. 85 is a flow diagram of a method of emplacing a neural stimulation device.

FIG. 85 is a flow diagram of a method of emplacing a neural stimulation device, which may include causing a self-propelling neural stimulation device to travel within a body tube tree of a subject toward a target site (at step 5502); if a branch point including two or more branches within the body tube tree is reached by the self-propelling neural stimulation device, causing the self-propelling neural stimulation device to enter a branch leading toward the target site (at step 5504); and causing the self-propelling neural stimulation device to stop traveling upon reaching the target site (at 5506). As noted elsewhere herein, various applications are known for neural stimulation devices and systems. The method may be used for emplacing a single neural stimulation device at a time, or for expanding to emplace multiple neural stimulation devices. In one variant, the method may include carrying at least one additional neural stimulation device with the self-propelling neural stimulation device. The neural stimulation devices may remain connected during use, or the method may include resealing the at least one additional neural stimulation device from the self-propelling neural stimulation device.

Figure 86:
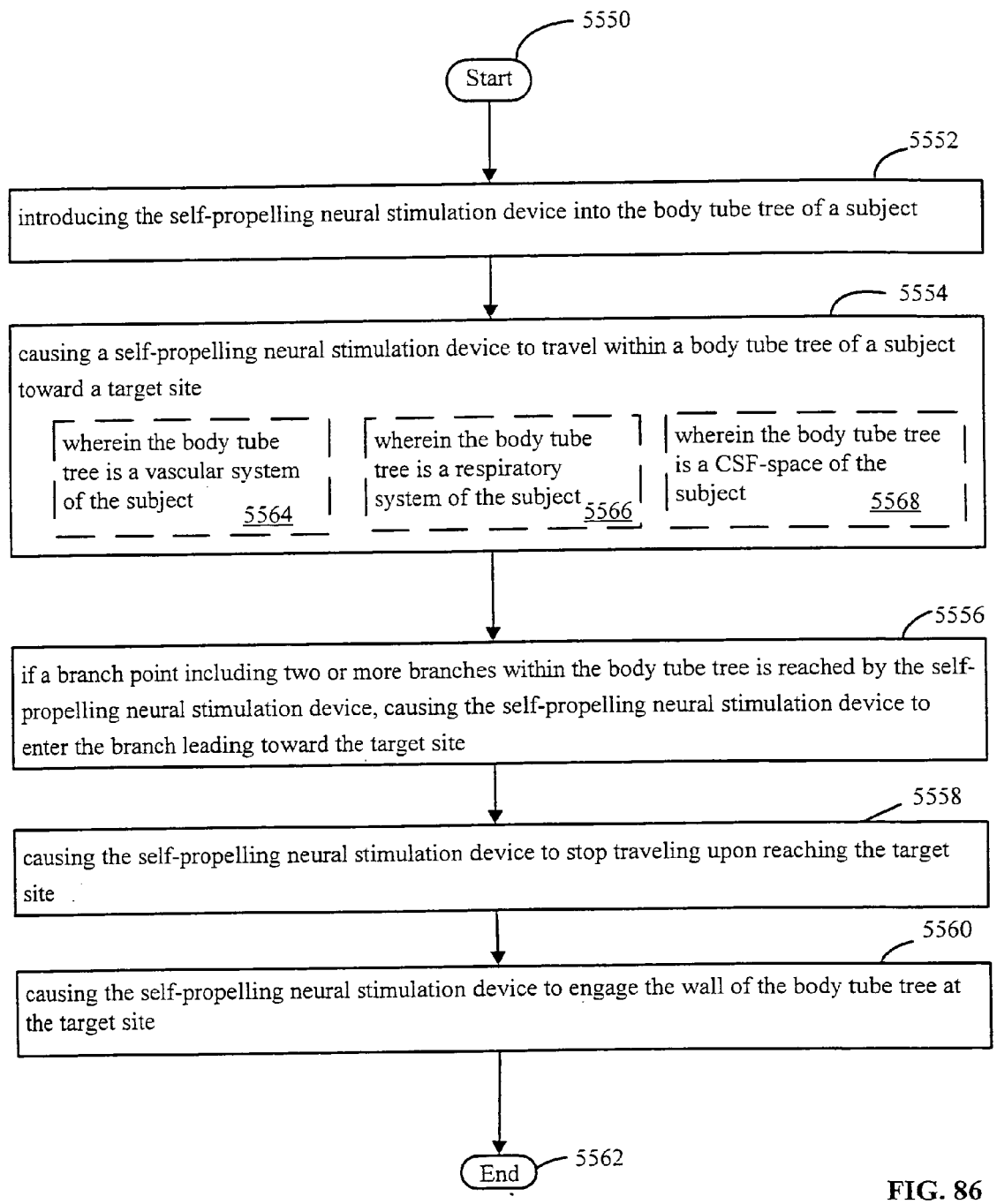
FIG. 86 is a flow diagram showing several variants of the method of FIG. 85.

FIG. 86 is a flow diagram showing further details of a method as outlined in FIG. 85. The method may include introducing the self-propelling neural stimulation device into the body tube tree of a subject (at step 5552), causing a self-propelling neural stimulation device to travel within a body tube tree of a subject toward a target site (at step 5554); if a branch point including two or more branches within the body tube tree is reached by the self-propelling neural stimulation device, causing the self-propelling neural stimulation device to enter a branch leading toward the target site (at step 5556); causing the self-propelling neural stimulation device to stop traveling upon reaching the target site (at 5558), and, optionally, causing the self-propelling neural stimulation device to engage the wall of the body tube tree at the target site (at step 5560). The body tube tree may be the vascular system of the subject, as indicated at 5564, the respiratory system of the subject, as indicated at 5566, or the CSF-space of the subject, as indicated at 5568, for example.

Figure 87:
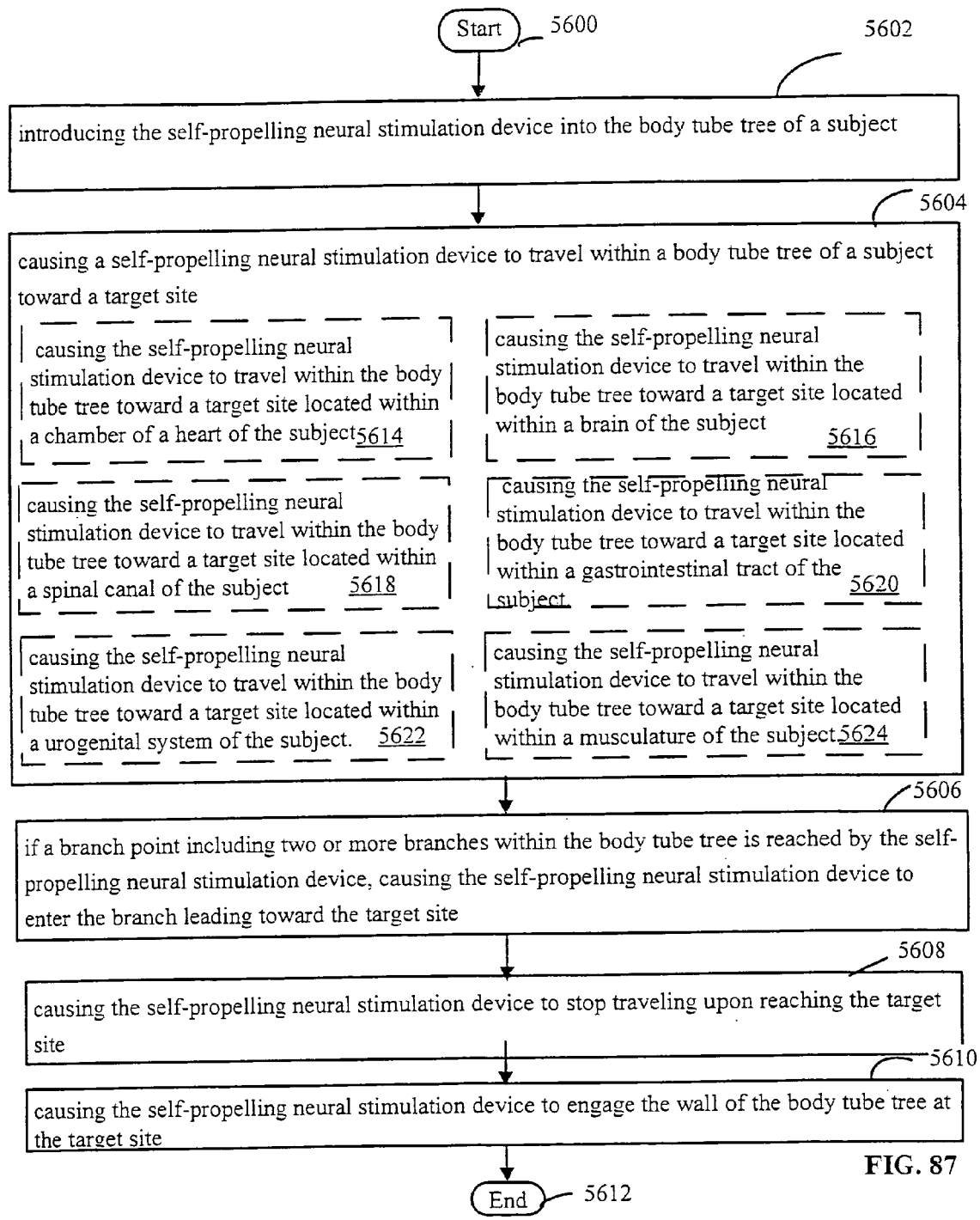
FIG. 87 is a flow diagram showing further variants of the method of FIG. 85.

FIG. 87 is a flow diagram showing further details of a method as outlined in FIG. 86. The method may include introducing the self-propelling neural stimulation device into the body tube tree of a subject (at step 5602), causing a self-propelling neural stimulation device to travel within a body tube tree of a subject toward a target site (at step 5604); if a branch point including two or more branches within the body tube tree is reached by the self-propelling neural stimulation device, causing the self-propelling neural stimulation device to enter a branch leading toward the target site (at step 5606); causing the self-propelling neural stimulation device to stop traveling upon reaching the target site (at 5608), and, optionally, causing the self-propelling neural stimulation device to engage the wall of the body tube tree at the target site (at step 5610). The method may include causing the self-propelling neural stimulation device to travel within the body tube tree toward a target site located within a chamber of the heart of the subject, as indicated at 5614. In another embodiment, the method may include causing the self-propelling neural stimulation device to travel within the body tube tree toward a target site located within the brain of the subject, as indicated at 5616. In another embodiment, the method may include causing the self-propelling neural stimulation device to travel within the body tube tree toward a target site located within the spinal canal of the subject, as indicated at 5618. In another embodiment, the method may include causing the self-propelling neural stimulation device to travel within the body tube tree toward a target site located within the gastrointestinal tract of the subject, as indicated at 5620. In still another embodiment, the method may include causing the self-propelling neural stimulation device to travel within the body tube tree toward a target site located within the urogenital system of the subject, as indicated at 5622. And in yet another embodiment, the method may include causing the self-propelling neural stimulation device to travel within the body tube tree toward a target site located within the musculature of the subject, as indicated at 5624.

Figure 88:
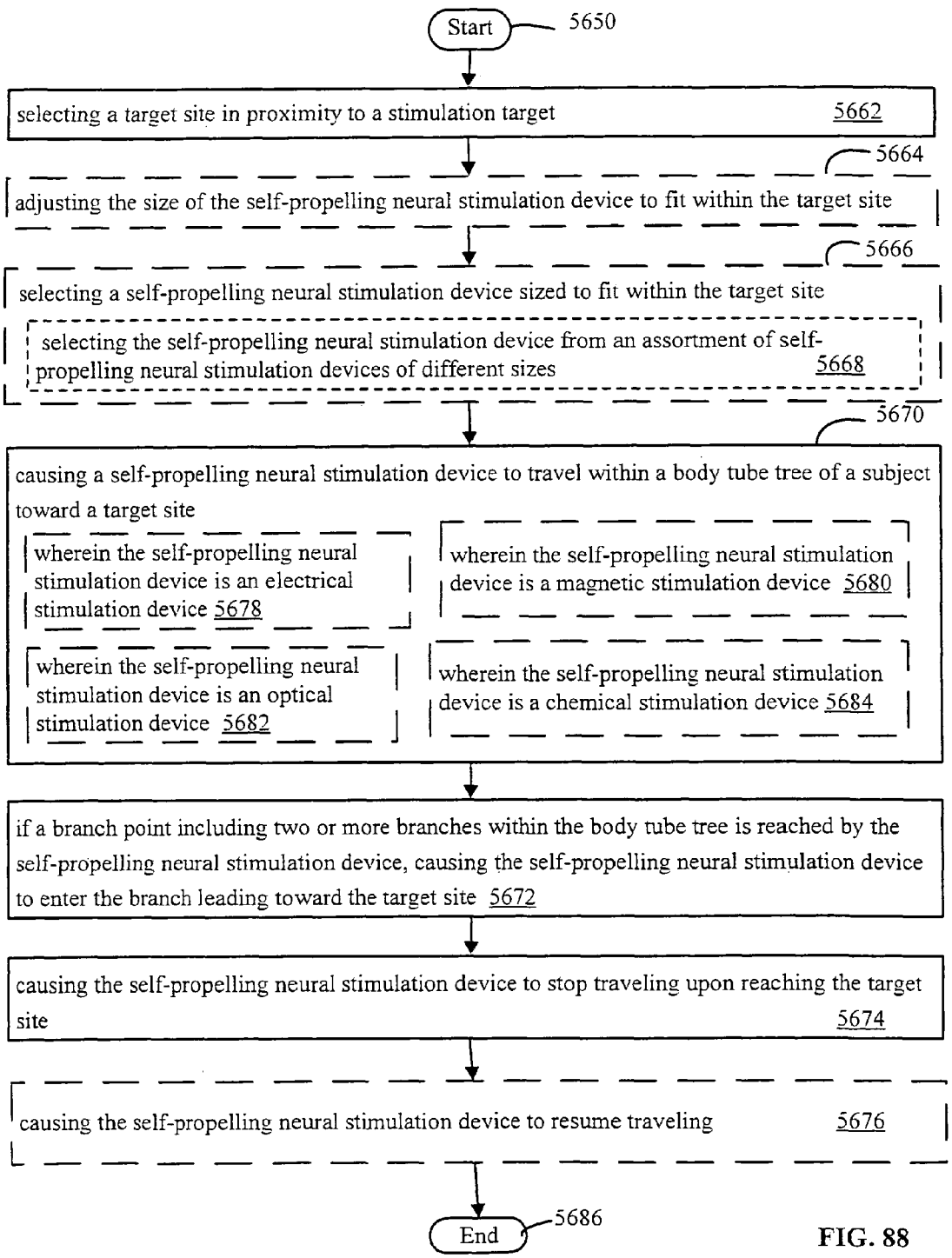
FIG. 88 is a flow diagram showing further variants of the method of FIG. 85.

FIG. 88 is a flow diagram showing a further expansion of the method of FIG. 85. The method includes selecting a target site in proximity to a stimulation target (at step 5652) and performing one or more of adjusting the size of the self-propelling neural stimulation device to fit within the target site (at 5664) or selecting a self-propelling neural stimulation device sized to fit within a target size (at 5666), e.g. by selecting the self-propelling neural stimulation device from an assortment of self-propelling neural stimulation devices of different sizes (at 5668). The method may also include the steps of causing a self-propelling neural stimulation device to travel within a body tube tree of a subject toward a target site (at 5670), if a branch point including two or more branches within the body tube tree is reached by the self-propelling neural stimulation device, causing the self-propelling neural stimulation device to enter a branch leading toward the target site (at 5672), and causing the self-propelling neural stimulation device to stop traveling upon reaching the target site (at 5674). In some embodiments, the method may include causing the self-propelling neural stimulation device to resume traveling, as indicated at 5676. The self-propelling neural stimulation device may be an electromagnetic stimulation device, as indicated at 5678, a magnetic stimulation device, as indicated at 5680, an optical stimulation device, as indicated at 5682, or a chemical stimulation device, as indicated at 5684.

Figure 89:
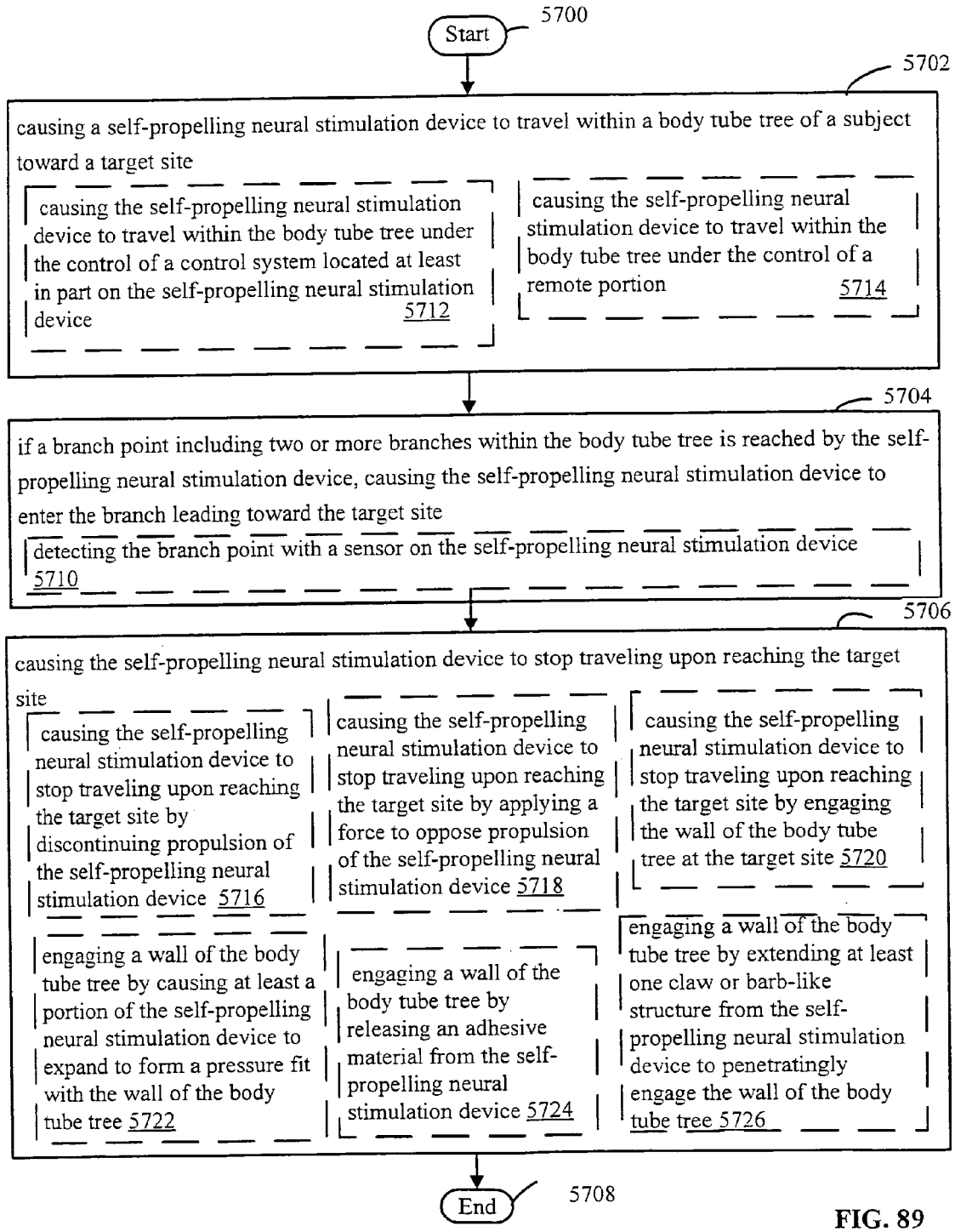
FIG. 89 is a diagram showing still further variants of the method of FIG. 85.

FIG. 89 is a flow diagram showing a further expansion of the method of FIG. 85, including the steps of causing a self-propelling neural stimulation device to travel within a body tube tree of a subject toward a target site at 5702; if a branch point including two or more branches within the body tube tree is reached by the self-propelling neural stimulation device, causing the self-propelling neural stimulation device to enter a branch leading toward the target site at 5704; and causing the self-propelling neural stimulation device to stop traveling upon reaching the target site at 5706. The method may include detecting the branch point with a sensor on the self-propelling neural stimulation device, as indicated at 5710. As indicated at 5712, the method may include causing the self-propelling neural stimulation device to travel within the body tube tree under the control of a control system located at least in part on the self-propelling neural stimulation device. Alternatively, the method may include causing the self-propelling neural stimulation device to travel within the body tube tree under the control of a remote portion, as indicated at 5714. The method may include causing the self-propelling neural stimulation device to stop traveling upon reaching the target site by discontinuing propulsion of the self-propelling neural stimulation device, as shown at 5716, by causing the self-propelling neural stimulation device to stop traveling upon reaching the target site by applying a force to oppose propulsion of the self-propelling neural stimulation device, as shown at 5718, or by engaging the wall of the body tube tree at the target site, as shown at 5720. The self-propelling neural stimulation device may be caused to engage a wall of the body tube tree by causing at least a portion of the self-propelling neural stimulation device to expand to form a pressure fit with the wall of the body tube tree, as indicated at 5722, by releasing an adhesive material from the self-propelling neural stimulation device, as indicated at 5724, or extending at least one claw or barb-like structure from the self-propelling neural stimulation device to penetratingly engage the wall of the body tube tree, as indicated at 5726. Examples of such structures are illustrated in FIGS. 5A, 5B, and 8B, for example.

Figure 90:
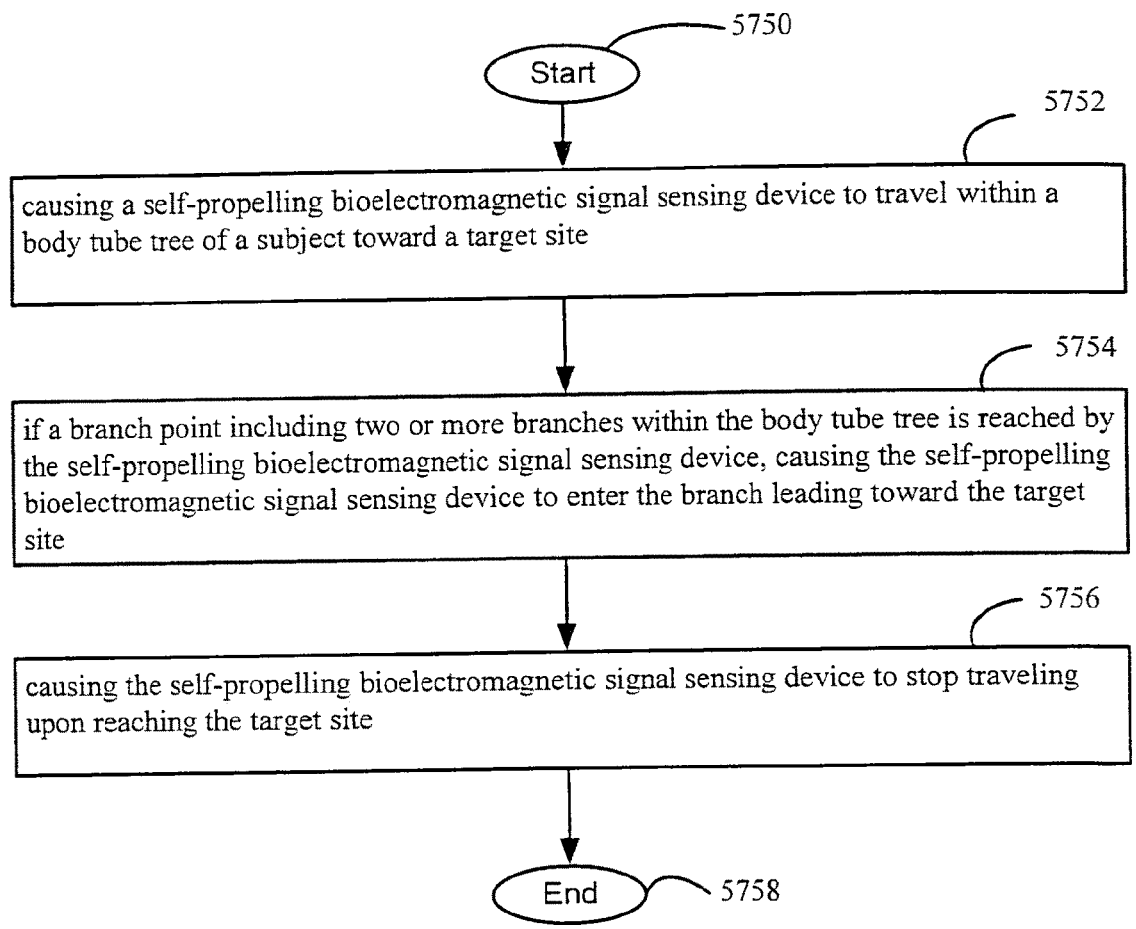
FIG. 90 is a flow diagram of a method of emplacing a bioelectromagnetic signal sensing device.

FIG. 90 depicts steps of method of emplacing a bioelectromagnetic signal sensing device, which may include: causing a self-propelling bioelectromagnetic signal sensing device to travel within a body tube tree of a subject toward a target site (step 5752); if a branch point including two or more branches within the body tube tree may be reached by the self-propelling bioelectromagnetic signal sensing device, causing the self-propelling bioelectromagnetic signal sensing device to enter a branch leading toward the target site (step 5754); and causing the self-propelling bioelectromagnetic signal sensing device to stop traveling upon reaching the target site (step 5756).

In some embodiments, sensing of bioelectromagnetic signals with bioelectromagnetic signal sensing devices as described herein may be used in research or diagnostic applications. In some embodiments, sensing of bioelectromagnetic signals may be used in combination with stimulation (electrical, magnetic, chemical, optical, etc.), delivery of drugs, or various treatments, stimuli, etc. to provide a therapeutic or beneficial effect, for providing control or feedback. Such applications are provided by way of example, and are not intended to be limiting.

Figure 91:
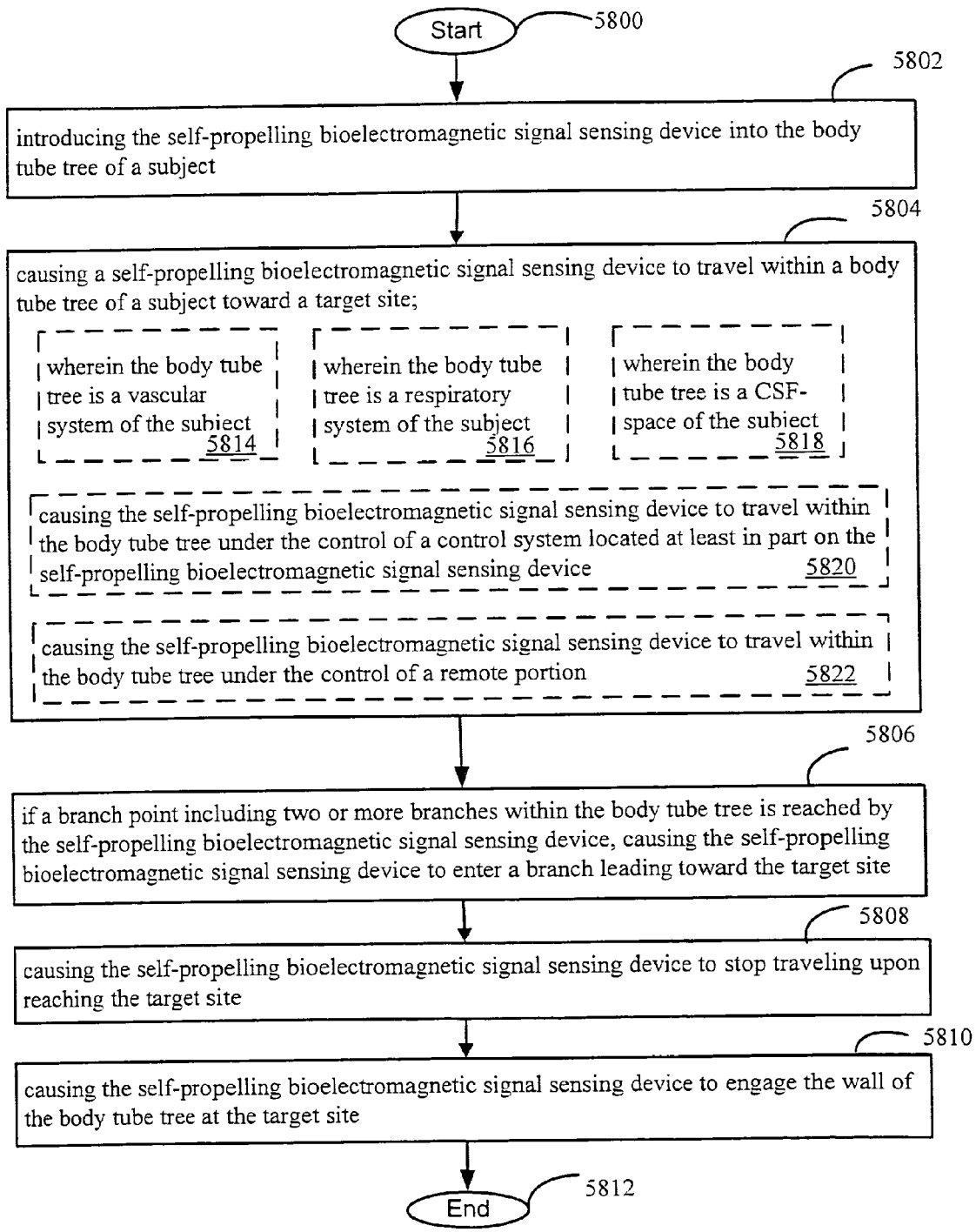
FIG. 91 is a flow diagram showing several variations of the method of FIG. 90.

FIG. 91 shows an expanded version of the method of FIG. 90, which includes introducing the self-propelling bioelectromagnetic signal sensing device into the body tube tree of a subject at 5802; causing the self-propelling bioelectromagnetic signal sensing device to travel within a body tube tree of a subject toward a target site at 5804; if a branch point including two or more branches within the body tube tree is reached by the self-propelling bioelectromagnetic signal sensing device, causing the self-propelling bioelectromagnetic signal sensing device to enter a branch leading toward the target site at 5806 causing the self-propelling bioelectromagnetic signal sensing device to stop traveling upon reaching the target site at 5808; and causing the self-propelling bioelectromagnetic signal sensing device to engage the wall of the body tube tree at the target site at 5810. The body tube tree may be any of various body tube trees, including, but not limited to, a vascular system of the subject, as indicated at 5814, a respiratory system of the subject, as indicated at 5816, or a CSF-space of the subject, as indicated at 5818. The bioelectromagnetic signal sensing device may be caused to travel within the body tube tree under the control of a control system located at least in part on the self-propelling bioelectromagnetic signal sensing device, as indicated at 5820, or alternatively, the method may include causing the self-propelling bioelectromagnetic signal sensing device to travel within the body tube tree under the control of a remote portion, as indicated at 5822.

Figure 92:
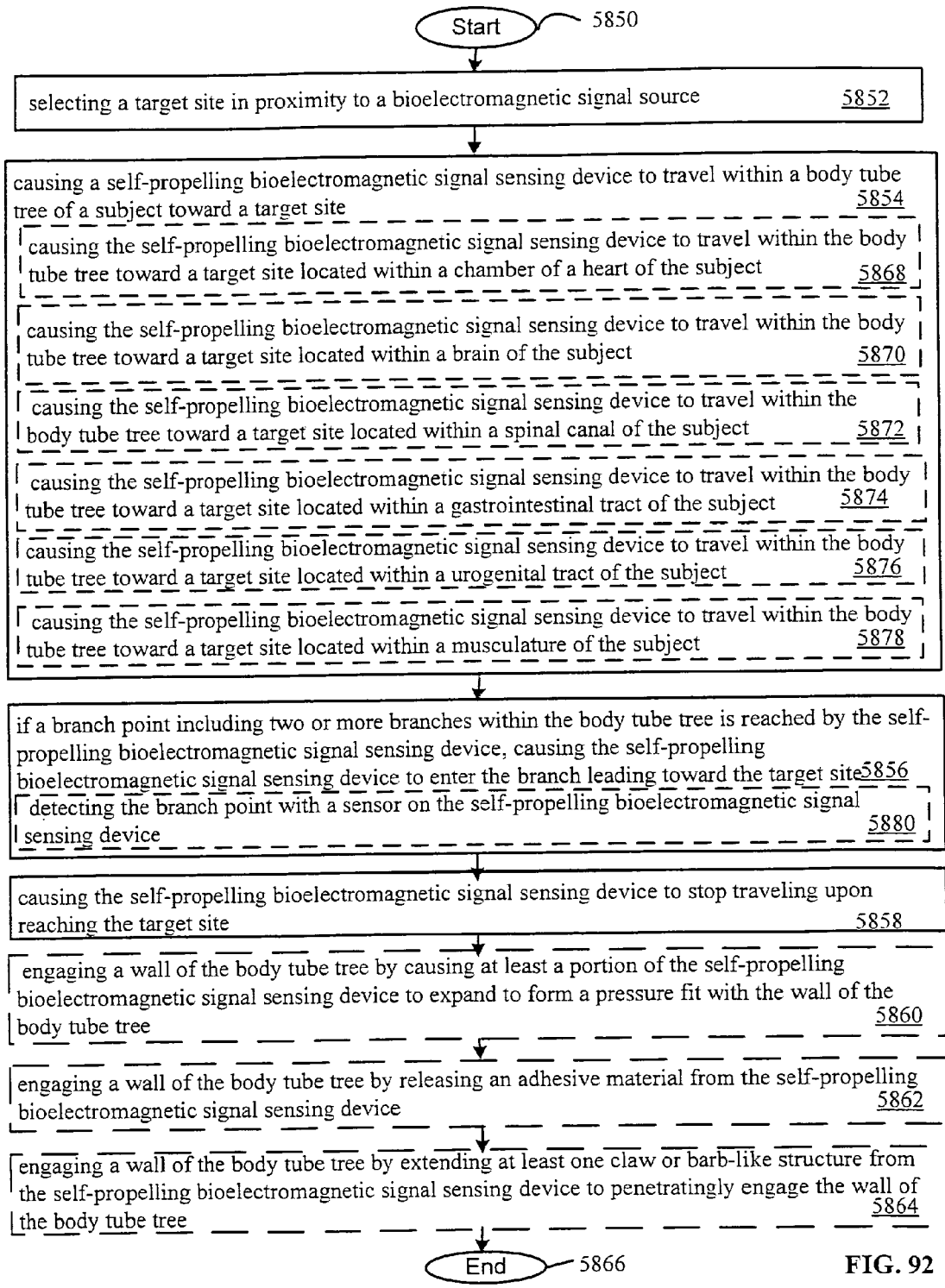
FIG. 92 is a flow diagram showing further variations of the method of FIG. 90.

FIG. 92 provides still further details of a method as shown in FIG. 90. The method includes selecting a target site in proximity to a bioelectromagnetic signal source (step 5852); causing a self-propelling bioelectromagnetic signal sensing device to travel within a body tube tree of a subject toward a target site (step 5854); if a branch point including two or more branches within the body tube tree is reached by the self-propelling bioelectromagnetic signal sensing device, causing the self-propelling bioelectromagnetic signal sensing device to enter a branch leading toward the target site (step 5856); and causing the self-propelling bioelectromagnetic signal sensing device to stop traveling upon reaching the target site (step 5858). As in various previously described embodiments, the method may include a step of engaging a wall of the body tube tree by various methods including, but not limited to, causing at least a portion of the self-propelling bioelectromagnetic signal sensing device to expand to form a pressure fit with the wall of the body tube tree (as shown at 5860), releasing an adhesive material from the self-propelling bioelectromagnetic signal sensing device (as shown at 5862), or extending at least one claw or barb-like structure from the self-propelling bioelectromagnetic signal sensing device to penetratingly engage the wall of the body tube tree (as shown at 5864). Step 5854 may include causing the self-propelling bioelectromagnetic signal sensing device to travel with the body tube tree toward a target site located within a chamber of a heart of the subject (as shown at 5868), within the brain of the subject, of the subject (as shown at 5870), within a spinal canal of the subject (as shown at 5872), within a gastrointestinal tract of the subject (as shown at 5874), within a urogenital system of the subject (as shown at 5876), or within a musculature of the subject of the subject (as shown at 5878). A target site may be selected that is in proximity to a bioelectromagnetic signal source, for example, a target site within a chamber of the heart may be selected if a signal is to be detected from the heart, a target site within a cerebral ventrical or a blood vessel in the brain may be selected for detecting a signal from a region of the brain, and so on. As shown at 5880, the method may include detecting the branch point with a sensor on the self-propelling bioelectromagnetic signal sensing device. Various types of signals may provide information about the presence of a branch point, including, for example, optical signals, acoustic signals, and electromagnetic signals, among others.

Figure 93:
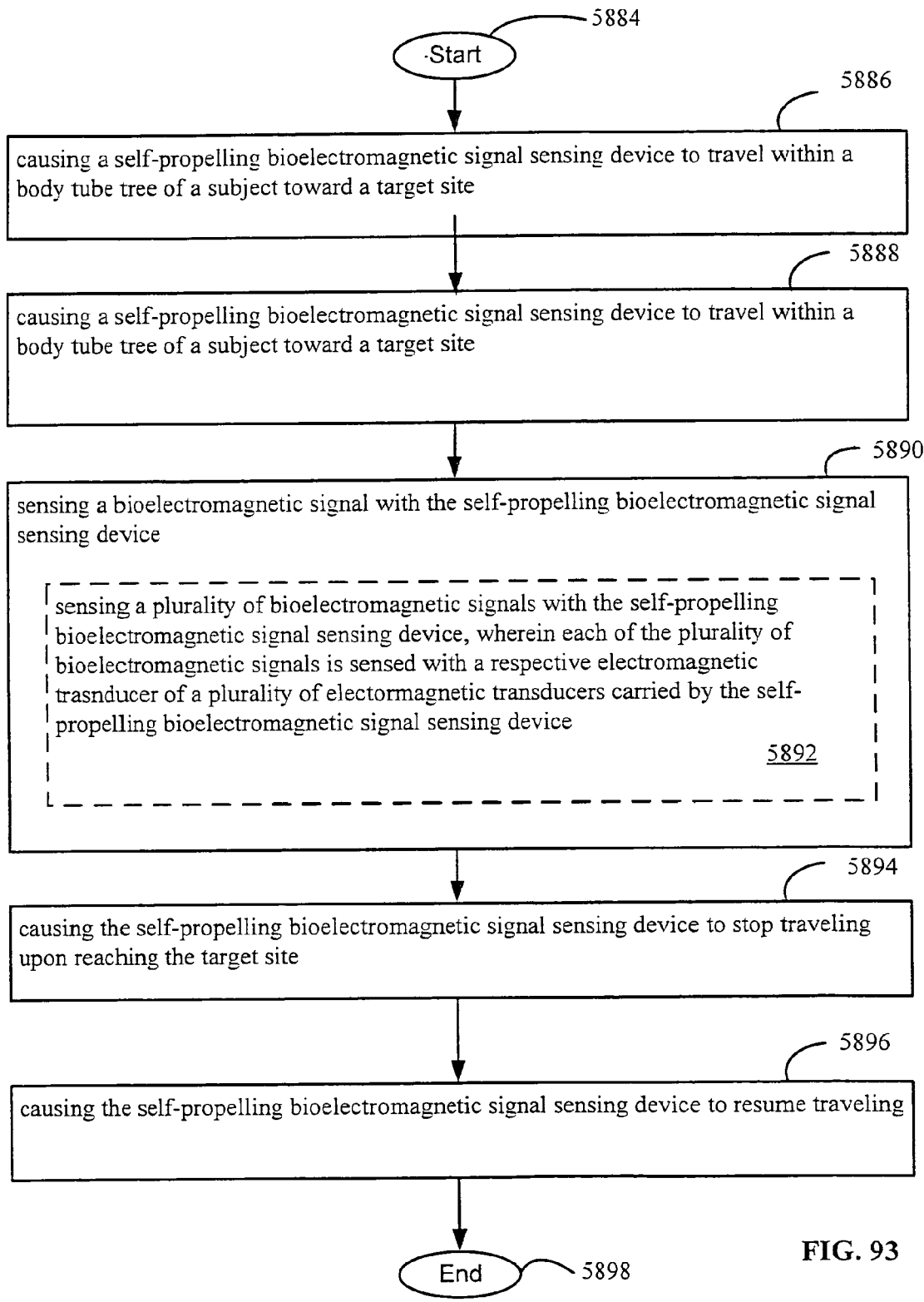
FIG. 93 is a flow diagram showing further variations of the method of FIG. 90.

FIG. 93 is a flow diagram showing a further variant of the method of FIG. 90, which includes the steps of causing a self-propelling bioelectromagnetic signal sensing device to travel within a body tube tree of a subject toward a target site (step 5886), causing a self-propelling bioelectromagnetic signal sensing device to travel within a body tube tree of a subject toward a target site (step 5888), and sensing a bioelectromagnetic signal with the self-propelling bioelectromagnetic signal sensing device (step 5890). In some embodiments, the method may include, sensing a plurality of bioelectromagnetic signals with the self-propelling bioelectromagnetic signal sensing device, wherein each of the plurality of bioelectromagnetic signals is sensed with a respective electromagnetic transducer of a plurality of electromagnetic transducers carried by the self-propelling bioelectromagnetic signal sensing device, as indicated at 5892. The method may also include causing the self-propelling bioelectromagnetic signal sensing device to stop traveling upon reaching the target site (step 5894) and causing the self-propelling bioelectromagnetic signal sensing device to resume traveling (step 5896).

Figure 94:
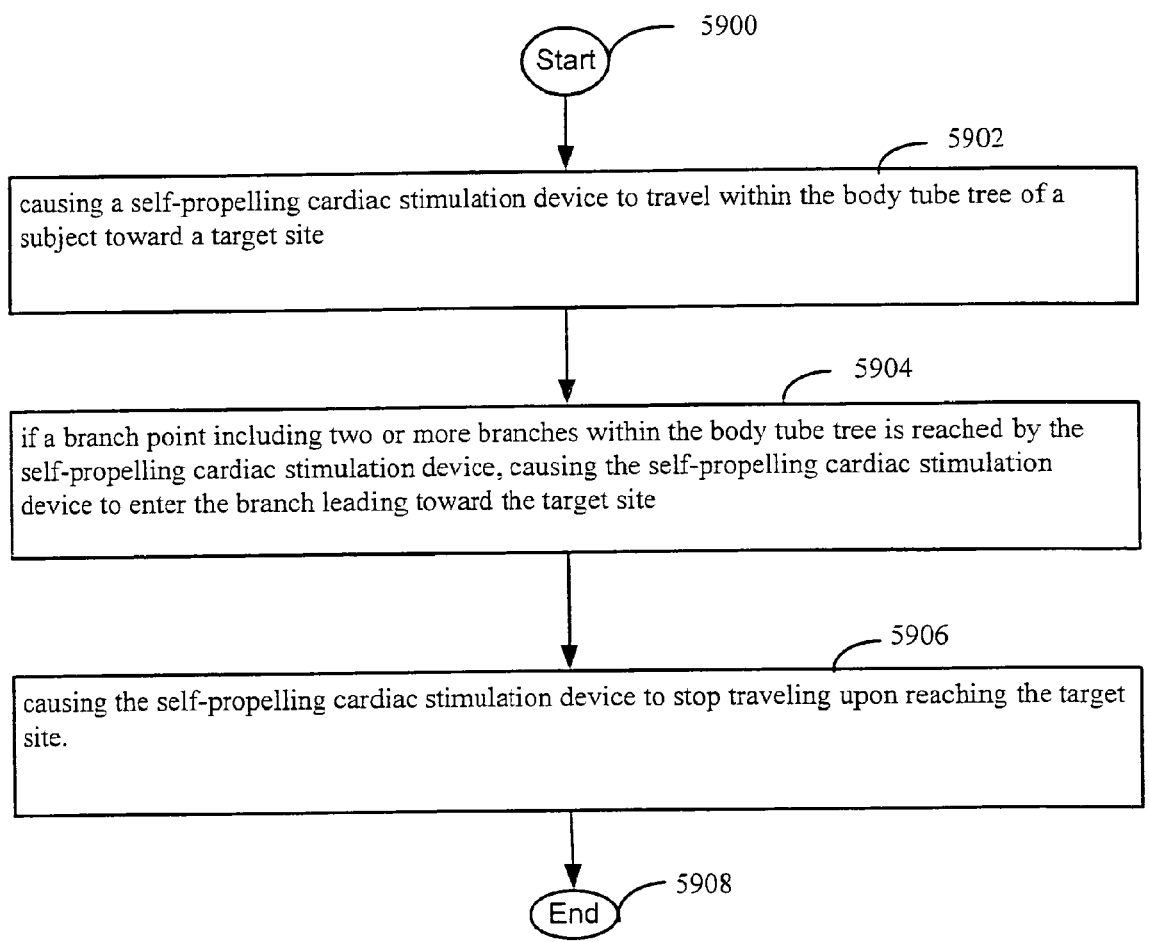
FIG. 94 is a flow diagram of a method of emplacing a cardiac stimulation device.

Another application for methods and devices as described herein is in cardiac stimulation. FIG. 94 shows steps of method for emplacing a cardiac stimulation device. The method may include causing a self-propelling cardiac stimulation device to travel within the body tube tree of a subject toward a target site at 5902; if a branch point including two or more branches within the body tube tree is reached by the self-propelling cardiac stimulation device, causing the self-propelling cardiac stimulation device to enter a branch leading toward the target site at 5904; and causing the self-propelling cardiac stimulation device to stop traveling upon reaching the target site at 5906.

Figure 95:
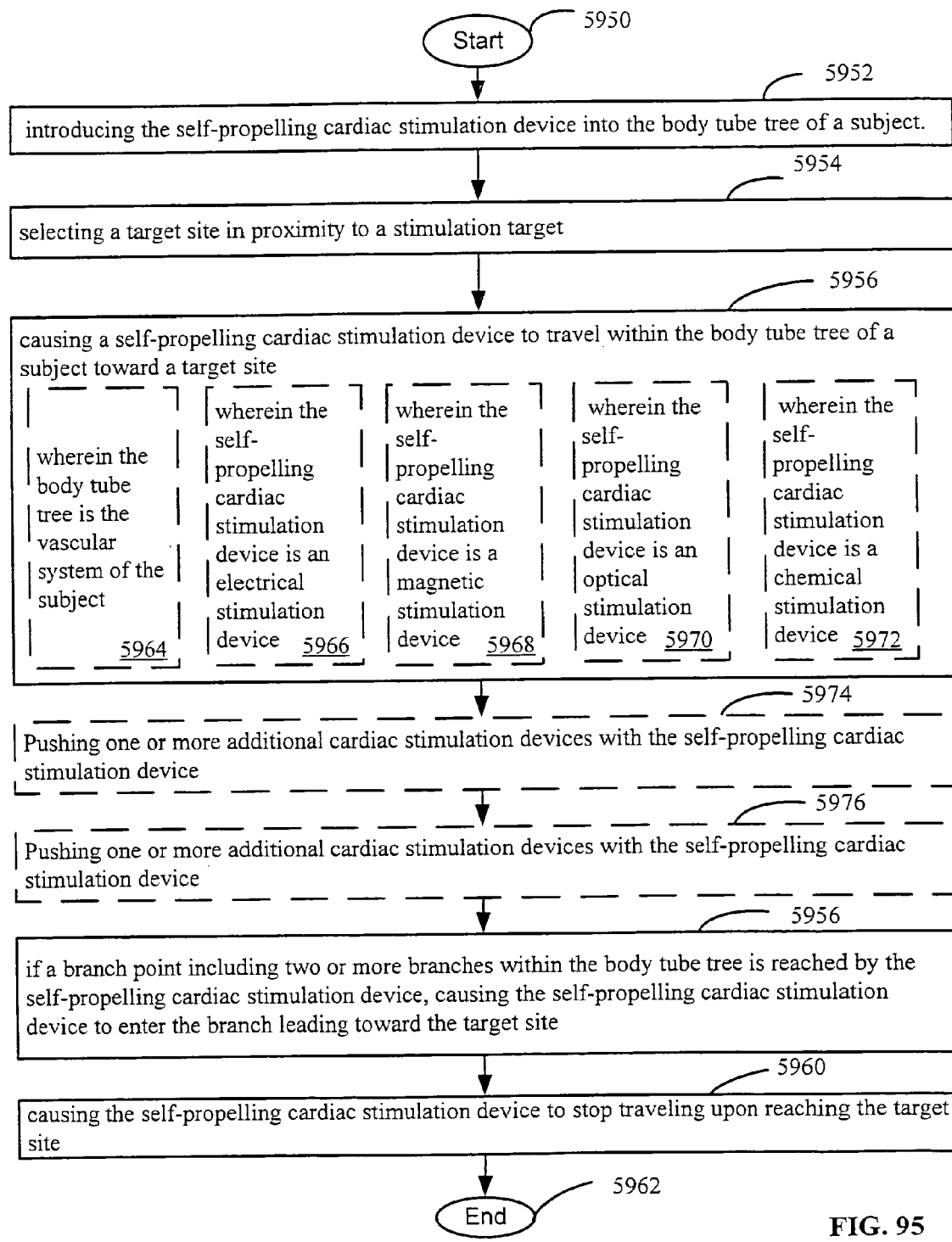
FIG. 95 is a flow diagram showing several variants of the method of FIG. 94.

FIG. 95 shows an expansion of the method of FIG. 94, which includes introducing the self-propelling cardiac stimulation device into the body tube tree of a subject (step 5952); selecting a target site in proximity to a stimulation target (step 5954); causing a self-propelling cardiac stimulation device to travel within the body tube tree of a subject toward a target site at 5956; if a branch point including two or more branches within the body tube tree is reached by the self-propelling cardiac stimulation device, causing the self-propelling cardiac stimulation device to enter a branch leading toward the target site at 5958; and causing the causing the self-propelling cardiac stimulation device to stop traveling upon reaching the target site at 5960. The self-propelling cardiac stimulation device may be introduced into a body tube tree of the subject at step 5952 by injection, or by being released from a catheter, for example. In some embodiments, the body tube tree may be the vascular system of the subject, as indicated in 5964; as illustrated in FIG. 64, a self-propelling cardiac stimulation device introduced into the vascular system (e.g. via a vein in the arm) can travel to the heart, where it may be used to deliver stimulation within a chamber of the heart. The self-propelling cardiac stimulation device may be an electromagnetic stimulation device, as indicated in 5966, a magnetic stimulation device, as indicated in 5968, an optical stimulation device, as indicated in 5970, or a chemical stimulation device, as indicated in 5972. The stimulation target referenced in step 5954 may be, for example, a particular region of the heart, and the target site may be a particular location within the heart, on the exterior of the heart, or in a blood vessel supplying the heart, for example. As described generally elsewhere herein, the method may include causing the self-propelling cardiac stimulation device to travel within the body tube tree under the control of a control system located at least in part on the self-propelling cardiac stimulation device, or causing the self-propelling cardiac stimulation device to travel within the body tube tree under the control of a remote portion. FIG. 95 also depicts two additional optional steps: in some embodiments, as indicated in 5974, the method may include pushing one or more additional cardiac stimulation devices with the self-propelling cardiac stimulation device, while in other embodiments, as indicated in 5976, the method may include pulling one or more additional cardiac stimulation devices with the self-propelling cardiac stimulation device.

Figure 96:
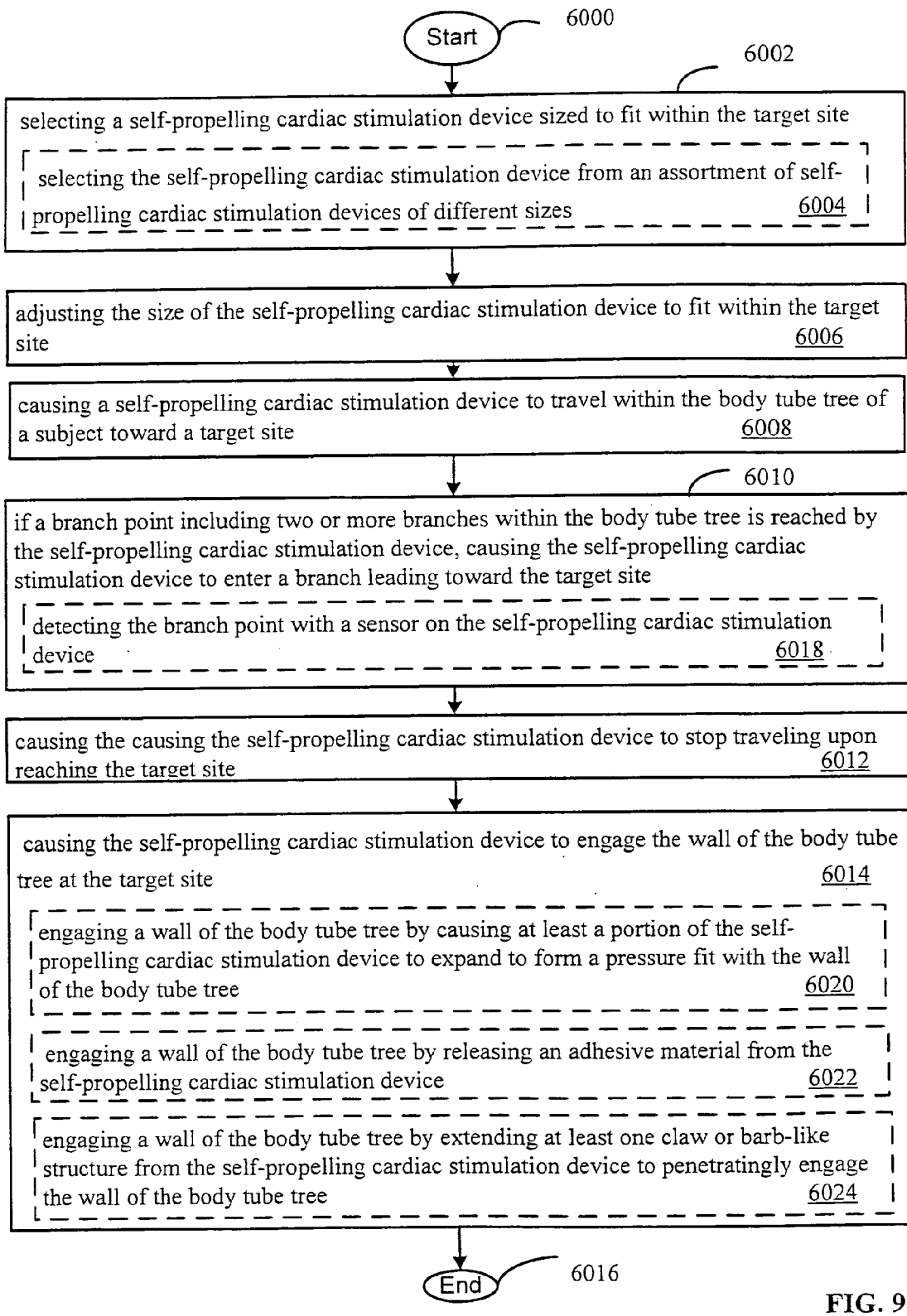
FIG. 96 is a flow diagram showing several additional variants of the method of FIG. 94.

A further variant of the method of emplacing a cardiac stimulation device outlined in FIG. 94 is shown in FIG. 96. The method may include selecting a self-propelling cardiac stimulation device that is sized to fit within the target site, as indicated at 6002. This may be accomplished, for example by selecting the self-propelling cardiac stimulation device from an assortment of self-propelling cardiac stimulation devices of different sizes, as indicated in 6004. Alternatively, the method may include adjusting the size of the self-propelling cardiac stimulation device to fit within the target site, as indicated at 6006. The method may include causing a self-propelling cardiac stimulation device to travel within the body tube tree of a subject toward a target site at 6008; if a branch point including two or more branches within the body tube tree is reached by the self-propelling cardiac stimulation device, causing the self-propelling cardiac stimulation device to enter a branch leading toward the target site at 6010; and causing the self-propelling cardiac stimulation device to stop traveling upon reaching the target site at 6012. The method may further include causing the self-propelling cardiac stimulation device to engage the wall of the body tube tree at the target site, at 6014. The method may include detecting the branch point with a sensor on the self-propelling cardiac stimulation device, as indicated at 6018.

The method may include engaging a wall of the body tube tree by causing at least a portion of the self-propelling cardiac stimulation device to expand to form a pressure fit with the wall of the body tube tree, as indicated at 6020, by releasing an adhesive material from the self-propelling cardiac stimulation device, as indicated at 6022, or by extending at least one claw or barb-like structure from the self-propelling cardiac stimulation device to penetratingly engage the wall of the body tube tree, as indicated at 6024.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. It will further be understand that method steps may be presented in a particular order in flowcharts, and/or examples herein, but are not necessarily limited to being performed in the presented order. For example, steps may be performed simultaneously, or in a different order than presented herein, and such variations will be apparent to one of skill in the art in light of this disclosure. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will recognize that electro-mechanical as used herein is not necessarily limited to a system that has both electrical and mechanical actuation except as context may dictate otherwise. Non-electrical analogs of electrical circuitry may include fluid circuitry, electro-mechanical circuitry, mechanical circuitry, and various combinations thereof.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of emplacing a cardiac stimulation device, comprising:
   causing a self-propelling cardiac stimulation device to travel within a body tube tree of a subject toward a target site;
   pushing or pulling one or more additional cardiac stimulation devices with the self-propelling cardiac stimulation device;
   if a branch point including two or more branches within the body tube tree is reached by the self-propelling cardiac stimulation device, causing the self-propelling cardiac stimulation device to enter a branch leading toward the target site;
   causing the self-propelling cardiac stimulation device to stop traveling upon reaching the target site; and
   delivering a cardiac pacing stimulus at the target site.

2. The method of claim 1, including introducing the self-propelling cardiac stimulation device into the body tube tree of the subject.

3. The method of claim 1, wherein the body tube tree is a vascular system of the subject.

4. The method of claim 1, wherein causing the self-propelling cardiac stimulation device to travel within the body tube tree of the subject toward the target site includes causing the self-propelling cardiac stimulation device to travel within the body tube tree under the control of a control system located at least in part on the self-propelling cardiac stimulation device.

5. The method of claim 1, wherein causing the self-propelling cardiac stimulation device to travel within the body tube tree of the subject toward the target site includes causing the self-propelling cardiac stimulation device to travel within the body tube tree toward a target site located within a chamber of a heart of the subject.

6. The method of claim 1, wherein delivering the cardiac pacing stimulus includes delivering an electrical stimulus.

7. The method of claim 1, wherein delivering the cardiac pacing stimulus includes delivering a magnetic stimulus.

8. The method of claim 1, including selecting the target site by selecting a site in proximity to a stimulation target.

9. The method of claim 1, wherein causing the self-propelling cardiac stimulation device to travel within the body tube tree of the subject toward the target site includes causing the self-propelling cardiac stimulation device to travel within the body tube tree under the control of a remote portion.

10. The method of claim 1, further comprising recording electromagnetic activity from the heart of the subject with the self-propelling cardiac stimulation device.

11. A method of emplacing a cardiac stimulation device, comprising:
  selecting a self-propelling cardiac stimulation device sized to fit within a target site from an assortment of self-propelling cardiac stimulation devices of different sizes;
  causing the self-propelling cardiac stimulation device to travel within a body tube tree of a subject toward a target site;
  if a branch point including two or more branches within the body tube tree is reached by the self-propelling cardiac stimulation device, causing the self-propelling cardiac stimulation device to enter a branch leading toward the target site;
  causing the self-propelling cardiac stimulation device to stop traveling upon reaching the target site and
  delivering a cardiac pacing stimulus at the target site.

12. The method of claim 11, including causing the self-propelling cardiac stimulation device to engage a wall of the body tube tree at the target site.

13. The method of claim 11, adjusting the size of the self-propelling cardiac stimulation device to fit within the target site.

14. The method of claim 11, including detecting the branch point with a sensor on the self-propelling cardiac stimulation device.

15. The method of claim 11, including engaging a wall of the body tube tree by causing at least a portion of the self-propelling cardiac stimulation device to expand to form a pressure fit with the wall of the body tube tree.

16. The method of claim 11, including engaging a wall of the body tube tree by releasing an adhesive material from the self-propelling cardiac stimulation device.

17. The method of claim 11, including engaging a wall of the body tube tree by extending at least one claw or barb-like structure from the self-propelling cardiac stimulation device to penetratingly engage the wall of the body tube tree.

\* \* \* \* \*